(12) United States Patent
Zhou et al.

(10) Patent No.: US 9,976,167 B2
(45) Date of Patent: May 22, 2018

(54) GROUP OF GLYCOSYLTRANSFERASES AND USE THEREOF

(71) Applicant: Shanghai Institutes For Biological Sciences, Chinese Academy Of Sciences, Shanghai (CN)

(72) Inventors: Zhihua Zhou, Shanghai (CN); Xing Yan, Shanghai (CN); Yun Fan, Shanghai (CN); Pingping Wang, Shanghai (CN); Yongjun Wei, Shanghai (CN); Wei Wei, Shanghai (CN); Jun Zhang, Shanghai (CN)

(73) Assignee: Shanghai Institutes For Biological Sciences, Chinese Academy Of Sciences, Shanghai (CN)

( * ) Notice: Subject to any disclaimer, the term of this patent is extended or adjusted under 35 U.S.C. 154(b) by 409 days.

(21) Appl. No.: 14/650,203

(22) PCT Filed: Dec. 6, 2013

(86) PCT No.: PCT/CN2013/088819
§ 371 (c)(1),
(2) Date: Dec. 18, 2015

(87) PCT Pub. No.: WO2014/086317
PCT Pub. Date: Jun. 12, 2014

(65) Prior Publication Data
US 2016/0115515 A1    Apr. 28, 2016

(30) Foreign Application Priority Data

Dec. 6, 2012   (CN) .......................... 2012 1 0520787
Jun. 7, 2013   (CN) .......................... 2013 1 0227689

(51) Int. Cl.
C12P 33/00     (2006.01)
C12P 19/56     (2006.01)
C12N 9/10      (2006.01)

(52) U.S. Cl.
CPC ............ *C12P 33/00* (2013.01); *C12N 9/1048* (2013.01); *C12N 9/1051* (2013.01); *C12P 19/56* (2013.01)

(58) Field of Classification Search
None
See application file for complete search history.

(56) References Cited

U.S. PATENT DOCUMENTS 6,294,714 B1 * 9/2001 Matsunaga ............ A01H 4/005
                                                    435/320.1

FOREIGN PATENT DOCUMENTS

| CN | 1225366 A | 8/1999 |
|---|---|---|
| CN | 1105781 C | 4/2003 |
| CN | 1587273 A | 3/2005 |
| CN | 101307082 A | 11/2008 |
| CN | 102549155 A | 7/2012 |
| EP | 1 544300 A1 | 6/2005 |
| EP | 1816193 A1 | 8/2007 |
| JP | H08-208688 A | 8/1996 |
| JP | 2011051933 A | 3/2011 |
| WO | WO 2008/062165 A2 | 5/2008 |
| WO | WO 2011/016260 A1 | 2/2011 |
| WO | WO 2014/051214 A1 | 4/2014 |
| WO | WO 2014/051215 A1 | 4/2014 |

OTHER PUBLICATIONS

Augustin et al. (Plant Physiology, Dec. 2012, vol. 160, pp. 1881-1895, Electronically published on Oct. 1, 2012).*
GenBank Submission; NIH/NCBI, Accession No. AED99883. Luo et al., Mar 19, 2012. 2 pages.
GenBank Submission; NIH/NCBI, Accession No. GU997660. Luo et al., Mar 19, 2012. 2 pages.
Jung et al., Discovery of genes for ginsenoside biosynthesis by analysis of ginseng expressed sequence tags. Plant Cell Rep. Oct. 2003;22(3):224-30. Epub Aug. 13, 2003.
Kim et al., Ginsensoside $Rh_2$ prepared from enzyme reaction. Journal of Dalian Institute Light Industry. Jun. 2001;20(2):99-104.
Luo et al., Analysis of the transcriptome of Panax notoginseng root uncovers putative triterpene saponin-biosynthetic genes and genetic markers. BMC Genomics. Dec. 23, 2011;12 Suppl 5:S5. doi: 10.1186/1471-2164-12-S5-S5. Epub Dec. 23, 2011.
Shi et al., Advances on biosynthesis of panax notoginseng saponins and regulation of key enzymes. Acta Bot. Boreal.—Occident. Sin. 2010;30(11):2358-64.
Vogt et al., Glycosyltransferases in plant natural product synthesis: characterization of a supergene family. Trends in Plant Science. Sep. 2000;5(9):380-6.
Chen et al., 454 EST analysis detects genes putatively involved in ginsenoside biosynthesis in Panax ginseng. Plant Cell Rep. Sep. 2011;30(9):1593-601. doi:10.1007/s00299-011-1070-6. Epub Apr. 12, 2011. Supplementary material.
Genbank Submission. FJ477891.1. Apr. 27, 2010. Naoumkina et al.
Genbank Submission. GU997660.1. Mar. 19, 2012. Luo et al.
Genbank Submission. JQ291613. Oct. 25, 2012. Augustin et al.
Genbank Submission. JQ291615.1. Oct. 25, 2012. Augustin et al.

(Continued)

*Primary Examiner* — Suzanne M Noakes
*Assistant Examiner* — Jae W Lee
(74) *Attorney, Agent, or Firm* — Wolf, Greenfield & Sacks, P.C.

(57) ABSTRACT

Provided are the use of glycosyltransferases gGT25, gGT13, gGT30, gGT25-1, gGT25-3, gGT25-5, gGT29, gGT29-3, gGT29-4, gGT29-5, gGT29-6, gGT29-7, 3GT1, 3GT2, 3GT3, 3GT4 and derived polypeptides therefrom in the catalyzed glycosylation of terpenoid compounds and the synthesis of new saponins, wherein the glycosyltransferases can specifically and efficiently catalyze tetracyclic triterpenoid compound substrates at positions C-20 and/or C-6 and/or C-3 during hydroxyl glycosylation, and/or transfer the glycosyl from a glycosyl donor to the first glycosyl of the tetracyclic triterpenoid compounds at position C-3, so as to extend the sugar chain. The glycosyltransferases can also be used for constructing man-made synthetic rare ginsenosides and a variety of new ginsenosides and derivatives thereof.

10 Claims, 30 Drawing Sheets

(56) References Cited

OTHER PUBLICATIONS

Han et al., Cytochrome P450 CYP716A53v2 catalyzes the formation of protopanaxatriol from protopanaxadiol during ginsenoside biosynthesis in Panax ginseng. Plant Cell Physiol. Sep. 2012;53(9):1535-45. doi: 10.1093/pcp/pcs106. Epub Aug. 7, 2012.
Jin et al. Biotransformation of Ginsenosides (Ginseng Saponins). Int J Biomedical Pharma Sci. Jul. 26, 2011. 34-44.
Kim et al., Upregulation of ginsenoside and gene expression related to triterpene biosynthesis in ginseng hairy root cultures elicited by methyl jasmonate. Plant Cell Tiss Organ Cult. 2009;98:25-33.
Kim et al., Ginseng metabolic engineering: Regulation of genes related to ginsenoside biosynthesis. J Med Plants Res. Dec. 2009;3(13):1270-1276.
Naouumkina et al., Genomic and coexpression analyses predict multiple genes involved in triterpene saponin biosynthesis in Medicago truncatula. Plant Cell.Mar. 2010;22(3):850-66. doi: 10.1105/tpc.109.073270. Epub Mar. 26, 2010.
Wei et al., Characterization of Panax ginseng UDP-Glycosyltransferases Catalyzing Protopanaxatriol and Biosyntheses of Bioactive Ginsenosides F1 and Rh1 in Metabolically Engineered Yeasts. Mol Plant. Sep. 2015;8(9):1412-24. doi:10.1016/j.molp.2015.05.010. Epub May 30, 2015.
Yue et al., Purification and characterization of UDPG:ginsenoside Rd glucosyltransferase from suspended cells of Panax no to ginseng. Process Biochem. 2005;40:3742-3748.

\* cited by examiner (a) 3GT1 and 3GT2  (b) 3GT3  (c) 3GT4

(a) 3GT1 and 3GT2  (b) 3GT3  (c) 3GT4

(a) 3GT1 and 3GT2      (b) 3GT3      (c) 3GT4

(A)

(B)

(a) PPD catalyzed by the combination of gGT29 and 3GT1

(b) PPD catalyzed by the combination of gGT29 and 3GT4

GROUP OF GLYCOSYLTRANSFERASES AND USE THEREOF

RELATED APPLICATIONS

This application is a national stage filing under 35 U.S.C. § 371 of International Application PCT/CN2013/088819 entitled "GROUP OF GLYCOSYLTRANSFERASES AND USE THEREOF" filed Dec. 6, 2013, which claims priority to CN Application No. 201310227689.7, filed Jun. 7, 2013, and CN Application No. 201210520787.5, filed Dec. 6, 2012, the entire disclosure of each of which is incorporated by reference in its entirety.

TECHNICAL FIELD

The present invention relates to the biotechnology and the phytobiology field. Specifically, the present invention relates to glycosyltransferases and use thereof.

BACKGROUND ART

Saponins isolated from *Panax ginseng* and the congener plants thereof (including *Panax. notoginseng* and *Panax quinguefolium* etc.) are collectively named as ginsenosides. Ginsenosides belong to triterpene saponins and they are the main active ingredient of *Panax*. At present, at least 60 kinds of ginsenosides have been isolated from *Panax*, some of which were proved to have broad physiological functions and pharmaceutical values including anti-cancer, immuno-regulation, anti-fatigue, heart protection, hepatoprotection, etc.

Structurally, ginsenosides are small molecules with biological activity formed by the glycosylation of sapogenins. The types of ginsenoside sapogenins are limited, mainly including dammarane-type protopanaxadiol (PPD), protopanaxatriol (PPT), and oleanolic acid. Recently, two new sapogenins, 25-OH-PPD and 25-OCH3-PPD, were isolated from *P. notoginseng*. Both of these new sapogenins present excellent anti-tumor activities.

Upon glycosylation, the water solubility of sapogenins is enhanced and different biological activities are exhibited. The carbohydrate chain of PPD saponin usually binds to C3 and (or) C20 hydroxyl(s) of sapogenin(s). Compared with PPD saponin, PPT saponin has one more hydroxyl at position C6. The glycosylation bindings all occur at C6 (and) or C20 hydroxyl(s) of PPT saponin according to the present findings. Glycosylation binding at C-3 of PPT saponin was not yet reported. The glycosyl can be glucose, rhamnose, xylose or arabinose.

The physiological functions and pharmaceutical values of ginsenosides can dramatically vary with different glycosyl binding sites, and composition and length of carbohydrate chains. For example, ginsenoside Rb1, Rd and Rc are all saponins with PPD as their sapogenins; they only vary in glycosyl modification, but their physiological functions differ a lot. Rb1 possesses the function of stabilizing the central neural system; while the function of Rc is to inhibit the function of the central neural system. Rb1 presents broad physiological functions while the functions of Rd are quite limited.

Structural diversities of ginsenoside sapogenins and saponins are also embodied in their stereo structures. Despite many chiral carbon atoms on tetracyclic triterpenoids skeleton, C20 is the dominant site for forming stereo structures. C20 epimers exist in almost every kind of ginsenosides and sapogenins. The content of ginsenosides and sapogenins with S-configuration at C20 in *ginseng* is far above that of R-configuration. Thus, in most cases, ginsenosides and sapogenins generally refer to C20 S-configuration ginsenosides and sapogenins. However, physiological activities of C20 epimers of ginsenosides and sapogenins are distinctly different. For example, the S-type ginsenoside Rh2 (3-O-β-(D-glucopyranosyl)-20(S)-protopanaxadiol) can significantly inhibit prostate cancer cells, while the inhibiting effect of R-type ginsenosides Rh2 (3-O-β-(D-glucopyranosyl)-20(R)-protopanaxadiol) is quite poor. The R-type ginsenoside Rh2 can selectively inhibit the generation of osteoclasts without any cytotoxicity, while the S-type ginsenoside Rh2 poorly inhibits the osteoclasts generation with strong cytotoxicity to osteoclasts. Besides, the regulatory effects of the S-type and R-type ginsenoside Rh2s on P-glycoprotein are substantially different.

The function of glycosyltransferases is transferring glycosyl(s) from glycosyl donor(s) (nucleotide diphosphate sugar, such as, UDP-glucose) to different glycosyl receptor(s). At present, glycosyltransferases have been classified into 94 families based on different amino acid sequences. More than one hundred different glycosyltransferases were identified among the sequenced plant genomes for now. Glycosyl acceptors for these glycosyltransferases include saccharides, lipids, proteins, nucleic acids, antibiotics, and other small molecules. The function of glycosyltransferases involved in saponin glycosylation in *ginseng* is transferring glycosyls from glycosyl donors to hydroxyls at position C-3, C-6, or C-20 of sapogenins or aglycones, thereby forming saponins with various pharmaceutical values.

At present, upon analyzing the transcriptome of *P. ginseng, P. quinguefolium* and *P. notoginseng*, researchers have identified huge amounts of glycosyltransferase genes. However, which of them are involved in ginsenosides synthesis remained ambiguous. The studies on isolation and purification of glycosyltransferases are making slow progress due to the numerous kinds of glycosyltransferases in *ginseng* and the extremely low content thereof.

Rare ginsenosides refer to the saponins with extremely low content in *P. ginseng*. Ginsenoside CK (20-O-β-(D-glucopyranosyl)-20(S)-protopanaxadiol) belongs to PPD-type saponins with a glucosyl group attached to C-20 hydroxyl of sapogenins. The content of ginsenoside CK in *P. ginseng* is extremely low, and it is the main metabolite produced by microbiological hydrolysis of PDD-type saponins in human intestinal tract. Researches indicated that most PDD-type saponins can be absorbed by human body only upon being metabolized into CK. Thus, ginsenosides CK is the real entity which can be directly absorbed by human body and take effects, while other saponins are only prodrugs. Ginsenoside CK has excellent anti-tumor activity. It can induce tumor cell apoptosis and inhibit tumor cell metastasis. The assays using it with combination of radiotherapy or chemotherapy came out to possess the effect of radiotherapy or chemotherapy enhancement. Besides, ginsenoside CK has the activities of anti-allergy, anti-inflammation, neural protection, anti-diabetes, and anti-skin aging. The pharmacological activities of ginsenoside CK are characterized by its multiple-targets, high activity, and low toxicity.

Ginsenoside F1 (20-O-β-D-glucopyranosyl-20(S)-protopanaxatriol) belonging to PPT saponins also has a very low content in *P. ginseng* and is one of the rare ginsenosides as well. Ginsenoside F1 is quite similar to CK in structure, also having a glucosyl group attached to C-20 hydroxyl of sapogenin. Ginsenoside F1 also possesses unique pharmaceutical values. It has the function of anti-aging and anti-oxidization.

Ginsenoside Rh1 (6-O-β-D-glucopyranosyl-20(S)-protopanaxatriol) belonging to PPT saponins also has a very low content in *P. ginseng* and is one of the rare ginsenosides as well. Ginsenoside Rh1 is quite similar to F1 in structure, but its glycosylation site is the hydroxyl at the C-6 position. Ginsenoside Rh1 also possesses unique physiological functions, such as anti-allergy and anti-inflammation.

Ginsenoside Rh2 (3-O-β-(D-glucopyranosyl)-20(S)-protopanaxadiol) with an extremely low content in *P. ginseng* of about 0.01% of *ginseng* dry weight is one of the rare ginsenosides as well. However, ginsenoside Rh2 has an excellent anti-tumor activity, which enabling it to be one of the most primary anti-tumor active ingredients in *ginseng*. It can inhibit tumor cell growth, induce tumor cell apoptosis, and inhibit tumor cell metastasis. Researches showed that ginsenoside Rh2 can inhibit the proliferation of lung cancer cells 3LL (mice), Morris liver cancer cells (rats), B-16 melanoma cells (mice), and HeLa cells (human). Clinically, treatments by combing ginsenoside Rh2 with radiotherapy or chemotherapy can improve the effects of theses therapies. Moreover, ginsenoside Rh2 also has the function of anti-allergy, improving body immunity, and inhibiting the inflammation produced by NO and PEG.

Ginsenoside Rg3 with a low content in *ginseng* has a significant anti-tumor effect, and it is complementary to ginsenoside Rh2 in anti-tumor effect. Clinic uses demonstrated that the combination of Rg3 and Rh2 can further enhance their synergetic effect on tumor treatment.

Because of the extremely low content of rare ginsenosides CK, F1, Rh1, Rh2 and Rg3 in *P. ginseng*, the present preparation method is, starting from the large amounts of saponins in *P. ginseng*, extracting and purifying upon conversion by selectively hydrolyzing glycosyls. Total saponins or protopanaxadiol type saponins of *panax* plants are used as raw materials for converting, isolating, and extracting 20(S)-protoginsenoside-Rh2. This preparation method is advantaged in that the huge amounts of diol type saponins are utilized. However, the reaction must be conducted under high temperature and high pressure (Changchun SONG etc. Preparation Method of 20(S)-ginsenosides-Rh2, Pharmaceutical Composition and Use Thereof, CN patent No. 1225366, 1999). Two methods of preparing 20(R&S)-ginsenosides-Rh2 from *ginseng* ingredients are disclosed by Korea *Ginseng* and Tobacco Institution; wherein the PPD saponin ingredients are obtained first, and then subjected to acidic hydrolysis to give 20(R&S)-ginsenosides-Rg3, the ginsenoside Rg3 is then treated to obtain ginsenoside Rh2. The major defect of the above methods is that they need a set of PPD-type saponin monomers as the starting materials for the products, which results in the complicated reaction steps, great loss of raw materials and complicated operations, thereby leading to the increased costs and difficulty in improving the yield. Since the glycosyls at C-20 of CK and F1 can be easily destroyed during the hydrolysis process, chemical methods are unsuitable for CK and F1 production. The yield of Rh1 by hydrolyzing saponins through acid or alkaline method is very low and many by-products are produced as well.

Enzymatic conversion method is characterized with its mild condition, high specificity, and easy isolation and purification of products, and hence it is the major method for CK, F1 and Rh1 production at present. The enzymes used for preparing ginsenosides CK, F1, Rh1 and Rh2 mainly include naringinase, pectinase, cellulase, lactase and the like. Ginsenoside CK can be also obtained by microbiological conversion which mainly utilizes anaerobion originated from intestinal tracts. Although great progresses have been made for preparing rare ginsenosides CK, F1, Rh1 and Rh2 by biological conversion (enzymatic method and microbiological method), the cost for preparing CK1, F1, Rh1 and Rh2 is still high and the yield is quite limited due to the fact that these methods use ginsenosides as the raw material (CN patent: CN1105781C; Dongshi J I N, Journal of Dalian Light Industry Academy, 2001).

In view of the important biological activities and tremendous economic values of ginsenoside Rh2, continuous efforts have been made for decades to produce such ginsenoside through chemical synthesis, the basic principle of which is the condensation reaction of PPD and the corresponding glycosyls, namely semi-synthesis (JP patent: JP8-208688, 1996). This method uses PPD as the raw material for semi-synthesizing 20(S)-protoginsenoside-Rh2. Its synthesis comprises six steps, and equivalent silver carbonate is used as catalyst in the glycosylation reaction. The high price of the catalyst results in a high cost, and at the same time, the poor stereoselectivity of the catalyst results in a low yield of product. In an alternative method, PPD with its C-12 hydroxyl substituted by aromatic acyl or alkyl is used and glucosyl group donor with activated C1 hydroxyl is added under the protection of organic solvents and inert gas for condensation reaction catalyzed by Lewis acid with the presence of molecular sieve. The resultant product is subjected to column chromatography or recrystallization purification and then the protecting groups are removed, thereby obtaining 20(S)-ginsenosides-Rh2 (Yongzheng H U I, A Method for Preparing 20(S)-ginsenosides-Rh2, CN patent: CN 1587273A, 2005).

At present, there is no method to effectively prepare rare ginsenosides CK, F1, Rh1, Rh2 and Rg3 in this field. Therefore, there is an urgent need to develop various glycosyltransferases with high specificity and efficiency.

Content of the Invention

The object of the present invention is to provide a group of glycosyltransferases and use thereof.

The first aspect of the present invention is to provide a method for in vitro glycosylation, comprising the steps of:

in the presence of a glycosyltransferase, transferring a glycosyl from a glycosyl donor to the following site on tetracyclic triterpenoid compounds:

positions C-20, C-6, C-3 or the first glycosyl at position C-3;

thereby forming glycosylated tetracyclic triterpenoid compounds;

wherein, said glycosyltransferase is selected from the group consisting of:

a glycosyltransferase as set forth by SEQ ID NOs.: 2, 16, 18, 20, 22, 24, 26, 28, 43, 55, 57, 59 or 61.

The second aspect of the present invention is to provide an isolated polypeptide; said polypeptide is selected from the group consisting of:

(a) a polypeptide having the amino acid sequence as set forth by any one of SEQ ID NOs.: 2, 16, 18, 20, 26, 28, 43, 55, 57, 59 or 61;

(b) a derivative polypeptide, which is derived from a polypeptide having the amino acid sequence as set forth by any one of SEQ ID NOs.: 2, 16, 18, 20, 26, 28, 43, 55, 57, 59 or 61 by substitution, deletion, or addition of one or more amino acid residues, or by addition of a signal peptide sequence, and has the activity of glycosyltransferase;

(c) a derivative polypeptide, which has the polypeptide sequence of (a) or (b) in its sequence;

(d) a derivative polypeptide, which has ≥85% or ≥90% (preferably ≥95%) sequence homology with the amino acid sequence as set forth by any one of SEQ ID NOs: 2, 16, 18, 20, 26, 28, 43, 55, 57, 59 or 61 and has the activity of glycosyltransferase.

In another preferred embodiment, said sequence (c) is a fusion protein derived from (a) or (b) by addition of a tag sequence, signal sequence, or secretory signal sequence.

In another preferred embodiment, said polypeptide is set forth by SEQ ID NOs: 2, 16, 18, 20, 26, 28, 3, 55, 57, 59 or 61.

The third aspect of the present invention is to provide an isolated polypeptide; said polypeptide is selected from the group consisting of:
(a1) a polypeptide having the amino acid sequence as set forth by any one of SEQ ID NOs.: 22, 24 and 41;
(b1) a polypeptide having the polypeptide sequence of (a1) in its sequence; and/or
said polypeptide is selected from the group consisting of:
(a2) a polypeptide having the amino acid sequence as set forth by any one of SEQ ID NOs.: 4 and 6;
(b2) a derivative polypeptide, which is derived from a polypeptide having the amino acid sequence as set forth by any one of SEQ ID NOs.: 4 and 6 by substitution, deletion, or addition of one or more amino acid residues, or by addition of a signal peptide sequence, and has the activity of glycosyltransferase;
(c2) a derivative polypeptide, which has the polypeptide sequence of (b2) in its sequence;
(d2) a derivative polypeptide, which has ≥85% or ≥90% (preferably ≥95%) sequence homology with the amino acid sequence as set forth by any one of SEQ ID NOs: 4 and 6 and has the activity of glycosyltransferase.

In another preferred embodiment, sequence (c2) is a fusion protein derived from (a2) or (b2) by addition of a tag sequence, signal sequence, or secretory signal sequence.

The fourth aspect of the present invention is to provide an isolated polynucleotide; said polynucleotide is selected from the group consisting of:
(A) a nucleotide sequence encoding the polypeptide of the first or the second aspect;
(B) a nucleotide sequence encoding the polypeptide as set forth by SEQ ID NOs.: 2, 4, 6, 16, 18, 20, 22, 24, 26, 28, 41, 43, 55, 57, 59 or 61;
(C) a nucleotide sequence as set forth by SEQ ID NOs.: 1, 3, 5, 15, 17, 19, 21, 23, 25, 27, 40, 42, 54, 56, 58 or 60;
(D) a nucleotide sequence, which has ≥95% (preferably ≥98%) homology with the sequence as set forth by SEQ ID NOs.: 1, 3, 5, 15, 17, 19, 21, 23, 25, 27, 40, 42, 54, 56, 58 or 60;
(E) a nucleotide sequence derived from the nucleotide sequence as set forth by SEQ ID NOs.: 1, 3, 5, 15, 17, 19, 21, 23, 25, 27, 40, 42, 54, 56, 58 or 60 by deletion or addition of 1-60 (preferably 1-30, more preferably 1-10) nucleotides at its 5' end and/or 3' end;
(F) a nucleotide sequence complementary to (preferably completely complementary to) any one of the nucleotide sequence of (A)-(E).

In another preferred embodiment, said nucleotide sequence is as set forth by SEQ ID NOs.: 1, 3, 5, 15, 17, 19, 21, 23, 25, 27, 40, 42, 54, 56, 58 or 60.

In another preferred embodiment, the polynucleotide with a sequence as set forth by SEQ ID NOs.: 1, 3, 5, 15, 17, 19, 21, 23, 25, 27, 40, 42, 54, 56, 58 or 60 encodes the polypeptide with an amino acid sequence as set forth by SEQ ID NOs.: 2, 4, 6, 16, 18, 20, 22, 24, 26, 28, 41, 43, 55, 57, 59 or 61, respectively.

The fifth aspect of the present invention is to provide a vector; said vector contains the polynucleotide in the third aspect of the present invention. Preferably, said vector includes expression vector, shuttle vector, or integration vector.

The fifth aspect of the present invention is to provide use of said isolated polypeptide in the first or the second aspect for catalyzing one or more of the following reactions, or for preparing a catalyst preparation used in the catalyzation of one or more of the following reactions: transferring glycosyl(s) from glycosyl donor(s) to hydroxyl(s) at position(s) C-20 and/or C-6 and/or C-3 of tetracyclic triterpenoid compound(s) so as to substitute H in said hydroxyl, and transferring glycosyl(s) from glycosyl donor(s) to the first glycosyl at position C-3 of tetracyclic triterpenoid compound(s) so as to extend carbohydrate chain.

In another preferred embodiment, said glycosyl donor(s) includes a nucleoside diphosphate sugar selected from the group consisting of: UDP-glucose, ADP-glucose, TDP-glucose, CDP-glucose, GDP-glucose, UDP-acetyl glucose, ADP-acetyl glucose, TDP-acetyl glucose, CDP-acetyl glucose, GDP-acetyl glucose, UDP-xylose, ADP-xylose, TDP-xylose, CDP-xylose, GDP-xylose, UDP-galacturonic acid, ADP-galacturonic acid, TDP-galacturonic acid, CDP-galacturonic acid, GDP-galacturonic acid, UDP-galactose, ADP-galactose, TDP-galactose, CDP-galactose, GDP-galactose, UDP-arabinose, ADP-arabinose, TDP-arabinose, CDP-arabinose, GDP-arabinose, UDP-rhamnose, ADP-rhamnose, TDP-rhamnose, CDP-rhamnose, GDP-rhamnose, or other nucleoside diphosphate hexose or nucleoside diphosphate pentose, or the combination thereof.

In another preferred embodiment, said glycosyl donor(s) includes uridine diphosphate (UDP) sugars selected from the group consisting of: UDP-glucose, UDP-galacturonic acid, UDP-galactose, UDP-arabinose, UDP-rhamnose, or other uridine diphosphate hexose or uridine diphosphate pentose, or the combination thereof.

In another preferred embodiment, said isolated polypeptide is used for catalyzing one or more of the following reactions or for preparing a catalyst preparation used in the catalyzation of one or more of the following reactions:

(A)

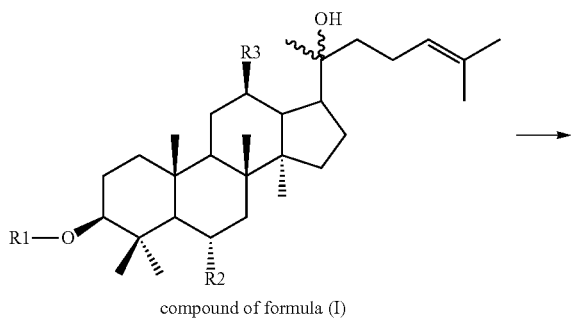

compound of formula (I)

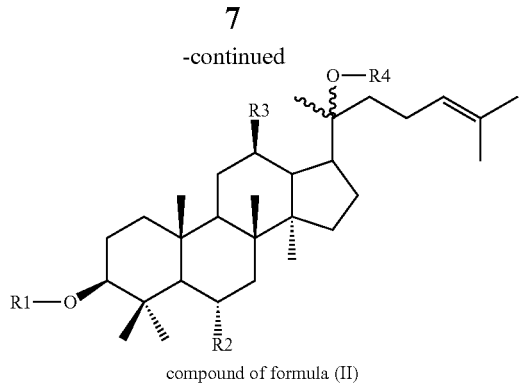

compound of formula (II)

wherein, R1 is H, monosaccharide glycosyl or polysaccharides glycosyl; R2 or R3 is H or OH; R4 is glycosyl; said polypeptide is selected from SEQ ID NOs.: 2, 16 or 18 or a derivative polypeptide thereof.

In another preferred embodiment, said monosaccharide includes glucose (Glc), rhamnose (Rha), acetyl glucose (Glc (6) Ac), arabinofuranose (Araf), arabopyranose (Arap), and xylose (Xyl), etc.

In another preferred embodiment, said polysaccharide includes polysaccharides composed of 2-4 monosaccharides, such as Glc(2-1)Glc, Glc(6-1)Glc, Glc(6)Ac, Glc(2-1)Rha, Glc(6-1)Arap, Glc(6-1)Xyl, Glc(6-1)Araf, Glc(3-1) Glc(3-1), Glc(2-1) Glu(6)Ac, Glc(6-1)Arap(4-1)Xyl, Glc(6-1)Arap(2-1)Xyl, or Glc(6-1)Arap(3-1)Xyl, etc.

Compounds with R1-R4 substituted are shown in the following table:

| substrate | R1 | R2 | R3 | R4 | product |
|-----------|----|----|----|----|---------|
| PPD | H | H | OH | glycosyl | CK |
| Rh2 | 1 glycosyl | H | OH | glycosyl | F2 |
| Rg3 | 2 glycosyls | H | OH | glycosyl | Rd |
| PPT | H | OH | OH | glycosyl | F1 |
| DM | H | H | H | glycosyl | 20-G-DM |

That is, when both of said R1 and R2 are H, and R3 is OH, said compound of formula (I) is protopanaxadiol (PPD);

when R1 is a glucosyl, R2 is H, and R3 is OH, said compound of formula (I) is ginsenoside Rh2;

when R1 is two glucosyls, R2 is H, and R3 is OH, said compound of formula (I) is ginsenoside RG3;

when R1 is H, R2 is OH, and R3 is OH, said compound of formula (I) is protopanaxatriol (PPT);

when R1 is H, R2 is H, and R3 is H, said compound of formula (I) is dammarenediol II (DM).

(B)

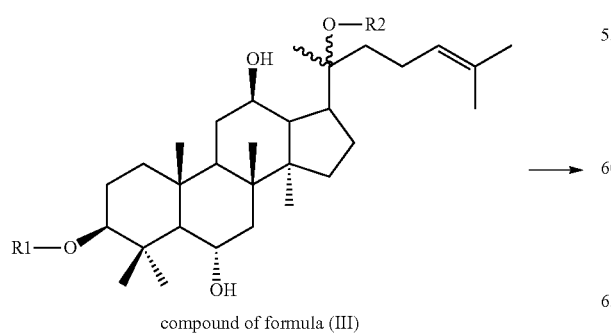

compound of formula (III)

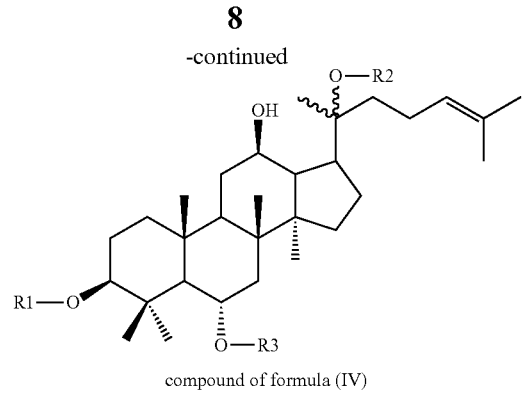

compound of formula (IV)

wherein, R1 is H or a glycosyl, R2 is a glycosyl, R3 is a glycosyl, said polypeptide is selected from SEQ ID NOs.: 2, 16, 18, or 20 or a derivative polypeptide thereof;

or, R1 is H or a glycosyl; R2 is H; R3 is a glycosyl, said polypeptide is selected from SEQ ID NO.: 20 or a derivative polypeptide thereof.

Compounds with R1-R3 substituted are shown in the following table:

| substrate | R1 | R2 | R3 | product |
|-----------|----|----|----|---------|
| F1 | H | glycosyl | glycosyl | Rg1 |
| PPT | H | H | glycosyl | Rh1 |

When both of said R1 and R2 are H, said compound of formula (III) is protopanaxatriol (PPT).

When R1 is H, R2 is a glucosyl, said compound of formula (III) is ginsenoside F1.

(C)

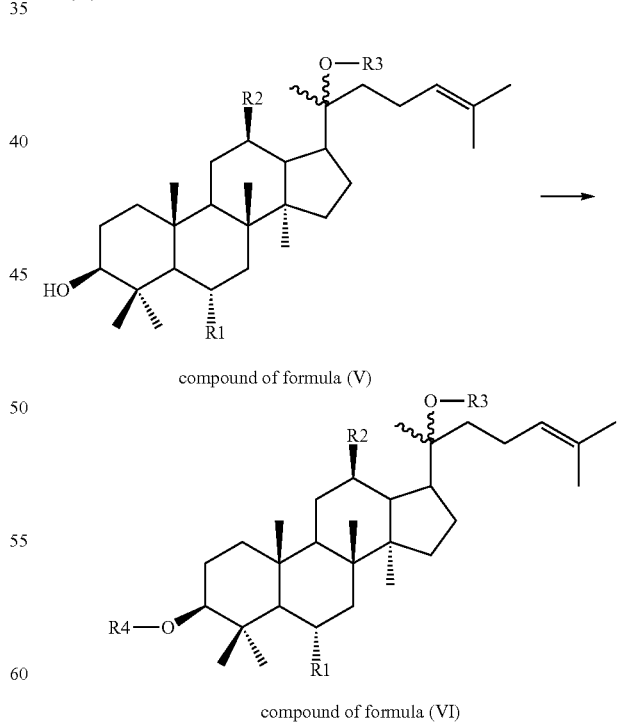

compound of formula (V)

compound of formula (VI)

wherein, R1 is H or OH; R2 is H or OH; R3 is H or a glycosyl; R4 is a glycosyl, said polypeptide is selected from SEQ ID NOs.: 22, 24, 41 or 43 or a derivative polypeptide thereof.

Compounds with R1-R4 substituted are shown in the following table:

| substrate | R1 | R2 | R3 | R4 | product |
|---|---|---|---|---|---|
| PPD | H | OH | H | glycosyl | Rh2 |
| CK | H | OH | glycosyl | glycosyl | F2 |
| PPT | OH | OH | H | glycosyl | 3-G-PPT |
| F1 | OH | OH | glycosyl | glycosyl | 3-G-F1 |
| DM | H | H | H | glycosyl | 3-G-DM |

When both of R1 and R3 are H, R2 is OH, said compound of formula (V) is PPD;

R1 is H, R2 is OH, R3 is a glucosyl, said compound of formula (V) is ginsenoside CK;

R1 is OH, R2 is OH, R3 is H, said compound of formula (V) is PPT;

R1 is OH, R2 is OH, R3 is a glucosyl, said compound of formula (V) is ginsenoside F1;

R1 is H, R2 is OH, R3 is H, said compound of formula (V) is dammarenediol II (DM).

When the substrate is PPD, said polypeptide is selected from SEQ ID NOs.: 22, 24, 41 or 43 or a derivative polypeptide thereof; when the substrate is CK, said polypeptide is selected from SEQ ID NOs.: 22, 24 or 43 or a derivative polypeptide thereof; when the substrate is PPT, said polypeptide is selected from SEQ ID NOs.: 22, 24 or 41 or a derivative polypeptide thereof; when the substrate is F1 and DM, said polypeptide is selected from SEQ ID NOs.: 22 or 24 or a derivative polypeptide thereof.

(D)

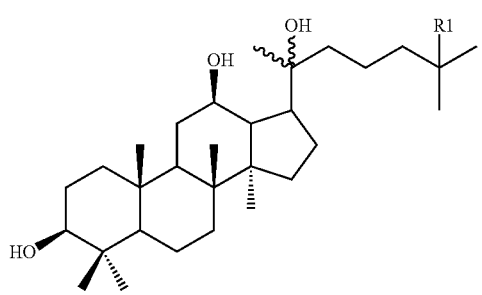

compound of formula (VII)

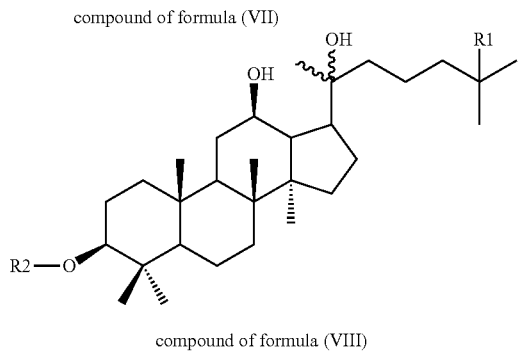

compound of formula (VIII)

wherein, R1 is OH or OCH$_3$; R2 is glycosyl, said polypeptide is selected from SEQ ID NOs.: 22, 24, 41 or 43 or a derivative polypeptide thereof.

Compounds with R1-R2 substituted are shown in the following table:

| substrate | R1 | R2 | product |
|---|---|---|---|
| 25-OH-PPD | OH | glycosyl | 3-G-25-OH-PPD |
| 25-OCH$_3$-PPD | OCH$_3$ | glycosyl | 3-G-25-OCH$_3$-PPD |

When R1 is OH, said compound of formula (VII) is 25-OH-PPD;

R1 is OCH, said compound of formula (VII) is 25-OCH$_3$-PPD.

(E)

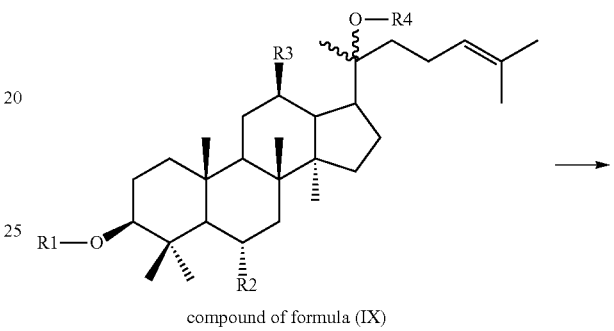

compound of formula (IX)

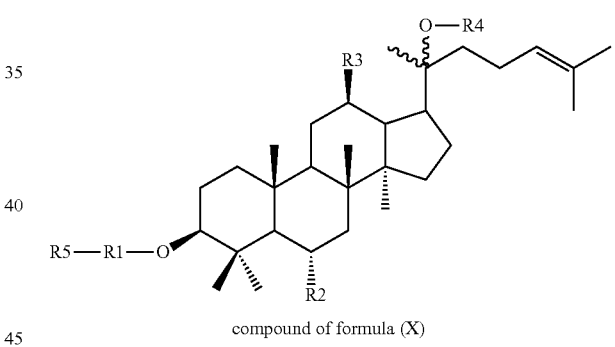

compound of formula (X)

wherein, R1 is glycosyl; R2 or R3 is OH or H; R4 is glycosyl or H; R5 is glycosyl, R5-R1-0 is a glycosyl derived from the first glycosyl at C-3, said polypeptide is selected from SEQ ID NOs.: 26, 28, 55, 57, 59 or 61 or a derivative polypeptide thereof.

Compounds with R1-R4 substituted are shown in the following table:

| substrate | R1 | R2 | R3 | R4 | product |
|---|---|---|---|---|---|
| Rh2 | glycosyl | H | OH | H | Rg3 |
| F2 | glycosyl | H | OH | glycosyl | Rd |

When R1 is a glucosyl; R2 is H, R3 is OH, R4 is H, compound of formula (IX) is Rh2.

When R1 is a glucosyl; R2 is H, R3 is OH, R4 is a glucosyl, compound of formula (IX) is F2.

(F)

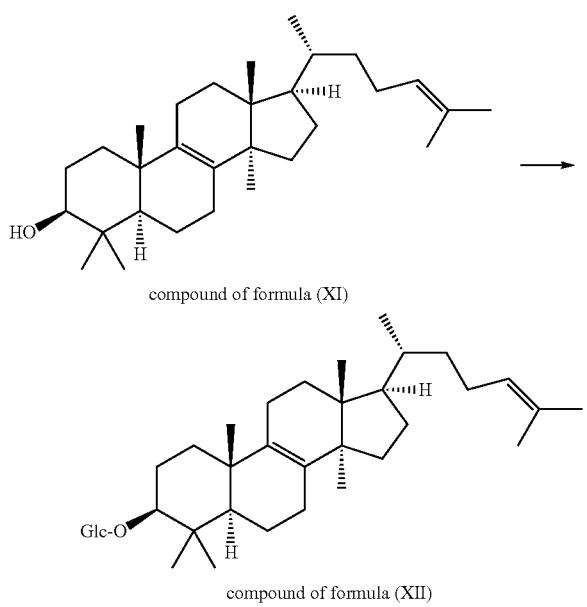

compound of formula (XI)

compound of formula (XII)

said polypeptide is selected from SEQ ID NO: 22 or SEQ ID NO: 24 or a derivative polypeptide thereof. The compound of formula (XI) is lanosterol, and the compound of formula (XII) is 3-O-β-(D-glucopyranosyl)-lanosterol.

In another preferred embodiment, said glycosyl is selected from glucosyl, galacturonic acid radical, galactosyl, arabinosyl, rhamnosyl, and other hexosyls or pentosyls.

In another preferred embodiment, said compounds of formulas (I), (III), (V), (VII), (IX) or (XI) include but are not limited to S- or R-dammarane-type tetracyclic triterpene compounds, lanostane-type typetetracyclic triterpene compounds, tirucallane-type typetetracyclic triterpene compounds, cycloartane-type typetetracyclic triterpene compounds, cucurbitane-type typetetracyclic triterpene compounds, or meliacane-type typetetracyclic triterpene compounds.

In another preferred embodiment, said polypeptide is selected from the group consisting of:
(a) a polypeptide having the amino acid sequence as set forth by any one of SEQ ID NOs.: 2, 16, 18, 20, 26, 28, 41, 43, 55, 57, 59 or 61;
(b) a derivative polypeptide, which is derived from a polypeptide having the amino acid sequence as set forth by any one of SEQ ID NOs.: 2, 16, 18, 20, 26, 28, 41, 43, 55, 57, 59 or 61 by substitution, deletion, or addition of one or more amino acid residues, or by addition of a signal peptide sequence, and has the activity of glycosyltransferase;
(c) a derivative polypeptide, which has the polypeptide sequence of (a) or (b) in its sequence;
(d) a derivative polypeptide, which has ≥85% or ≥90% (preferably ≥95%) sequence homology with the amino acid sequence as set forth by any one of SEQ ID NOs: 2, 16, 18, 20, 26, 28, 41, 43, 55, 57, 59 or 61 and has the activity of glycosyltransferase.

In another preferred embodiment, said polypeptide is selected from the group consisting of:
(a1) a polypeptide having the amino acid sequence as set forth by any one of SEQ ID NOs.: 22 and 24;
(b1) a polypeptide having the polypeptide sequence of (a1) in its sequence; and/or said polypeptide is selected from the group consisting of:
(a2) a polypeptide having the amino acid sequence as set forth by any one of SEQ ID NOs.: 4 and 6;
(b2) a derivative polypeptide, which is derived from a polypeptide having the amino acid sequence as set forth by any one of SEQ ID NOs.: 4 and 6 by substitution, deletion, or addition of one or more amino acid residues, or by addition of a signal peptide sequence, and has the activity of glycosyltransferase;
(c2) a derivative polypeptide, which has the polypeptide sequence of (b2) in its sequence;
(d2) a derivative polypeptide, which has ≥85% or ≥90% (preferably ≥95%) sequence homology with the amino acid sequence as set forth by any one of SEQ ID NOs: 4 and 6 and has the activity of glycosyltransferase.

In another embodiment, the polynucleotide encoding said polypeptide is selected from the group consisting of:
(A) a nucleotide sequence encoding the polypeptide of the first or the second aspect;
(B) a nucleotide sequence encoding the polypeptide as set forth by SEQ ID NOs.: 2, 4, 6, 16, 18, 20, 22, 24, 26, 28, 41, 43, 55, 57, 59 or 61;
(C) a nucleotide sequence as set forth by SEQ ID NOs.: 1, 3, 5, 15, 17, 19, 21, 23, 25, 27, 40, 42, 54, 56, 58 or 60;
(D) a nucleotide sequence, which has ≥95% (preferably ≥98%) homology with the sequence as set forth by SEQ ID NOs.: 1, 3, 5, 15, 17, 19, 21, 27, 40, 42, 54, 56, 58 or 60;
(E) a nucleotide sequence derived from the nucleotide sequence as set forth by SEQ ID NOs.: 1, 3, 5, 15, 17, 19, 21, 23, 25, 27, 40, 42, 54, 56, 58 or 60 by deletion or addition of 1-60 (preferably 1-30, more preferably 1-10) nucleotides at its 5' end and/or 3' end;
(F) a nucleotide sequence complementary to (preferably completely complementary to) any one of the nucleotide sequence of (A)-(E).

In another preferred embodiment, said nucleotide sequence is as set forth by SEQ ID NOs.: 1, 3, 5, 15, 17, 19, 21, 23, 25, 27, 40, 42, 54, 56, 58 or 60.

In another preferred embodiment, the polynucleotide with a sequence as set forth by SEQ ID NOs.: 1, 3, 5, 15, 17, 19, 21, 23, 25, 27, 40, 42, 54, 56, 58 or 60 encodes the polypeptide with an amino acid sequence as set forth by SEQ ID NOs.: 2, 4, 6, 16, 18, 20, 22, 24, 26, 28, 41, 43, 55, 57, 59 or 61, respectively.

The sixth aspect of the present invention is to provide a method for conducting catalytic glycosylation, comprising the following steps: in the presence of a polypeptide and a derivative polypeptide according to the second and third aspects of the present invention, conducting the catalytic glycosylation.

In another preferred embodiment, said method further comprises the step of:
In the presence of a glycosyl donor and a polypeptide or a derivative polypeptide according to the second or third aspect of the present invention, transforming said compound of formula (I) into said compound of formula (II), or transforming said compound of formula (III) into said compound of formula (IV), or transforming said compound of formula (V) into said compound of formula (VI), or transforming said compound of formula (VII) into said compound of formula (VIII), or transforming said formula (IX) compound into said compound of formula (X), or transforming said compound of formula (XI) into said compound of formula (XII);

In another preferred embodiment, said method further comprises: adding said polypeptide or a derivative polypeptide thereof into the catalytic reaction, respectively; and/or adding said polypeptide or a derivative polypeptide thereof into the catalytic reaction simultaneously.

In another preferred embodiment, said method further comprises: in the co-presence of a glycosyl donor and at least two of the polypeptide or the derivative polypeptide according to the second and third aspects of the present invention, transforming the compound of formula (I) into the compound of formula (IV), (VI), (VIII), (X), or transforming the compound of formula (III) into the compound of formula (II), (VI), (VIII), (X), or transforming the compound of formula (V) into the compound of formula (II), (IV), (VIII), (X), or transforming the compound of formula (VII) into the compound of formula (II), (IV), (VI), (X), or transforming the compound of formula (IX) into the compound of formula (II), (IV), (VI), (VIII).

In another preferred embodiment, said method further comprises: co-expressing the nucleotide sequence encoding the glycosyltransferase and the key gene(s) in the anabolism pathway of dammarenediol II and/or protopanaxadiol and/or protopanaxatriol in a host cell, thereby obtaining said compound of formula (II), (IV), (VI), (VIII), (X) or (XII).

In another preferred embodiment, said host cell is saccharomycetes or E. coli.

In another preferred embodiment, said polypeptide is a polypeptide having the amino acid sequence as set forth by SEQ ID NOs.: 2, 4, 6, 16, 18, 20, 22, 24, 26, 28, 41, 43, 55, 57, 59 or 61 and a derivative polypeptide thereof.

In another preferred embodiment, the nucleotide sequence encoding said polypeptide is as set forth by SEQ ID NOs.: 1, 3, 5, 15, 17, 19, 21, 23, 25, 27, 40, 42, 54, 56, 58 or 60.

In another preferred embodiment, said method further comprises: providing additive(s) for modulating enzyme activity to the reaction system.

In another preferred embodiment, said additive(s) for modulating enzyme activity is: additive(s) enhancing enzyme activity or inhibiting enzyme activity.

In another preferred embodiment, said additive(s) for modulating enzyme activity is selected from the group consisting of $Ca^{2+}$, $Co^{2+}$, $Mn^{2+}$, $Ba^{2+}$, $Al^{3+}$, $Ni^{2+}$, $Zn^{2+}$, and $Fe^{2+}$.

In another preferred embodiment, said additive(s) for modulating enzyme activity is a material(s) capable of producing $Ca^{2+}$, $Co^{2+}$, $Mn^{2+}$, $Ba^{2+}$, $Al^{3+}$, $Ni^{2+}$, $Zn^{2+}$, or $Fe^{2+}$.

In another preferred embodiment, said glycosyl donor(s) is nucleoside diphosphate sugar(s) selected from the group consisting of: UDP-glucose, ADP-glucose, TDP-glucose, CDP-glucose, GDP-glucose, UDP-acetyl glucose, ADP-acetyl glucose, TDP-acetyl glucose, CDP-acetyl glucose, GDP-acetyl glucose, UDP-xylose, ADP-xylose, TDP-xylose, CDP-xylose, GDP-xylose, UDP-galacturonic acid, ADP-galacturonic acid, TDP-galacturonic acid, CDP-galacturonic acid, GDP-galacturonic acid, UDP-galactose, ADP-galactose, TDP-galactose, CDP-galactose, GDP-galactose, UDP-arabinose, ADP-arabinose, TDP-arabinose, CDP-arabinose, GDP-arabinose, UDP-rhamnose, ADP-rhamnose, TDP-rhamnose, CDP-rhamnose, GDP-rhamnose, or other nucleoside diphosphate hexose or nucleoside diphosphate pentose, or the combination thereof.

In another preferred embodiment, said glycosyl donor(s) is uridine diphosphate (UDP) sugars selected from the group consisting of: UDP-glucose, UDP-galacturonic acid, UDP-galactose, UDP-arabinose, UDP-rhamnose, or other uridine diphosphate hexose or uridine diphosphate pentose, or the combination thereof.

In another preferred embodiment, the pH of the reaction system is: pH4.0-10.0, preferably 5.5-9.0.

In another preferred embodiment, the temperature of the reaction system is: 10° C.-105° C., preferably 20° C.-50° C.

In another preferred embodiment, the key gene(s) in the anabolism pathway of dammarenediol II includes but are not limited to dammarenediol synthase gene.

In another preferred embodiment, the key gene(s) in the anabolism pathway of PPD includes but is not limited to: dammarenediol synthase gene, cytochrome P450 CYP716A47 gene, and P450 CYP716A47 reductase gene, or the combination thereof.

In another preferred embodiment, the key gene(s) in the anabolism pathway of PPT includes but is not limited to: dammarenediol synthase gene, cytochrome P450 CYP716A47 gene, P450 CYP716A47 reductase gene, cytochrome P450 CYP716A53V2 gene and the reductase gene thereof, or the combination thereof.

In another preferred embodiment, the substrate of the catalytic glycosylation is the compound of formula (I), (III), (V), (VII), (IX) or (XI), and said product is the compound of (II), (IV), (VI), (VIII), (X) or (XII);

In another preferred embodiment, said compound of formula (I) is PPD (Protopanaxadiol), and the compound of formula (II) is ginsenoside CK (20-O-β-(D-glucopyranosyl)-protopanaxadiol);

or, said compound of formula (I) is ginsenoside Rh2 (3-O-β-(D-glucopyranosyl)-protopanaxadiol)), and the compound of formula (II) is ginsenoside F2 (3-O-β-(D-glucopyranosyl)-20-O-β-(D-glucopyranosyl)-protopanaxadiol);

or, said compound of formula (I) is ginsenoside Rg3, and the compound of formula (II) is ginsenoside Rd;

or, said compound of formula (I) is PPT (Protopanaxatriol), and the compound of formula (II) is ginsenoside F1 (20-O-β-(D-glucopyranosyl)-protopanaxatriol);

or, said compound of formula (I) is DM (Dammarenediol II), and the compound of formula (II) is ginsenoside 20-O-β-(D-glucopyranosyl)-Dammarenediol II;

or, said compound of formula (III) is PPT, and the compound of formula (IV) is ginsenoside Rh1 (6-O-β-(D-glucopyranosyl)-protopanaxatriol);

or, said compound of formula (III) is ginsenoside F1, and the compound of formula (IV) is ginsenoside Rg1 (6-O-β-(D-glucopyranosyl)-20-O-β-(D-glucopyranosyl)-protopanaxadiol);

or, said compound of formula (V) is PPD, and the compound of formula (VI) is ginsenoside Rh2 (3-O-β-(D-glucopyranosyl)-protopanaxadiol);

or, said compound of formula (V) is CK, and the compound of formula (VI) is ginsenoside F2 (3-O-β-(D-glucopyranosyl)-20-O-β-(D-glucopyranosyl)-protopanaxadiol);

or, said compound of formula (V) is PPT, and the compound of formula (VI) is ginsenoside 3-O-β-(D-glucopyranosyl)-protopanaxatriol;

or, said compound of formula (V) is ginsenoside F1, and the compound of formula (VI) is ginsenoside 3-O-β-(D-glucopyranosyl)-F1;

or, said compound of formula (V) is DM, and the compound of formula (VI) is ginsenoside 3-O-β-(D-glucopyranosyl)-Dammarenediol II;

or, said compound of formula (VII) is 25-OH-PPD (25-OH-protopanaxadiol), and the compound of formula (VIII) is ginsenoside 3-O-β-(D-glucopyranosyl)-25-OH-protopanaxadiol;

or, said compound of formula (VII) is 25-$OCH_3$-PPD (25-$OCH_3$-protopanaxadiol), and the compound of formula (VIII) is ginsenoside 3-O-β-(D-glucopyranosyl)-25-$OCH_3$- protopanaxadiol; or, said compound of formula (IX) is ginsenoside Rh2, and the compound of formula (X) is ginsenoside Rg3;

or, said compound of formula (IX) is ginsenoside F2, and the compound of formula (X) is ginsenoside Rd.

Or, said compound of formula (XI) is lanosterol, and the compound of formula (XII) is 3-O-β-(D-glucopyranosyl)-lanosterol.

The seventh aspect of the present invention is to provide a genetically engineered host cell; said host cell contains the vector according to the fifth aspect of the present invention, or has a polynucleotide according to the fourth aspect of the present invention integrated in its genome.

In another preferred embodiment, said glycosyltransferase is the polypeptide or the derivative polypeptide according to the second or third aspect of the present invention.

In another preferred embodiment, the nucleotide sequence encoding said glycosyltransferase is as described in the fourth aspect of the present invention.

In another preferred embodiment, said cell is a prokaryocyte or a eukaryocyte.

In another preferred embodiment, said host cell is a eukaryocyte, such as a yeast cell or a plant cell.

In another preferred embodiment, said host cell is a *Saccharomyces cerevisiae* cell.

In another preferred embodiment, said host cell is a prokaryocyte, such as *E. coli*.

In another preferred embodiment, said host cell is a ginseng cell.

In another preferred embodiment, said host cell is not a cell naturally producing the compound of formula (II), (IV), (VI), (VIII), (X) or (XII).

In another preferred embodiment, said host cell is not a cell naturally producing rare ginsenoside CK and/or rare ginsenoside F1 and/or rare ginsenoside Rh2 and/or Rg3 and/or Rh1, and/or novel ginsenoside 20-O-β-(D-glucopyranosyl)-dammarendiol II, 3-O-β-(D-glucopyranosyl)-PPT, 3-O-β-(D-glucopyranosyl)-F1, 3-O-β-(D-glucopyranosyl)-DM, 3-O-β-D-glucopyranosyl)-25-OH-PPD, 3-O-β-(D-glucopyranosyl)-25-OCH$_3$-PPD, and/or Rh1, F2, Rd and Rg1 etc.

In another preferred embodiment, said key gene(s) in the anabolism pathway of dammarenediol II includes but is not limited to: dammarenediol synthase gene.

In another preferred embodiment, the key gene(s) in the anabolism pathway of PPD contained in said host cell includes but is not limited to dammarenediol synthase gene, cytochrome P450 CYP716A47 gene, and P450 CYP716A47 reductase gene, or the combination thereof.

In another preferred embodiment, the key gene(s) in the anabolism pathway of PPT contained in said host cell includes but is not limited to dammarenediol synthase gene, cytochrome P450 CYP716A47 gene, P450 CYP716A47 reductase gene, and cytochrome P450 CYP716A53V2 gene, or the combination thereof.

The eighth aspect of the present invention is to provide use of the host cell according to the seventh aspect, for preparing an enzymatic catalyzation preparation, or for producing a glycosyltransferase, or as a catalytic cell, or for producing the compound of formula (II), (IV), (VI), (VIII), (X) or (XII).

In another preferred embodiment, said host cell is used for producing new saponins 20-O-β-(D-glucopyranosyl)-dammarendiol II and/or 3-O-β-(D-glucopyranosyl)-dammarendiol II, 3-O-β-(D-glucopyranosyl)-protopanaxatriol, 3-O-β-(D-glucopyranosyl)-F1 and/or rare ginsenoside CK and/or rare ginsenoside F1 and or rare ginsenoside Rh1 and/or ginsenoside Rh2 and/or rare ginsenoside Rg3 through glycosylation of dammarenediol II (DM) and/or protopanaxadiol (PPD), and/or protopanaxatriol (PPT).

The ninth aspect of the present invention is to provide a method for producing a transgenic plant, comprising the following step: regenerating said genetically engineered host cell according to the seventh aspect of the present invention into a plant, and said genetically engineered host cell is a plant cell.

In another preferred embodiment, said genetically engineered host cell is a ginseng cell.

It should be understood that in the present invention, the technical features specifically described above and below (such as in the Examples) can be combined with each other, thereby constituting a new or preferred technical solution which needs not be described one by one.

DESCRIPTION OF FIGURES

The following figures are used to describe the specific embodiments of the present invention and should not be used as limitation to the scope defined by the claims.

FIG. 45 shows Western Blot detection of the gene gGT29-4, gGT29-5, gGT29-6 and gGT29-7 expression in E. coli; lane 1, total protein in the lysate of the gGT29-4-pET28a recombinant E. coli; lane 2, lysate supernatant of the recombinant E. coli gGT29-4-pET28a; lane 3, total protein in the lysate of the recombinant E. coli gGT29-5-pET28a; lane 4, lysate supernatant of the recombinant E. coli gGT29-5-pET28a; lane 5, total protein in the lysate of the recombinant E. coli gGT29-6-pET28a; lane 6, lysate supernatant of the recombinant E. coli gGT29-6-pET28a; lane 7, total protein in the lysate of the recombinant E. coli gGT29-7-pET28a; lane 8, lysate supernatant of the recombinant E. coli gGT29-7-pET28a.

SPECIFIC MODES FOR CARRYING OUT THE INVENTION

Figure 1:
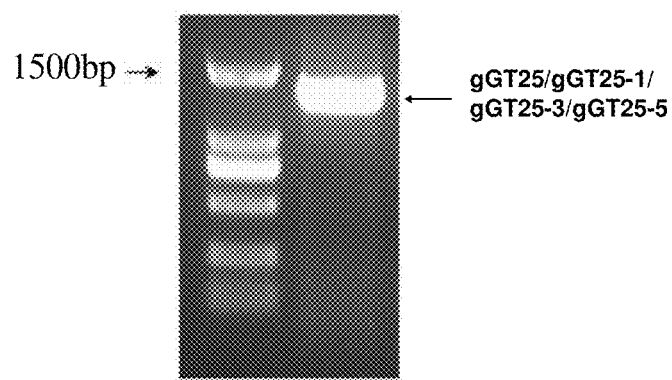
FIG. 1 shows the agarose gel electrophoretogram of the PCR products of the genes gGT25, gGT25-1, gGT25-3 and gGT25-5.

Upon extensive and intensive studies, for the first time, the inventors provided use of the glycosyltransferases gGT25 (SEQ ID NO.: 2), gGT25-1 (SEQ ID NO.: 16), gGT25-3 (SEQ ID NO.: 18), gGT25-5 (SEQ ID NO.: 20), gGT29 (SEQ ID NO.: 26), gGT29-3 (SEQ ID NO.: 28), gGT29-4 (SEQ ID NO.:55), gGT29-5 (SEQ ID NO.:57), gGT29-6 (SEQ ID NO.:59), gGT29-7 (SEQ ID NO.:61) and 3GT1 (SEQ ID NO.: 22), 3GT2 (SEQ ID NO.: 24), 3GT3 (SEQ ID NO.: 41), 3GT4 (SEQ ID NO.: 43), gGT13 (SEQ ID NO.: 4), and gGT30 (SEQ ID NO.: 6) for the catalytic glycosylation of terpenoids and synthesis of new saponins Specifically, the glycosyltransferases according to the present invention are capable of specifically and efficiently catalyzing the glycosylation of the hydroxyl group(s) at position(s) C-20 and/or C-6 and/or C3 of a tetracyclic triterpenoid substrate, and/or transferring glycosyl(s) from glycosyl donors to the first glycosyl at position C-3 of a tetracyclic triterpenoid compound to extend the carbohydrate chain. The glycosyltransferases according to the present invention are particularly capable of converting protopanaxadiol into rare ginsenosides CK and Rh2 with anti-tumor activity, converting protopanaxatriol into rare ginsenoside F1 with anti-aging activity and rare ginsenoside Rh1 with anti-allergy activity, converting Rh2 into rare ginsenoside Rg3 with excellent anti-tumor activity. The glycosyltransferases of the present invention can also synthesize unreported novel saponins such as 20-O-β-(D-glucopyranosyl)-dammarendiol II, 3-O-β-(D-glucopyranosyl)-dammarendiol II, 3-O-β-(D-glucopyranosyl)-PPT, 3-O-β-(D-glucopyranosyl)-F1, 3-O-β-(D-glucopyranosyl)-25-OH- PPD, and 3-O-β-(D-glucopyrano-syl)-25-OCH₃-PPD by using dammarendiol, PPT, F1, 25-OH-PPD, or 25-OCH₃-PPD.

The glycosyltransferases according to the present invention can also convert Rh2, CK, or Rg3 into ginsenosides F2, Rd, or Rg1, respectively. The present invention further provides a method for transformation and catalyzation. The glycosyltransferases according to the present invention can also be co-expressed with the key enzymes in the anabolism pathways of dammarenediol II and/or PPD and/or PPT in host cells, or can be used in preparation of the genetically engineered host cells for DM, PPD and PPT, or used in the construction of the metabolic pathways for artificially synthesizing the rare ginsenosides CK, F1, Rh1, Rh2, Rg3, as well as the novel ginsenosides 20-O-β-(D-glucopyranosyl)-dammarendiol II, 3-O-β-(D-glucopyranosyl)-PPT, 3-O-β-(D-glucopyranosyl)-F1, 3-O-β-(D-glucopyranosyl)-dammarendiol II, 3-O-β-(D-glucopyranosyl)-25-OH-PPD, and 3-O-β-(D-glucopyranosyl)-25-OCH₃-PPD, and F2, Rd and Rg1, etc. Based on the above, the present invention was completed.

Definitions

As used herein, the terms "active peptide(s)", "the polypeptide(s) and derivative polypeptide(s) thereof according to the present invention", "enzyme(s) according to the present invention", "glycosyltransferase(s)", "proteins gGT25, gGT13, gGT30, gGT25-1, gGT25-3, gGT25-5, gGT29, gGT29-3, 3GT1, 3GT2, 3GT3, or 3GT4 according to the present invention" and "glycosyltransferase(s) according to the present invention" all refer to the polypeptides of glycosyltransferases gGT25 (SEQ ID NO.: 2), gGT13 (SEQ ID NO.: 4), gGT30 (SEQ ID NO.: 6), gGT25-1 (SEQ ID NO.: 16), gGT25-3 (SEQ ID NO.: 18), gGT25-5 (SEQ ID NO.: 20), gGT29 (SEQ ID NO.: 26), gGT29-3 (SEQ ID NO.: 28), gGT29-4 (SEQ ID NO.:55), gGT29-5 (SEQ ID NO.:57), gGT29-6 (SEQ ID NO.:59), gGT29-7 (SEQ ID NO.:61), 3GT1 (SEQ ID NO.: 22), 3GT2 (SEQ ID NO.: 24), 3GT3 (SEQ ID NO.: 41), and 3GT4 (SEQ ID NO.: 43), and the derivative polypeptides thereof.

Unless stated otherwise, said ginsenoside and sapogenin according to the present invention refer to the ginsenosides and sapogenins with a C20 of S-configuration.

As used herein, "isolated polypeptide" means that the polypeptides almost has no other proteins, lipids, sugars or other substances that are naturally related to the polypeptide. Said polypeptide(s) can be purified by those skilled in the art using standard protein purification techniques. The substantially purified polypeptide can generate a single main band on nonreductive polyacrylamide gel electrophoresis. The purity of said polypeptide(s) can be further analyzed by using amino acids sequencing.

The active polypeptide(s) according to the present invention can be recombinant polypeptide(s), natural polypeptide(s), or synthetic polypeptide(s). The polypeptide(s) according to the present invention can be a purified natural product or chemically synthesized product, or can be produced from protokaryotic or eukaryotic hosts (e.g. bacteria, yeast, or plant) by recombination techniques. According to the hosts used in the recombinant production procedure, the polypeptide(s) according to the present invention can be glycosylated or non-glycosylated. The polypeptide(s) according to the present invention can or can not include an initiate residue of methionine.

The present invention further includes the fragments, derivatives and analogues of said polypeptides. As used herein, the terms "fragments", "derivatives" and "analogues" refer to peptides that substantially maintain the same biological function or activity with said polypeptides.

The polypeptide fragments, derivatives or analogs of the present invention could be (i) a polypeptide with one or more conservative or non-conservative amino acid residues (preferably, conservative amino acid residues) being substituted, wherein said amino acid residue substitution can be or not be encoded by genetic code; or (ii) a polypeptide having substitution group(s) in one or more amino acid residues, or (iii) a polypeptide formed by fusion of a mature polypeptide with another compound (such as a compound that prolongs the half life of a polypeptide, such as polyethylene glycol), or (iv) a polypeptide with an additional amino acid sequence fused to said polypeptide sequence (such as a fusion protein formed by fusion with a leader sequence, secretion sequence, a sequence for purifying the peptide, proteinogen sequence, or a fusion protein formed with the IgG fragment of an antigen). According to the teachings of the present application, these fragments, derivatives and analogs are within the scope commonly known by a skilled person.

The active polypeptides of the present invention possess the activity of glycosyltransferases and are able to catalyze one or more of following reaction(s):

(A)

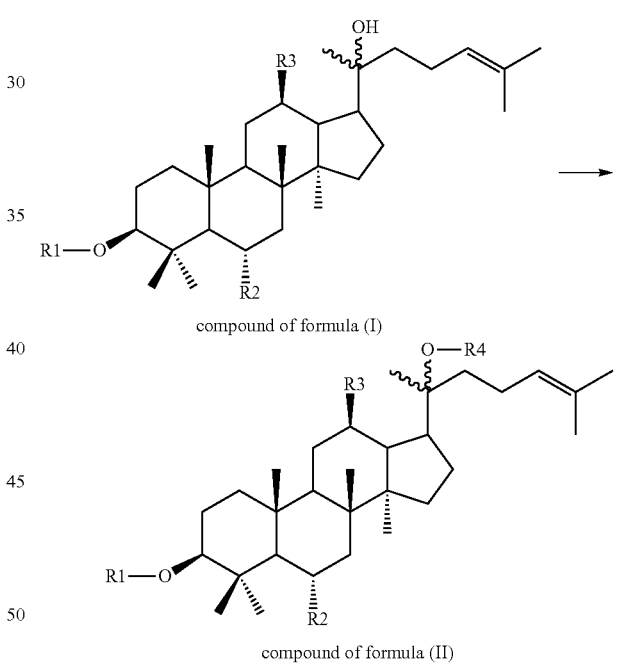

compound of formula (I)

compound of formula (II)

wherein, R1 is H, monosaccharide glycosyl or polysaccharides glycosyl; R2 or R3 is H or OH; R4 is glycosyl; said polypeptide is selected from SEQ ID NOs.: 2, 16 or 18 or a derivative polypeptide thereof.

In another embodiment, said monosaccharide includes glucose (Glc), rhamnose (Rha), acetyl glucose (Glc (6)Ac), arabinofuranose (Araf), arabopyranose (Arap), and xylose (Xyl), etc.

In another embodiment, said polysaccharides include polysaccharides composed of 2-4 monosaccharides, such as Glc(2-1)Glc, Glc(6-1)Glc, Glc(6)Ac, Glc(2-1)Rha, Glc(6-1)Arap, Glc(6-1)Xyl, Glc(6-1)Araf, Glc(3-1)Glc(3-1), Glc(2-1) Glu(6)Ac, Glc(6-1)Arap(4-1)Xyl, Glc(6-1)Arap(2-1)Xyl, or Glc(6-1)Arap(3-1)Xyl, etc.

Compounds with R1-R4 substituted are shown in the following table:

| substrate | R1 | R2 | R3 | R4 | product |
|---|---|---|---|---|---|
| PPD | H | H | OH | glycosyl | CK |
| Rh2 | 1 glycosyl | H | OH | glycosyl | F2 |
| Rg3 | 2 glycosyls | H | OH | glycosyl | Rd |
| PPT | H | OH | OH | glycosyl | F1 |
| DM | H | H | H | glycosyl | 20-G-DM |

When both of said R1 and R2 are H, R3 is OH, said compound of formula (I) is PPD.

R1 is one glucosyl, R2 is H, R3 is OH, said compound of formula (I) is ginsenoside Rh2.

R1 is two glucosyls, R2 is H, R3 is OH, said compound of formula (I) is ginsenoside Rg3.

R1 is H, R2 is OH, R3 is OH, said compound of formula (I) is PPT.

R1 is H, R2 is H, R3 is H, said compound of formula (I) is dammarenediol II (DM).

(B):

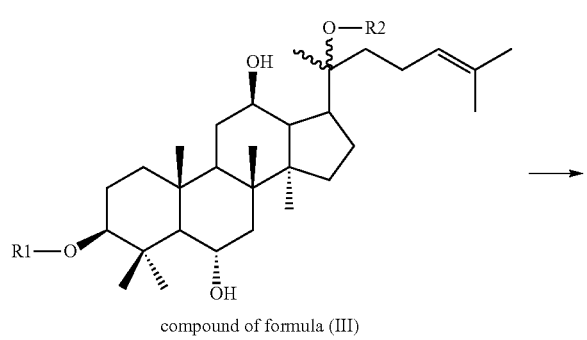

compound of formula (III)

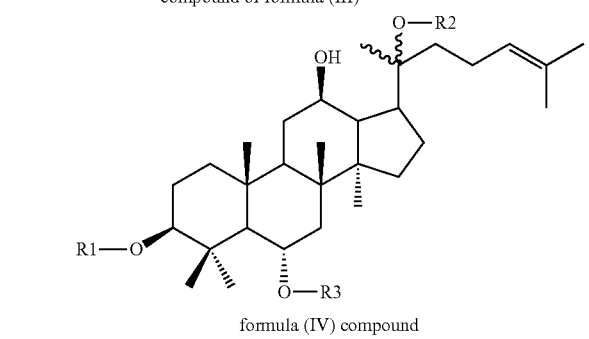

formula (IV) compound wherein, R1 is H or glycosyl, R2 is glycosyl, R3 is glycosyl, said polypeptide is selected from SEQ ID NOs.: 2, 16, 18, or 20 or a derivative polypeptide thereof;

or, R1 is H or glycosyl; R2 is H; R3 is glycosyl, said polypeptide is selected from SEQ ID NO.: 20 or a derivative polypeptide thereof.

Compounds with R1-R3 substituted are shown in the following table:

| substrate | R1 | R2 | R3 | product |
|---|---|---|---|---|
| F1 | H | glycosyl | glycosyl | Rg1 |
| PPT | H | H | glycosyl | Rh1 |

When both of said R1 and R2 are H, said compound of formula (III) is PPT.

R1 is H, R2 is glucose, said compound of formula (III) is ginsenoside F1.

(C):

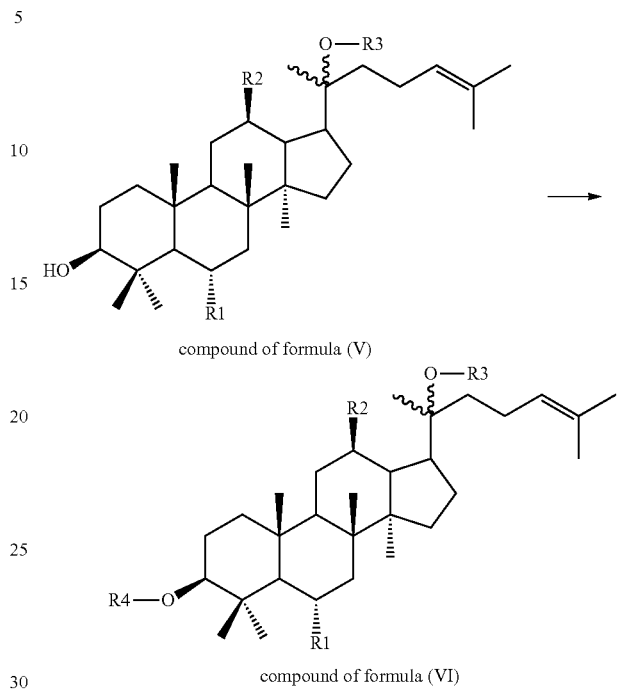

compound of formula (V)

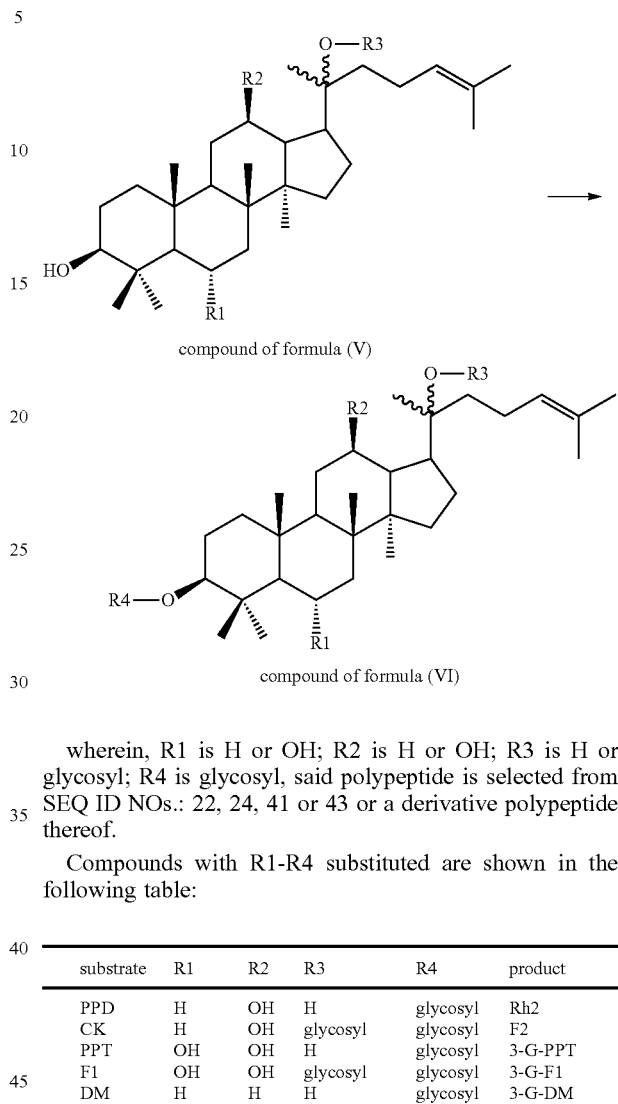

compound of formula (VI)

wherein, R1 is H or OH; R2 is H or OH; R3 is H or glycosyl; R4 is glycosyl, said polypeptide is selected from SEQ ID NOs.: 22, 24, 41 or 43 or a derivative polypeptide thereof.

Compounds with R1-R4 substituted are shown in the following table:

| substrate | R1 | R2 | R3 | R4 | product |
|---|---|---|---|---|---|
| PPD | H | OH | H | glycosyl | Rh2 |
| CK | H | OH | glycosyl | glycosyl | F2 |
| PPT | OH | OH | H | glycosyl | 3-G-PPT |
| F1 | OH | OH | glycosyl | glycosyl | 3-G-F1 |
| DM | H | H | H | glycosyl | 3-G-DM |

When both of R1 and R3 are H, R2 is OH, said compound of formula (V) is PPD; said polypeptide is selected from SEQ ID NOs.: 22, 24, 41 or 43 or a derivative polypeptide thereof;

when R1 is H, R2 is OH, R3 is glucosyl, said compound of formula (V) is ginsenoside CK; said polypeptide is selected from SEQ ID NOs.: 22, 24, or 43 or a derivative polypeptide thereof; when R1 is OH, R2 is OH, R3 is H, said compound of formula (V) is PPT; said polypeptide is selected from SEQ ID NOs.: 22, 24, or 41 or a derivative polypeptide thereof;

when R1 is OH, R2 is OH, R3 is glucosyl, said compound of formula (V) is ginsenoside F1; said polypeptide is selected from SEQ ID NOs.: 22, or 24 a derivative polypeptide thereof;

when R1 is H, R2 is OH, R3 is H, said compound of formula (V) is dammarenediol II (DM); said polypeptide is selected from SEQ ID NOs.: 22, or 24 a derivative polypeptide thereof;

(D):

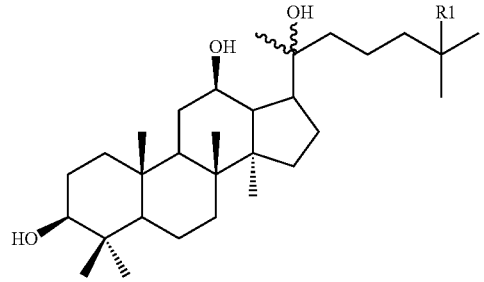

compound of formula (VII)

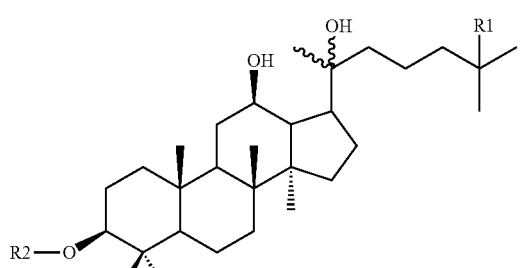

compound of formula (VIII)

wherein, R1 is OH or OCH₃; R2 is glycosyl, said polypeptide is selected from SEQ ID NOs.: 22, 24, 41 or 43 or a derivative polypeptide thereof.

Compounds with R1-R2 substituted are shown in the following table:

| substrate | R1 | R2 | product |
|---|---|---|---|
| 25-OH-PPD | OH | glycosyl | 3-G-25-OH-PPD |
| 25-OCH₃-PPD | OCH₃ | glycosyl | 3-G-25-OCH₃-PPD |

When R1 is OH, said compound of formula (VII) is 25-OH-PPD;

R1 is OCH, said compound of formula (VII) is 25-OCH₃-PPD.

(E)

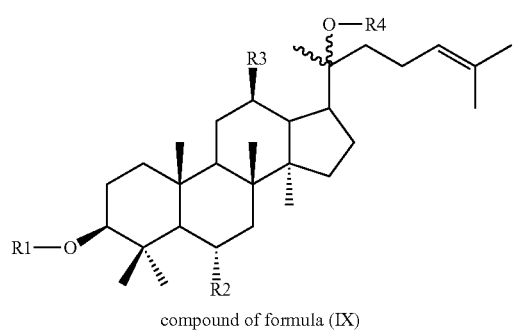

compound of formula (IX)

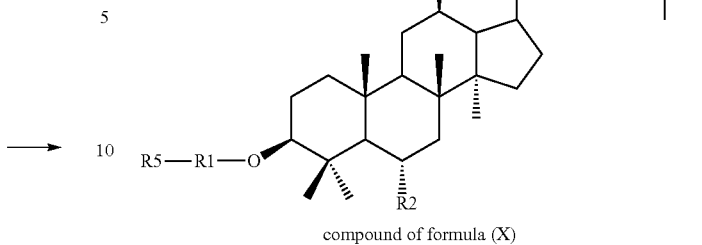

compound of formula (X)

wherein, R1 is glycosyl; R2 or R3 is OH or H; R4 is glycosyl or H; R5 is glycosyl, said polypeptide is selected from SEQ ID NOs.: 26, 28, 55, 57, 59 or 61 or a derivative polypeptide thereof.

Compounds with R1-R4 substituted are shown in the following table.

| substrate | R1 | R2 | R3 | R4 | product |
|---|---|---|---|---|---|
| Rh2 | glycosyl | H | OH | H | Rg3 |
| F2 | glycosyl | H | OH | glycosyl | Rd |

When R1 is glucosyl; R2 is H, R3 is OH, R4 is H, the compound of formula (IX) is Rh2.

R1 is glucosyl; R2 is H, R3 is OH, R4 is glucosyl, the compound of formula (IX) is F2.

(F)

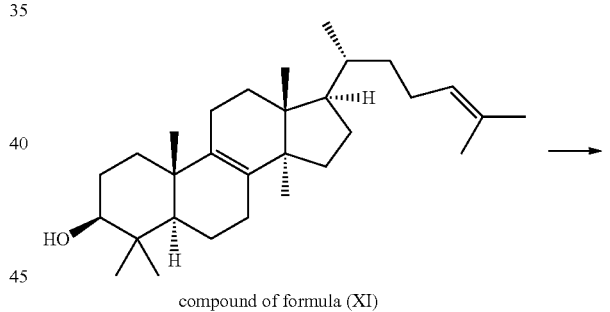

compound of formula (XI)

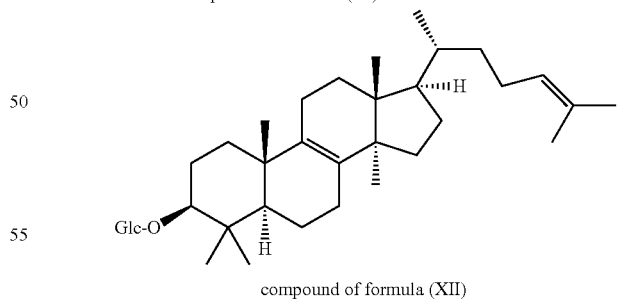

compound of formula (XII)

said polypeptide is selected from SEQ ID NO: 22 or SEQ ID NO: 24 or a derivative polypeptide thereof.

The preferred sequence of said polypeptides is as set forth by SEQ ID NOs.: 2, 16, 18, 20, 22, 24, 41, 26, 28, 43, 55, 57, 59 or 61. The term also comprises variants of the sequences as set forth by SEQ ID NOs.: 2, 16, 18, 20, 22, 24, 41, 26, 28, 43, 55, 57, 59 or 61, which have the same function with said polypeptide, as well as the derivative polypeptide thereof. These variants include but are not limited to, deletions, insertions and/or substitutions of one or more (typically 1-50, preferably 1-30, more preferably 1-20, most preferably 1-10) amino acids, and addition of one or more (typically not more than 20, preferably not more than 10, more preferably not more than 5) amino acids at C-terminus and/or N-terminus. For example, the functions of a protein are usually unchanged when an amino acid is substituted by another amino acid with similar or analogous properties in the art. Further, addition of one or several amino acids at C-terminus and/or N-terminus generally will not change the function of a protein. The terms further includes the active fragment and active derivatives of said protein. The present invention further provides the analogues of said polypeptides. These analogues could differ from the naturally occurring polypeptide either in amino acid sequence or in modifications that do not affect the sequence, or in both. These polypeptides comprise natural or induced genetic variants. These variants can be obtained by various techniques, such as random mutagenesis through radiation or being exposed to mutagenic agents, site directed mutagenesis, or other known molecular biology techniques. Also included are analogues which include residues other than those naturally occurring L-amino acids (e.g., D-amino acids) or which include non-naturally occurring or synthetic amino acids (e.g., beta- or gamma-amino acids). It is understood that the polypeptides of the present invention are not limited to the representative polypeptides listed herein above.

Modifications (which do not normally alter the primary sequence) include in vivo or in vitro chemical derivation of polypeptides, e.g., acelylation, or carboxylation. Glycosylation is also included in modification, e.g., polypeptides that are produced by glycosylation modification during its synthesis and processing or in the further processing steps. These modifications can be achieved by exposing the polypeptide to enzymes for glycosylation (e.g, mammalian glycosylating or deglycosylating enzymes). Also included are sequences that have phosphorylated amino acid residues (e.g., phosphotyrosine, phosphoserine, phosphothronine), as well as sequences that have been modified to improve their resistance to proteolytic degradation or to optimize solubility properties.

The N-terminal or C-terminal of the proteins gGT25, gGT13, gGT30, gGT25-1, gGT25-3, gGT25-5, gGT29, gGT29-3, gGT29-4, gGT29-5, gGT29-6, gGT29-7 and 3GT1, 3GT2, 3GT3, 3GT4 of the present invention can further comprise one or more polypeptide fragments as a protein tag. Any suitable tag can be used in the present invention. For example, said tag can be FLAG, HA, HA1, c-Myc, Poly-His, Poly-Arg, Strep-TagII, AU1, EE, T7, 4A6, E, B, gE, or Ty1. These tags can be used for protein purification. Some of the tags and sequences thereof are listed in Table 1.

TABLE 1

| Tag | Residue numbers | Sequence |
|---|---|---|
| Poly-Arg | 5-6(generally 5) | RRRRR |
| Poly-His | 2-10(generally 6) | HHHHHH |
| FLAG | 8 | DYKDDDDK |
| Strep-TagII | 8 | WSHPQFEK |
| C-myc | 10 | WQKLISEEDL |
| GST | 220 | followed with 6 LVPRGS |

In order to achieve the secretory expression of the translated proteins (e.g. secrete out of cells), a signal peptide sequence, such as the signal peptide pelB, can be added to the N-terminal of said amino acids gGT25, gGT13, gGT30, gGT25-1, gGT25-3, gGT25-5, gGT29, gGT29-3, gGT29-4, gGT29-5, gGT29-6, gGT29-7 and 3GT1, 3GT2, 3GT3, 3GT4. The signal peptides can be cut off during the secretion process of the polypeptide from the cells.

The polynucleotide of the present invention can be in a form of DNA or RNA. The form of DNA includes cDNA, genome DNA or artificially synthesized DNA. DNA can be single strand or double strands. DNA can be a coding strand or a non-coding strand. The coding sequence encoding the mature polypeptide can be identical to the coding sequence indicated by SEQ ID NO: 1 or can be a degenerate variant thereof. As used herein, "degenerate variant" of the present invention refers to a nucleic acid sequence which encodes the protein having the amino acid sequence of SEQ ID NOs.: 2, 4, 6, 16, 18, 20, 22, 24, 26, 28, 41, 43, 55, 57, 59 or 61, but is different from the coding sequence indicated by SEQ ID NOs.: 1, 3, 5, 15, 17, 19, 21, 23, 25, 27, 40, 42, 54, 56, 58 or 60.

The polynucleotides encoding the mature polypeptides of SEQ ID NOs.: 2, 4, 6, 16, 18, 20, 22, 24, 26, 28, 41, 43, 55, 57, 59 or 61 include: coding sequences that only encodes mature polypeptides; coding sequences of mature polypeptides and various additional coding sequences; coding sequences of mature polypeptides (and optionally additional coding sequences) and non-coding sequences.

The term "polynucleotide encoding the polypeptide" can be a polynucleotide encoding said polypeptide, and can also be a polynucleotide further including an additional coding sequence and/or non-coding sequence.

The present invention further encompasses variants of the above-noted polynucleotides, which encodes polypeptides that have the same amino acid sequences with that of the present invention, or fragments, analogues and derivatives thereof. The variants of these polynucleotides can be naturally occurred allelic variants or non-naturally occurred variants. These polynucleotides variants include substitution variants, deletion variants and insertion variants. As known in the art, an allelic variant is the substituted form of polynucleotides, and they can be the substitution, deletion, or insertion of one or more polynucleotides, but do not substantially change the function of the encoded polypeptides.

The present invention further relates to polynucleotides that hybridize with the above-noted sequences and have an identity of at least 50%, preferably 70%, more preferably 80% between the two sequences. Particularly, the present invention relates to the polynucleotides capable of hybridizing with the polynucleotides of the present invention under stringent conditions. According to the present invention, "stringent condition" refers to: (1) hybridization and elution under a low ion strength and a high temperature, such as 0.2×SSC, 0.1% SDS, 60° C.; or (2) hybridization in the presence of an added denaturant, such as 50% (v/v) of formamide, 0.1% of fetal bovine serum/0.1% Ficoll, 42° C., etc; or (3) hybridization only occurring under the condition that the identity between the two sequences is at least more than 90%, preferably more than 95%. Moreover, the polypeptides encoded by the hybridizable polynucleotides have identical biological functions and activities with the mature polypeptide as set forth by SEQ ID NOs.: 2, 4, 6, 16, 18, 20, 22, 24, 26, 28, 41, 43, 55, 57, 59 or 61.

The present invention further relates to nucleic acid fragments which can hybridize with the sequences described above. As used herein, the length of the "nucleic acid fragments" is at least 15 nucleotides, preferably at least 30 nucleotides, more preferably at least 50 nucleotides, most preferably at least 100 nucleic acids. The nucleic acid fragments can be used in the nucleic acid amplification techniques (such as PCR) for determining and/or isolating the polynucleotides encoding the proteins gGT25, gGT13, gGT30, gGT25-1, gGT25-3, gGT25-5, gGT29, gGT29-3, gGT29-4, gGT29-5, gGT29-6, gGT29-7 and 3GT1, 3GT2, 3GT3, 3GT4.

The polypeptides and polynucleotides of the present invention are preferably provided in the isolated form, more preferably are purified to be homogenous.

The full-length nucleotide sequences of gGT25, gGT13, gGT30, gGT25-1, gGT25-3, gGT25-5, gGT29, gGT29-3, gGT29-4, gGT29-5, gGT29-6, gGT29-7 and 3GT1, 3GT2, 3GT3, 3GT4 or the fragments thereof can be obtained by PCR amplification, recombination, or artificial synthesis. For PCR amplification, the primers can be designed according to the relevant nucleotide sequences (especially the Open Reading Frame) disclosed herein, and the commercially available cDNA library or the cDNA library prepared through the conventional methods known by those skilled in the art can be used as the template, thereby amplifying and obtaining the corresponding sequences. Twice or more PCR amplifications are typically needed for a longer sequence, and then, the respectively amplified fragments are spliced together in correct order.

Once the corresponding sequences are obtained, recombination can be used for giving the corresponding sequences massively. Generally, they are cloned into vectors, followed, transformed into cells, and then, the corresponding sequences are isolated from the host cells upon proliferation by conventional methods.

Furthermore, the corresponding sequences can be synthesized by artificial synthesis, especially when the fragment length is short. Generally, multiple small peptides are synthesized first and then can be connected to obtain fragments with longer sequences.

At present, the DNA sequences encoding the proteins of the present invention (or the fragments or derivatives thereof) can be obtained entirely via chemical synthesis. After that, the DNA sequences can be introduced into the various existing DNA molecules (or, such as, vectors) and cells known in the art. Moreover, mutations can be introduced into the protein sequences of the present invention through chemical synthesis.

Methods for amplifying DNA/RNA by using PCR amplification is preferably used for obtaining the genes of the present invention. A RACE method (RACE-rapid amplification of cDNA end) is preferred when it is difficult to obtain the full length of cDNA from a library. The primers used for PCR can be properly selected according to the sequence information disclosed in the present invention and can be synthesized by conventional methods. The amplified DNA/RNA fragments can be isolated and purified by conventional methods such as gel electrophoresis.

The present invention further relates to the vectors containing the polynucleotides of the present invention, the host cells produced by genetic engineering using the vectors of the present invention or the sequences encoding the proteins gGT25, gGT13, gGT30, gGT25-1, gGT25-3, gGT25-5, gGT29, gGT29-3, gGT29-4, gGT29-5, gGT29-6, gGT29-7 and 3GT1, 3GT2, 3GT3, 3GT4, and the method for producing polypeptides of the present invention by recombination techniques.

The polynucleotides sequences can be used for expressing or producing the recombinant polypeptides of gGT25, gGT13, gGT30, gGT25-1, gGT25-3, gGT25-5, gGT29, gGT29-3, gGT29-4, gGT29-5, gGT29-6, gGT29-7 and 3GT1, 3GT2, 3GT3, 3GT4 by conventional DNA recombination techniques. Generally, the following steps are included:

(1). transforming or transducing suitable host cells by using the polynucleotides (or the variants) encoding the polypeptides gGT25, gGT13, gGT30, gGT25-1, gGT25-3, gGT25-5, gGT29, gGT29-3, gGT29-4, gGT29-5, gGT29-6, gGT29-7 and 3GT1, 3GT2, 3GT3, 3GT4 of the present invention, or by using the recombinant expression vectors containing said polynucleotides;

(2). culturing the host cells in a proper medium;

(3). isolating and purifying the proteins from the medium or the cells.

In the present invention, the polynucleotides of gGT25, gGT13, gGT30, gGT25-1, gGT25-3, gGT25-5, gGT29, gGT29-3, gGT29-4, gGT29-5, gGT29-6, gGT29-7 and 3GT1, 3GT2, 3GT3 can be inserted into a recombinant expression vector. The term "recombinant expression vector" refers to a bacterial plasmid, phage, yeast plasmid, virus for plant cells, virus for mammal cells such as adenovirus, retrovirus or other vectors well known in the art. Any plasmids or vectors can be used as long as it can replicate and stabilize inside the hosts. A major characteristic of the expression vector is that it generally contains a replication origin, a promoter, a marker gene and a translation control element.

The well-known methods in the art can be use to construct the vectors containing the DNA sequences encoding gGT25, gGT13, gGT30, gGT25-1, gGT25-3, gGT25-5, gGT29, gGT29-3, gGT29-4, gGT29-5, gGT29-6, gGT29-7 and 3GT1, 3GT2, 3GT3, 3GT4 and suitable transcription/translation control signals. These methods include in vitro DNA recombination techniques, DNA synthesis techniques, and in vivo recombination techniques, etc. Said DNA sequences can be effectively connected to a proper promoter in the expression vector so as to guide the mRNA synthesis. The representative examples of these promoters are: lac or trp promoter of *E. coli*; PL promoter of λ phage; eukaryotic promoters including CMV immediate-early promoter, HSV thymidine kinase promoter, early and late SV40 promoters, LTRs of retrovirus and some other known promoters capable of controlling the gene expression in protokaryocytes or eukaryocytes or the viruses thereof. The expression vectors further comprise ribosome binding sites for initiating translation and transcription terminators.

Furthermore, the expression vectors preferably contain one or more selective marker genes so as to provide the phenotypic characteristics for selecting the transformed host cells, such as dihydrofolate reductase, neomycin resistance and green fluorescent protein (GFP) used for eukaryocytes culturing, or tetracycline or ampicillin resistance used for *E. coli*.

The vectors containing the suitable DNA sequences and suitable promoters or regulating sequences described above can be used for transforming suitable host cells to express proteins.

The host cells can be prokaryocytes, such as bacterial cells; or lower eukaryocytes, such as yeast cells; or higher eukaryocytes, such as mammal cells. The representative examples are: bacterial cells of *E. coli, streptomyces, salmonella typhimurium*; fungal cells such as yeast; plant cells; insect cells of *Drosophila* S2 or Sf9; animal cells, such as CHO, COS, 293 cells, or Bowes melanoma cells.

When the polynucleotides of the present invention are expressed in higher eukaryocytes, the insertion of an enhancer sequence into the vector will enhance the transcription. The enhancer is a cis-acting element of DNA generally containing about 10-300 base-pairs and acting on promoters to enhance gene transcription. The available examples include the SV40 enhancer of 100-270 base-pairs located at the late-stage side of the replication origins, the polyma enhancer located at the late-stage side of the replication origins, and the adenovirus enhancers, etc.

It is all clear for those skilled in the art to choose suitable vectors, promoters, enhancers and host cells.

The transformation of host cells by using DNA recombination can be conducted by conventional techniques well-known to those skilled in the art. When prokaryotes such as E. coli are used as host cells, competent cells capable of absorbing DNA can be harvested after the exponential growth phase, and then treated with the $CaCl_2$ method, wherein the steps used are well known in the art. Another method is using $MgCl_2$. The transformation can also be conducted by electroporation if desired. When the host cell is a eucaryote, the following methods for DNA transfection are for selection: calcium phosphate co-precipitation, conventional mechanical methods such as micro-injection, electroporation, and liposome packing, etc.

The obtained transformants can be cultured by conventional methods, thereby expressing the polypeptides encoded by the genes of the present invention. According to the host cells used, the medium for culturing can be selected from various conventional medium. Upon culturing under the condition suitable for host cell growth, proper methods (such as temperature conversion or chemical induction) are used to induce the selected promoters when the host cells grow to a proper cells density, and then the cells are cultured for another period.

The recombinant polypeptide according to the methods above can be intracellular or membrane expression, or secreted out of the cells. The recombinant proteins can be isolated and purified by various isolating methods according to the physical, chemical, and other characteristics. These methods are well known to those skilled in the art. The examples of these methods include, but are not limited to: conventional renaturation treatment, treatment with protein precipitant (the salting-out method), centrifugation, bacterial-breaking by permeation, ultra-treatment, ultracentrifugation, molecular sieve chromatography (gel filtration), adsorption chromatography, ion-exchange column chromatography, high performance liquid chromatography (HPLC) and various other liquid chromatography techniques and the combination thereof.

Applications

The use of the active polypeptides or glycosyltransferases gGT25, gGT13, gGT30, gGT25-1, gGT25-3, gGT25-5, gGT29, gGT29-3, gGT29-4, gGT29-5, gGT29-6, gGT29-7 and 3GT1, 3GT2, 3GT3, 3GT4 of the present invention includes, but is not limited to: specifically and efficiently catalyzing glycosylation of the hydroxyl groups at positions C-20 and/or C-6 and/or C-3 of tetracyclic triterpenoid substrates, or transferring glycosyl(s) from glycosyl donor(s) to the first glycosyl at position C-3 of tetracyclic triterpenoid compound(s) so as to extend the carbohydrate chain. Particularly, they can convert PPD into rare ginsenosides CK and Rh2 with anti-tumor activity, convert PPT into rare ginsenoside F1 with anti-aging activity and rare ginsenoside Rh1 with anti-allergy activity, convert Rh2 into rare ginsenoside Rg3 with better anti-tumor activity. The glycosyltransferases of the present invention can further synthesize novel saponins such as 20-O-β-(D-glucopyranosyl)-dammarendiol II, 3-O-β-(D-glucopyranosyl)-dammarendiol II, 3-O-β-(D-glucopyranosyl)-PPT, 3-O-β-(D-glucopyrano-syl)-F1, 3-O-β-(D-glucopyranosyl)-25-OH-PPD, 3-O-β-(D-glucopyrano-syl)-25-$OCH_3$-PPD by using DM, PPT, F1, 25-OH-PPD, or 25-$OCH_3$-PPD. The glycosyltransferases of the present invention can further convert Rh2, CK, or Rg3 into ginsenoside F2, Rd, or Rg1.

Said tetracyclic triterpenoid compounds include but are not limited to: S- or R-dammarane-type, lanostane-type, tirucallane-type, cycloartane-type, cucurbitane type, or meliacane type typetetracyclic triterpenoid compounds.

The present invention provides a method for industrial catalyzation, comprises: under the condition of provided glycosyl donors, obtaining compound (II), (IV), (VI), (VIII), (X) and (XII) by using the active peptides or glycosyltransferases gGT25, gGT13, gGT30, gGT25-1, gGT25-3, gGT25-5, gGT29, gGT29-3, gGT29-4, gGT29-5, gGT29-6, gGT29-7, 3GT1, 3GT2, 3GT3 and/or 3GT4 of the present invention. Specifically, said polypeptide used in reaction (a) is selected from SEQ ID NOs.: 2, 16 or 18; said polypeptide used in reaction (b) is selected from SEQ ID NOs.: 20, 2, 16 or 18; said polypeptide used in reaction (c) and (d) is selected from SEQ ID NOs.: 22, 24, 41 and 43; said polypeptide used in reaction (e) is selected from SEQ ID NOs.: 26, 28, 55, 57, 59 or 61; said polypeptide used in reaction (F) is selected from the active polypeptide as set forth by SEQ ID NOs.: 22 or 24.

Said glycosyl donor(s) is nucleoside diphosphate sugar(s) selected from the group consisting of: UDP-glucose, ADP-glucose, TDP-glucose, CDP-glucose, GDP-glucose, UDP-acetyl glucose, ADP-acetyl glucose, TDP-acetyl glucose, CDP-acetyl glucose, GDP-acetyl glucose, UDP-xylose, ADP-xylose, TDP-xylose, CDP-xylose, GDP-xylose, UDP-galacturonic acid, ADP-galacturonic acid, TDP-galacturonic acid, CDP-galacturonic acid, GDP-galacturonic acid, UDP-galactose, ADP-galactose, TDP-galactose, CDP-galactose, GDP-galactose, UDP-arabinose, ADP-arabinose, TDP-arabinose, CDP-arabinose, GDP-arabinose, UDP-rhamnose, ADP-rhamnose, TDP-rhamnose, CDP-rhamnose, GDP-rhamnose, or other nucleoside diphosphate hexose or nucleoside diphosphate pentose, or the combination thereof.

Said glycosyl donor(s) is preferably uridine diphosphate (UDP) sugars selected from the group consisting of: UDP-glucose, UDP-galacturonic acid, UDP-galactose, UDP-arabinose, UDP-rhamnose, or other uridine diphosphate hexose or uridine diphosphate pentose, or the combination thereof.

For said method, additives for modulating enzyme activity (additives enhancing enzyme activity or inhibiting enzyme activity) can be further added. Said additive(s) for modulating enzyme activity can be selected from the group consisting of $Ca^{2+}$, $Co^{2+}$, $Mn^{2+}$, $Ba^{2+}$, $Al^{3+}$, $Ni^{2+}$, $Zn^{2+}$ and $Fe^{2+}$; or material(s) capable of producing $Ca^{2+}$, $Co^{2+}$, $Mn^{2+}$, $Ba^{2+}$, $Al^{3+}$, $Ni^{2+}$, $Zn^{2+}$, or $Fe^{2+}$.

The pH condition for said method is: pH 4.0-10.0, preferably pH 6.0-pH 8.5, more preferably 8.5.

The temperature condition for said method is: 10° C.-105° C., preferably 25° C.-35° C., more preferably 35° C.

The present invention further provide a composition, which contains an effective amount of the active polypeptide or glycosyltransferases gGT25, gGT13, gGT30, gGT25-1, gGT25-3, gGT25-5, gGT29, gGT29-3, gGT29-4, gGT29-5, gGT29-6, gGT29-7, 3GT1, 3GT2, 3GT3 and 3GT4 of the present invention, and a bromatologically or industrially acceptable carrier or excipient. Such carriers include, but are not limited to: water, buffer solution, glucose, water, glycerol, ethanol, and the combination thereof.

Additive(s) for modulating the activity of enzyme gGT25 of the present invention can be further added into said composition. Any additive(s) having the function of enhancing enzyme activity can be used. Preferably, said additive(s) for enhancing the activity of enzyme gGT25 of the present invention is mercaptoethanol. Furthermore, enzyme activity can be inhibited by many substances, which include but are not limited to $Ca^{2+}$, $Co^{2+}$, $Mn^{2+}$, $Ba^{2+}$, $Al^{3+}$, $Ni^{2+}$, $Zn^{2+}$ and $Fe^{2+}$; or substances capable of producing $Ca^{2+}$, $Co^{2+}$, $Mn^{2+}$, $Ba^{2+}$, $Al^{3+}$, $Ni^{2+}$, $Zn^{2+}$, or $Fe^{2+}$ by hydrolysis after being added to the substrate.

Upon obtaining gGT25, gGT13, gGT30, gGT25-1, gGT25-3, gGT25-5, gGT29, gGT29-3, gGT29-4, gGT29-5, gGT29-6, gGT29-7 and 3GT1, 3GT2, 3GT3, 3GT of the present invention, these enzymes can be readily used by the skilled in the art for transferring glycosyls, especially for transferring glycosyls by using DM, PPD and PPT as substrates. As a preferred embodiment for the present invention, two methods for generating rare ginsenosides are further provided, the first of said methods comprises: treating the substrate for transglycosylation with the enzymes gGT25, gGT13, gGT30, gGT25-1, gGT25-3, gGT25-5, gGT29, gGT29-3, gGT29-4, gGT29-5, gGT29-6, gGT29-7, 3GT1 and/or 3GT2, 3GT3, 3GT4 of the present invention, wherein said substrate includes tetracyclic triterpenoid compounds such as DM, PPD, PPT, and the derivatives thereof; preferably, under the condition of pH3.5-10, treating the substrate for transglycosylation with the enzymes gGT25, gGT13, gGT30, gGT25-1, gGT25-3, gGT25-5, gGT29, gGT29-3, gGT29-4, gGT29-5, gGT29-6, gGT29-7, 3GT1 and/or 3GT2, 3GT3, 3GT4; preferably, under the condition of a temperature of 30-105° C., treating the substrate for transglycosylation with the enzymes gGT25, gGT13, gGT30, gGT25-1, gGT25-3, gGT25-5, gGT29, gGT29-3, gGT29-4, gGT29-5, gGT29-6, gGT29-7, 3GT1 and/or 3GT2, 3GT3, 3GT4. The second of said methods comprises: transferring the genes of gGT25, gGT13, gGT30, gGT25-1, gGT25-3, gGT25-5, gGT29, gGT29-3, gGT29-4, gGT29-5, gGT29-6, gGT29-7 and 3GT1, 3GT2, 3GT3, 3GT4 of the present invention into an engineered strain (such as a yeast or E. coli engineered strain) capable of synthesizing DM, PPD or PPT, or alternatively co-expressing the genes of gGT25, gGT13, gGT30, gGT25-1, gGT25-3, gGT25-5, gGT29, gGT29-3, gGT29-4, gGT29-5, gGT29-6, gGT29-7 and 3GT1, 3GT2, 3GT3, 3GT4 with the key genes in the anabolism pathways of DM, PPD and PPT in a host cell (such as yeast cells or E. coli), thereby obtaining the recombinant strains for directly producing rare ginsenosides CK, Rh2, Rg3, Rh1 or F1.

Said key gene(s) in the anabolism pathway of dammarenediol includes but is not limited to dammarenediol synthase gene.

In another preferred embodiment, the key gene(s) in the anabolism pathway of PPD includes but is not limited to dammarenediol synthase gene, cytochrome P450 CYP716A47 gene, cytochrome P450 CYP716A47 reductase gene, or the combination thereof; or the isoenzymes of the above enzymes, and the combination thereof. Wherein, oxidosqualene (produced by Saccharomyces cerevisiae itself) is transformed into DM by dammarenediol synthase, and DM is transformed into PPD by cytochrome P450 CYP716A47 and the reductase thereof. (Han et al, plant & cell physiology, 2011, 52.2062-73)

In another preferred embodiment, the key gene(s) in anabolism pathway of PPT includes but is not limited to dammarenediol synthase gene, cytochrome P450 CYP716A47 gene, cytochrome P450 CYP716A47 reductase gene, cytochrome P450 CYP716A53V2 gene, or the combination thereof; or the isoenzymes of the above enzymes, and the combination thereof. Wherein, oxidosqualene (produced by Saccharomyces cerevisiae itself) is transformed into DM by dammarenediol synthase, and then DM is transformed into PPD by cytochrome P450 CYP716A47 and the reductase thereof, and PPD is further transformed into PPT by cytochrome P450 CYP716A53V2 (JX036031) and cytochrome P450 CYP716A47 reductase. (Han et al, plant & cell physiology, 2012, 53. 1535-45)

The Major Advantages of the Present Invention (1) Glucosyl(s) can be transferred to the hydroxyl(s) at position(s) C-20 and/or C-6 and/or C-3 of tetracyclic triterpenoid substrates specifically and efficiently by the glycosyltransferases of the present invention.

(2) Glycosyl(s) from glycosyl donor(s) can be transferred to the first glycosyl at position C-3 of tetracyclic triterpenoid compounds for extending the carbohydrate chain by using glycosyltransferases gGT29 and gGT29-3 of the present invention.

(3) PPD and PPT can be transformed into rare ginsenoside CK, Rh2 or Rg3 with anti-tumor activity, rare ginsenoside F1 with anti-aging activity, and rare ginsenoside Rh1 with anti-allergy activity respectively by the glycosyltransferases of the present invention.

(4) Unreported novel compounds of 20-O-β-(D-glucopyranosyl)-dammarendiol II, 3-O-β-(D-glucopyranosyl)-dammarendiol II, 3-O-β-(D-glucopyranosyl)-PPT, 3-O-β-(D-glucopyranosyl)-F1, 3-O-β-(D-glucopyranosyl)-25-OH-PPD, and 3-O-β-D-glucopyranosyl)-25-OCH$_3$-PPD, 3-O-β-(D-glucopyranosyl)-lanosterol can be synthesized from DM, PPT, F1, 25-OH-PPD, and 25-OCH$_3$-PPD by using the glycosyltransferases of the present invention.

(5) The catalytic activities of 3GT1, 3GT2, gGT29, gGT29-3 and gGT25-5 are not affected by the steric configuration of the hydroxyl or glycosyl at position 20 of tetracyclic triterpenoid compounds. These enzymes can catalyze the ginsenosides (sapogenins) of 20(S)-type as well as the ginsenosides (sapogenins) of 20(R)-type.

(6) The synthetic pathway of ginsengenins (DM, PPD, and PPT) are constructed in yeast, thereby realizing the production of novel compounds of 20-O-β-(D-glucopyranosyl)-dammarendiol II, 3-O-β-(D-glucopyranosyl)-dammarendiol II, 3-O-β-(D-glucopyranosyl)-PPT, 3-O-β-(D-glucopyranosyl)-F1, and 3-O-β-(D-glucopyranosyl)-lanosterol and rare ginsenosides CK, F1, Rh1, Rh2 and Rg3 through yeasts by using monosaccharide (such as glucose, etc) as substrates. Not only the problem of material source for saponin production is solved, but also the production costs of rare saponins CK, F1, Rh1, Rh2 and Rg3 are significantly decreased.

The invention is further illustrated by the following examples. These examples are only intended to illustrate the invention, but not to limit the scope of the invention. For the experimental methods in the following examples the specific conditions of which are not specifically indicated, they are performed under routine conditions, e.g., those described by Sambrook. et al., in Molecular Cloning: A Laboratory Manual, New York: Cold Spring Harbor Laboratory Press, 1989, or as instructed by the manufacturers, unless otherwise specified.

EXAMPLE 1

1. Isolation of Glycosyltransferases and their Encoding Genes

More than 100 predicted cDNA sequences of glycosyltransferases were extracted from the published expression profile data of the Panax plant. 60 cDNAs with full length were cloned, expressed, and subjected to the analysis of glycosyltransfering reaction. Wherein, 11 of the expression products showed glycosyltransfering activities on ginsengenins and saponins.

Figure 19:
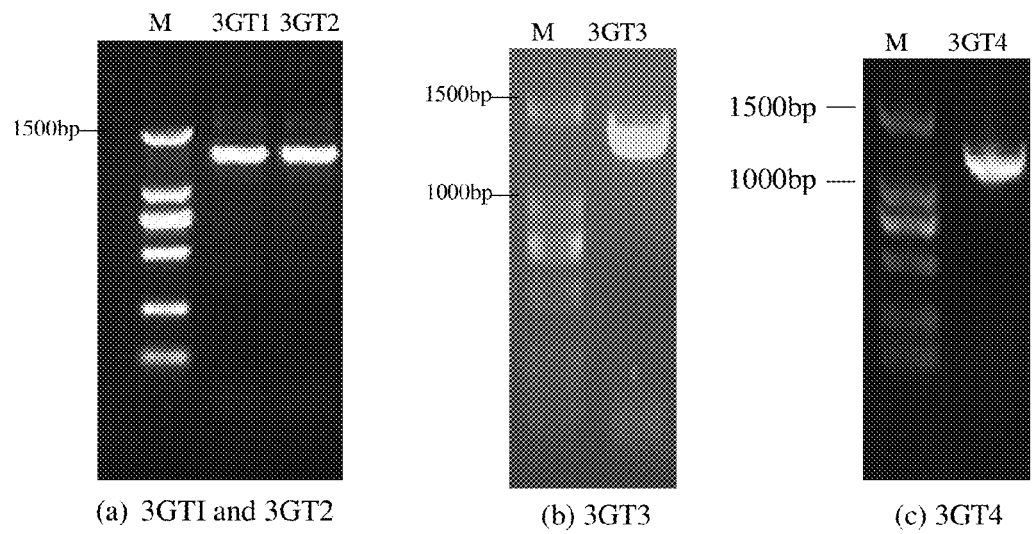
FIG. 19 shows agarose gel electrophoresis detection of the PCR products of genes (a) 3GT1 and 3GT2, (b) 3GT3 and (c) 3GT4.

The RNA of *P. ginseng* was extracted and reverse transcribed to obtain the cDNA of *P. ginseng*. PCR amplification was conducted using the cDNA as the template. Wherein, amplification products were all obtained by using primer pair 1 (SEQ ID NOs.: 7, 8), primer pair 2 (SEQ ID NOs.: 9, 10), primer pair 3 (SEQ ID NOs.: 11, 12), primer pair 5 (SEQ ID NOs.: 34, 35), primer pair 7 (SEQ ID NOs.: 46, 47), primer pair 8 (SEQ ID NOs.:62, 63) and primer pair 9 (SEQ ID NOs.:64, 65). The high-fidelity DNA Polymerase KOD purchased from Takara Bio Inc. was used as the DNA polymerase. The PCR products were detected by agarose gel electrophoresis (FIGS. 1, 19(*c*) and 31). The target DNA bands were cut out under a UV lamp. Then, the DNA was recovered from the agarose gel using Axygen Gel Extraction Kit (Axygen Inc.) to give the amplified DNA fragments. An adenine was added to the end of the DNA fragments using the rTaq DNA polymerase (Takara Bio Inc.) and then the product was ligated into the commercially available cloning vector pMD18-T. The ligated products were transformed into the commercially available *E. coli* competent cells EPI300. The liquid containing the transformed *E. coli* strains was plated on a LB plate supplemented with 50 ug/mL of ampicillin, 0.5 mM of IPTG and 25 μg/mL of X-Gal. The recombinant clones were verified by PCR and enzyme digestion. Recombinant plasmids extracted from each clone were subjected to sequencing. The Open Reading Frame (ORF) was searched using software BESTORF. Through sequence alignment, the conserved domain of the glycosyltransferases family 1 was encoded by the ORF, indicating that these genes were glycosyltransferase genes.

The genes obtained by primer pair 1 (SEQ ID NOs.: 7, 8) are as set forth by SEQ ID NOs.: 1, 15, 17 and 19, and named as gGT25, gGT25-1, gGT25-3 and gGT25-5, respectively. The protein coding sequence (CDS) of gGT25 is shown as the nucleotides of positions 1-1425 from the 5' end of SEQ ID NO.: 1 according to the sequence listing. The start codon ATG of gene gGT25 is shown as the nucleotides of positions 1-3 from the 5' end of SEQ ID NO.: 1. The Open Reading Frame (ORF) of gGT25-1 is shown as the nucleotides of positions 1-1428 from the 5' end of SEQ ID NO.: 15 according to the sequence listing. The start codon ATG of gGT25-1 is shown as the nucleotides of position 1-3 from the 5' end of SEQ ID NO.: 15 and the stop codon TAA of gGT25-1 is shown as the nucleotides of positions 1426-1428 from the 5' end of SEQ ID NO.: 15. The Open Reading Frame (ORF) of gGT25-3 is shown as the nucleotides of positions 1-1428 from the 5' end of SEQ ID NO.: 17 according to the sequence listing. The start codon ATG of gGT25-3 is shown as the nucleotides of position 1-3 from the 5' end of SEQ ID NO.: 17 and the stop codon TAA of gGT25-3 is shown as the nucleotides of position 1426-1428 from the 5' end of SEQ ID NO.: 17. The Open Reading Frame (ORF) of gGT25-5 is shown as the nucleotides of position 1-1419 from the 5' end of SEQ ID NO.: 19 according to the sequence listing. The start codon ATG of gGT25-5 is shown as the nucleotides of position 1-3 from the 5' end of SEQ ID NO.: 19 and the stop codon TAA of gGT25-5 is shown as the nucleotides of position 1426-1428 from the 5' end of SEQ ID NO.: 19.

The gene obtained by primer pair 2 (SEQ ID NOs.: 9, 10) is as set forth by SEQ ID NO.: 3, and named as gGT13. The Open Reading Frame (ORF) of gGT13 is shown as the nucleotides of position 1-1431 from the 5' end of SEQ ID NO.: 3 according to the sequence listing. The start codon ATG of gGT13 is shown as the nucleotides of position 1-3 from the 5' end of SEQ ID NO.: 3 and the stop codon TAA of gGT13 is shown as the nucleotides of position 1429-1431 from the 5' end of SEQ ID NO.: 1.

The gene obtained by primer pair 3 (SEQ ID NOs.: 11, 12) is as set forth by SEQ ID NO.: 5, and named as gGT30. The Open Reading Frame (ORF) of gGT30 is shown as the nucleotides of position 1-1353 from the 5' end of SEQ ID NO.: 5 according to the sequence listing. The start codon ATG of gGT30 is shown as the nucleotides of position 1-3 from the 5' end of SEQ ID NO.: 5 and the stop codon TAA of gGT30 is shown as the nucleotides of position 1351-1353 from the 5' end of SEQ ID NO.: 5.

The genes obtained by primer pair 5 (SEQ ID NOs.: 34, 35) are as set forth by SEQ ID NOs.: 25 and 27, and named as gGT29 and gGT29-3. The Open Reading Frame (ORF) of gGT29 is shown as the nucleotides of position 1-1329 from the 5' end of SEQ ID NO.: 25 according to the sequence listing. The start codon ATG of gene gGT29 is shown as the nucleotides of position 1-3 from the 5' end of SEQ ID NO.: 25 and the stop codon TAG of gene gGT29 is shown as the nucleotides of position 1327-1329 from the 5' end of SEQ ID NO.: 25. The start codon ATG of gene gGT29-3 is shown as the nucleotides of position 1-3 from the 5' end of SEQ ID NO.: 27 and the stop codon TAG of gGT29 is shown as the nucleotides of position 1327-1329 from the 5' end of SEQ ID NO.: 27.

The gene obtained by primer pair 6 (SEQ ID NOs.: 46, 47) is as set forth by SEQ ID NO.: 42, and named as 3GT4. The Open Reading Frame (ORF) of 3GT4 is shown as the nucleotides of position 1-1374 from the 5' end of SEQ ID NO.: 42 according to the sequence listing. The start codon ATG of gene 3GT4 is shown as the nucleotides of position 1-3 from the 5' end of SEQ ID NO.: 42 and the stop codon TAG of gene 3GT4 is shown as the nucleotides of position 1372-1374 from the 5' end of SEQ ID NO.: 42.

The genes obtained by primer pair 7 (SEQ ID NOs.: 62, 63) are as set forth by SEQ ID NOs.: 54, 56, and 58, and named as gGT29-4, gGT29-5 and gGT29-6. The Open Reading Frame (ORF) of gGT29-4 is shown as the nucleotides of position 1-1341 from the 5' end of SEQ ID NO.: 54 according to the sequence listing. The start codon ATG of gene gGT29-4 is shown as the nucleotides of position 1-3 from the 5' end of SEQ ID NO.: 54 and the stop codon TAG of gene gGT29-4 is shown as the nucleotides of position 1339-1341 from the 5' end of SEQ ID NO.: 54. The Open Reading Frame (ORF) of gGT29-5 is shown as the nucleotides of position 1-1341 from the 5' end of SEQ ID NO.: 56 according to the sequence listing. The start codon ATG of gene gGT29-5 is shown as the nucleotides of position 1-3 from the 5' end of SEQ ID NO.: 56 and the stop codon TAG of gene gGT29-5 is shown as the nucleotides of position 1339-1341 from the 5' end of SEQ ID NO.: 56. The Open Reading Frame (ORF) of gGT29-6 is shown as the nucleotides of position 1-1341 from the 5' end of SEQ ID NO.: 58 according to the sequence listing. The start codon ATG of gene gGT29-6 is shown as the nucleotides of position 1-3 from the 5' end of SEQ ID NO.: 58 and the stop codon TAG of gene gGT29-6 is shown as the nucleotides of position 1339-1341 from the 5' end of SEQ ID NO.: 58.

The gene obtained by primer pair 8 (SEQ ID NOs.: 64, 65) is as set forth by SEQ ID NO.: 60, and named as gGT29-7. The Open Reading Frame (ORF) of gGT29-7 is shown as the nucleotides of position 1-1341 from the 5' end of SEQ ID NO.: 60 according to the sequence listing. The start codon ATG of gene gGT29-7 is shown as the nucleotides of position 1-3 from the 5' end of SEQ ID NO.: 60 and the stop codon TAG of gene gGT29-7 is shown as the nucleotides of position 1339-1341 from the 5' end of SEQ ID NO.: 60. The nucleotide sequences as set forth by SEQ ID NOs.: 21, 23 and 40 were artificially synthesized and named as 3GT1, 3GT2 and 3GT3, respectively. The Open Reading Frame (ORF) of 3GT1 is shown as the nucleotides of position 1-1488 from the 5' end of SEQ ID NO.: 21 according to the sequence listing. The start codon ATG of gene 3GT1 is shown as the nucleotides of position 1-3 from the 5' end of SEQ ID NO.: 21 and the stop codon TAA of gene 3GT1 is shown as the nucleotides of position 1486-1488 from the 5' end of SEQ ID NO.: 21. The Open Reading Frame (ORF) of 3GT2 is shown as the nucleotides of position 1-1488 from the 5' end of SEQ ID NO.: 23 according to the sequence listing. The start codon ATG of gene 3GT2 is shown as the nucleotides of position 1-3 from the 5' end of SEQ ID NO.: 23 and the stop codon TAA of gene 3GT2 is shown as the nucleotides of position 1486-1488 from the 5' end of SEQ ID NO.: 23. The Open Reading Frame (ORF) of 3GT3 is shown as the nucleotides of position 1-1494 from the 5' end of SEQ ID NO.: 40 according to the sequence listing. The start codon ATG of gene 3GT3 is shown as the nucleotides of position 1-3 from the 5' end of SEQ ID NO.: 40 and the stop codon TAA of gene 3GT3 is shown as the nucleotides of position 1492-1494 from the 5' end of SEQ ID NO.: 40. PCR was employed to amplify two of the synthesized genes as set forth by SEQ ID NO.: 21 and SEQ ID NO.: 23 using primer pair 4 (SEQ ID NOs.: 29, 30), and the obtained PCR products had the nucleotides sequences as set forth by SEQ ID NO.: 21 and SEQ ID NO.: 23 (FIG. 19(a)). PCR was employed to amplify another synthesized gene as set forth by SEQ ID NO.: 40 using primer pair 6 (SEQ ID NOs.: 44, 45), and the obtained PCR products had the nucleotides sequences as set forth by SEQ ID NO.: 40 (FIG. 19(b)).

The glycosyltransferase gene gGT25 encodes a protein gGT25 with 475 amino acids having the amino acid sequence as set forth by SEQ ID NO.: 2 of the sequence listing. The theoretical molecular weight of the protein was predicted to be 53 kDa and the isoelectric point (PI) 5.14 by software. Positions 344-387 from the N-terminal of SEQ ID NO.: 2 correspond to the conserved domain of the glycosyltransferase family 1. The amino acid sequence identity between said glycosyltransferase and the amino acid sequence of the predicted glycosyltransferase gene of saponin in P. ginseng transcriptome is lower than 52%.

The glycosyltransferase gene gGT25-1 encodes a protein gGT25-1 with 475 amino acids having the amino acid sequence as set forth by SEQ ID NO.: 16 of the sequence listing. The theoretical molecular weight of the protein was predicted to be 53 kDa and the isoelectric point (PI) 4.91 by software. Positions 344-387 from the N-terminal of SEQ ID NO.: 16 correspond to the conserved domain of the glycosyltransferase family 1. The amino acid sequence identity between said glycosyltransferase and the amino acid sequence of the predicted glycosyltransferase gene of saponin in P. ginseng transcriptome is lower than 52%.

The glycosyltransferase gene gGT25-3 encodes a protein gGT25-3 with 475 amino acids having the amino acid sequence as set forth by SEQ ID NO.: 18 of the sequence listing. The theoretical molecular weight of the protein was predicted to be 53 kDa and the isoelectric point (PI) 5.05 by software. Positions 344-387 from the N-terminal of SEQ ID NO.: 18 correspond to the conserved domain of the glycosyltransferase family 1. The amino acid sequence identity between said glycosyltransferase and the amino acid sequence of the predicted glycosyltransferase gene of saponin in P. ginseng transcriptome is lower than 52%.

The glycosyltransferase gene gGT25-5 encodes a protein gGT25-5 with 472 amino acids having the amino acid sequence as set forth by SEQ ID NO.: 20 of the sequence listing. The theoretical molecular weight of the protein was predicted to be 53 kDa and the isoelectric point (PI) 4.98 by software. Positions 343-386 from the N-terminal of SEQ ID NO.: 20 correspond to the conserved domain of the glycosyltransferase family 1. The amino acid sequence identity between said glycosyltransferase and the amino acid sequence of the predicted glycosyltransferase gene of saponin in P. ginseng transcriptome is lower than 52%.

The glycosyltransferase gene gGT13 encodes a protein gGT13 with 476 amino acids having the amino acid sequence as set forth by SEQ ID NO.: 4 of the sequence listing. The theoretical molecular weight of the protein was predicted to be 53 kDa and the isoelectric point (PI) 4.91 by software. Positions 343-386 from the N-terminal of SEQ ID NO.: 4 correspond to the conserved domain of the glycosyltransferase family 1. The highest amino acid sequence identity between said glycosyltransferase and the amino acid sequence of the predicted glycosyltransferase gene of saponin in P. ginseng transcriptome is 99.5%.

The glycosyltransferase gene gGT30 encodes a protein gGT30 with 451 amino acids having the amino acid sequence as set forth by SEQ ID NO.: 6 of the sequence listing. The theoretical molecular weight of the protein was predicted to be 51 kDa and the isoelectric point (PI) 6.79 by software. Positions 318-361 from the N-terminal of SEQ ID NO.: 6 correspond to the conserved domain of the glycosyltransferase family 1. This glycosyltransferase has the highest similarity with the glycosyltransferase of *Vitis vinifera* (XP_002271587)(53%), indicating that this glycosyltransferase is a novel enzyme.

The glycosyltransferase gene 3GT1 encodes a protein 3GT1 with 495 amino acids having the amino acid sequence as set forth by SEQ ID NO.: 22 of the sequence listing. The theoretical molecular weight of the protein was predicted to be 56 kDa and the isoelectric point (PI) 5.52 by software. Positions 355-398 from the N-terminal of SEQ ID NO.: 22 correspond to the conserved domain of the glycosyltransferase family 1. The homology between said glycosyltransferase and the glycosyltransferase UGT73C10 originated from *Barbarea vulgaris* is higher than 99%.

The glycosyltransferase gene 3GT2 encodes a protein 3GT2 with 495 amino acids having the amino acid sequence as set forth by SEQ ID NO.: 24 of the sequence listing. The theoretical molecular weight of the protein was predicted to be 56 kDa and the isoelectric point (PI) 5.62 by software. Positions 355-398 from the N-terminal of SEQ ID NO.: 24 correspond to the conserved domain of the glycosyltransferase family 1. The homology between said glycosyltransferase and the glycosyltransferase UGT73C12 originated from *Barbarea vulgaris* is higher than 99%.

The glycosyltransferase gene gGT29 encodes a protein gGT29 with 442 amino acids having the amino acid sequence as set forth by SEQ ID NO.: 26 of the sequence listing. The theoretical molecular weight of the protein was predicted to be 49 kDa and the isoelectric point (PI) 5.93 by software. Positions 317-360 from the N-terminal of SEQ ID NO.: 26 correspond to the conserved domain of the glycosyltransferase family 1. The sequence similarity between said glycosyltransferase and the glycosyltransferase originated from *Vitis vinifera* is lower than 56%.

The glycosyltransferase gene gGT29-3 encodes a protein gGT29-3 with 442 amino acids having the amino acid sequence as set forth by SEQ ID NO.: 28 of the sequence listing. The theoretical molecular weight of the protein was predicted to be 49 kDa and the isoelectric point (PI) 5.48 by software. Positions 317-360 from the N-terminal of SEQ ID NO.: 26 correspond to the conserved domain of the glycosyltransferase family 1. The sequence similarity between said glycosyltransferase and the glycosyltransferase originated from *Vitis vinifera* is lower than 56%.

The glycosyltransferase gene 3GT3 encodes a protein 3GT3 with 497 amino acids having the amino acid sequence as set forth by SEQ ID NO.: 41 of the sequence listing. The theoretical molecular weight of the protein was predicted to be 55 kDa and the isoelectric point (PI) 5.50 by software. Positions 350-393 from the N-terminal of SEQ ID NO.: 41 correspond to the conserved domain of the glycosyltransferase family 1. The homology between said glycosyltransferase and the glycosyltransferase originated from *Medicago truncatula* is higher than 99%.

The glycosyltransferase gene 3GT4 encodes a protein 3GT4 with 458 amino acids having the amino acid sequence as set forth by SEQ ID NO.: 43 of the sequence listing. The theoretical molecular weight of the protein was predicted to be 51 kDa and the isoelectric point (PI) 5.10 by software. Positions 333-376 from the N-terminal of SEQ ID NO.: 43 correspond to the conserved domain of the glycosyltransferase family 1. The sequence homology between said glycosyltransferase and the glycosyltransferase originated from *Vitis vinifera* is lower than 50%.

The glycosyltransferase gene gGT29-4 encodes a protein gGT29-4 with 446 amino acids having the amino acid sequence as set forth by SEQ ID NO.: 55 of the sequence listing. The theoretical molecular weight of the protein was predicted to be 50 kDa and the isoelectric point (PI) 5.78 by software. Positions 321-364 from the N-terminal of SEQ ID NO.: 55 correspond to the conserved domain of the glycosyltransferase family 1. The sequence similarity between said glycosyltransferase and the glycosyltransferase originated from *Bupleurunt chinense* is lower than 57%.

The glycosyltransferase gene gGT29-5 encodes a protein gGT29-5 with 446 amino acids having the amino acid sequence as set forth by SEQ ID NO.: 57 of the sequence listing. The theoretical molecular weight of the protein was predicted to be 50 kDa and the isoelectric point (PI) 5.93 by software. Positions 321-364 from the N-terminal of SEQ ID NO.: 57 correspond to the conserved domain of the glycosyltransferase family 1. The sequence similarity between said glycosyltransferase and the glycosyltransferase originated from *Bupleurum chinense* is lower than 58%.

The glycosyltransferase gene gGT29-6 encodes a protein gGT29-6 with 446 amino acids having the amino acid sequence as set forth by SEQ ID NO.: 59 of the sequence listing. The theoretical molecular weight of the protein was predicted to be 50 kDa and the isoelectric point (PI) 6.03 by software. Positions 321-364 from the N-terminal of SEQ ID NO.: 59 correspond to the conserved domain of the glycosyltransferase family 1. The sequence similarity between said glycosyltransferase and the glycosyltransferase originated from *Bupleurum chinense* is lower than 59%.

The glycosyltransferase gene gGT29-7 encodes a protein gGT29-7 with 446 amino acids having the amino acid sequence as set forth by SEQ ID NO.: 61 of the sequence listing. The theoretical molecular weight of the protein was predicted to be 50 kDa and the isoelectric point (PI) 5.80 by software. Positions 321-364 from the N-terminal of SEQ ID NO.: 61 correspond to the conserved domain of the glycosyltransferase family 1. The sequence similarity between said glycosyltransferase and the glycosyltransferase originated from *Bupleurum chinense* is lower than 57%.

TABLE 2

| Glycosyltransferase | C-3 | The first glycosyl at C-3 | C6 | C20 |
|---|---|---|---|---|
| gGT25 (SEQ ID NO.: 2) | | | ✓ | ✓ |
| gGT25-1 (SEQ ID NO.: 16) | | | ✓ | ✓ |
| gGT25-3 (SEQ ID NO.: 18) | | | ✓ | ✓ |
| gGT25-5 (SEQ ID NO.: 20) | | | ✓ | |
| gGT29 (SEQ ID NO.: 26) | | ✓ | | |
| gGT29-3 (SEQ ID NO.: 28) | | ✓ | | |
| gGT29-4 (SEQ ID NO.: 55) | | ✓ | | |
| gGT29-5 (SEQ ID NO.: 57) | | ✓ | | |
| gGT29-6 (SEQ ID NO.: 59) | | ✓ | | |
| gGT29-7 (SEQ ID NO.: 61) | | ✓ | | |
| 3GT1 (SEQ ID NO.: 22) | ✓ | | | |
| 3GT2 (SEQ ID NO.: 24) | ✓ | | | |
| 3GT3 (SEQ ID NO.: 40) | ✓ | | | |
| 3GT4 (SEQ ID NO.: 43) | ✓ | | | |
| gGT13 (SEQ ID NO.: 4) | ND | ND | ND | ND |
| gGT30 (SEQ ID NO.: 6) | ND | ND | ND | ND |

EXAMPLE 2

Construction of the Recombinant Yeast Expression Vectors for Glycosyltransferase Genes gGT25, gGT25-1, gGT25-3 and gGT25-5

The target genes were amplified using the plasmids gGT25-pMD18T, gGT25-1-pMD18T, gGT25-3-pMD18T and gGT25-5-pMD18T containing genes gGT25, gGT25-1, gGT25-3 and gGT25-5 constructed in Example 1 as templates.

The collective forward primer is:
5'-GCCGGAGCTCATGAAGTCAGAATTGATATTC-3' (SEQ ID NO.: 13) with a SacI recognition site added to its 5' end: GAGCTC;

The collective reverse primer is:
5'-GCCGCTCGAGTTAATGATGATGATGATGATG-CATAATTTCCTCAAATAGCTTC-3' (SEQ ID NO.: 14) with a XhoI recognition site added to its 5' end: CTCGAG. A 6×His Tag was introduced into the reverse primer for expression detection by Western Blot and purification.

The above primers and templates were used for amplifying genes gGT25, gGT25-1, gGT25-3 and gGT25-5 by PCR method. The high-fidelity DNA polymerase KOD (Toyobo Inc) was selected as DNA polymerase and the PCR program was set according to the instructions: 94° C. 2 min; 94° C. 15 s, 58° C. 30 s, 68° C. 1.5 min for 30 cycles; 68° C. 10 min; the temperature was kept at 10° C. The PCR product was detected by agarose gel electrophoresis and the band with a size of the target DNA was cut under a UV lamp. Then, the DNA fragments were recovered from the agarose gel using AxyPrep DNA Gel Extraction Kit (AXYGEN Inc.). The recovered DNA fragments were digested using two Quickcut restricted enzymes Kpn I and Xba I from Takara Inc. for 30 mins. The enzyme-digested products were rinsed and recovered by AxyPrep PCR Cleanup Kit from AXYGEN Inc. The digested products was ligated to the *Saccharomyces cerevisiae* expression plasmid pYES2 (also digested by Kpn I and Xba I and then cut out and recovered) at 25° C. for 2 hrs by using T4 DNA ligase (NEB Inc.). The ligated products were transformed into *E. coli* TOP 10 competent cells and coated on a LB plate supplemented with 100 µg/mL ampicillin. The positive clones were verified by colony PCR and further verified by sequencing. The results indicated that the expression plasmids gt25-pYES2, gt25-1-pYES2, gt25-3-pYES2 and gt25-5-pYES2 were successfully constructed.

EXAMPLE 3

Expression of Glycosyltransferases gGT25, gGT25-1, gGT25-3 and gGT25-5 Genes in *S. cerevisiae*

Figure 2:
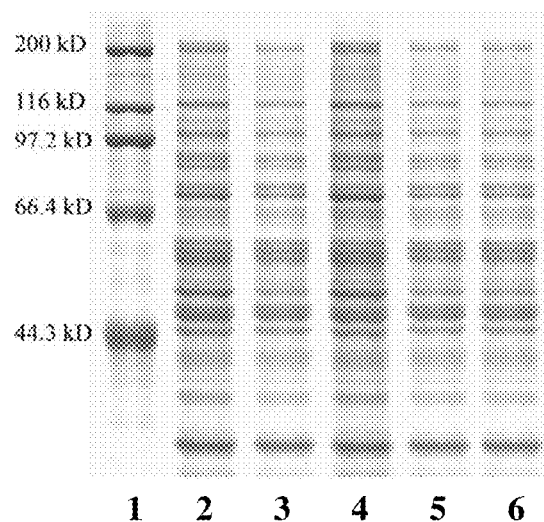
FIG. 2 shows the SDS-PAGE detection of gGT25, gGT25-1, gGT25-3 and gGT25-5 gene expression in *Saccharomyces cerevisiae*; lane 1, electrophoresis results of the protein marker (molecular weight from top to bottom: 200, 116, 97.2, 66.4 and 44.3 kDa); lane 2, lysate supernatant of the GT25-pYES2 recombinant yeast; lane 3, lysate supernatant of the gt25-1-pYES2 recombinant yeast; lane 4, lysate supernatant of the gt25-3-pYES2 recombinant yeast; lane 5, lysate supernatant of the gt25-5-pYES2 recombinant yeast; lane 6, lysate supernatant of the empty vector pYES2 recombinant.
Figure 3:
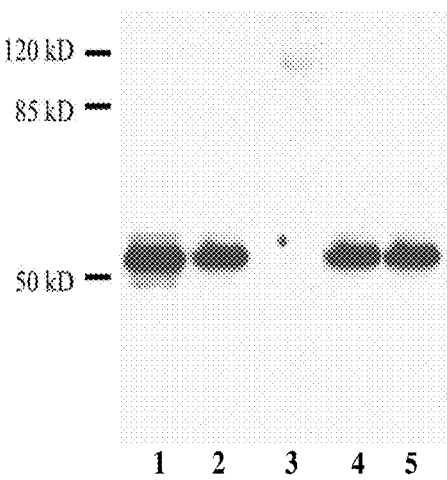
FIG. 3 shows the Western Blot detection of gGT25, gGT25-1, gGT25-3 and gGT25-5 gene expression in *S. cerevisiae*; lane 1, lysate supernatant of the recombinant yeast gt25-pYES2; lane 2, lysate supernatant of the recombinant yeast gt25-1-pYES2; lane 4, lysate supernatant of the recombinant yeast gt25-3-pYES2; lane 5, lysate supernatant of the recombinant yeast gt25-5-pYES2; lane 3, lysate supernatant of the empty vector pYES2 recombinant.

The constructed expression vectors gt25-pYES2 were transformed into *Saccharomyces cerevisiae* through electroporation and then coated on screening plates SC-Ura (0.67% yeast nitrogen base without amino acids, 2% glucose). The recombinant yeasts were verified by colony PCR. A recombinant yeast colony was inoculated into 10 mL of the SC-Ura (2% glucose) medium and then cultured at 200 rpm under 30° C. for 20 h. The pellets were collected by centrifuge (3500 g) at 4° C. The pellets were washed with sterile deionized water for twice, resuspended in the induction medium SC-Ura (2% galactose) and inoculated into 50 mL of the induction medium with an $OD_{600}$ of about 0.4 so as to induce the expression at 200 rpm under 30° C. After expression induction for 12 hours, the pellets were collected by centrifugation (3500 g) at 4° C., washed with sterile deionized water for twice and then resuspended in the yeast lysis buffer to keep $OD_{600}$ between 50 and 100. The yeast cells were shook and disrupted by the Fastprep cell disruption system. The cell debris was removed by centrifugation (12000 g) at 4° C. for 10 mins and the supernatant of the cell lysis was collected. An appropriate amount of supernatant of the cell lysis was subjected to SDS-PAGE electrophoresis detection. Compared with empty vector pYES2 recombinants, no obvious characteristic band was shown for gt25-pYES2, gt25-1-pYES2, gt25-3-pYES2, or gt25-5-pYES2 recombinants, see FIG. 2. The expression was detected by using anti-6×His Tag Western Blot. As shown in FIG. 3, the *S. cerevisiae* recombinants expressing gGT25, gGT25-1, gGT25-3 or gGT25-5 showed strong Western Blot signals, indicating the soluble expression of gGT25, gGT25-1, gGT25-3 and gGT25-5 in yeasts. In contrast, no anti-6×His Tag Western Blot signal was shown for the recombinants transformed with empty vector pYES2.

EXAMPLE 4

Glycosyltransfering Reaction of the Yeast Expression Products gGT25, gGT25-1, gGT25-3 and gGT25-5 and the Product Identification The glycosyltransfering reactions of the substrates PPD, PPT or DM were catalyzed by using lysate supernatant of the recombinant yeasts expressing gGT25, gGT25-1, gGT25-3 or gGT25-5 as crude enzymes. The lysate supernatant of the recombinant yeasts expressing the empty vector was used as control. The 100 µL reaction system is shown in Table 3:

TABLE 3

| 9% Tween 20 | 11.1 µL |
| 50 mM UDP-glucose | 10 µL |
| 1M Tris-HCl pH8.5 | 5 µL |
| 100 mM substrate (dissolved in ethanol) | 0.5 µL |
| crude enzyme | 73.4 µL |

The reaction was conducted under 35° C. for 12 hrs, then stopped by adding 100 µL of butanol. The product were extracted, dried in vacuum, and dissolved in methanol.

Figure 6:
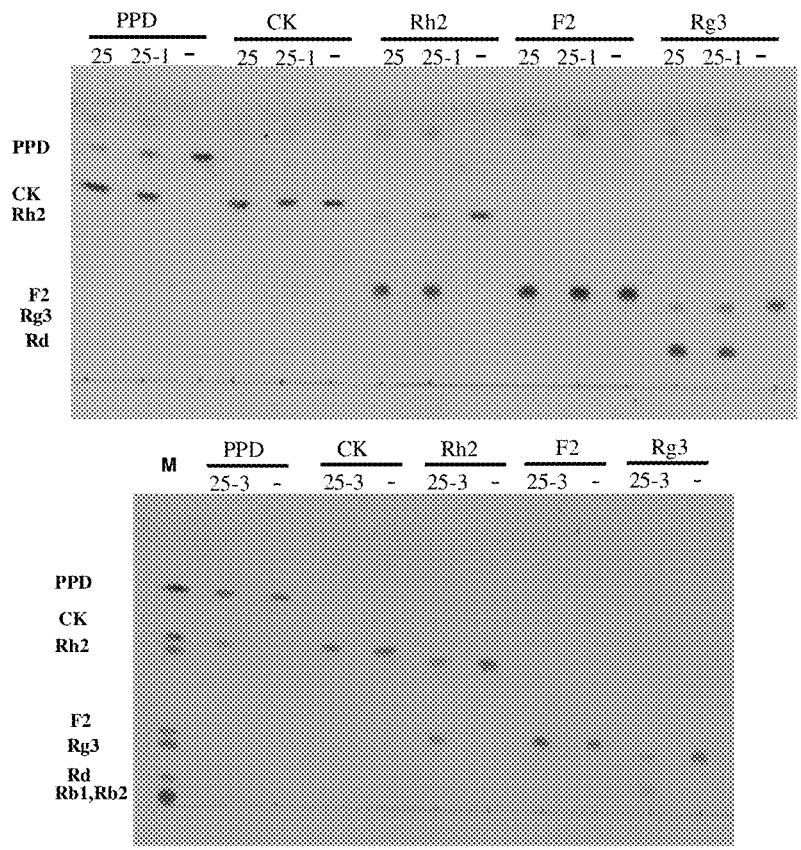
FIG. 6 shows the TLC detection of the products obtained by catalyzing protopanaxadiol (PPD) and PPD-type ginsenosides using the glycosyltransferases gGT25, gGT25-1 and gGT25-3. Lane 25, gGT25 crude enzyme (lysate supernatant of the recombinant yeast gt25-pYES2); lane 25-1, gGT25-1 crude enzyme (lysate supernatant of the recombinant yeast gt25-1-pYES2); lane 25-3, gGT25-3 crude enzyme (lysate supernatant of the recombinant yeast gt25-3-pYES2); lane "−", negative control, crude enzyme was substituted by lysate supernatant of the empty vector yeast; lane M, mixed standard samples of PPD and PPD-type ginsenosides.
Figure 7:
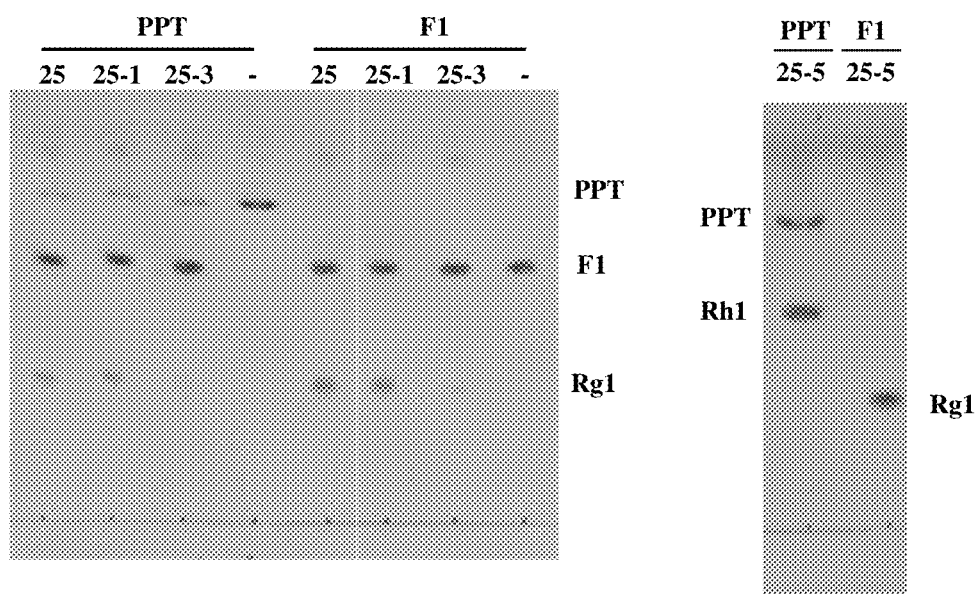
FIG. 7 shows the TLC detection of the products obtained by catalyzing protopanaxatriol (PPT) and PPT-type ginsenosides using the glycosyltransferases gGT25, gGT25-1 and gGT25-3. Lane M, mixed standard sample of PPT and PPT-type ginsenosides; lane 25, gGT25 crude enzyme (lysate supernatant of the recombinant yeast gt25-pYES2); lane 25-1, gGT25-1 crude enzyme (lysate supernatant of the recombinant yeast gt25-1-pYES2); lane 25-3, gGT25-3 crude enzyme (lysate supernatant of the recombinant yeast gt25-3-pYES2); lane 25-5, gGT25-5 crude enzyme (lysate supernatant of the recombinant yeast gt25-5-pYES2); lane "–", negative control, crude enzyme was substituted by lysate supernatant of the empty vector yeast.
Figure 8:
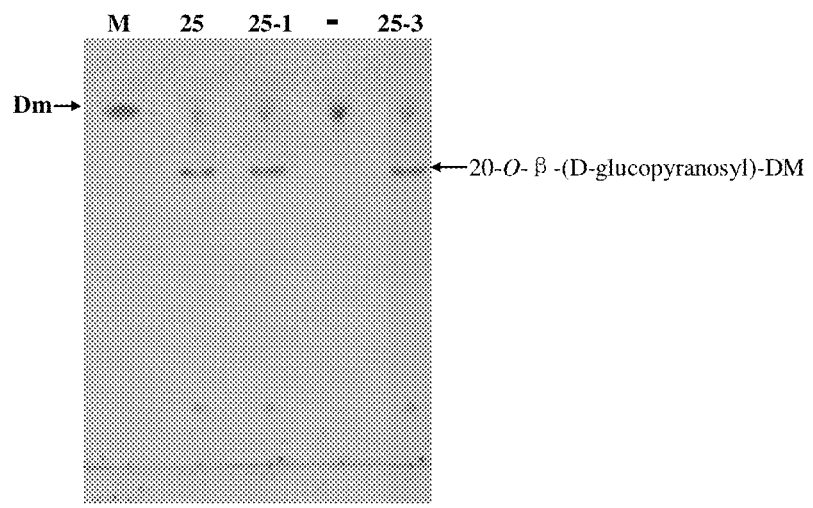
FIG. 8 shows the TLC detection of the products obtained by catalyzing dammarenediol II using the glycosyltransferases gGT25, gGT25-1 and gGT25-3. Lane 25, gGT25 crude enzyme (lysate supernatant of the recombinant yeast gt25-pYES2); lane 25-1, gGT25-1 crude enzyme (lysate supernatant of the recombinant yeast gt25-1-pYES2); lane 25-3, gGT25-3 crude enzyme (lysate supernatant of the recombinant yeast gt25-3-pYES2); lane "–", negative control, crude enzyme was substituted by lysate supernatant of the empty vector yeast; lane M, dammarenediol II (DM) standard sample.

The reaction products were first detected by thin layer chromatography (TLC). The lysate supernatant (used as the crude enzyme) of the recombinant yeasts expressing gGT25, gGT25-1 or gGT25-3 glycosylated the C20-OH of PPD and PPT, thereby converting them into rare ginsenosides CK and F1 (FIG. 6 and FIG. 7). PPD-type saponins Rh2 and Rg3 with glycosylated C3-OH were further glycosylated at C20-OH, with the catalyzation by gGT25, gGT25-1 and gGT25-3, to produce F2 and Rd, respectively (FIG. 6). Upon the catalyzation of gGT25, gGT25-1 and gGT25-3, not only the C20-OH of PPT could be glycosylated to produce F1, but also C6-OH could be further glycosylated to produce Rg1 (FIG. 7). Besides, gGT25, gGT25-1 and gGT25-3 could also glycosylate C20-OH of DM (the precursor of PPD) to produce an unreported saponin 20-O-β-(D-glucopyranosyl)-dammarendiol II (FIG. 8). However, PPT-type saponins (Rh1, Rg2, and Rf) with a glycosylated C6-OH could not be catalyzed by gGT25, gGT25-1 or gGT25-3 to produce glycosylated C20-OH. Meanwhile, gGT25, gGT25-1 or gGT25-3 could not catalyze the extension of carbohydrate chain. The glycosyltransferase gGT25-5 has different catalytic activities with gGT25, or gGT25-1, or gGT25-3; unlike gGT25, gGT25-1 and gGT25-3, it could not glycosylate the C20-OH of PPD, PPT or DM, but can only glycosylate C6-OH of PPT to produce rare ginsenoside Rh1 (FIG. 7).

Figure 10:
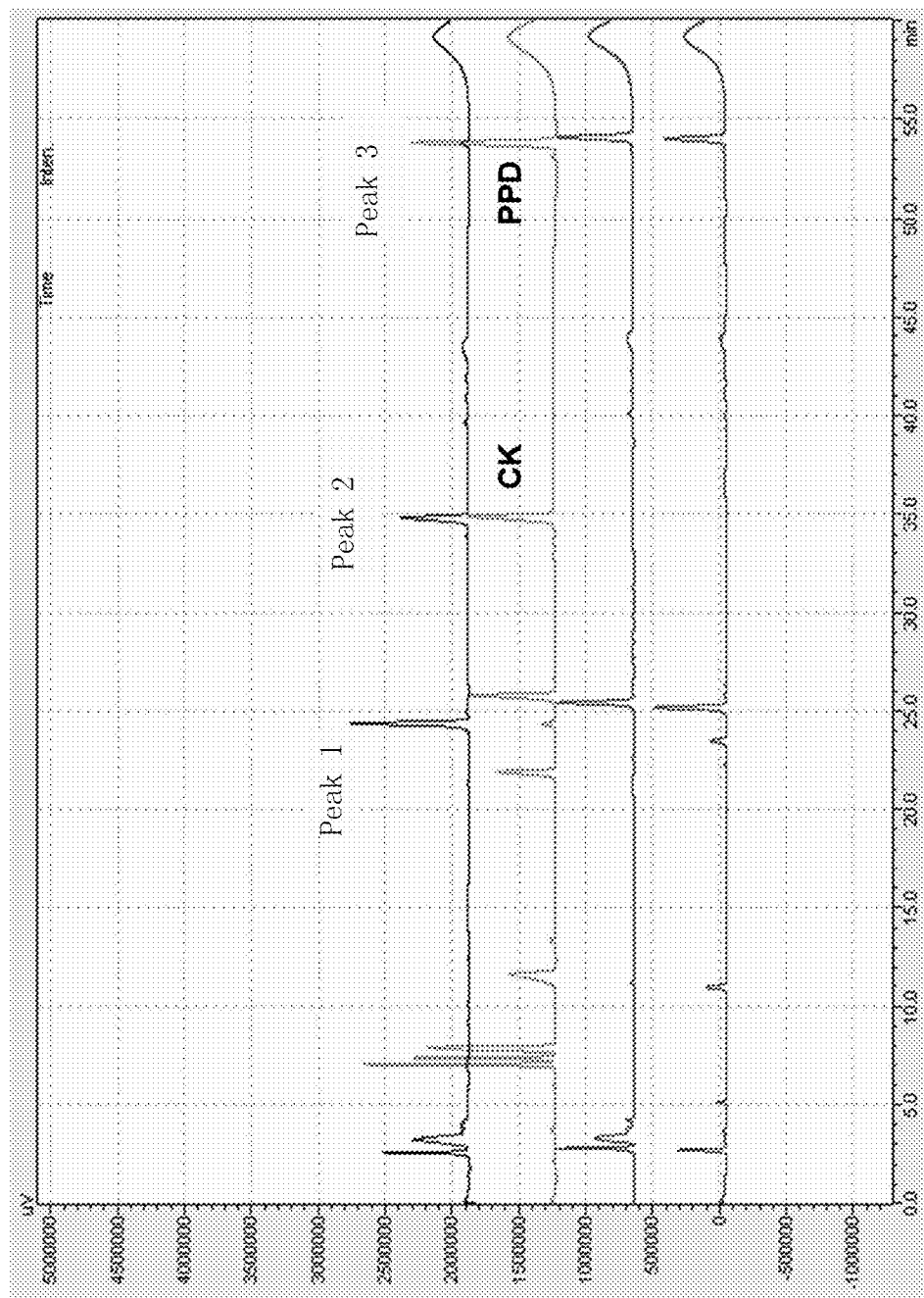
FIG. 10 shows the HPLC detection of the products obtained by catalyzing PPD using the glycosyltransferase gGT25, the sample of line 2: mixed standard sample of PPD and various ginsenosides (CK, Rh2, F2 and Rg3); the sample of line 1: PPD catalyzed by gGT25 crude enzyme; the sample of the third line: the negative control 1, PPD catalyzed by lysate supernatant of the empty vector recombinant yeast; the sample of the fourth line: negative control 2, dH2O.
Figure 11:
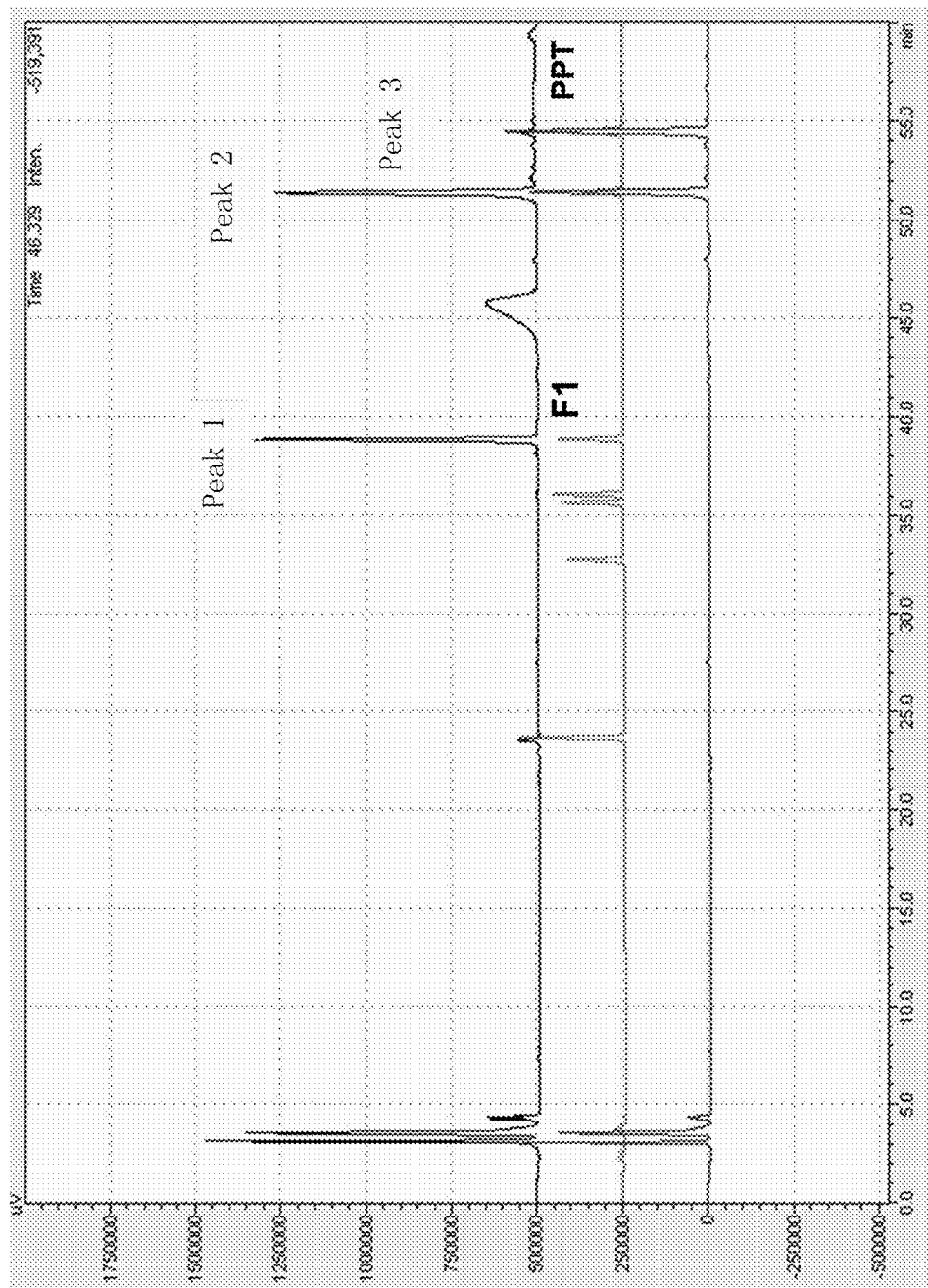
FIG. 11 shows the HPLC detection of the products obtained by catalyzing PPT using the glycosyltransferase gGT25, the sample of line 2: mixed standard sample of PPT and various PPT-type ginsenosides (F1, Rh1 and Rg1); the sample of line 1: PPT catalyzed by gGT25 crude enzyme; the sample of the third line; the negative control 1, PPT catalyzed by lysate supernatant of the empty vector recombinant yeast.

The converted products of gGT25 were further identified by HPLC (FIG. 10 and FIG. 11). As shown in FIG. 10, there were 3 peaks. The retention time of peak 2 was identical to that of the CK standard sample; the retention time of peak 3 was identical to that of PPD. The small peak 3 indicated that PPD had been substantially transformed into CK. Peak 1, also present in the profile of the negative control, indicated its irrelevance to the conversion of PPD. 3 peaks were shown in FIG. 11, the retention time of peak 1 was identical to that of F1 standard sample and peak 3 was identical to that of PPT. The small peak 3 indicated that PPT had been substantially transformed into F1. Peak 2, also present in the profile of the negative control, indicated its irrelevance to the conversion of PPT.

Figure 12:
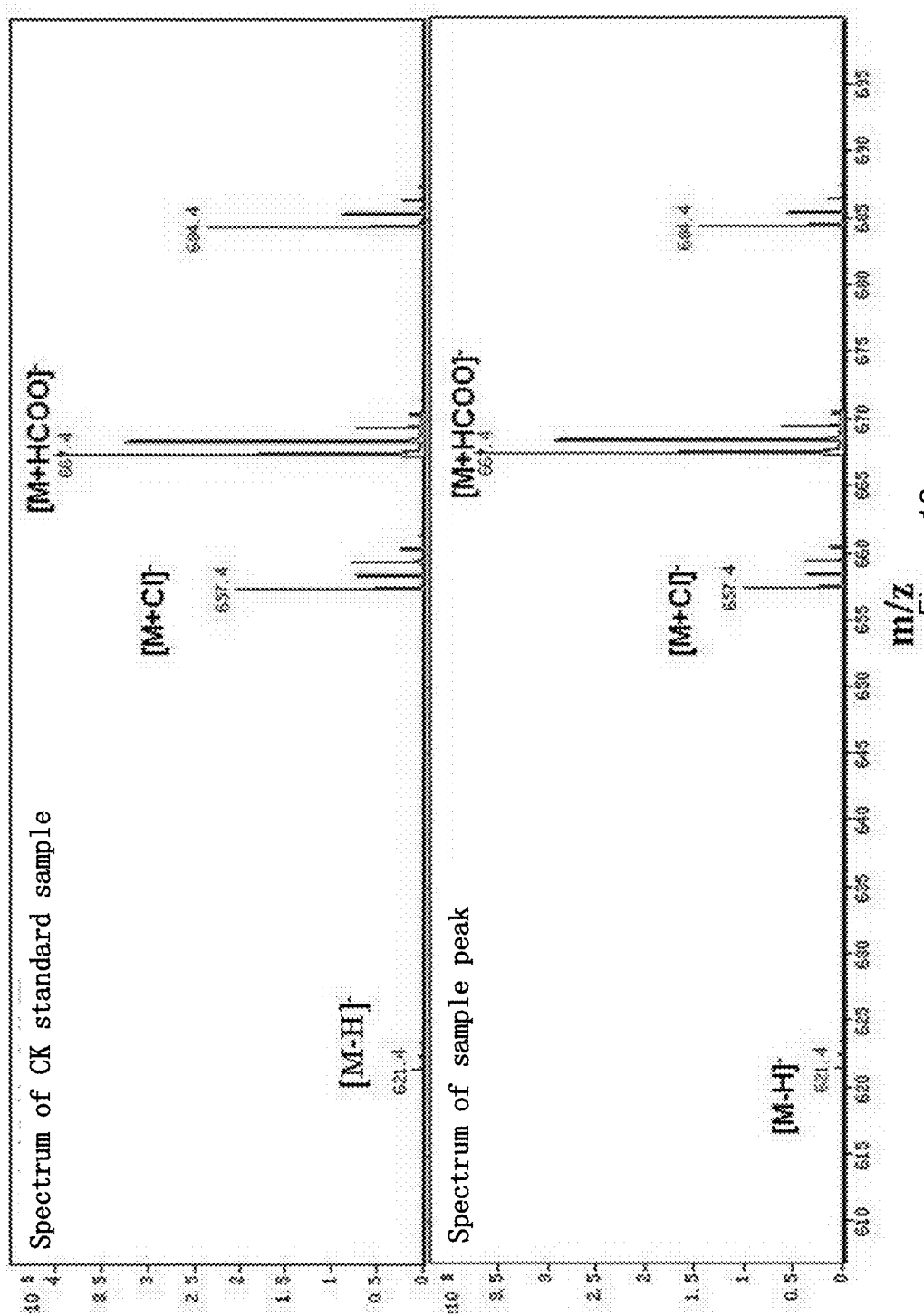
FIG. 12 shows the LC/MS detection of the products obtained by catalyzing PPD using the glycosyltransferase gGT25. The mass spectrums of peak 2 (product peak) in FIG. 10 and the standard CK sample are presented.
Figure 13:
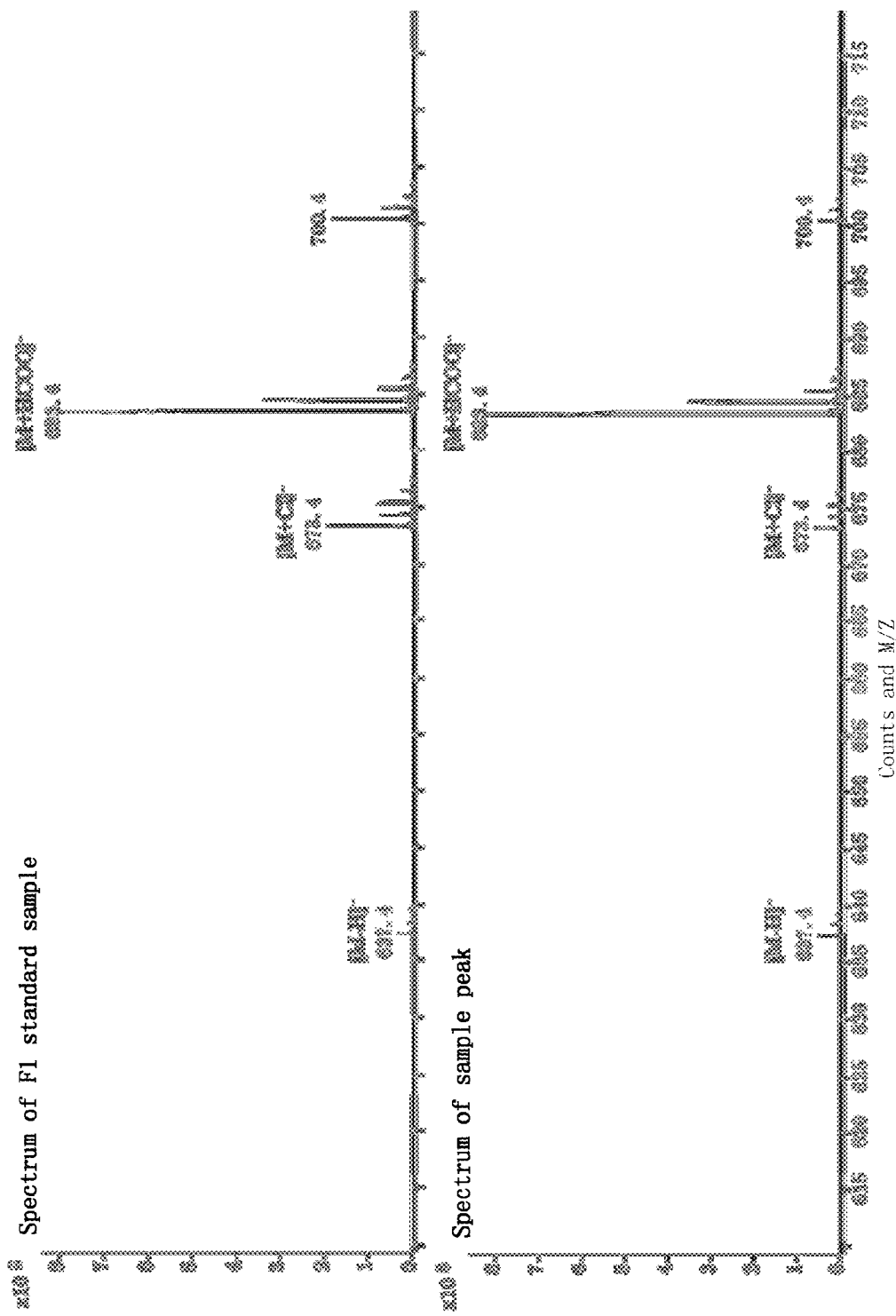
FIG. 13 shows the LC/MS detection of the products obtained by catalyzing PPT using the glycosyltransferase gGT25. The mass spectrums of peak 1 (product peak) in FIG. 11 and the standard F1 sample are presented.

Finally, LC/MS was employed to further confirm the products (FIG. 12 and FIG. 13). FIG. 12 showed the mass spectrum of the CK peak from the PPD conversion products (Peak 2 in FIG. 10). Its MS was completely identical to that of the CK standard sample. FIG. 13 showed the mass spectrum of F1 peak from the PPT conversion products (Peak 1 in FIG. 11). Its MS was completely identical to that of the standard sample of F1. These results further confirmed that the conversion product of PPD and PPT by gGT25 is CK and F1, respectively.

EXAMPLE 5

Figure 4:
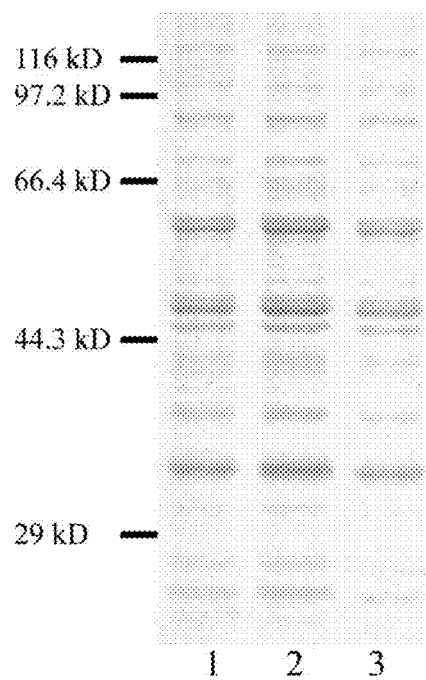
FIG. 4 shows the SDS-PAGE detection of gGT13 and gGT30 expression in *S. cerevisiae*; lane 1, lysate supernatant of the recombinant yeast gt30-pYES2; lane 2, lysate supernatant of the recombinant yeast gt13-pYES2; lane 3, lysate supernatant of the empty vector pYES2 recombinant.
Figure 5:
FIG. 5 shows the Western Blot detection of gGT13 and gGT30 expression in *S. cerevisiae*; lane 1, lysate supernatant of the recombinant yeast gt30-pYES2; lane 2, lysate supernatant of the recombinant yeast gt13-pYES2; lane 3, lysate supernatant of the empty vector pYES2 recombinant.

The Cloning and Expression of Glycosyltransferases gGT13 and gGT30, and the Glycosyltransfering Reaction of the Expression Products Thereof Using the same method as in Example 2, clones of gGT13 and gGT30 were obtained and recombinant yeast expression vectors were constructed and then transformed into *Saccharomyces cerevisiae*. Glycosyltransferases were induced to express as the steps in Example 3. Although there was no apparent band of target protein on SDS-PAGE (FIG. 4), obvious hybridization signals were detected by Western Blot, indicating expressions of gGT13 and gGT30 in the yeasts (FIG. 5).

According to the method as in Example 4, the cell lysate of recombinant yeasts expressing gGT13 and gGT30 were used to catalyze PPD and PPT.

Figure 9:
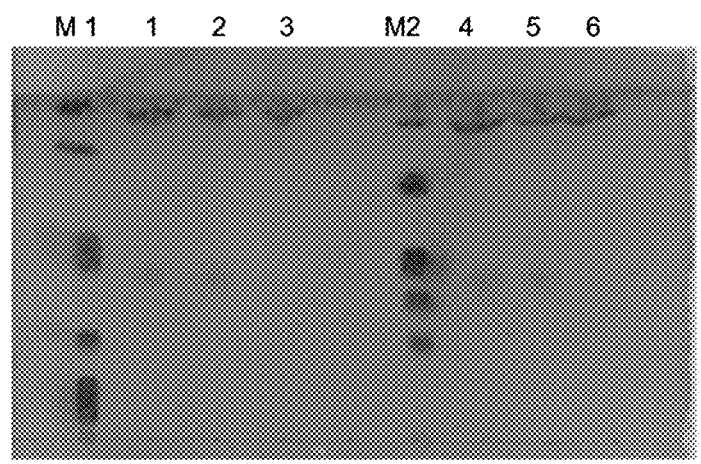
FIG. 9 shows the TLC detection of the products obtained by catalyzing PPD and PPT using the glycosyltransferases gGT13 and gGT30. Lane M1, mixed standard sample of PPD and PPD-type ginsenosides; lane M2, mixed standard sample of PPT and PPT-type ginsenosides; lane 1, PPD catalyzed by gGT13 crude enzyme; lane 2, PPD catalyzed by gGT30 crude enzyme; lane 3, negative control, crude enzyme was substituted with ddH2O; lane 4, PPT catalyzed by gGT13 crude enzyme; lane 5, PPT catalyzed by gGT30 crude enzyme; lane 6, negative control, crude enzyme was substituted with ddH2O.

Results turned out that the protein expression products of gGT13 and gGT30 neither converted PPD or PPT (FIG. 9), nor PPD-type saponins Rh2, CK, F2 or Rg3, or PPT-type saponins F1, Rh1 or Rg1.

The above results indicated that gGT13 and gGT30 exhibited no glycosyltransfering effect on the above substrates in spite of the high identity (99.5%) between gGT13 and amino acid sequence of the predicted ginsenoside glycosyltransferase in *P. ginseng* transcriptome.

EXAMPLE 6

The Expression of Glycosyltransferase gGT25 in *E. coli* and the Glycosyltransfering Reaction of the Expression Product Thereof The target gene gGT25 was amplified by using the plasmid gGT25-pMD18T containing gene gGT25 constructed in Example 1 as a template, cloned to the *E. coli* expression vector pet28a (purchased from Merck company) to construct an *E. coli* expression vector gt25-pet28a. The product was transformed into the commercial available *E. coli* BL21. The recombinant was inoculated in LB medium and cultured under 30° C. at 200 rpm until $OD_{600}$ reached about 0.6-0.8. Then the culture liquid was cooled to 4° C., and IPTG with a final concentration of 50 μM was added for inducing expression under 18° C. at 200 rpm for 15 hrs. The pellets were collected by centrifugation under 4° C. and then subjected to ultrasonic disruption. The cell lysis supernatant was collected by centrifugation at 12000 g under 4° C. and then an sample was taken for SDS-PAGE electrophoresis.

Figure 14:
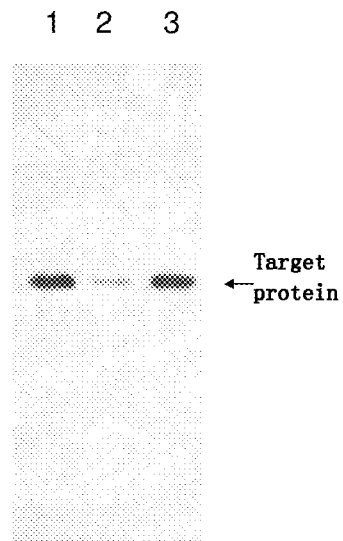
FIG. 14 shows the Western Blot detection of gGT25-pET28a expression in *E. coli* BL21; lanes 1-3 illustrate the total protein, supernatant and precipitate upon 50 µM IPTG induction, respectively.

Western blot (FIG. 14) showed that glycosyltransferase gGT25 could also be expressed in *E. coli* under the induction condition of 50 μM IPTG. The cell lysis supernatant of the recombinant *E. coli* was used as crude enzyme to conduct the glycosyltransfering reaction, and the reaction condition was identical to that of Example 4.

Figure 15:
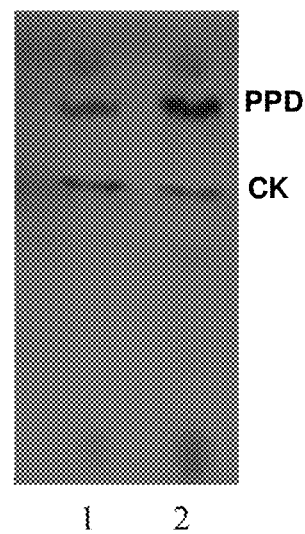
FIG. 15 shows the TLC detection of the products obtained by catalyzing PPD in vitro using lysate supernatant of the gGT25-pET28a recombinant *E. coli*; lane 1, mixed standard sample of PPD and CK; lane 2, PPD catalyzed by lysate supernatant of the gGT25-pET28a recombinant *E. coli* upon IPTG induction (50 µM IPTG).

The reaction was conducted under 35° C. for 12 hrs. 100 μL of butanol was added to stop the reaction and the products were extracted. Upon vacuum drying, the product was dissolved by methanol. TLC was first used to detect the reaction product. As shown in FIG. 15, the crude enzyme containing gGT25 could transform PPD into CK.

EXAMPLE 7

Construction of the Engineered Yeast Strain for Producing CK and the Product Characterization Dammarenediol synthase (ACZ71036.1) (GAL1/GAL10 GAL10 side promoter, ADH1 terminator), cytochrome P450 CYP716A47 (AEY75213.1) (FBA1 promoter, CYC1 terminator), and glycosyltransferase gene GT25 (GAL1/GAL10 GAL1 side promoter, TDH2 terminator) were assembled in the plasmid pESC-HIS (Stratagene, Agilent), thereby constructing an episomal plasmid. The plasmid was used to transform *Saccharomyces cerevisiae* BY4742. Cytochrome P450 reductase gene ATR2-1 (NP_849472.2) from *Arabidopsis thaliana* was also integrated to the site of gene trp1 (GAL1 promoter; using the original terminator of trp1) in the chromosome of *Saccharomyces cerevisiae* BY4742 so as to construct the recombinant yeast A. Recombinant yeast B was also constructed by the same method except that the reductase gene ATR2-1 from *A. thaliana* was integrated to the recombinant plasmid containing DM synthetase, cytochrome P450 CYP716A47 and glycosyltransferases GT25. The promoter and terminator of ART2-1 were TEF2 promoter and TPI1 terminator, respectively. The promoters or terminators of other 3 genes were identical to the corresponding genes of recombinant strain A.

Recombinant yeast strain C was constructed using the method as for recombinant yeast strain B except the replanned promoter and terminator of each gene as shown in Table 4.

TABLE 4

Constitution of promoters and terminators of the major enzymes:

| Major enzymes | Promoter | Terminator |
| --- | --- | --- |
| DM synthetase | GAL1/GAL10 GAL10 side | ADH1 |
| CYP716A47 | GAL1/GAL10 GAL1 side | TDH2 |
| ATR2-1 | TEF2 | TPI1 |
| GT25 | FBA1 | CYC1 |

The recombinant yeast strains A, B, C were fermented in SC-Ura culture medium (0.67% yeast nitrogen base without amino acids, and 2% galactose). Additional added amino acids or uracil needed for each recombinant strain was shown in Table 5. 50 mL of the fermentation broth of the recombinant yeast was subjected to centrifugation, and the precipitated pellets were resuspended in 5 mL of yeast lysis buffer (50 mM Tris-Hcl, 1 mM EDTA, 1 mM PMSF, 5% glycerol, pH 7.5). Then the yeasts were shook and disrupted by Fastprep. 7-8 times of shaking with the power of 6M/S enabled the complete disruption of the yeast. The lysate was transferred into 2 mL EP tubes with 1 mL for each tube, subjected to extraction by adding n-butanol of equivalent volume (1 mL) for about 30 mins, and then centrifuged for 10 mins at 12000 g. The supernatant was transferred to a new EP tube. n-butanol was evaporated to dry in vacuum under 45° C. Upon being dissolved in methanol (100 μL), the product was subjected to HPLC detection.

Figure 16:
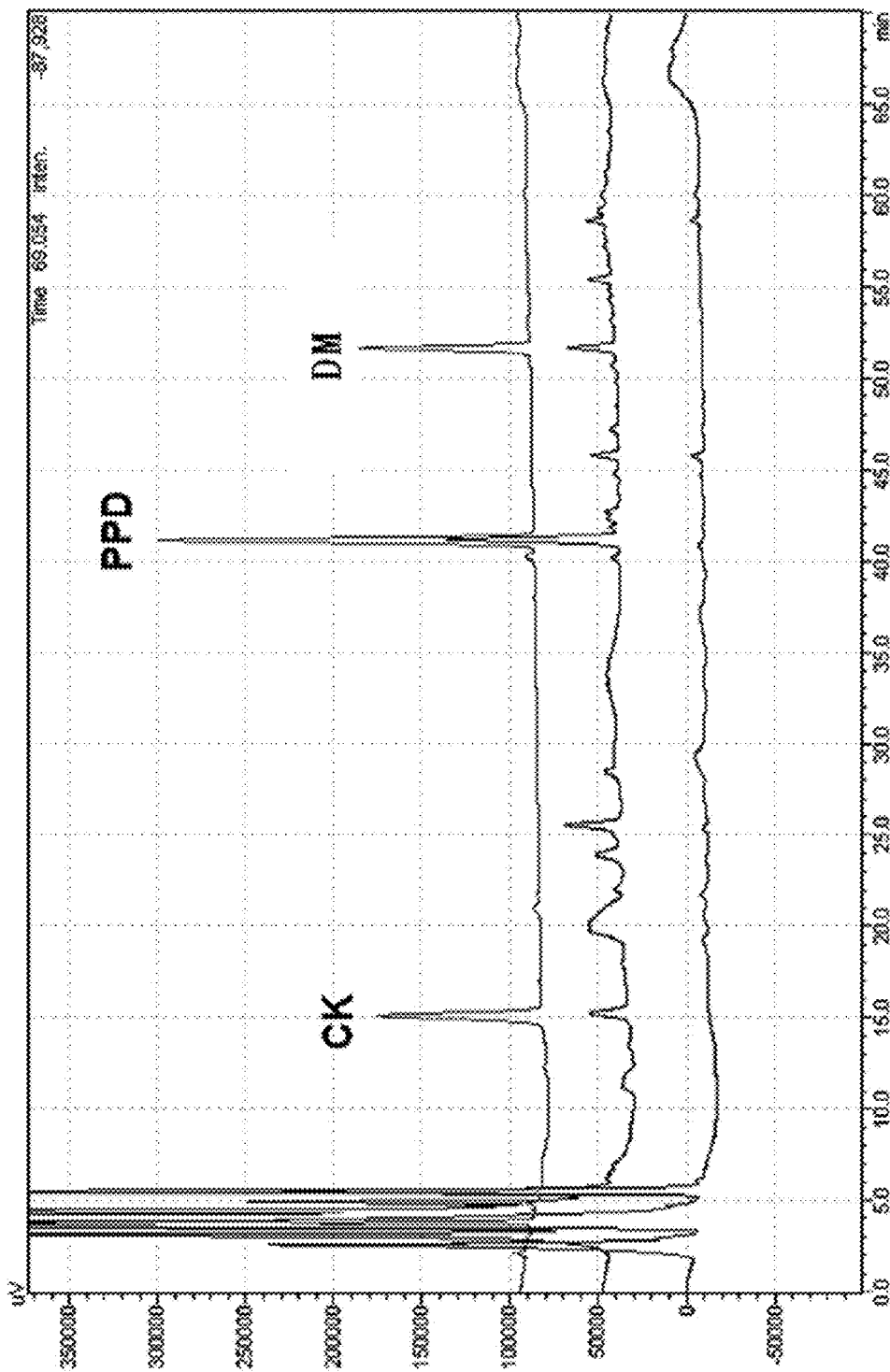
FIG. 16 shows the HPLC detection of the cell lysate extract of the engineered yeast strain A for CK production, the sample of line 1: mixed standard sample of PPD, dammarenediol II, and CK; the sample of line 2: cell lysate of the engineered yeast A which can produce CK; the sample of line 3: negative control, cell lysate of starting yeast strain.
Figure 17:
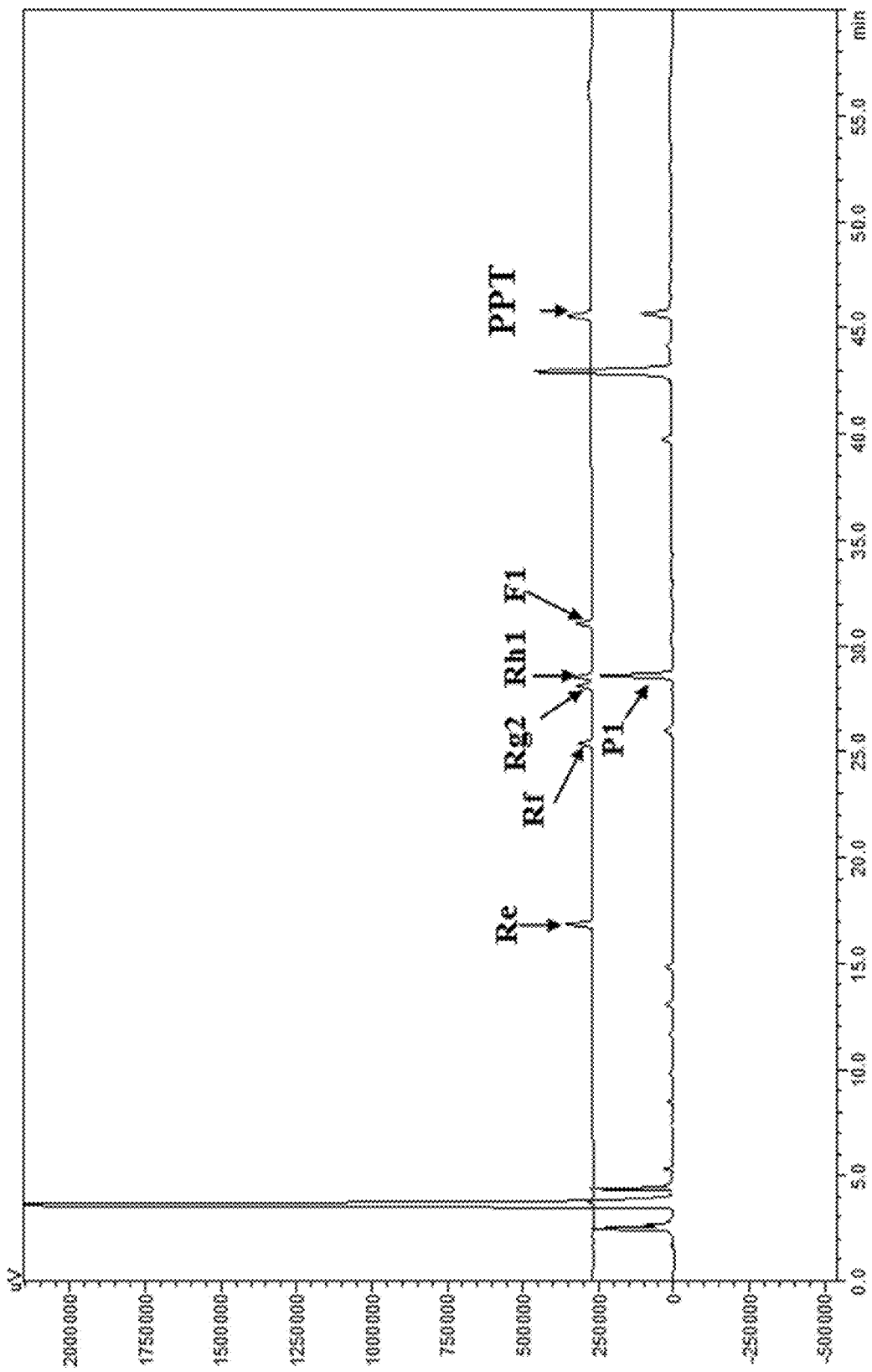
FIG. 17 shows the HPLC detection of the products obtained by catalyzing PPT using the glycosyltransferase gGT25-5, the sample of line 1: mixed standard sample of PPT and PPT-type saponins (F1, Rh1, Rg1 and Re); the sample of line 2: the product obtained by catalyzing PPT using gGT25-5 crude enzyme.
Figure 18:
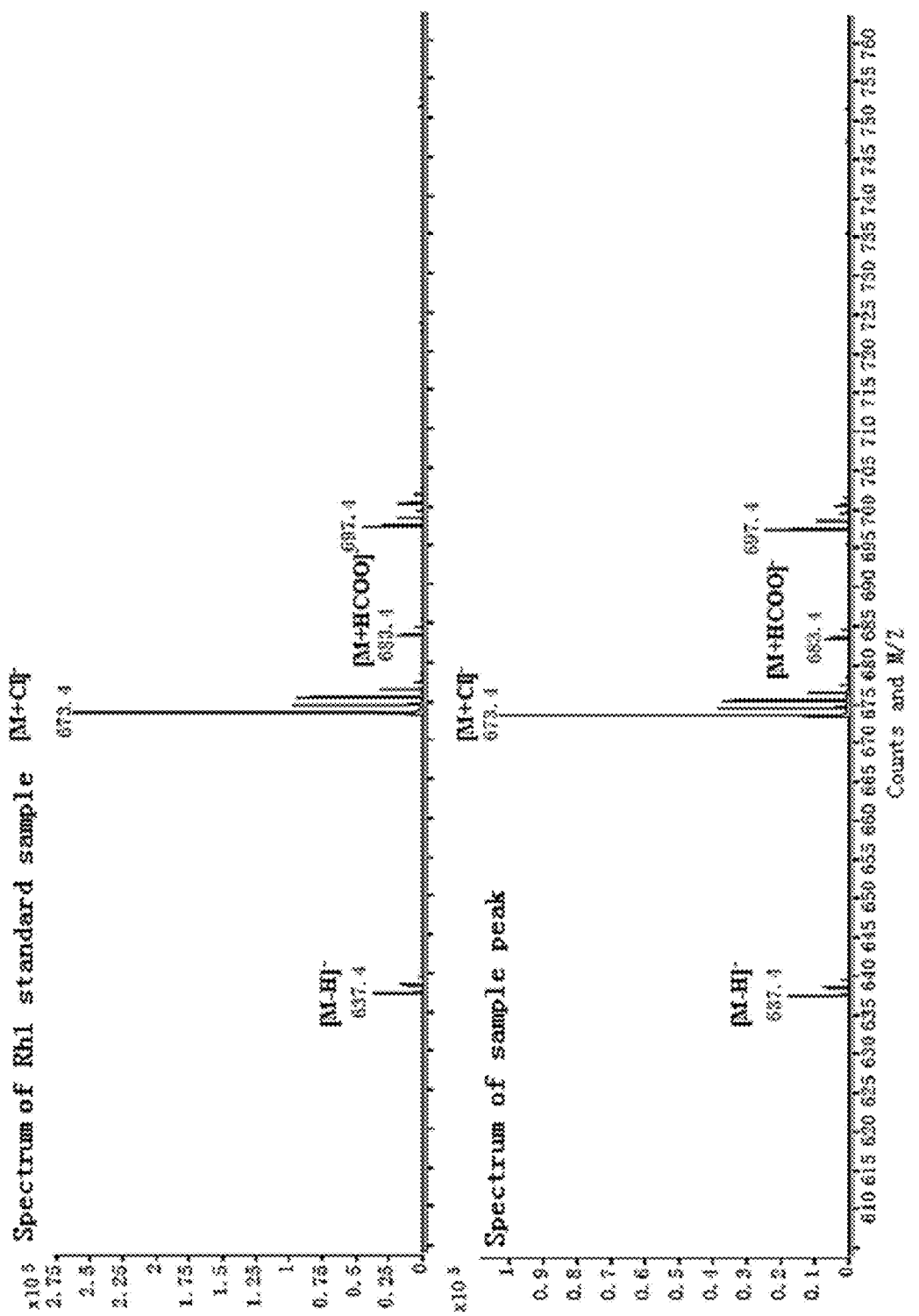
FIG. 18 shows the LC/MS detection of the products obtained by catalyzing PPT using the glycosyltransferase gGT25-5. The mass spectrums of peak P1 in FIG. 17 (product Rh1 peak) and the standard sample of Rh1 are shown.

Upon HPLC analyze, DM, PPD and the ginsenoside active metabolite (CK) were detected in the cell lysate of recombinant yeast A (FIG. 16). The yield of CK synthesized by yeast A reached to 0.6 mg/L. It could also be concluded from HPLC analyze that there were trace amounts of CK contained in the cell lysate of recombinant yeasts B and C.

TABLE 5

The corresponding amino acids or uracil additionally needed for recombinant yeast strains

| recombinant yeast strains | Additional amino acids or uracil |
|---|---|
| A | 0.01% of tryptophan, leucine, lysine |
| B | 0.01% of uracil, leucine, lysine |
| C | 0.01% of uracil, leucine, lysine |

EXAMPLE 8

Construction of Engineered Yeast Strain for Rh1 Production and the Product Identification Dammarenediol synthase (ACZ71036.1) (GAL1/GAL10 GAL10 side promoter, ADH1 terminator), cytochrome P450 CYP716A47 (AEY75213.1) (FBA1 promoter, CYC1 terminator), cytochrome P450 CYP716A53V2 gene (ENO2 promoter, CYC1 terminator) and glycosyltransferase gene GT25-5 (GAL1/GAL10 GAL1 side promoter, TDH2 terminator) were assembled in the plasmid pESC-HIS (Stratagene, Agilent), thereby constructing an episomal plasmid. The product was used to transform *S. cerevisiae* BY4742. Cytochrome P450 reductase ATR2-1 (NP_849472.2) from *A. thaliana* was also integrated to the site of gene trp1 (GAL1 promoter; and the original terminator of trp1 was used) in the chromosome of *S. cerevisiae* BY4742 so as to construct the recombinant yeast A3. Additional added amino acids or uracil needed for each recombinant strain was shown in Table 5.

The lysate of recombinant yeast was transferred into 2 mL EP tubes with 1 mL for each tube, subjected to extraction by adding n-butanol of equivalent volume (1 mL) for about 30 mins, and then centrifuged for 10 mins at 12000 g. The supernatant was transferred to a new EP tube. n-butanol was evaporated to dry in vacuum under 45° C. Upon being dissolved in methanol (100 μL), the product was subjected to HPLC detection.

Figure 41:
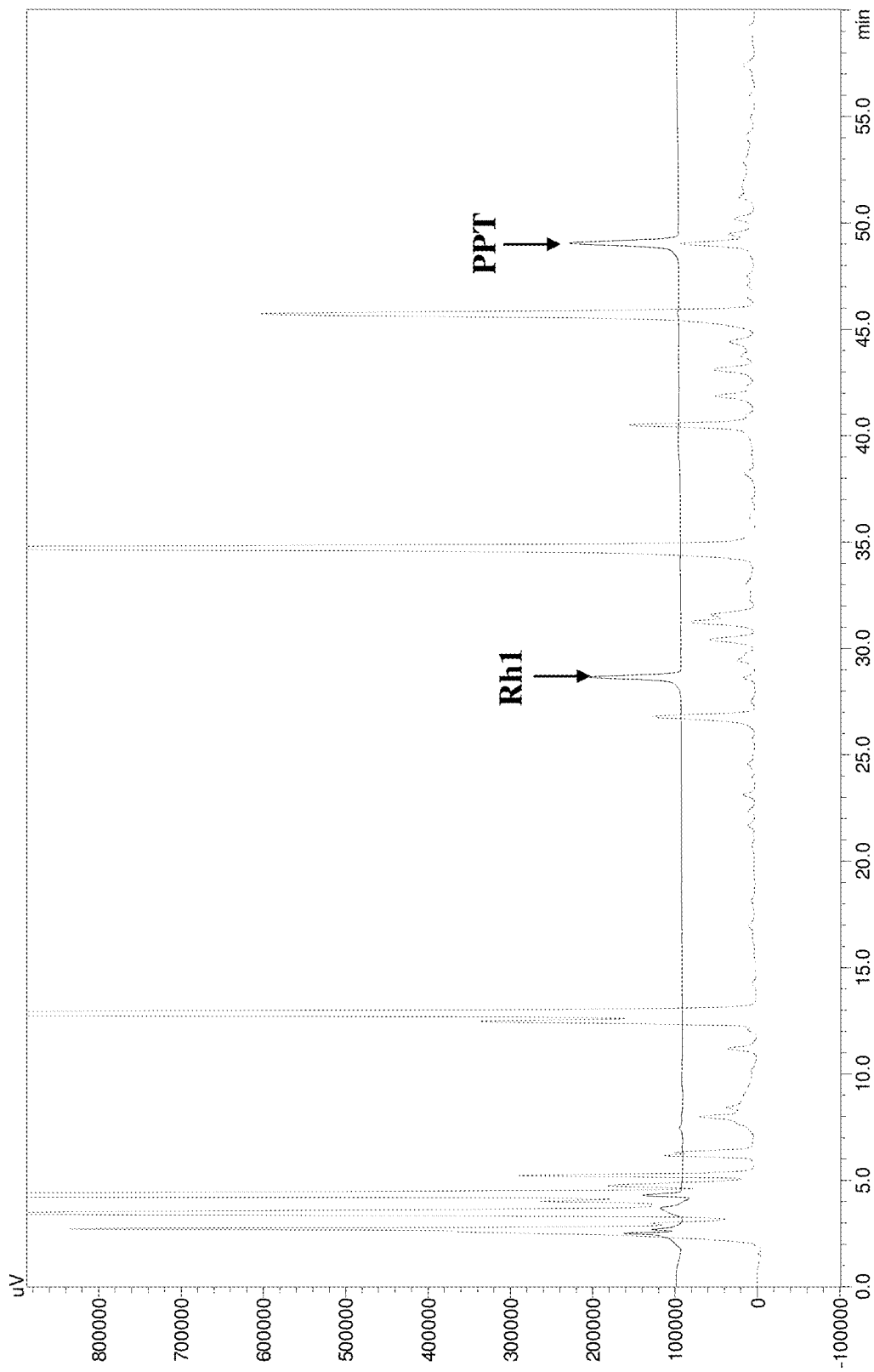
FIG. 41 shows HPLC detection of the cell lysate extracts of the engineered yeast strain A3 for Rh1 production, the sample of line 1: a mixed standard sample of PPT and ginsenoside Rh1; the sample of line 2: cell lysate extracts of the engineered yeast strain A3 which can produce Rh1.

Upon HPLC analysis, PPT and the active metabolite of ginsenoside (Rh1) were detected in the cell lysate of recombinant yeast A3 (FIG. 41).

EXAMPLE 9

The Construction of *E. coli* Recombinant Expression Vectors for Glycosyltransferase Genes 3GT1, 3GT2, 3GT3 and 3GT4

The target genes were amplified using the plasmids 3GT1-pMD18T and 3GT2-pMD18T containing genes 3GT1 and 3GT2 constructed in Example 1 as templates.

The collective forward primer of 3GT1 and 3GT2 is SEQ ID NO.: 31 with a BamHI recognition site added to its 5' end: GGATCC; the reverse primer of 3GT1 is SEQ ID NO.: 32 with a SalI recognition site added to its 5' end: CTCGAG; the reverse primer of 3GT2 is SEQ ID NO.: 33 with a Sal I recognition site added to its 5' end CTCGAG.

The above primers and templates were used for amplifying genes 3GT1 and 3GT2 by PCR. The high-fidelity DNA polymerase KOD (Toyobo Inc) were selected as DNA polymerase and the PCR program was set according to the instructions: 94° C. 2 min; 94° C. 15 s, 58° C. 30 s, 68° C. 1.5 min, for 30 cycles; 68° C. 10 min; the temperature was kept at 10° C. The PCR product was detected by agarose gel electrophoresis and the band with a size of the target DNA was cut out under the UV lamp. Then, the DNA fragments were recovered from the agarose gel using AxyPrep DNA Gel Extraction Kit (AXYGEN Inc.). The recovered DNA fragments were digested using two Quickcut restricted enzymes Kpn I and Xba I from Takara Inc. for 30 mins. The enzyme-digested products were washed and recovered by AxyPrep PCR Cleanup Kit from AXYGEN Inc. The digested products were ligated to the *E. coli* expression plasmid pET28a (also digested by BamHI and SalI and then cut and recovered) under 16° C. for 4 hrs by using a T4 DNA ligase (NEB Inc.). The ligated products were transformed into *E. coli* EPI300 competent cells and coated on LB plate supplemented with 50 μg/mL kanamycin, respectively. The positive clones were verified by colony PCR and the expression plasmids of 3GT1-pET28a and 3GT2-pET28a were further confirmed by sequencing.

The target genes were amplified using the plasmids 3GT3-pMD18T and 3GT4-pMD18T containing genes 3GT3 and 3GT4 constructed in Example 1 as templates.

The forward primer of 3GT3 is SEQ ID NO.: 48 with a sequence homologous with vector pET28a added to its 5' end: ACTTTAAGAAGGAGATATACC; the reverse primer of 3GT3 is SEQ ID NO.: 49 with a sequence homologous with vector pET28a added to its 5' end:CTCGAGTGCG-GCCGCAAGCTT.

The forward primer of 3GT4 is SEQ ID NO.: 50 with a sequence homologous with vector pET28a added to its 5' end: ACTTTAAGAAGGAGATATACC; the reverse primer of 3GT4 is SEQ ID NO.: with a sequence of 18 bases homologous with vector pET28a added to its 5' end:CTC-GAGTGCGGCCGCAAGCTT.

The above primers were used for amplifying genes 3GT3 and 3GT4 by PCR. The high-fidelity DNA polymerase Q5 (NEB Inc) was selected for gene amplification and the PCR program was set according to the instructions: 98° C. 30 sec; 98° C. 15 s, 58° C. 30 s, 72° C. 1 min for 35 cycles; 72° C. 2 min; the temperature was kept at 10° C.

Further, the vector pET28a was amplified by using SEQ ID NO.: 52 and SEQ ID NO.: 53 as the forward and reverse primer respectively so as to obtain the linearized vector pET28a. The high-fidelity DNA polymerase Q5 (NEB Inc) was also chosen for amplifying the linearized vector pET28a and the PCR program was set according to the instructions: 98° C. 30 sec; 98° C. 15 s, 58° C. 30 s, 72° C. 1 min for 35 cycles; 72° C. 2 min; the temperature was kept at 10° C. The PCR products of the above genes 3GT3 and 3GT4 and the linearized vector pET28a were detected by agarose gel electrophoresis and the bands with size of the target DNAs were cut out under a UV lamp. Then, the DNA fragments were recovered from the agarose gel using AxyPrep DNA Gel Extraction Kit (AXYGEN Inc.). The recovered fragment of the linearized vector pET28a, the recovered gene fragments of 3GT3 and 3GT4 and BGclonart seamless cloning reaction solution (Rockgene Biotech Inc.) were mixed up to 20 μl in suitable proportions according to the instructions of BGclonart seamless cloning kit from Rockgene Biotech Inc. Upon mixed to homogenous, the product was incubated under 50° C. for 30 mins and the mixed reacting solution was transferred onto ice. *E. coli* EPI300 competent cells were transformed by 5 μl of the reacting solution and then coated on a LB plate supplemented with 50 μg/mL of kanamycin. The positive clones were verified by colony PCR and the successful expression plasmids of 3GT3-pET28a and 3GT4-pET28a were further confirmed by sequencing.

EXAMPLE 10

The Expression of Glycosyltransferase 3GT1, 3GT2, 3GT3 and 3GT4 in E. coli

Figure 20:
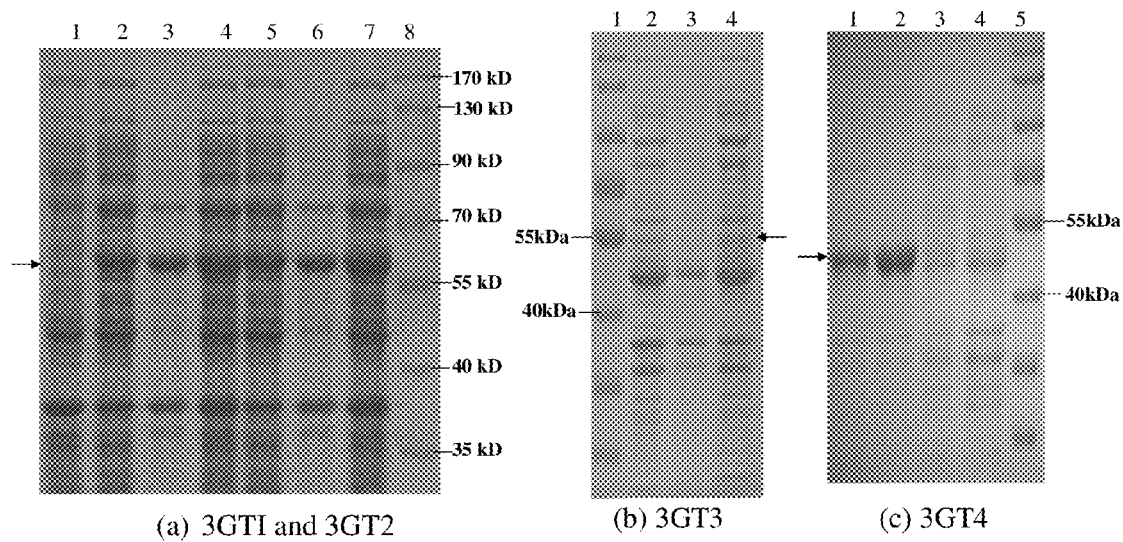
FIG. 20 shows SDS-PAGE detection of (a) 3GT1 and 3GT2, (b) 3GT3 and (c) 3GT4 expressions in *E. coli*; (a) lane 1, total protein in the lysate of the empty vector pET28a-transformed-*E. coli*; lane 2, lysate supernatant of recombinant *E. coli* 3GT1-pET28a; lane 3, lysate precipitation of the recombinant *E. coli* 3GT1-pET28a; lane 4, total protein in the lysate of the recombinant *E. coli* 3GT1-pET28a; lane 5, lysate supernatant of the recombinant *E. coli* 3GT2-pET28a; lane 6, lysate precipitation of the recombinant *E. coli* 3GT2-pET28a; lane 7, total protein of the recombinant *E. coli* 3GT2-pET28a; lane 8, protein molecular-weight Marker. (b) Lane 1, Protein molecular-weight Marker; lane 2, lysate supernatant of the recombinant *E. coli* 3GT3-pET28a; lane 3, lysate precipitation of the recombinant *E. coli* 3GT3-pET28a; lane 4, total protein of the recombinant *E. coli* 3GT3-pET28a lysate. (c) lane 1, lysate supernatant of the recombinant *E. coli* 3GT4-pET28a; lane 2, lysate precipitation of the recombinant *E. coli* 3GT4-pET28a; lane 3, lysate supernatant of the recombinant *E. coli* 3GT4-pET28a; lane 4, lysate of the empty vector pET28a-transformed *E. coli*; lane 5, protein molecular-weight Marker. The target protein is indicated with an arrow.
Figure 21:
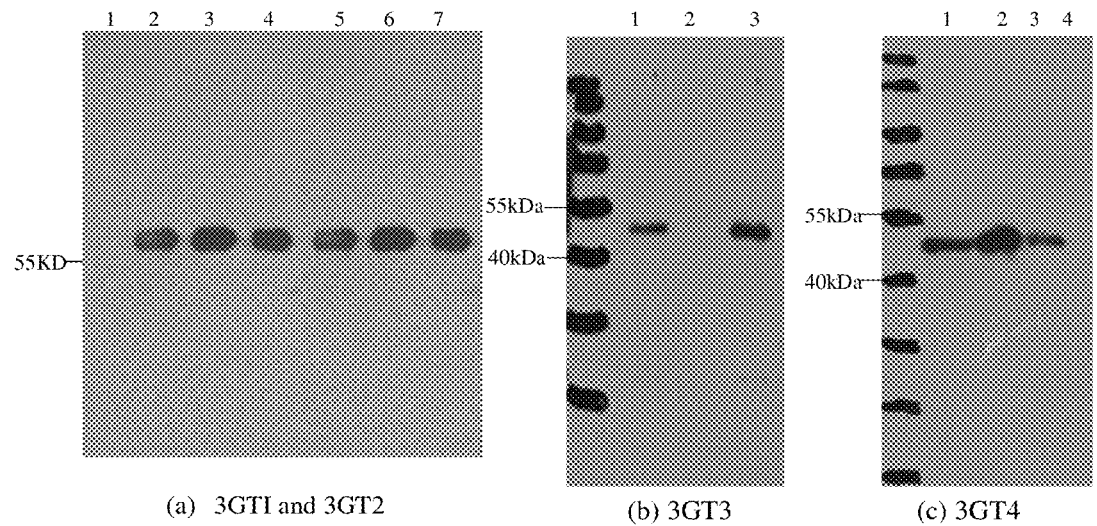
FIG. 21 shows Western Blot detection of (a) 3GT1 and 3GT2, (b) 3GT3 and (c) 3GT4 expression in *E. coli*; (a) lane 1, total protein in the lysate of the empty vector pET28a-transformed-*E. coli*; lane 2, lysate supernatant of recombinant *E. coli* 3GT1-pET28a; lane 3, lysate precipitation of the recombinant *E. coli* 3GT1-pET28a; lane 4, total protein in the lysate of the recombinant *E. coli* 3GT1-pET28a; lane 5, lysate supernatant of the recombinant *E. coli* 3GT2-pET28a; lane 6, lysate precipitation of the recombinant *E. coli* 3GT2-pET28a; lane 7, total protein of the recombinant *E. coli* 3GT2-pET28a; (b) lane 1, lysate supernatant of the recombinant *E. coli* 3GT3-pET28a; lane 2, lysate precipitation of the recombinant *E. coli* 3GT3-pET28a; lane 3, total protein in the lysate of the recombinant *E. coli* 3GT3-pET28a; (c) lane 1, total protein in the lysate of the recombinant *E. coli* 3GT4-pET28a; lane 2, lysate precipitation of the recombinant *E. coli* 3GT4-pET28a; lane 3, lysate supernatant of the recombinant *E. coli* 3GT4-pET28a; lane 4, lysate of the empty vector pET28a-transformed *E. coli*.
Figure 22:
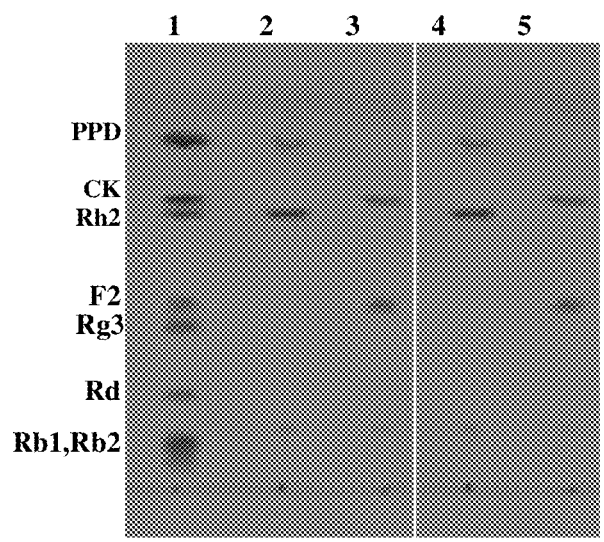
FIG. 22 shows the TLC detection of the products obtained by catalyzing PPD and CK using the glycosyltransferases 3GT1 and 3GT2. Lane 1, standard samples of PPD-type ginsenosides; lane 2, ginsenoside Rh2 produced by catalyzing PPD using the glycosyltransferase 3GT1; lane 3, ginsenoside F2 produced by catalyzing ginsenoside CK using glycosyltransferase 3GT1; lane 4, ginsenoside Rh2 produced by catalyzing PPD using glycosyltransferase 3GT2; lane 5, ginsenoside F2 produced by catalyzing ginsenoside CK using glycosyltransferase 3GT2.
Figure 23:
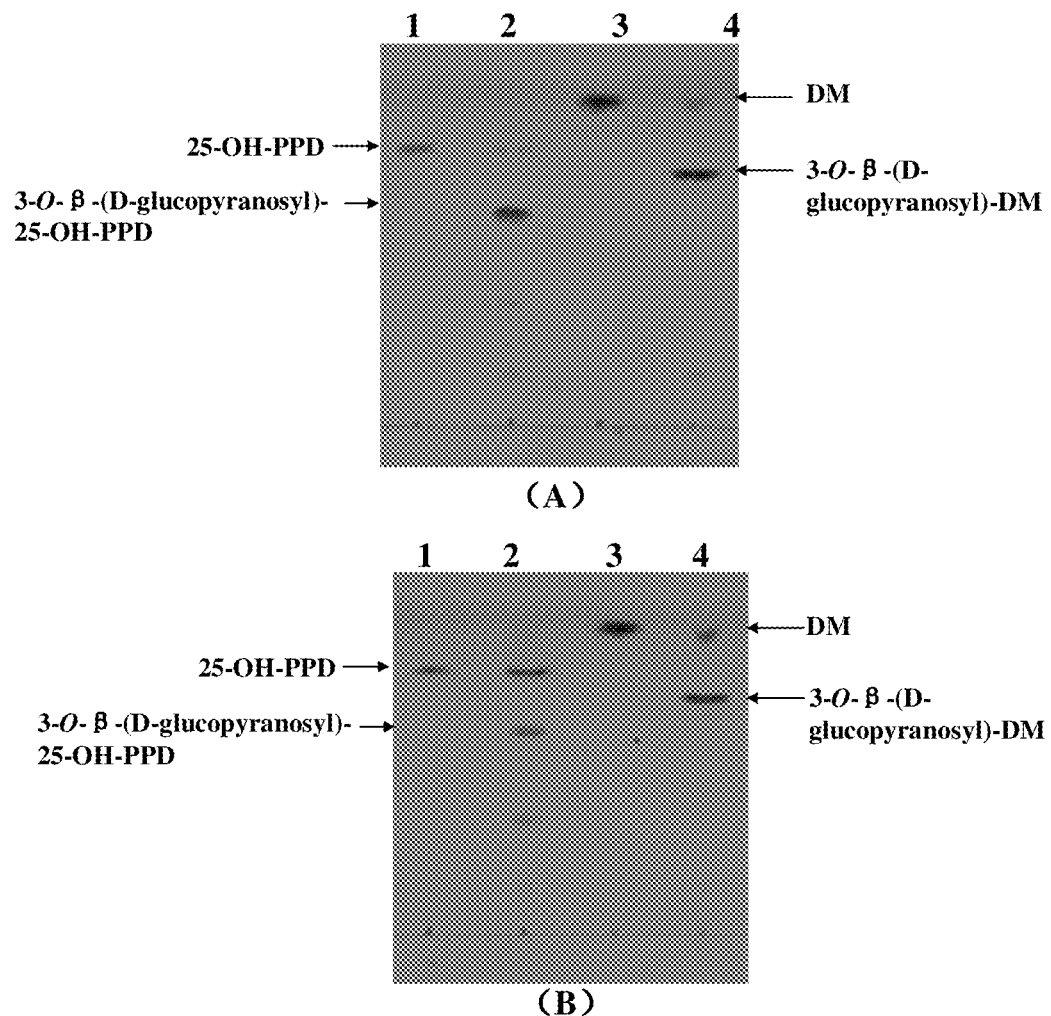
FIG. 23 shows the TLC detection of the products obtained by catalyzing DM and 25-OH-PPD using glycosyltransferases 3GT1 and 3GT2. (A) Catalyzation of DM and 25-OH-PPD by 3GT1 crude enzyme (lysate supernatant of the recombinant E. coli 3GT1-pET28a). Lane 1, 25-OH-PPD standard sample; lane 2, 3-O-β-(D-glucopyranosyl)-25-OH-protopanaxadiol generated by catalyzing 25-OH-PPD using 3GT1 crude enzyme; lane 3, DM standard sample; lane 4, 3-O-β-(D-glucopyranosyl)-dammarenediol II produced by catalyzing DM using 3GT1 crude enzyme; (B) Catalyzation of DM and 25-OH-PPD by 3GT2 crude enzyme (lysate supernatant of the recombinant E. coli 3GT2-pET28a). Lane 1, 25-OH-PPD standard sample; lane 2, 3-O-β-(D-glucopyranosyl)-25-OH-protopanaxadiol produced by catalyzing 25-OH-PPD using 3GT2; lane 3, DM standard sample; lane 4, 3-O-β-(D-glucopyranosyl)-dammarenediol II produced by catalyzing DM using 3GT2.
Figure 24:
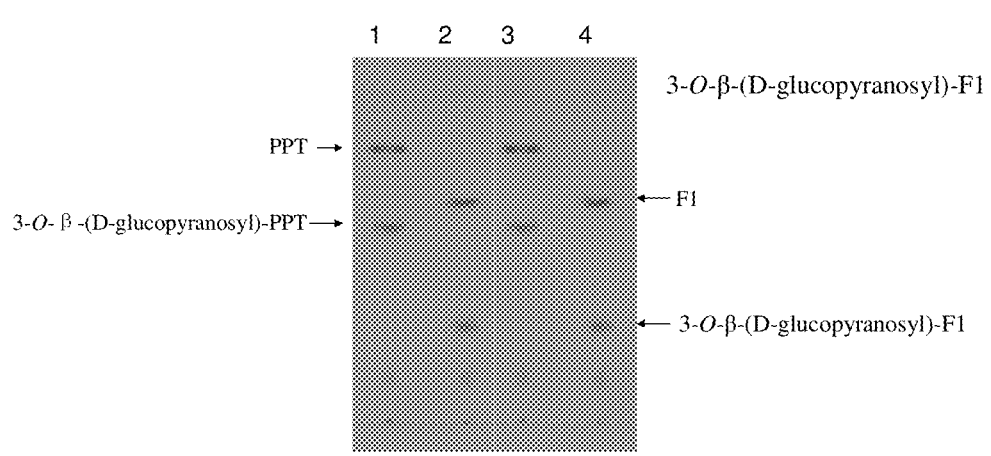
FIG. 24 shows TLC detection of the products obtained by catalyzing PPT and F1 using glycosyltransferases 3GT1 and 3GT2. Lane 1, 3-O-β-(D-glucopyranosyl)-protopanaxatriol obtained by catalyzing PPT using 3GT1 crude enzyme (lysate supernatant of the recombinant E. coli 3GT1-pET28a); lane 2, 3-O-β-(D-glucopyranosyl)-F1 obtained by catalyzing F1 using 3GT1 crude enzyme; lane 3, 3-O-β-(D-glucopyranosyl)-PPT obtained by catalyzing PPT using 3GT2 crude enzyme (lysate supernatant of the recombinant E. coli 3GT2-pET28a); lane 4, 3-O-β-(D-glucopyranosyl)-F1 obtained by catalyzing F1 using 3GT2 crude enzyme.

The E. coli expression vectors 3GT1-pET28a, 3GT2-pET28a, 3GT3-pET28a and 3GT4-pET28a constructed in Example 9 were transformed into the commercially available E. coli BL21. A recombinant was inoculated into LB medium and cultured under 30° C. at 200 rpm until $OD_{600}$ reached about 0.6-0.8. Then the culture liquid was cooled to 4° C., and IPTG with a final concentration of 50 µM was added for inducing expression under 18° C. at 200 rpm for 15 hrs. The pellets were collected under 4° C. and then subjected to ultrasonic disruption. The cell lysis supernatant was collected by centrifugation at 12000 g and then a sample was taken for SDS-PAGE electrophoresis (FIG. 20). Compared with empty vector pYES2 recombinant, obvious bands (about 55 kDa) representing 3GT1, 3GT2, 3GT3 and 3GT4 were shown for the 3GT1-pET28a, 3GT2-pET28a, 3GT3-pET28a and 3GT4-pET28a recombinants. The results of Western Blot (FIG. 21) also indicate that the soluble expression of target proteins 3GT1, 3GT2, 3GT3 and 3GT4 were realized in the hosts.

EXAMPLE 11

Glycosyltransfering Reaction of the E. coli Expression Products of 3GT1, 3GT2, 3GT3 and 3GT4 and Product Identification The glycosyltransfering reactions of ginsenosides and ginsengenins were catalyzed by using the lysis supernatant of the recombinant yeasts expressing 3GT1, 3GT2, 3GT3 and 3GT4 as crude enzymes. The lysis supernatant of recombinant E. coli expressing empty vectors was used as control. The 100 µL reaction system is shown as Table 3. The reaction was conducted under 35° C. for 12 hrs, then stopped by adding 100 µL of butanol. The product were extracted, dried in vacuum, and dissolved in methanol.

Figure 25:
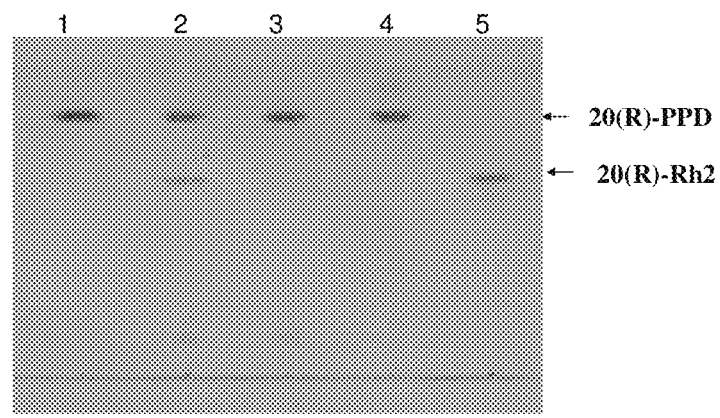
FIG. 25 shows TLC detection of the products obtained by catalyzing 20 (R)-PPD using glycosyltransferases 3GT1 and 3GT2. Lane 1, 20 (R)-PPD standard sample; lane 2, 20 (R)-Rh2 obtained by catalyzing 20 (R)-PPD using 3GT1 crude enzyme (lysate supernatant of the recombinant E. coli 3GT1-pET28a); lane 3, 20 (R)-Rh2 obtained by catalyzing 20 (R)-PPD using 3GT2 crude enzyme (lysate supernatant of the recombinant E. coli 3GT2-pET28a); lane 4, control, the crude enzyme was substituted by lysate supernatant of the empty vector pET28a-transformed E. coli; lane 5, 20 (R)-Rh2 standard sample.
Figure 26:
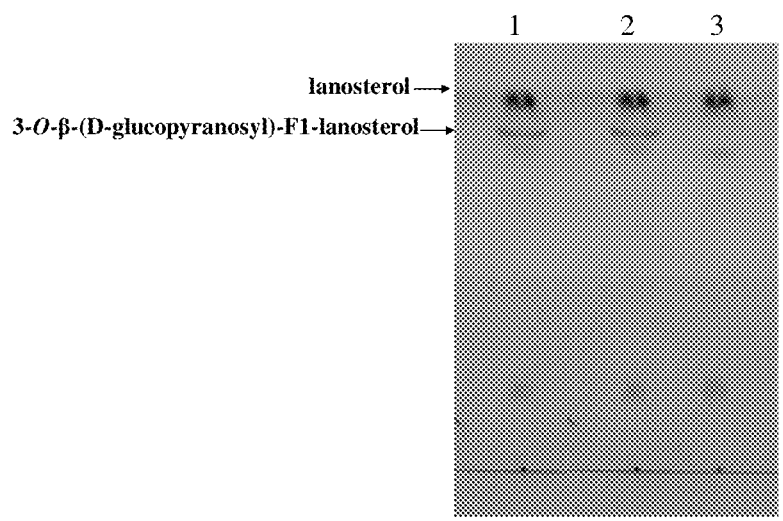
FIG. 26 shows the TLC detection of the products obtained by catalyzing lanosterol using glycosyltransferase 3GT1. Lane 1, lanosterol catalyzed by 3GT1 crude enzyme (lysate supernatant of the recombinant E. coli 3GT1-pET28a); lane 2, lanosterol catalyzed by 3GT2 crude enzyme (lysate supernatant of the recombinant E. coli 3GT2-pET28a); lane 3, control, the crude enzyme was substituted by lysate supernatant of the empty vector pET28a-transformed E. coli.
Figure 27:
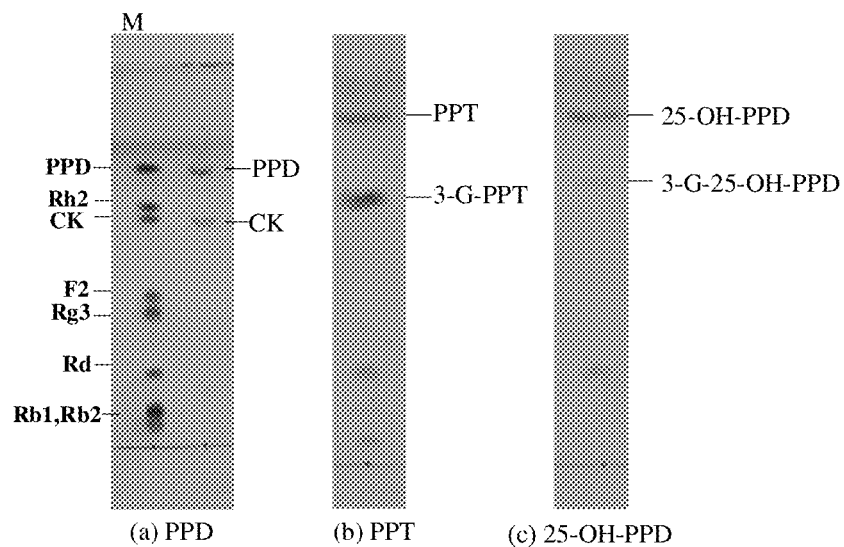
FIG. 27 shows TLC detection of the products obtained by catalyzing PPD, PPT and 25-OH-PPD using glycosyltransferase 3GT3. (a) ginsenoside Rh2 produced by catalyzing PPD using 3GT3 crude enzyme (lysate supernatant of the recombinant E. coli 3GT3-pET28a); (b) 3-O-β-(D-glucopyranosyl)-PPT (3-G-PPT) produced by catalyzing PPT using 3GT3 crude enzyme; (c) 3-O-β-(D-glucopyranosyl)-25-OH-PPD (3-G-25-OH-PPD) produced by catalyzing 25-OH-PPD using 3GT3 crude enzyme.
Figure 28:
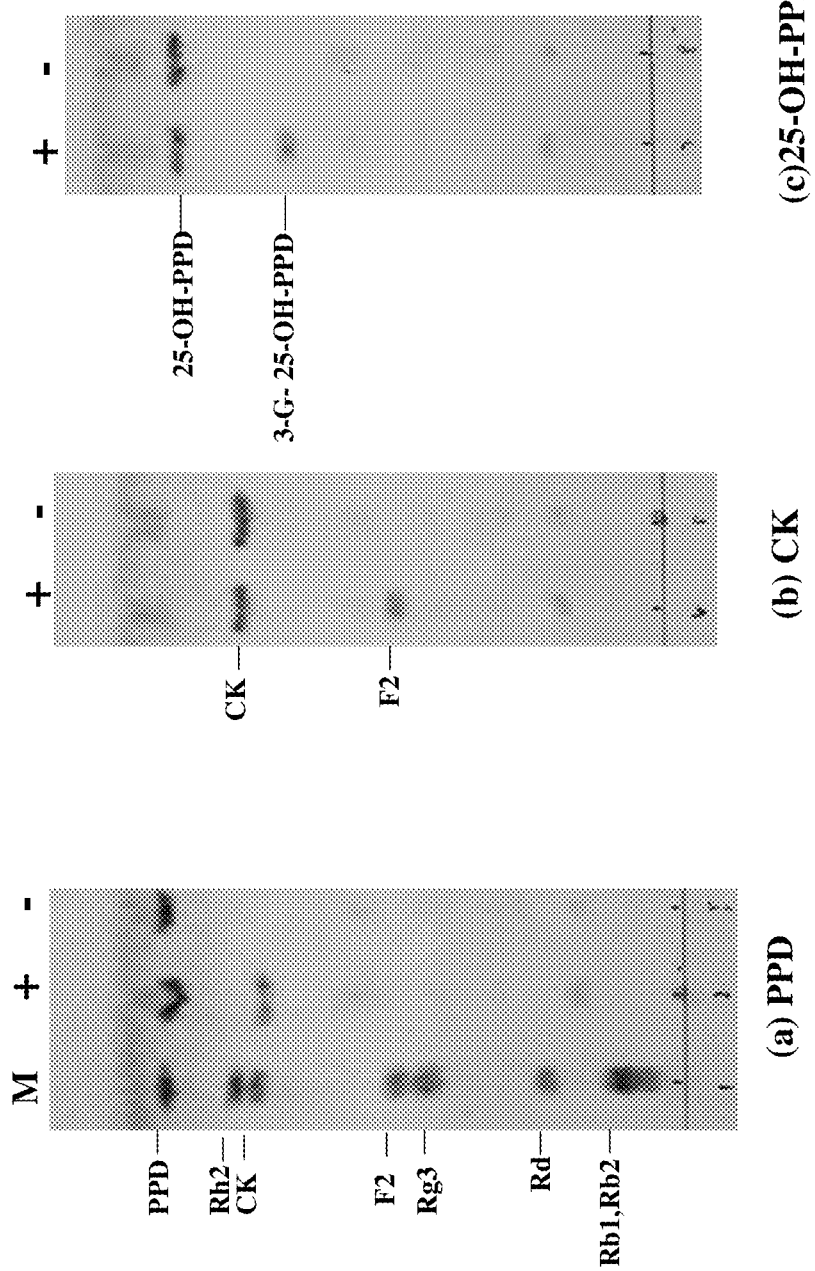
FIG. 28 shows TLC detection of the products obtained by catalyzing PPD, CK and 25-OH-PPD using glycosyltransferase 3GT4. (a) ginsenoside Rh2 produced by catalyzing PPD using 3GT4 crude enzyme (lysate supernatant of the recombinant E. coli 3GT4-pET28a); M represents the mixed standard sample of PPD-type ginsenosides; "+" represents samples with 3GT4 crude enzyme added, "−" represents control, that is, the crude enzyme being substituted by lysate supernatant of pET28a-transformed E. coli; (b) F2 produced by catalyzing ginsenoside CK using 3GT4 crude enzyme; "+" represents samples with 3GT4 crude enzyme added, "−" represents control, that is, the crude enzyme being substituted by lysate supernatant of pET28a-transformed E. coli; (c) 3-O-β-(D-glucopyranosyl)-25-OH-PPD (3-G-25-OH-PPD) produced by catalyzing 25-OH-PPD using glycosyltransferase 3GT4, "+" represents samples with 3GT4 crude enzyme added, "−" represents control, that is, the crude enzyme being substituted by lysate supernatant of the pET28a-transformed E. coli.

The reaction products were first detected by thin layer chromatography (TLC) (FIG. 22-28). The C3-OH of PPD was glycosylated by the crude enzymes expressing 3GT1, 3GT2, 3GT3 and 3GT4 to respectively produce rare ginsenoside Rh2 (FIGS. 22, 27(a) and 28(a)). PPD-type saponin CK with a glycosylated C20-OH was catalyzed by 3GT1, 3GT2, 3GT3 and 3GT4 for further glycosylating its C3-OH to respectively produce F2 (FIGS. 22 and 28(b)). C3-OH of DM could be glycosylated to produce a novel compound 3-O-β-(D-glucopyranosyl)-Dammarenediol II (FIG. 23) by using 3GT1 and 3GT2 for catalyzation. C3-OH of 25-OH-PPD could be glycosylated to produce a novel compound 3-O-β-(D-glucopyranosyl)-25-OH-PPD (FIG. 23, FIG. 27(c) and FIG. 28(c)) by using 3GT1, 3GT2, 3GT3 and 3GT4 for catalyzation. C3-OH of PPT could be glycosylated to produce an unreported novel compound 3-O-β-(D-glucopyranosyl)-PPT (FIG. 24 and FIG. 27(b)) by using 3GT1, 3GT2, and 3GT3 for catalyzation. C3-OH of F1 could be glycosylated to produce an unreported novel compound 3-O-β-(D-glucopyranosyl)-F1 (FIG. 24) by using 3GT1 and 3GT2 for catalyzation. C3-OH of lanosterol could be glycosylated to produce a novel compound 3-O-β-(D-glucopyranosyl)-lanosterol (FIG. 26) by using 3GT1 and 3GT2 for catalyzation. Moreover, the catalytic activities of 3GT1 and 3GT2 were not affected by the steric configuration of the hydoxyls or glycosyls at C20. For example, these enzymes could catalyze both 20(S)-PPD and 20(R)-PPD to produce rare ginsenoside 20(R)-ginsenoside Rh2 (FIG. 25). Although, all of the four glycosyltransferase 3GT1, 3GT2, 3GT3 and 3GT4 could introduce glycosyl into C3 of tetracyclic triterpenoid sapogenins, the substrate spectrums that they could catalyze were remarkably distinct. As shown in Table 6, 3GT1 and 3GT2 could catalyze the most number of substrates; 3GT3 could catalyze the least number of substrates; while 3GT4 showed the best specificity: it could only catalyze PPD and PPD-type saponin (CK).

Figure 29:
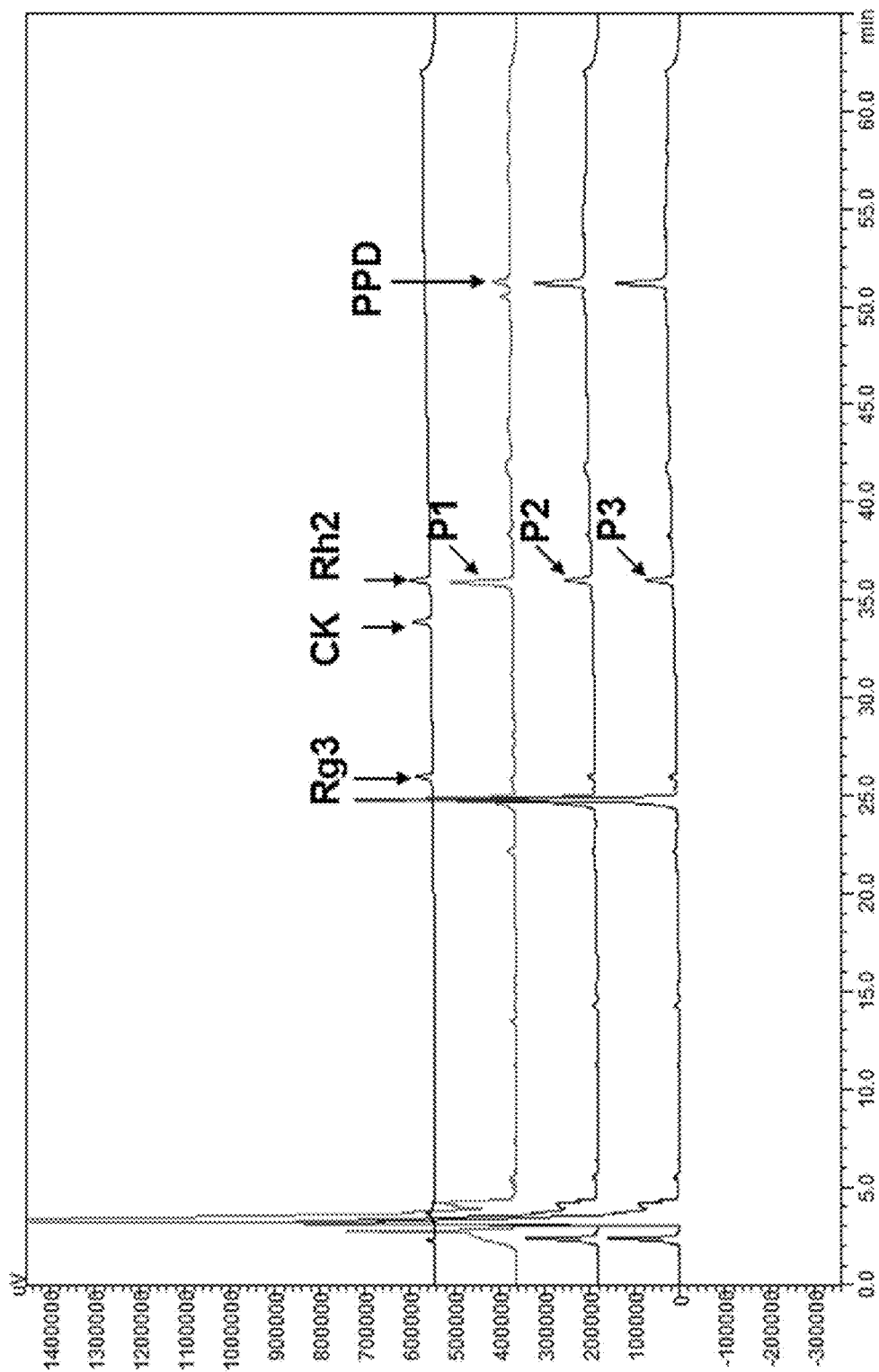
FIG. 29 shows HPLC detection of Rh2 obtained by catalyzing PPD using glycosyltransferases 3GT1, 3GT3 and 3GT4, the sample of line 1: mixed standard sample of CK, Rh2 and F2; the sample of line 2: the product obtained by catalyzing PPD using the glycosyltransferase 3GT1 crude enzyme (lysate supernatant of the recombinant E. coli 3GT1-pET28a); the sample of line 3: the product obtained by catalyzing PPD using 3GT3 crude enzyme (lysate supernatant of the recombinant E. coli 3GT3-pET28a); the sample of line 4: the product obtained by catalyzing PPD using 3GT4 crude enzyme (lysate supernatant of the recombinant E. coli 3GT4-pET28a).
Figure 30:
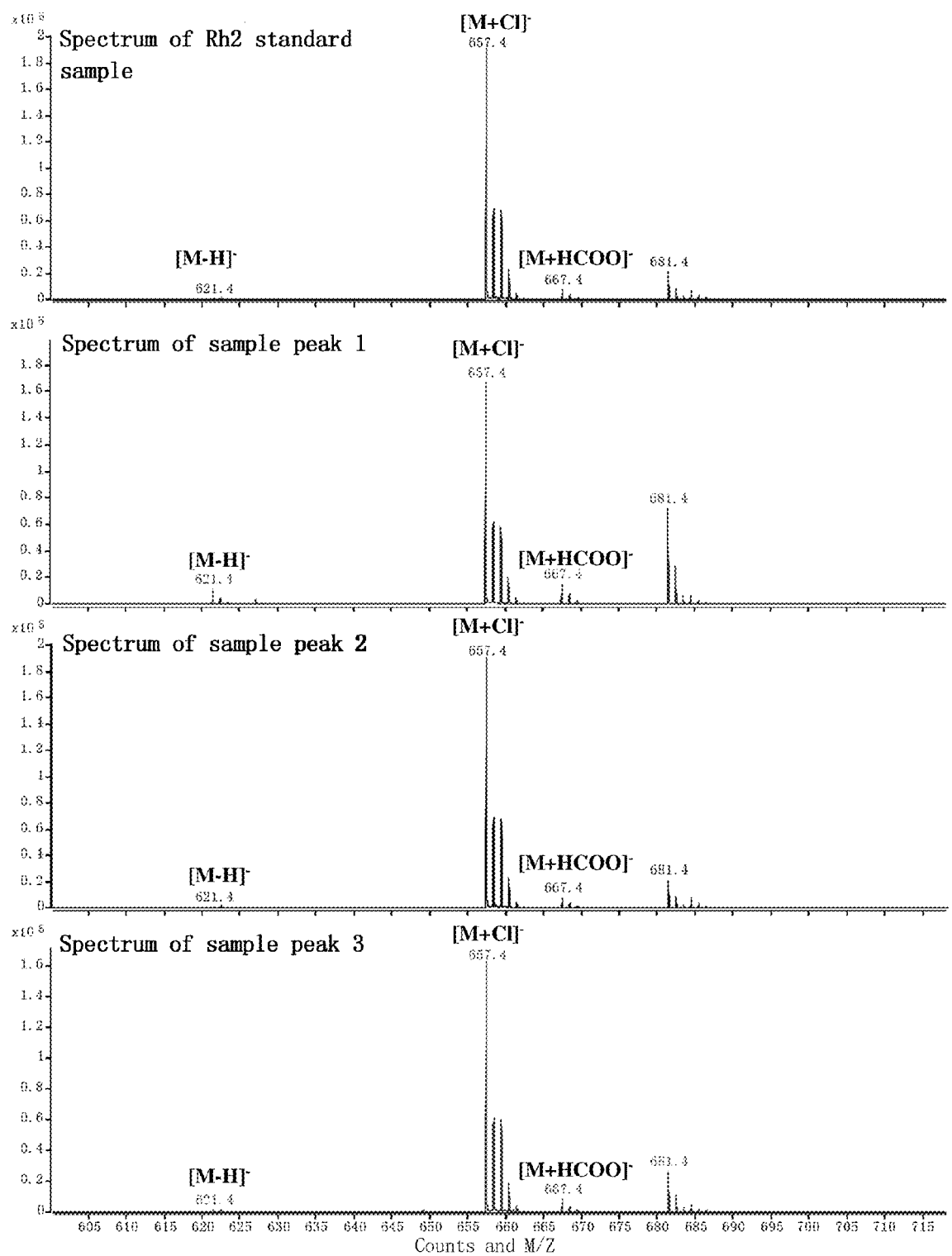
FIG. 30 shows LC/MS detection of the products obtained by catalyzing PPD using the glycosyltransferases 3GT1, 3GT3 and 3GT4. The mass spectrum of the standard sample of Rh2, P1 peak of FIG. 29 (product peak of 3GT1), P2 peak of FIG. 29 (product peak of 3GT2) and P3 peak of FIG. 29 (product peak of 3GT4) are shown.
Figure 31:
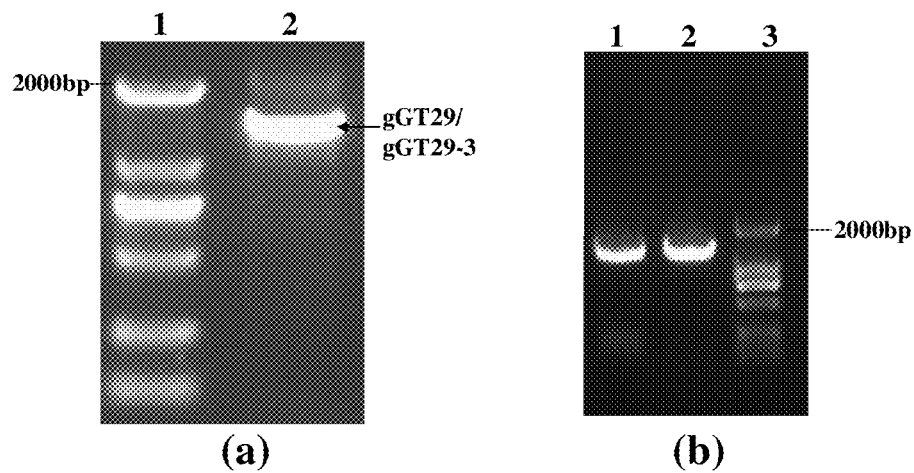
FIG. 31 shows agarose gel electrophoresis analysis of the PCR products of (a) gene gGT29/gGT29-3 and (b) gene gGT29-4/gGT29-5/gGT29-6 and gGT29-7. (b) Lane 1, nucleic acid Marker; lane 2, PCR product of gene gGT29/gGT29-3; (b) lane 1, PCR product of gene gGT29-4/gGT29-5/gGT29-6; lane 2, PCR product of gene gGT29-7; lane 3, nucleic acid Marker.

The products obtained by catalyzing PPD using 3GT1, 3GT2, 3GT3 and 3GT4 were further detected by HPLC (FIG. 29). Peaks with the same retention time (P1, P2, and P3) could be observed in products obtained by catalyzing PPD using glycosyltransferases 3GT1, 3GT2, 3GT3 and 3GT4. The retention time of these peaks is identical to that of the spectrum of ginsenoside Rh2 in standard sample, indicating that the product obtained by catalyzing PPD using glycosyltransferases 3GT1, 3GT2, 3GT3 and 3GT4 was Rh2. Finally, the three samples in FIG. 29, P1, P2, and P3, were subjected to mass spectrometry characterization by LC/MS (FIG. 30). Their spectrums were completely identical to that of ginsenoside Rh2 standard sample, further indicating that the product obtained by catalyzing PPD using glycosyltransferases 3GT1, 3GT2, 3GT3 and 3GT4 was Rh2.

The substrates that could be catalyzed by glycosyltransferases 3GT1, 3GT2, 3GT3 and 3GT4 are compared in Table 6:

TABLE 6

|  | PPD | 20(R)-PPD | CK | PPT | F1 | DM | 25-OH-PPD | lanosterol |
| --- | --- | --- | --- | --- | --- | --- | --- | --- |
| 3GT1/3GT2 | ✓ | ✓ | ✓ | ✓ | ✓ | ✓ | ✓ | ✓ |
| 3GT3 | ✓ | x | x | ✓ | x | x | ✓ | x |
| 3GT4 | ✓ | x | ✓ | x | x | x | ✓ | x |

EXAMPLE 12

Construction of the Engineered Yeast Strain for Rh2 Production and Product Identification 12.1 Dammarenediol synthase (ACZ71036.1) (GAL1/GAL10 GAL10 side promoter, ADH1 terminator), cytochrome P450 CYP716A47 (AEY75213.1) (FBA1 promoter, CYC1 terminator), and glycosyltransferase 3GT4 (GAL1/GAL10 GAL1 side promoter, TDH2 terminator) were assembled in the plasmid pESC-HIS (Stratagene, Agilent), thereby constructing an episomal plasmid. The plasmid was used to transform S. cerevisiae BY4742. Cytochrome P450 reductase ATR2-1 (NP_849472.2) from Arabidopsis thaliana was also integrated to the site of gene trp1 (GAL1 promoter, and the original terminator of trp1 was used) in the chromosome of S. cerevisiae BY4742 so as to construct the recombinant yeast A1. Additional added amino acids or uracil needed for each recombinant strain is shown in Table 5.

The lysate of recombinant yeast A1 was transferred into 2 mL EP tubes with 1 mL for each tube, subjected to extraction by adding n-butanol of equivalent volume (1 mL) for about 30 mins, and then centrifuged for 10 mins at 12000 g. The supernatant was transferred to a new EP tube. n-butanol was evaporated to dry in vacuum under 45° C.

Upon dissolved in methanol (100 μL), the product was subjected to HPLC detection.

Figure 39:
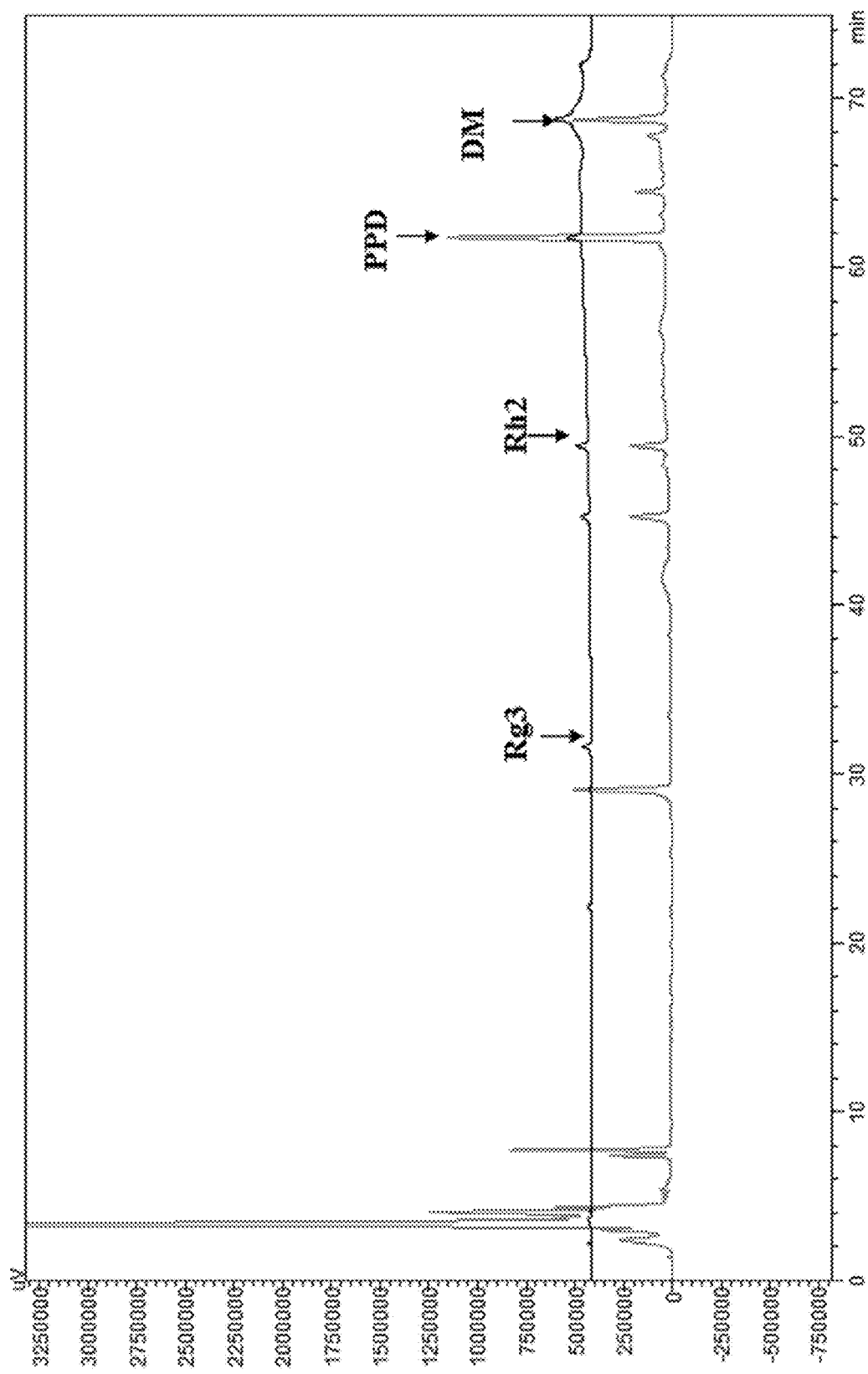
FIG. 39 shows HPLC detection of the cell lysate extracts of the engineered yeast strain A1 for Rh2 production, the sample of line 1: a mixed standard sample of PPD, DM, Rh2 and Rg3; the sample of line 2: cell lysate extracts of the engineered yeast strain A1 which can produce Rh2.

DM, PPD and the active metabolite of ginsenoside (Rh2) were detected in the cell lysate of recombinant yeast A1 according to HPLC analyze (FIG. 39).

12.2 The same method as 12.1 was used except that glycosyltransferase 3GT4 was substituted by 3GT1, thereby obtaining recombinant yeast A5.

Figure 43:
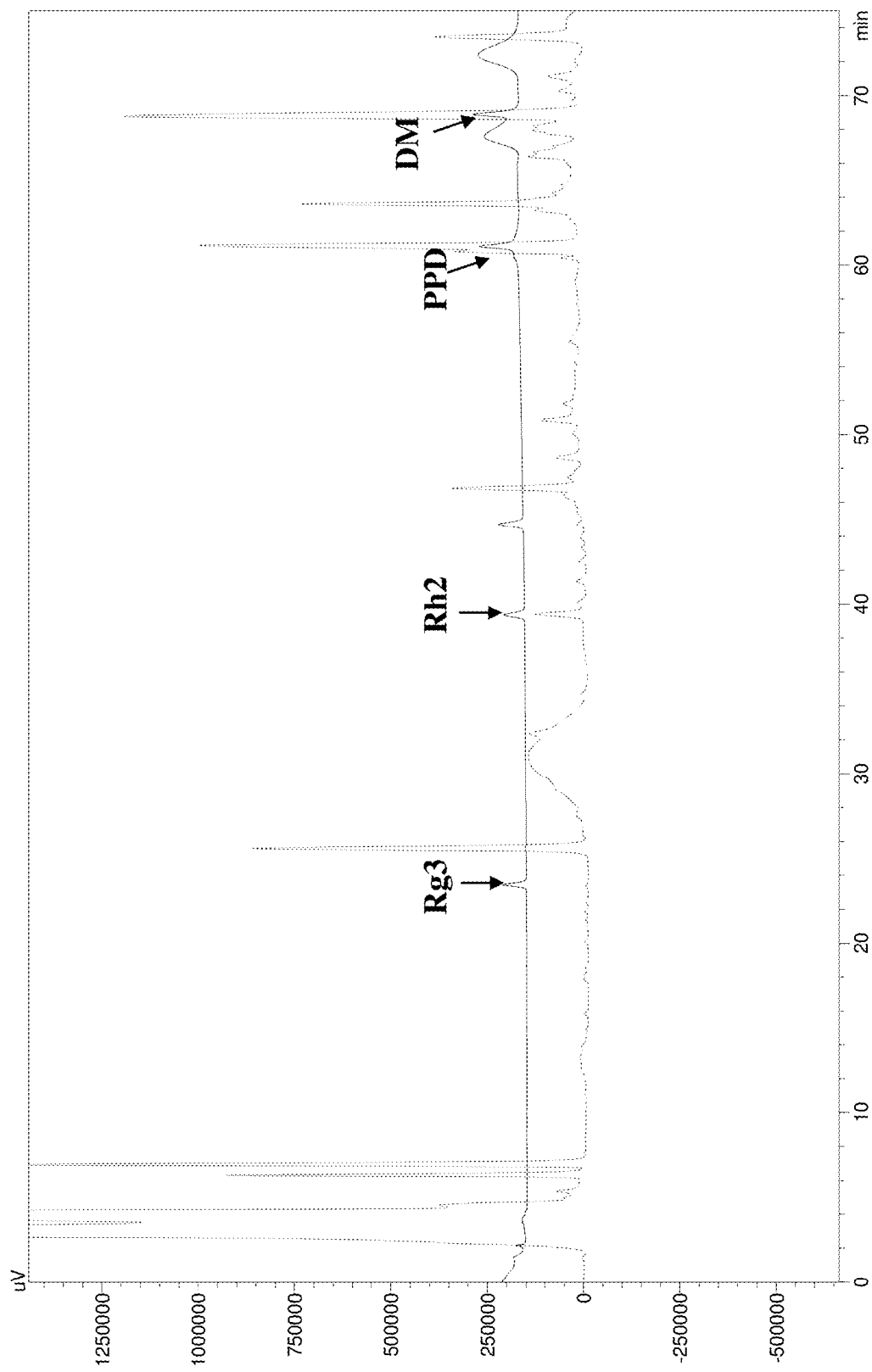
FIG. 43 shows HPLC detection of the cell lysate extracts of the engineered yeast strain A5 for Rh2 production, the sample of line 1: a mixed standard sample of DM, PPD, ginsenoside Rh2, and ginsenoside Rg3; the sample of line 2: cell lysate extracts of the engineered yeast strain A5 which can produce Rh2.

Results were shown in FIG. 43, DM, PPD and the active metabolite of ginsenoside (Rh2) were contained in the cell lysate of recombinant yeast A5 according to the HPLC analyze.

EXAMPLE 13

Construction of the Recombinant Yeast Expression Vectors for Glycosyltransferase Genes gGT29 and gGT29-3

The target genes were amplified using the plasmids gGT29-pMD18T, gGT29-3-pMD18T containing genes gGT29 and gGT29-3 constructed in Example 1 as templates.

The forward primer of gGT29 was SEQ ID NO.: 36 with a Kpn I recognition site added to its 5' end: GGATCC; the reverse primer was SEQ ID NO.: 37 with an XhoI recognition site added to its 5' end: CTCGAG; a 6×His Tag was introduced into the reverse primer for expression detection by Western Blot and purification.

The forward primer of gGT29-3 was SEQ ID NO.: 38 with a Kpn I recognition site added to its 5' end: GGATCC; the reverse primer was SEQ ID NO.: 39 with an XhoI recognition site added to its 5' end: CTCGAG; a 6×His Tag was introduced into the reverse primer for expression detection by Western Blot and purification.

By using plasmids gGT29-pMD18T and gGT29-3-pMD18T as templates and the primers above, genes gGT29 and gGT29-3 were amplified through PCR method. The high-fidelity DNA polymerase KOD (Toyobo Inc) were selected as DNA polymerase and the PCR program was set according to the instructions: 94° C. 2 min; 94° C. 15 s, 58° C. 30 s, 68° C. 1.5 min, for 30 cycles; 68° C. 10 min; the temperature was kept at 10° C. The PCR product was detected by agarose gel electrophoresis and the band with a size of the target DNA was cut out under a UV lamp. Then, the DNA fragments were recovered from the agarose gel using AxyPrep DNA Gel Extraction Kit (AXYGEN Inc.). The recovered DNA fragments were digested using two Quickcut restricted enzymes Kpn I and Xba I from Takara Inc. for 30 mins. The enzyme-digested products were washed and recovered by AxyPrep PCR Cleanup Kit from AXYGEN Inc. The digested products was ligated to the S. cerevisiae expression plasmid pYES2 (also digested by Kpn I and Xba I and then cut and recovered) under 25° C. for 2 hrs by using a T4 DNA ligase (NEB Inc.). The ligated products were transformed into E. coli TOP 10 competent cells and coated on LB plate supplemented with 100 μg/mL ampicillin. The positive clones were verified by colony PCR and the expression plasmids of gGT29-pYES2 and gGT29-3-pYES2 were further confirmed by sequencing.

EXAMPLE 14

The Expression of Glycosyltransferase Genes gGT29 and gGT29-3 in *S. cerevisiae*

Figure 32:
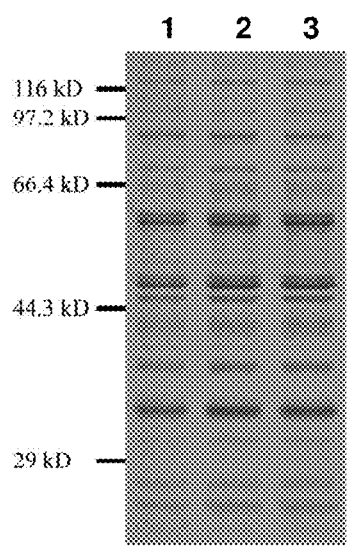
FIG. 32 shows SDS-PAGE detection of gGT29 and gGT29-3 expression in S. cerevisiae; lane 1, lysate supernatant of the pYES2-transformed yeast; lane 2, lysate supernatant of the recombinant yeast gGT29-pYES2; lane 3, lysate supernatant of the recombinant yeast gGT29-3-pYES2.
Figure 33:
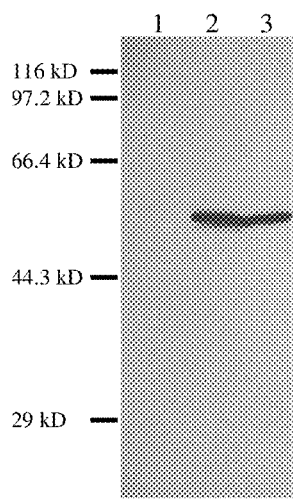
FIG. 33 shows Western Blot detection of gGT29 and gGT29-3 expression in S. cerevisiae; lane 1, lysate supernatant of the pYES2-transformed yeast; lane 2, lysate supernatant of the recombinant yeast gGT29-pYES2; lane 3, lysate supernatant of the recombinant yeast gGT29-3-pYES2.

The constructed expression plasmids gGT29-pYES2 and gGT29-3-pYES2 were transformed into *S. cerevisiae* by electrotransformation. The transformants were plated on a screening plate SC-Ura (0.67% yeast nitrogen base without amino acids, and 2% galactose). The recombinant yeast was verified by colony PCR. The recombinant yeast colony was inoculated into 10 mL of SC-Ura (2% glucose) medium and then cultured at 200 rpm under 30° C. for 20 h. The pellets were collected by centrifugation (3500 g) at 4° C. The pellets were washed with sterile deionized water for twice and resuspended in the induction medium SC-Ura (2% galactose) and inoculated to the 50 mL induction medium with an $OD_{600}$ of about 0.4 so as to induce the expression at 200 rpm under 30° C. for 12 hours. The pellets were collected by centrifugation (3500 g) at 4° C., washed with sterile deionized water for twice and then resuspended in the yeast lysis buffer to keep $OD_{600}$ between 50 and 100. The yeast cells were shook and disrupted by a cell disruption system (Fastprep). The cell debris was removed by centrifugation (12000 g) at 4° C. for 10 mins and the supernatant of the cell lysis was collected. An appropriate amount of the lysate supernatant was subjected to SDS-PAGE electrophoresis detection. Compared with the empty vector pYES2 recombinant, no obvious characteristic band was shown for gGT29-pYES2 or gGT29-3-pYES2 recombinant (FIG. 32). *S. cerevisiae* expressing gGT29 and gGT29-3 showed very strong Western Blot signals according to anti-6×His Tag Western Blot detection, indicating the soluble expression of gGT29 and gGT29-3 in the yeasts. In contrast, no anti-6×His Tag Western Blot signal was shown for the recombinants transformed with the empty vector pYES2 (FIG. 33).

EXAMPLE 15

Glycosyltransfering Reaction of the Yeast Expression Products of gGT29 and gGT29-3 and the Product Identification The glycosyltransfering reactions of ginsenoside Rh2 and F2 were catalyzed by using the lysate supernatant of the recombinant yeasts expressing gGT29 and gGT29-3 as crude enzyme. The lysate supernatant of the recombinant yeast expressing empty vectors was used as control. The 100 μL of reaction system is shown in Table 3. The reaction was conducted under 35° C. for 12 hrs, and then stopped by adding 100 μL of butanol. The product were extracted, dried in vacuum, and dissolved in methanol.

Figure 34:
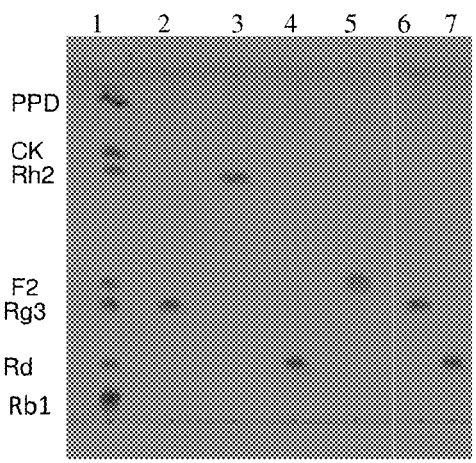
FIG. 34 shows TLC detection of the products obtained by catalyzing ginsenoside Rh2 and F2 using glycosyltransferases gGT29 and gGT29-3. Lane 1, mixed standard sample of PPD and PPD-type ginsenosides; lane 2, Rg3 produced by catalyzing Rh2 using gGT29 crude enzyme (lysate supernatant of the recombinant yeast gGT29-pYES2); lane 3, control for catalyzing Rh2 by gGT29 crude enzyme, wherein the crude enzyme was substituted by lysate of the empty vector pYES2-transformed yeast; lane 4, Rd produced by catalyzing F2 using gGT29; lane 5, control for catalyzing F2 by gGT29, wherein the crude enzyme was substituted by lysate of the empty vector pYES2-transformed yeast; lane 6, Rg3 produced by catalyzing Rh2 using gGT29-3 crude enzyme (lysate supernatant of the recombinant yeast gGT29-pYES2); lane 7, Rd produced by catalyzing F2 using gGT29-3 crude enzyme.

The reaction products were first detected by thin layer chromatography (TLC). C3 of ginsenosides Rh2 and F2 could be extended by one more glycosyl by using the lysate supernatant of yeast hosts expressing gGT29 and gGT29-3 as crude enzymes so as to produce ginsenosides Rg3 and Rd (FIG. 34). The catalytic activities of gGT29 and gGT29-3 were not affected by the steric configuration of hydroxyls or glycosyls at C20. These enzymes could convert 20(R)-Rh2 to 20(R)-Rg3 (FIG. 36).

EXAMPLE 16

Figure 35:
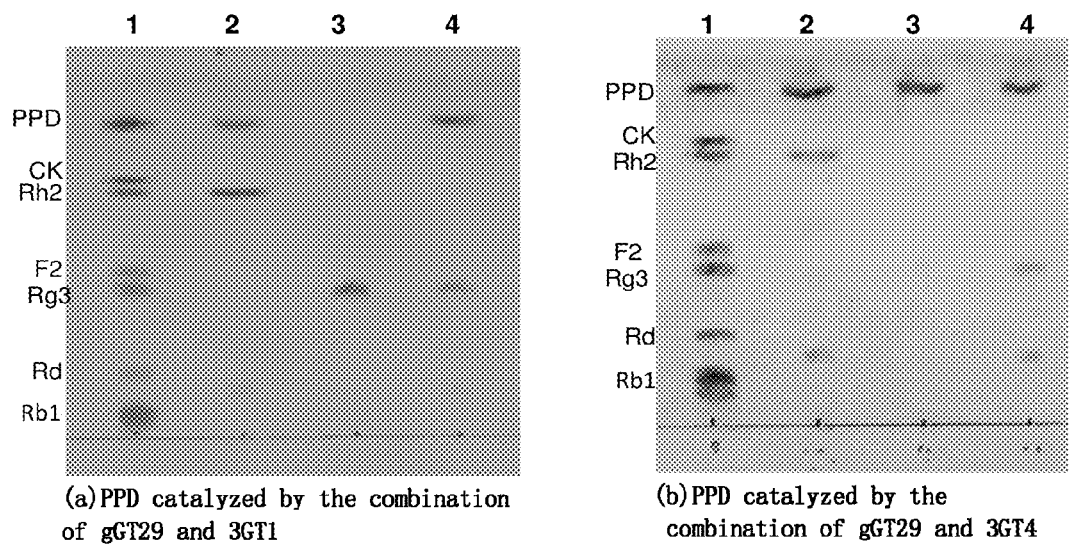
FIG. 35 shows TLC detection of the products obtained by catalyzing PPD using the combination of glycosyltransferases gGT29 and 3GT1, or the combination of glycosyltransferases gGT29 and 3GT4. (a) catalyzing PPD by using the combination of gGT29 and 3GT1; lane 1, mixed standard sample of PPD and PPD-type ginsenosides; lane 2, Rh2 produced by catalyzing PPD using 3GT1; lane 3, Rg3 produced by catalyzing Rh2 using gGT29; lane 4, Rg3 produced by catalyzing PPD using the combination of 3GT1 and gGT29; (b) PPD is catalyzed by the combination of gGT29 and 3GT4; lane 1, mixed standard sample of PPD and PPD-type ginsenosides; lane 2, Rh2 produced by catalyzing PPD using 3GT1; lane 3, PPD; lane 4, Rg3 produced by catalyzing PPD using the combination of 3GT4 and gGT29.

Glycosyltransfering Reaction by Combined Use of Glycosyltransferases 3GT1/3GT4 and gGT29 and the Product Identification PPD was catalyzed by using the combination of the lysate supernatant of *E. coli* host expressing 3GT1 or 3GT4 and the lysate supernatant of yeast host expressing gGT29 as crude enzymes. The 100 μL reaction system is shown in Table 3. In the 73.4 μL enzyme liquid, 40 μL was the supernatant of *E. coli* host expressing 3GT1, the rest 33.44, was the lysate supernatant of yeast host expressing gGT29. The reaction was conducted under 35° C. for 12 hrs, and then stopped by adding 100 μL of butanol. The product were extracted, dried in vacuum, and dissolved in methanol. The reaction products were first detected by thin layer chromatography (TLC) (FIG. 35). It could be observed that PPD could be transformed into Rg3 either by the combination of glycosyltransferase 3GT1 and gGT29 or the combination of 3GT4 and gGT29.

Figure 36:
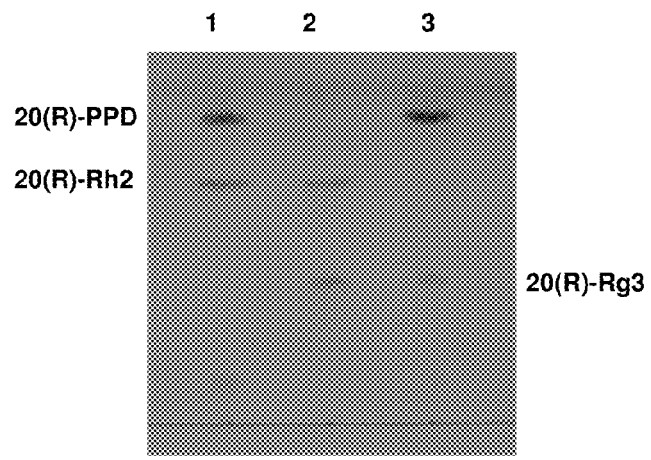
FIG. 36 TLC detection of the products obtained by catalyzing 20(R)-PPD or 20(R)-Rh2 using glycosyltransferase 3GT1 or gGT29 respectively or by catalyzing 20(R)-PPD using the combination of these two glycosyltransferases; lane 1, 20(R)-Rh2 produced by catalyzing 20(R)-PPD using 3GT1; lane 2, 20(R)-Rg3 produced by catalyzing 20(R)-Rh2 using gGT29; lane 3, 20(R)-Rg3 produced by catalyzing 20(R)-PPD using the combination of gGT29 and 3GT1.
Figure 37:
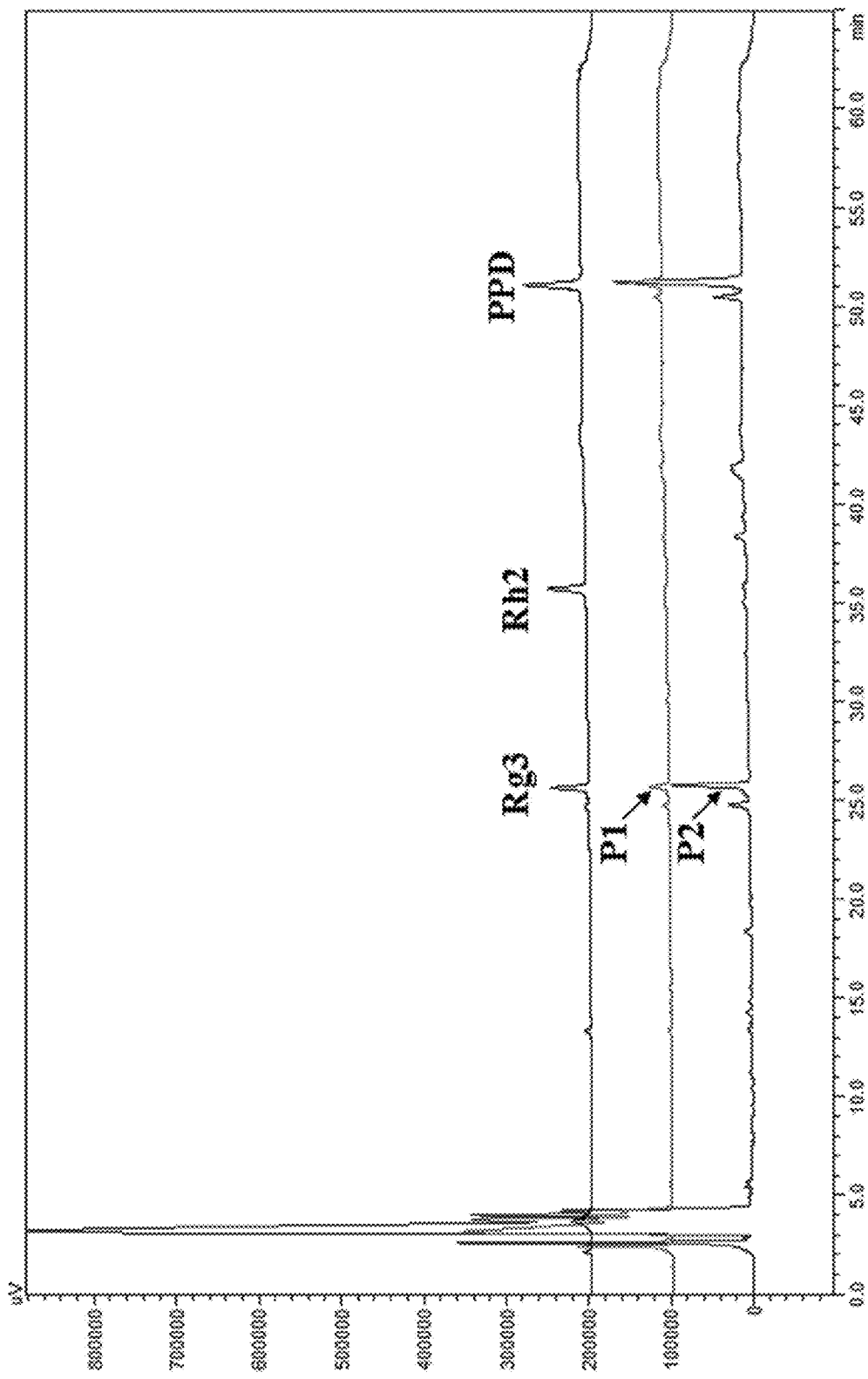
FIG. 37 shows HPLC detection of the products obtained by catalyzing PPD using the combination of glycosyltransferases gGT29 and 3GT1 or gGT29 and 3GT4. Line 1: a mixed standard sample of Rg3, Rh2 and PPD; line 2: PPD is catalyzed by the combination of glycosyltransferases gGT29 and 3GT1; line 3: PPD is catalyzed by the combination of glycosyltransferases gGT29 and 3GT4.
Figure 38:
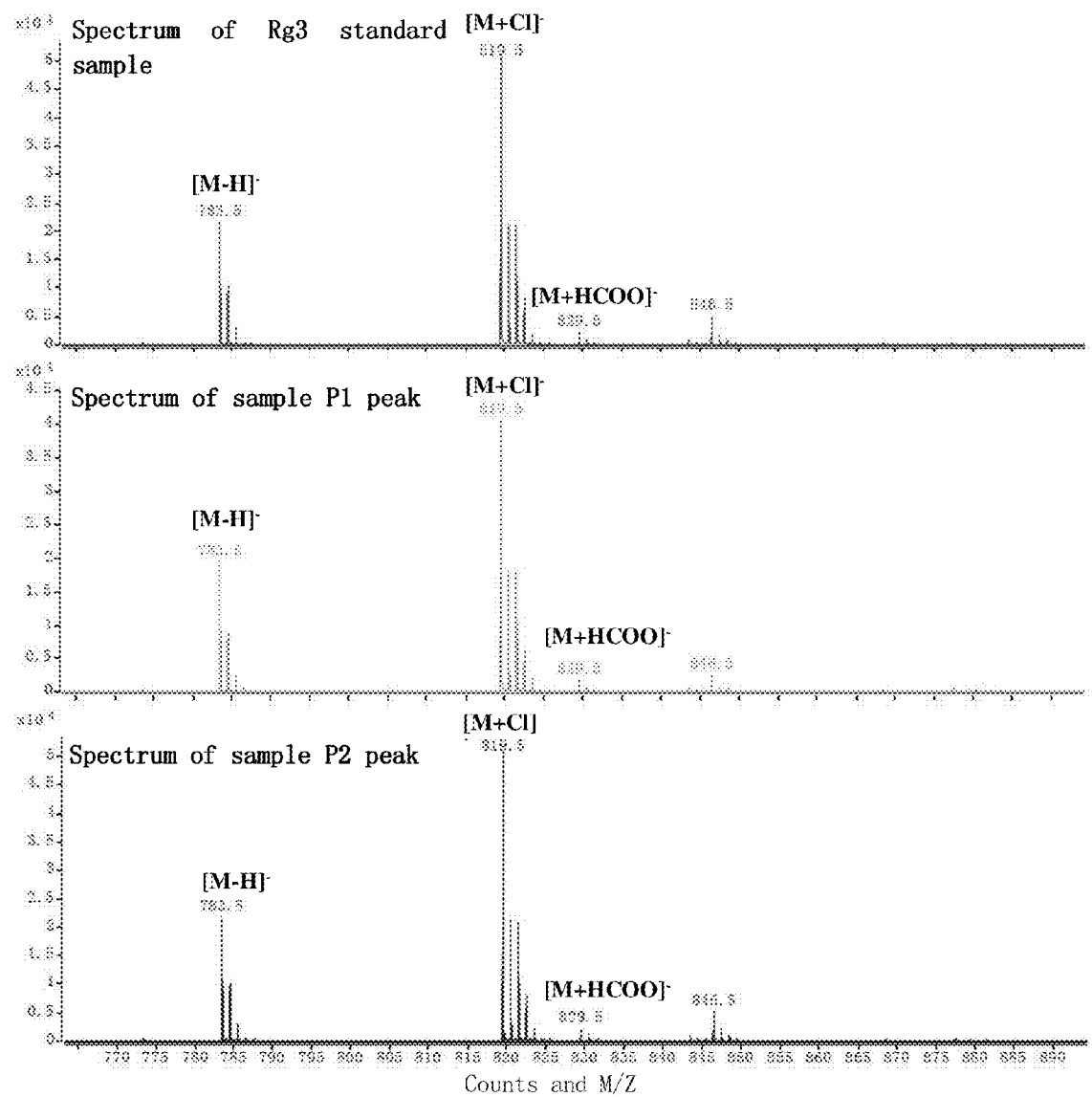
FIG. 38 shows LC/MS detection of the products obtained by catalyzing PPD using the combination of glycosyltransferases gGT29 and 3GT1 or gGT29 and 3GT4. The mass spectrum of the standard sample of Rg3, P1 peak (the product obtained by catalyzing PPD using the combination of gGT29 and 3GT1) and P2 peak of FIG. 37 (the product peak of the product obtained by catalyzing PPD using the combination of gGT29 and 3GT4) are shown.

20(R)-PPD could be transformed into 20(R)-Rg3 either by the combination of glycosyltransferase 3GT1 and gGT29 or the combination of 3GT4 and gGT29 (FIG. 36).

EXAMPLE 17

Construction of Engineered Yeast Strains for Rg3 Production and Product Identification 17.1 Dammarenediol synthase (ACZ71036.1) (GAL1/GAL10 GAL10 side promoter, ADH1 terminator), cytochrome P450 CYP716A47 (AEY75213.1) (FBA1 promoter, CYC1 terminator), glycosyltransferases 3GT4 and gGT29 (GAL1/GAL10 GAL1 side promoter, TDH2 terminator) were assembled in the plasmid pESC-HIS (Stratagene, Agilent), thereby constructing an episomal plasmid. The plasmid was used to transform $S.$ cerevisiae BY4742. Cytochrome P450 reductase ATR2-1 (NP_849472.2) from Arabidopsis thaliana was also integrated to the site of gene trp1 (GAL1 promoter, and the original terminator of trp1 was used) in the chromosome of $S.$ cerevisiae BY4742 so as to construct the recombinant yeast A2. Additional added amino acids or uracil needed for each recombinant strain is shown in Table 5.

The lysate of recombinant yeast A2 was transferred into 2 mL EP tubes with 1 mL for each, subjected to extraction by adding n-butanol in equivalent volume (1 mL) for about 30 mins, and then centrifuged for 10 mins at 12000 g. The supernatant was transferred to a new EP tube. n-butanol was dried in vacuum under 45° C. Upon dissolved in methanol (100 μL), the product was subjected to HPLC detection.

Figure 40:
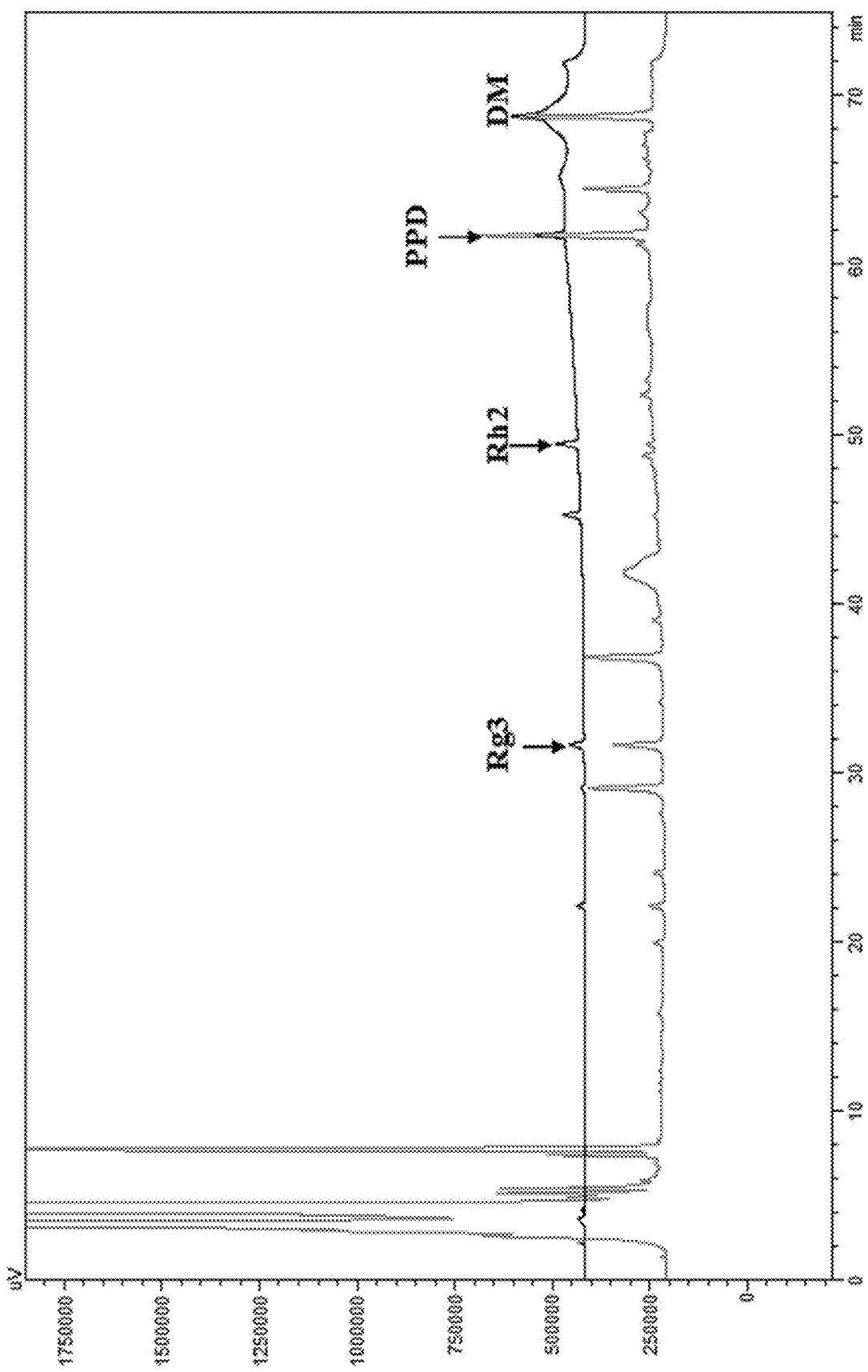
FIG. 40 shows HPLC detection of the cell lysate extracts of the engineered yeast strain A2 for Rg3 production, the sample of line 1: a mixed standard sample of PPD, DM, Rh2 and Rg3; the sample of line 2: cell lysate extracts of the engineered yeast strain A2 which can produce Rg3.

DM, PPD and the active metabolite of ginsenoside (Rg3) were contained in the cell lysate of recombinant yeast A2 according to HPLC analyze (FIG. 40).

17.2 The same method as 17.1 was used except that glycosyltransferase 3GT4 was substituted by 3GT1, thereby obtaining recombinant yeast A6. DM, PPD and the active metabolite of ginsenoside (Rg3) were also contained in the cell lysate of recombinant yeast A6 according to HPLC analyze.

EXAMPLE 18

Construction of Engineered Yeast Strains for F1 Production and Product Identification Dammarenediol synthase (ACZ71036.1) (GAL1/GAL10 GAL10 side promoter, ADH1 terminator), glycosyltransferase gGT25 (GAL1/GAL10 GAL1 side promoter, TDH2 terminator), cytochrome P450 CYP716A47 (AEY75213.1) (FBA1 promoter, FBA1 terminator), cytochrome P450 CYP716A53V2 (ENO2 promoter, CYC1 erminator) were assembled in the plasmid pESC-HIS (Stratagene, Agilent), thereby constructing an episomal plasmid. The product was used to transform $S.$ cerevisiae BY4742. Cytochrome P450 reductase ATR2-1 (NP_849472.2) from Arabidopsis thaliana was integrated to the site of gene trp1 (GAL1 promoter, and the original terminator of trp1 was used) in the chromosome of $S.$ cerevisiae BY4742 so as to construct the recombinant yeast A4. Additional added amino acids or uracil needed for each recombinant strain is shown in Table 5.

The lysate of recombinant yeast A4 was transferred into 2 mL EP tubes with 1 mL for each, subjected to extraction by adding n-butanol with equivalent volume (1 mL) for about 30 mins, and then centrifuged for 10 mins at 12000 g. The supernatant was transferred to a new EP tube. n-butanol was dried in vacuum under 45° C. Upon dissolved in methanol (100 μL), the product was subjected to HPLC detection.

Figure 42:
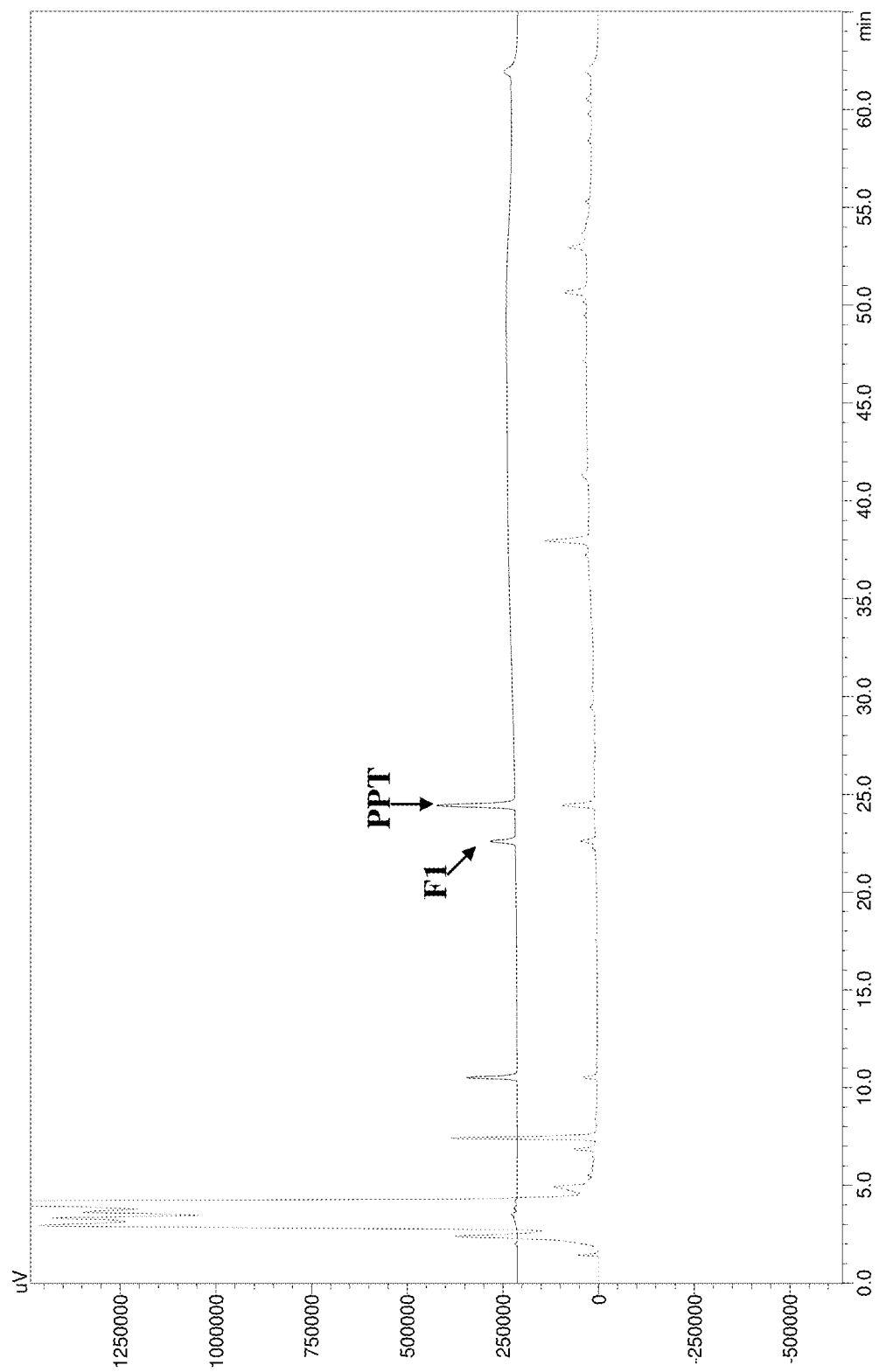
FIG. 42 shows HPLC detection of the cell lysate extracts of the engineered yeast strain A4 for F1 production, the sample of line 1: a mixed standard sample of PPT and ginsenoside F1; the sample of line 2: cell lysate extracts of the engineered yeast strain A4 which can produce F1.

PPT and the active metabolite of ginsenoside (F1) were contained in the cell lysate of recombinant yeast A4 according to HPLC analyze (FIG. 42).

EXAMPLE 19

Construction of the $E.$ coli Recombinant Expression Vectors for Glycosyltransferase Genes gGT29-4, gGT29-5, gGT29-6 and gGT29-7

The target genes were amplified using the plasmids gGT29-4-pMD18T, gGT29-5-pMD18T, gGT29-6-pMD18T and gGT29-7-pMD18T containing genes gGT29-4, gGT29-5, gGT29-6 and gGT29-7 constructed in Example 1 as templates.

The forward primer for gGT29-5 and gGT29-6 is as set forth by SEQ ID NO.: 66 with a sequence homologous to vector pET28a added to its 5' end: CTGGTGCCGCGCGGCAGC; the used reverse primer is as set forth by SEQ ID NO.: 68 with a sequence homologous to vector pET28a added to its 5' end: TGCGGCCGCAAGCTTGTC.

The forward primer for gGT29-4 and gGT29-7 is as set forth by SEQ ID NO.: 67 with a sequence homologous to vector pET28a added to its 5' end: CTGGTGCCGCGCGGCAGC; the used reverse primer is as set forth by SEQ ID NO.: 68 with a fragment of 18 bases homologous to vector pET28a added to its 5' end: TGCGGCCGCAAGCTTGTC.

The above primers were used to amplify genes gGT29-4, gGT29-5, gGT29-6 and gGT29-7 by PCR. The high-fidelity DNA polymerase Q5 (NEB Inc.) was selected for gene amplification. The PCR program was set according to the instructions: 98° C. 30 s; 98° C. 15 s, 58° C. 30 s, 72° C. 1 min, for 35 cycles; 72° C. 2 min; the temperature was kept at 10° C.

Further, the vector pET28a was amplified by using SEQ ID NO.: 69 and SEQ ID NO.: 70 as forward and reverse primer respectively so as to obtain the linearized vector pET28a. The high-fidelity DNA polymerase Q5 (NEB Inc) was also chosen for amplifying the linearized vector pET28a and the PCR program was set according to the instructions: 98° C. 30 sec; 98° C. 15 s, 58° C. 30 s, 72° C. 3 min for 35 cycles; 72° C. 2 min; the temperature was kept at 10° C.

The PCR products of above genes gGT29-4, gGT29-5, gGT29-6 and gGT29-7 and the linearized vector pET28a were detected by agarose gel electrophoresis and the bands with size of the target DNAs were cut out under a UV lamp. Then, the DNA fragments were recovered from the agarose gel using AxyPrep DNA Gel Extraction Kit (AXYGEN Inc.). The recovered fragment of the linearized vector pET28a, the recovered gene fragments of gGT29-4, gGT29-5, gGT29-6 and gGT29-7 and BGclonart seamless cloning reaction solution (Rockgene Biotech Inc.) were mixed up to 200 in suitable proportions according to the instruction of the BGclonart seamless cloning kit from Rockgene Biotech Inc. Upon mixed to homogenous, the product was incubated under 50° C. for 30 mins and the mixed reacting solution was transferred onto ice. *E. coli* EPI300 competent cells were transformed by 5 μl of reacting solution and then coated on the LB plate supplemented with 50 μg/mL of kanamycin. The positive clones were verified by colony PCR and the successful expression plasmids of gGT29-4-pET28a, gGT29-5-pET28a, gGT29-6-pET28a and gGT29-7-pET28a were further confirmed by sequencing

EXAMPLE 20

The Expression of Glycosyltransferases gGT29-4, gGT29-5, gGT29-6 and gGT29-7 in *E. coli*

Figure 44:
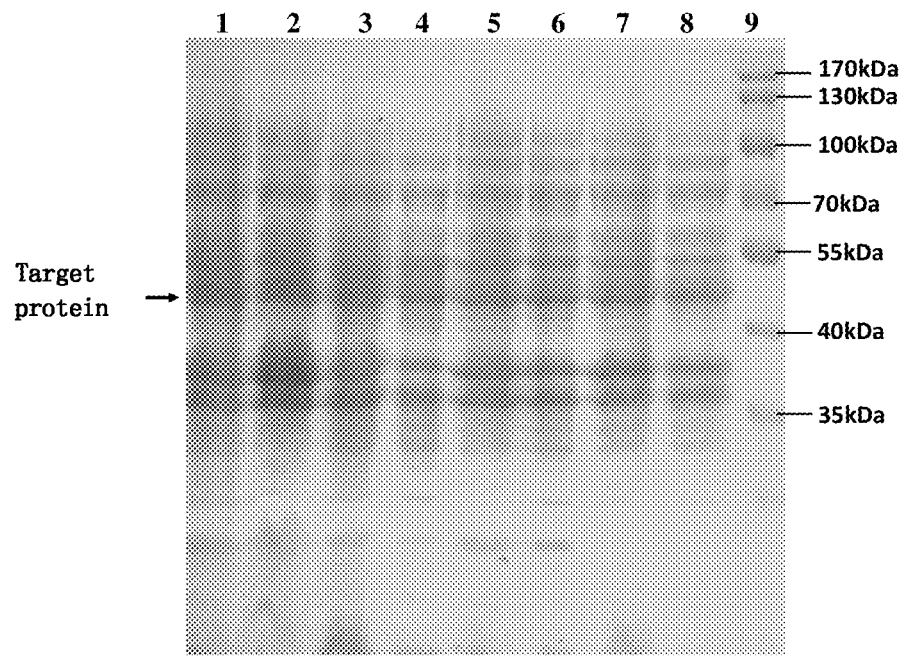
FIG. 44 shows SDS-PAGE detection of the gene gGT29-4, gGT29-5, gGT29-6 and gGT29-7 expression in E. coli. Lane 1, total protein in the lysate of the recombinant E. coli gGT29-4-pET28a; lane 2, lysate supernatant of the recombinant E. coli gGT29-4-pET28a; lane 3, total protein in the lysate of the recombinant E. coli gGT29-5-pET28a; lane 4, lysate supernatant of the recombinant E. coli gGT29-5-pET28a; lane 5, total protein in the lysate of the recombinant E. coli gGT29-6-pET28a; lane 6, lysate supernatant of the recombinant E. coli gGT29-6-pET28a; lane 7, total protein in the lysate of the recombinant E. coli gGT29-7-pET28a; lane 8, lysate supernatant of the recombinant E. coli gGT29-7-pET28a; lane 9, protein molecular-weight Marker.
Figure 45:
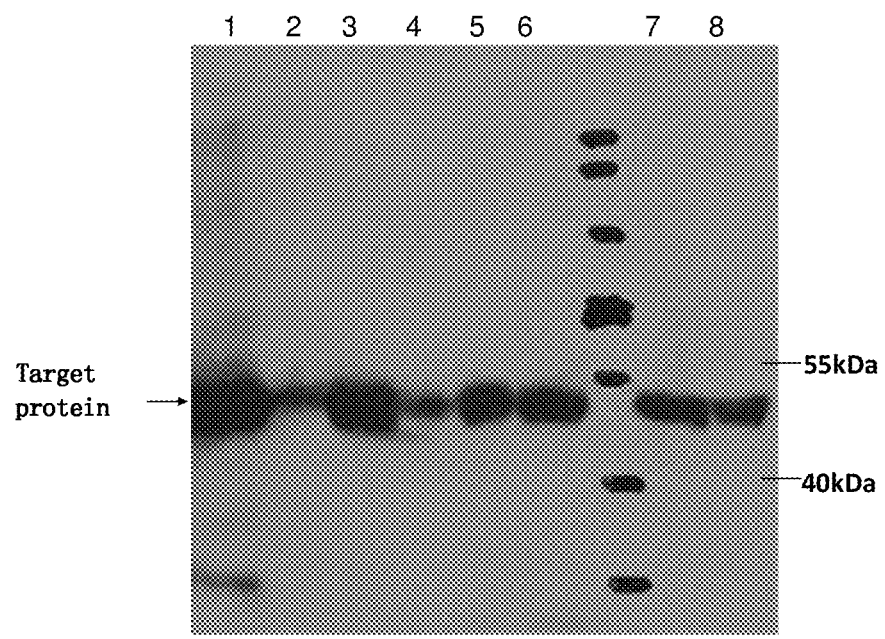

The *E. coli* expression vectors gGT29-4-pET28a, gGT29-5-pET28a, gGT29-6-pET28a and gGT29-7-pET28a constructed in Example 19 were transformed into the commercially available *E. coli* BL21. A recombinant was inoculated into LB medium and cultured under 30° C. at 200 rpm until $OD_{600}$ reached about 0.6-0.8. Then the culture liquid was cooled to 4° C., and IPTG with a final concentration of 50 μM was added for inducing expression under 18° C. at 200 rpm for 15 hrs. The pellets were collected under 4° C. and then subjected to ultrasionic cell-break. The cell lysis supernatant was collected by centrifugation at 12000 g and then a sample was taken for SDS-PAGE electrophoresis (FIG. 44). Obvious bands (about 50 kD) of target proteins could be observed in the lysate, total protein, and supernatant of the recombinants gGT29-4-pET28a, gGT29-5-pET28a, gGT29-6-pET28a and gGT29-7-pET28a, representing glycosyl-transferases gGT29-4, gGT29-5, gGT29-6 and gGT29-7, respectively. According to the Western Blot results (FIG. 45), target genes gGT29-4, gGT29-5, gGT29-6 and gGT29-7 achieved soluble expression in the hosts.

EXAMPLE 21

Glycosyltransfering Reaction of the *E. coli* Expression Products gGT29-4, gGT29-5, gGT29-6 and gGT29-7 and Product Identification The glycosyltransfering reactions of ginsenosides Rh2 and F2 were catalyzed by using the lysate supernatant of the recombinant yeasts expressing 3GT1, 3GT2, 3GT3 and 3GT4 as crude enzymes. The 100 μL reaction system is shown as Table 3. The reaction was conducted under 35° C. for 12 hrs, and then stopped by adding 100 μL of butanol. The product were extracted, dried in vacuum, and dissolved in methanol.

Figure 46:
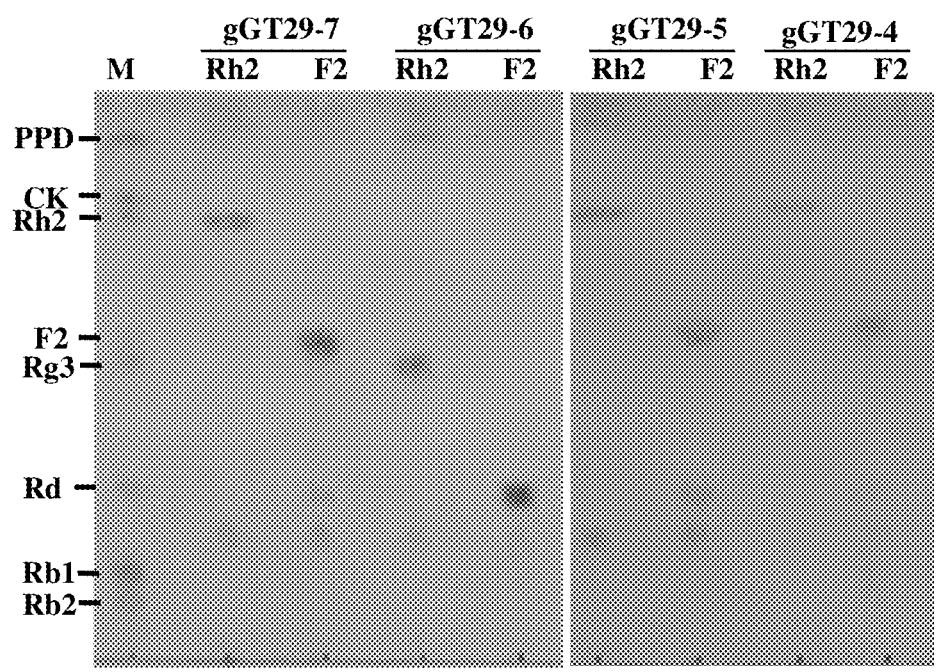
FIG. 46 shows TLC detection of the products obtained by catalyzing Rh2 and F2 using glycosyltransferases gGT29-4, gGT29-5, gGT29-6 and gGT29-7. Lane Rh2, saponin Rh2 is used as substrate; lane F2, saponin F2 is used as substrate. gGT29-4, gGT29-5, gGT29-6 or gGT29-7 represents reactions catalyzed by different enzymes respectively.

The reaction products were detected by thin layer chromatography (TLC). C3 glycosyl of ginsenosides Rh2 and F2 could be extended by one more glycosyl using the crude enzymes of gGT29-6 so as to produce ginsenosides Rg3 and Rd (FIG. 46); C3 glycosyl of ginsenoside F2 could be extended by one more glycosyl using the crude enzymes of gGT29-4, gGT29-5 and gGT29-7 so as to produce ginsenoside Rd; however, saponin Rh2 could not be catalyzed by them (FIG. 46).

All references mentioned in the present invention are incorporated herein by reference, as each of them is individually cited herein by reference. Further, it should be understood that, after reading the above contents, the skilled person can make various modifications or changes to the present invention. All these equivalents also fall into the scope defined by the appending claims of the present application.

The invention claimed is:

1. A vector, wherein said vector comprises the polynucleotide selected from the group consisting of:

(A1) a nucleotide sequence encoding a polypeptide having the amino acid sequence as set forth in SEQ ID NO: 20, 26, 28, 43, 55, 57, 59 or 61 or a derivative polypeptide thereof, wherein said derivative polypeptide thereof has at least 85% sequence identity to SEQ ID NO: 20, 26, 28, 43, 55, 57, 59 or 61 and has the activity of glycosyltransferase, optionally having substitution, deletion or addition of one or more amino acid residues or by addition of a signal peptide sequence;

(A2) a nucleotide sequence encoding a polypeptide having the amino acid sequence as set forth in SEQ ID NO: 2, 16, or 18; and (B) a nucleotide sequence as set forth in SEQ ID NO: 1, 15, 17, 19, 25, 27, 42, 54, 56, 58 or 60;

wherein said polynucleotide is under the control of a heterologous promoter.

2. The vector of claim 1, wherein the vector comprises the polynucleotide encoding a polypeptide having the amino acid sequence set forth in SEQ ID NO: 2, 16, 18, 20, 26, 28, 43, 55, 57, 59 or 61.

3. A genetically engineered host cell, wherein said host cell contains the vector according to claim 1.

4. A method for in vitro glycosylation, said method comprising:

providing the genetically engineered host cell of claim 3;

obtaining a recombinant glycosyltransferase expressed in said host cell; and catalyzing the transfer of a glycosyl from a glycosyl donor to the following site on a tetracyclic triterpenoid compound: positions C-20, C-6, C-3 or the first glycosyl at position C-3, thereby forming glycosylated tetracyclic triterpenoid compounds, wherein said recombinant glycosyltransferase catalyzes the transfer.

5. The method of claim 4, wherein said glycosyltransferase is used for catalyzing one or more of the following reactions, or for preparing a catalyst preparation used in the catalyzation of one or more of the following reactions:

(A)

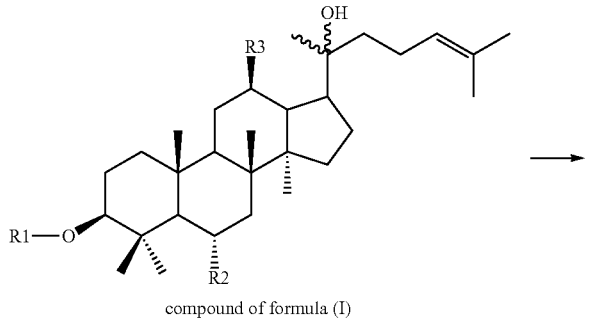

compound of formula (I)

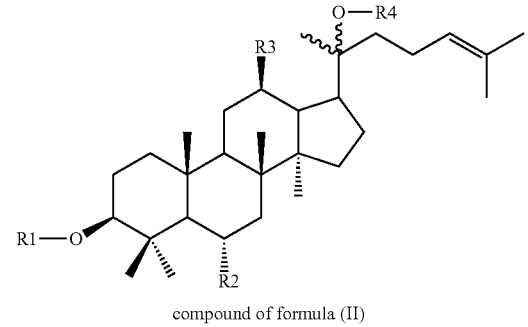

compound of formula (II)

wherein, R1 is H, monosaccharide glycosyl or polysaccharides glycosyl; R2 or R3 is H or OH; R4 is glycosyl; said polypeptide is selected from SEQ ID NOs: 2, 16 or 18 or the derivative polypeptide thereof;

(B)

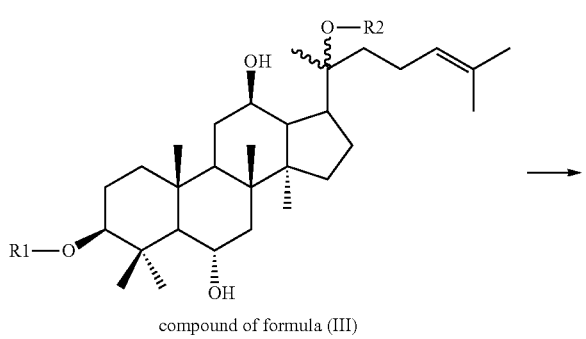

compound of formula (III)

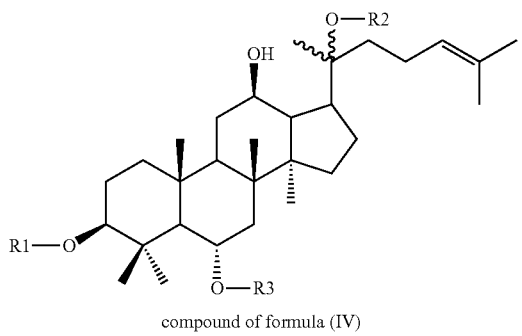

compound of formula (IV)

wherein, R1 is H or glycosyl; R2 is a glycosyl; R3 is a glycosyl; said polypeptide is selected from SEQ ID NOs: 2, 16, 18 or 20, or the derivative polypeptide thereof;

or, R1 is H or a glycosyl; R2 is H; R3 is a glycosyl; said polypeptide is selected from SEQ ID NO: 20 or the derivative polypeptide thereof;

(C)

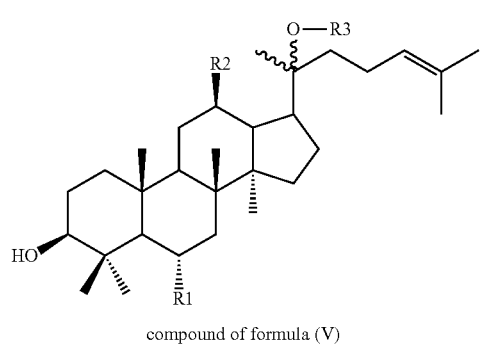

compound of formula (V)

→

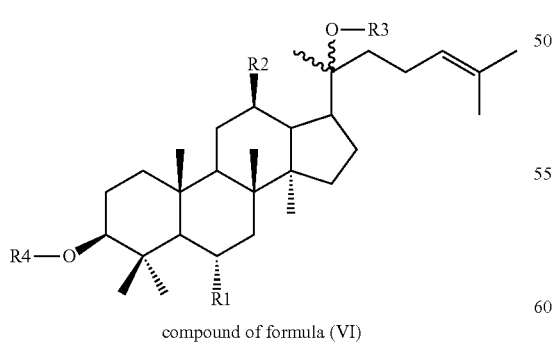

compound of formula (VI)

wherein, R1 is H or OH; R2 is H or OH; R3 is H or a glycosyl; R4 is a glycosyl; said polypeptide is selected from SEQ ID NO: 43 or the derivative polypeptide thereof;

(D)

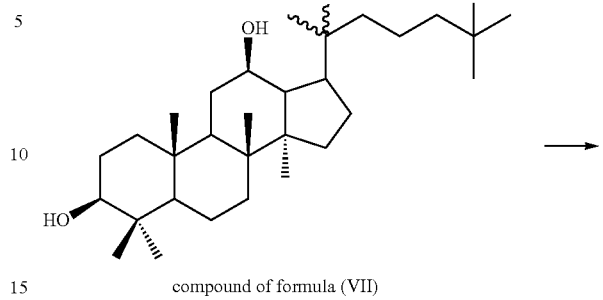

compound of formula (VII)

→ compound of formula (VIII)

wherein, R1 is OH or OCH$_3$; R2 is a glycosyl; said polypeptide is selected from SEQ ID NO: 43 or the derivative polypeptide thereof;

(E)

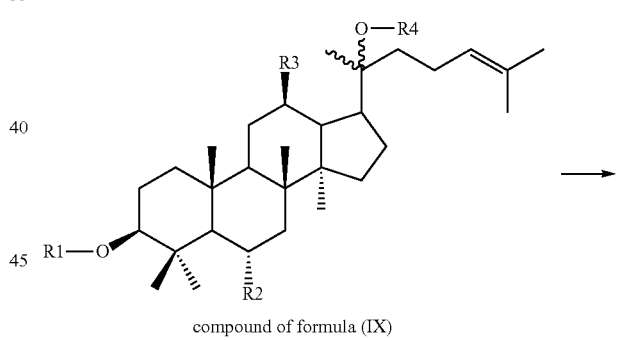

compound of formula (IX)

→ compound of formula (X)

wherein, R1 is glycosyl; R2 or R3 is OH or H; R4 is glycosyl or H; R5 is glycosyl, R5-R1-O is a glycosyl extended from the first glycosyl at C-3; said polypeptide is selected from SEQ ID NOs: 26, 28, 55, 57, 59 or 61 or the derivative polypeptide thereof;

(F)

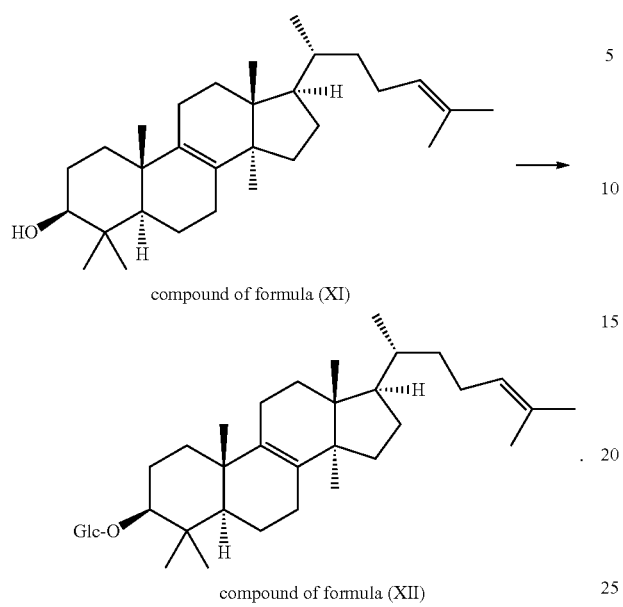

compound of formula (XI)

compound of formula (XII)

6. The method according to claim 4, said tetracyclic triterpenoid compounds comprises S- or R-dammarane-type, lanostane-type, tirucallane-type, cycloartane-type, cucurbitane type, or meliacane type typetetracyclic triterpenoid compounds.

7. The method according to claim 4, wherein said glycosyltransferase is selected from the group consisting of glycosyltransferases as set forth by SEQ ID NOs.: 2, 16, 18, 20, 22, 24, 26, 28, 43, 55, 57, 59 and 61.

8. A method for conducting catalytic glycosylation in vitro, said method comprising:
   providing the genetically engineered host cell of claim 3;
   obtaining a recombinant glycosyltransferase expressed in said host cell; and
   catalyzing a glycosylation reaction on a tetracyclic triterpenoid compound thereby forming a glycosylated tetracyclic triterpenoid compound,
   wherein said recombinant glycosyltransferase catalyzes the glycosylation reaction.

9. The method according to claim 8, wherein the substrate of the catalytic glycosylation is the compound of formula (I), (III), (V), (VII), (IX) or (XI), and the product is the compound of (II), (IV), (VI), (VIII), (X) or (XII); preferably, said compound of formula (I) is protopanaxadiol (PPD), and the compound of formula (II) is ginsenoside CK (20-O-β-(D-glucopyranosyl)-protopanaxadiol);
   or, said compound of formula (I) is ginsenoside Rh2 (3-O-β-(D-glucopyranosyl)-protopanaxadiol)), and the compound of formula (II) is ginsenoside F2 (3-O-β-(D-glucopyranosyl)-20-O-β-(D-glucopyranosyl)-protopanaxadiol);
   or, said compound of formula (I) is ginsenoside Rg3, and the compound of formula (II) is ginsenoside Rd;
   or, said compound of formula (I) is protopanaxatriol (PPT), and the compound of formula (II) is ginsenoside F1 (20-O-β-(D-glucopyranosyl)-protopanaxatriol);
   or, said compound of formula (I) is dammarenediol-II (DM), and the compound of formula (II) is ginsenoside 20-O-β-(D-glucopyranosyl)-dammarenediol II;
   or, said compound of formula (III) is protopanaxatriol, and the compound of formula (IV) is ginsenoside Rh1 (6-O-β-(D-glucopyranosyl)-protopanaxatriol);
   or, said compound of formula (III) is ginsenoside F1, and the compound of formula (IV) is ginsenoside Rg1 (6-O-β-(D-glucopyranosyl)-20-O-β-(D-glucopyranosyl)-protopanaxadiol);
   or, said compound of formula (V) is protopanaxadiol, and the compound of formula (VI) is ginsenoside Rh2 (3-O-β-(D-glucopyranosyl)-protopanaxadiol);
   or, said compound of formula (V) is CK, and the compound of formula (VI) is ginsenoside F2 (3-O-β-(D-glucopyranosyl)-20-O-β-(D-glucopyranosyl)-protopanaxadiol);
   or, said compound of formula (V) is protopanaxatriol, and the compound of formula (VI) is ginsenoside 3-O-β-(D-glucopyranosyl)-protopanaxatriol;
   or, said compound of formula (V) is ginsenoside F1, and the compound of formula (VI) is ginsenoside 3-O-β-(D-glucopyranosyl)-F1;
   or, said compound of formula (V) is DM, and the compound of formula (VI) is ginsenoside 3-O-β-(D-glucopyranosyl)-dammarenediol II;
   or, said compound of formula (VII) is 25-OH-protopanaxadiol, and the compound of formula (VIII) is ginsenoside 3-O-β-(D-glucopyranosyl)-25-OH-protopanaxadiol;
   or, said compound of formula (VII) is 25-OCH$_3$-protopanaxadiol), and the compound of formula (VIII) is ginsenoside 3-O-β-(D-glucopyranosyl)-25-OCH$_3$-protopanaxadiol;
   or, said compound of formula (IX) is ginsenoside Rh2, and the compound of formula (X) is ginsenoside Rg3;
   or, said compound of formula (IX) is ginsenoside F2, and the compound of formula (X) is ginsenoside Rd;
   or, said compound of formula (XI) is lanosterol, and the compound of formula (XII) is 3-O-β-(D-glucopyranosyl)-lanosterol.

10. The method according to claim 8, said tetracyclic triterpenoid compounds comprises S- or R-dammarane-type, lanostane-type, tirucallane-type, cycloartane-type, cucurbitane type, or meliacane type typetetracyclic triterpenoid compounds.

* * * * *

SEQUENCE LISTING

```
<160> NUMBER OF SEQ ID NOS: 70

<210> SEQ ID NO 1
<211> LENGTH: 1425
<212> TYPE: DNA
<213> ORGANISM: Panax ginseng
<220> FEATURE:
<221> NAME/KEY: misc_feature
<223> OTHER INFORMATION: gGT25

<400> SEQUENCE: 1
atgaagtcag aattgatatt cttgcccgcc ccggccatcg gacacctcgt gggaatggtg      60
gagatggcta aactcttcat cagtcgacat gaaaacctct cggtcaccgt cctcatcgcg     120
aaattctaca tggatacggg ggtagacaac tacaataaat cactcttaac aaaccctacc     180
ccgcgtctca caattgtaaa tctcccggaa accgaccccc aaaactatat gctcaaacca     240
cgccatgcca tcttttcctag cgtcatcgag actcagaaga cacacgtgcg agacataata     300
tcaggcatga ctcagtccga gtcgactcgg gtcgttggtt tgctggctga ccttttgttc     360
atcaacatta tggacattgc caatgagttc aatgttccaa cttatgtata ctcccctgcc     420
ggagccggtc atcttggcct cgcgttccat ctccagacac tcaacgacaa aaagcaagat     480
gtgaccgagt tcaggaactc ggacactgag ttattggtac cgagttttgc aaacccggtt     540
cccgccgagg tcttgccgtc gatgtatgtg gataaagaag gtgggtatga ttatttgttt     600
tcattgttcc ggaggtgcag agagtcaaag gcaattatta ttaacacgtt tgaggagctg     660
gaaccctatg cgatcaattc cctccggatg gatagtatga tccctccgat ctaccgggtg     720
```

-continued

```
ggacccatac taaatctcaa cggtgatggc caaaactccg atgaggctgc tgtgatcctt    780
ggttggttag atgatcaacc accttcatct gtggtgtttt tgtgctttgg tagctatgga    840
agctttcaag aaaccaggt gaaggagatt gcaatgggtc tagagcgcag tgggcatcgc    900
ttcttgtggt ccttgcgtcc gtctatccct aaaggcgaga caaagcttca gcttaaatac    960
tcaaatttga agaaattct cccagtagga ttcttggaca ggacatcatg cgtcggaaaa   1020
gtgattggat gggccccgca agtggccgtg ctcggacatg agtcagtcgg agggttcctg   1080
tctcattgcg gttggaattc gacattggag agtgtttggt gtggggtgcc cgttgcaaca   1140
tggccaatgt atggtgagca acaactcaat gcttttgaga tggttaagga gttaggtatt   1200
gcggtggaaa ttgaggtgga ctataagaaa gattatttta acatgaagaa tgatttatt    1260 gttagggcag aagaaatcga gacaaaaata aagaagttga tgatggatga aaataatagt   1320
gaaataagaa agaaggtaaa ggaaatgaaa gaaagagta gggctgcaat gtctgagaat   1380
ggatcatctt ataattcatt ggcgaagcta tttgaggaaa ttatg                   1425
```

<210> SEQ ID NO 2
<211> LENGTH: 475
<212> TYPE: PRT
<213> ORGANISM: Panax ginseng
<220> FEATURE:
<221> NAME/KEY: misc_feature
<223> OTHER INFORMATION: gGT25

<400> SEQUENCE: 2

```
Met Lys Ser Glu Leu Ile Phe Leu Pro Ala Pro Ala Ile Gly His Leu
1               5                   10                  15

Val Gly Met Val Glu Met Ala Lys Leu Phe Ile Ser Arg His Glu Asn
            20                  25                  30

Leu Ser Val Thr Val Leu Ile Ala Lys Phe Tyr Met Asp Thr Gly Val
        35                  40                  45

Asp Asn Tyr Asn Lys Ser Leu Leu Thr Asn Pro Thr Pro Arg Leu Thr
    50                  55                  60

Ile Val Asn Leu Pro Glu Thr Asp Pro Gln Asn Tyr Met Leu Lys Pro
65                  70                  75                  80

Arg His Ala Ile Phe Pro Ser Val Ile Glu Thr Gln Lys Thr His Val
                85                  90                  95

Arg Asp Ile Ile Ser Gly Met Thr Gln Ser Glu Ser Thr Arg Val Val
            100                 105                 110

Gly Leu Leu Ala Asp Leu Leu Phe Ile Asn Ile Met Asp Ile Ala Asn
        115                 120                 125

Glu Phe Asn Val Pro Thr Tyr Val Tyr Ser Pro Ala Gly Ala Gly His
    130                 135                 140

Leu Gly Leu Ala Phe His Leu Gln Thr Leu Asn Asp Lys Lys Gln Asp
145                 150                 155                 160

Val Thr Glu Phe Arg Asn Ser Asp Thr Glu Leu Leu Val Pro Ser Phe
                165                 170                 175

Ala Asn Pro Val Pro Ala Glu Val Leu Pro Ser Met Tyr Val Asp Lys
            180                 185                 190

Glu Gly Gly Tyr Asp Tyr Leu Phe Ser Leu Phe Arg Arg Cys Arg Glu
        195                 200                 205

Ser Lys Ala Ile Ile Ile Asn Thr Phe Glu Glu Leu Glu Pro Tyr Ala
    210                 215                 220

Ile Asn Ser Leu Arg Met Asp Ser Met Ile Pro Pro Ile Tyr Pro Val
225                 230                 235                 240
```

Gly Pro Ile Leu Asn Leu Asn Gly Asp Gly Gln Asn Ser Asp Glu Ala
            245                 250                 255

Ala Val Ile Leu Gly Trp Leu Asp Asp Gln Pro Pro Ser Ser Val Val
        260                 265                 270

Phe Leu Cys Phe Gly Ser Tyr Gly Ser Phe Gln Glu Asn Gln Val Lys
    275                 280                 285

Glu Ile Ala Met Gly Leu Glu Arg Ser Gly His Arg Phe Leu Trp Ser
290                 295                 300

Leu Arg Pro Ser Ile Pro Lys Gly Glu Thr Lys Leu Gln Leu Lys Tyr
305                 310                 315                 320

Ser Asn Leu Lys Glu Ile Leu Pro Val Gly Phe Leu Asp Arg Thr Ser
                325                 330                 335

Cys Val Gly Lys Val Ile Gly Trp Ala Pro Gln Val Ala Val Leu Gly
            340                 345                 350

His Glu Ser Val Gly Gly Phe Leu Ser His Cys Gly Trp Asn Ser Thr
        355                 360                 365

Leu Glu Ser Val Trp Cys Gly Val Pro Val Ala Thr Trp Pro Met Tyr
    370                 375                 380

Gly Glu Gln Gln Leu Asn Ala Phe Glu Met Val Lys Glu Leu Gly Ile
385                 390                 395                 400

Ala Val Glu Ile Glu Val Asp Tyr Lys Lys Asp Tyr Phe Asn Met Lys
                405                 410                 415

Asn Asp Phe Ile Val Arg Ala Glu Glu Ile Glu Thr Lys Ile Lys Lys
            420                 425                 430

Leu Met Met Asp Glu Asn Asn Ser Glu Ile Arg Lys Lys Val Lys Glu
        435                 440                 445

Met Lys Glu Lys Ser Arg Ala Ala Met Ser Glu Asn Gly Ser Ser Tyr
    450                 455                 460

Asn Ser Leu Ala Lys Leu Phe Glu Glu Ile Met
465                 470                 475

<210> SEQ ID NO 3
<211> LENGTH: 1431
<212> TYPE: DNA
<213> ORGANISM: Panax ginseng
<220> FEATURE:
<221> NAME/KEY: misc_feature
<223> OTHER INFORMATION: gGT13

<400> SEQUENCE: 3
atgggagcgg agctcatctt aatcccttct ccgggagttg gtcatctggt atctactgtt      60
gagattgcaa agctcctcat cagtcgagat gaacggcttt ccatcacagt ccttgtaatg     120
aagttctcgc atgacactgg tgtgactgcc tacactcggt cattgcagaa agatgctcct     180
aaccgcatag tctttgtgga ccttcctcag aacgagtctc ttatctcatc gcccaagtct     240
ttctttacta gcttcatcga gagtcagacg agtccggtta gagattctgt cagacaaatt     300
gtgagtcggt ctgattctaa taagctcgct ggcttcgtca tcgacatgtt ctgcacccca     360
atgatagacg tggcaaatga atttggagtc ccaacctatg tgttcttcac ttcaggtgct     420
gcatttcttg gcctccagtt ttaccatctg agtctcagtg atgaacataa ccaggacctt     480
accgagtata aggacacgga tgttgagtta tctatcccga gtttcatcaa cccagtgccc     540
gctaaggttt tgccttcggt gattctgaac aaggaaggat cgaccatgct ccaatctatt     600
tcccgaaggt ttaagaagc caaggccatt ctagtcaaca cgttcgcgga gctggaacca     660

-continued

```
catgccatta aggcccttgg tgataactgc aagatccctc ctatctatcc cgtgggaccc        720
ataatcaacc tcaagaacaa ggagggaaca acccaaaacc atagttctga agatggtatc        780
attagctggt tggacaatca gccaccatct tcggtagtgt ttttgtgctt tgggagcttt        840
gggagctttg atgaaggcca agtcagggag atagcaaacg gattgagca gagtggacag         900 cgattcttgt ggtctctacg ccggcggcca gaaaaaatgg aattgcctaa agactatgag        960
aatcccgaag aagtgttgcc agaaggattc atagaacgaa catcagggat ggggaaggtg       1020
atcggatggg cgccacaaac ggcgattctt tcccaccctg ctgtgggagg attcgtgtct       1080
cattgtggat ggaattctac attggagagt atatggtgtg gggttccaat ggctacttgg       1140
cctatatatg cagagcagca aatcaatgcg tttgagttgg tgaaggagtt gggaatggct       1200
gtggagatca aaatggatta cagagaagat tatattttg cacctgaaaa taatttagtt        1260
gtgaccgcag accagataga aaaggaatg cgatgtctga tgatggatgg agagagtgaa        1320
atgaggaaga aggtggaaga gatgaaagag aagagcagaa tggccatggt gaagggcggg       1380
tcttcttaca tttcactcgg gcattttatt gaggatgtca tgcgtaatta a                1431
```

<210> SEQ ID NO 4
<211> LENGTH: 476
<212> TYPE: PRT
<213> ORGANISM: Panax ginseng
<220> FEATURE:
<221> NAME/KEY: misc_feature
<223> OTHER INFORMATION: gGT13

<400> SEQUENCE: 4

```
Met Gly Ala Glu Leu Ile Leu Ile Pro Ser Pro Gly Val Gly His Leu
1               5                   10                  15

Val Ser Thr Val Glu Ile Ala Lys Leu Leu Ile Ser Arg Asp Glu Arg
            20                  25                  30

Leu Ser Ile Thr Val Leu Val Met Lys Phe Ser His Asp Thr Gly Val
        35                  40                  45

Thr Ala Tyr Thr Arg Ser Leu Gln Lys Asp Ala Pro Asn Arg Ile Val
    50                  55                  60

Phe Val Asp Leu Pro Gln Asn Glu Ser Leu Ile Ser Ser Pro Lys Ser
65                  70                  75                  80

Phe Phe Thr Ser Phe Ile Glu Ser Gln Thr Ser Pro Val Arg Asp Ser
                85                  90                  95

Val Arg Gln Ile Val Ser Arg Ser Asp Ser Asn Lys Leu Ala Gly Phe
            100                 105                 110

Val Ile Asp Met Phe Cys Thr Pro Met Ile Asp Val Ala Asn Glu Phe
        115                 120                 125

Gly Val Pro Thr Tyr Val Phe Phe Thr Ser Gly Ala Ala Phe Leu Gly
    130                 135                 140

Leu Gln Phe Tyr His Leu Ser Leu Ser Asp Glu His Asn Gln Asp Leu
145                 150                 155                 160

Thr Glu Tyr Lys Asp Thr Asp Val Glu Leu Ser Ile Pro Ser Phe Ile
                165                 170                 175

Asn Pro Val Pro Ala Lys Val Leu Pro Ser Val Ile Leu Asn Lys Glu
            180                 185                 190

Gly Ser Thr Met Leu Gln Ser Ile Ser Arg Arg Phe Lys Glu Ala Lys
        195                 200                 205

Ala Ile Leu Val Asn Thr Phe Ala Glu Leu Glu Pro His Ala Ile Lys
    210                 215                 220
```

| Ala | Leu | Gly | Asp | Asn | Cys | Lys | Ile | Pro | Pro | Ile | Tyr | Pro | Val | Gly | Pro |
|---|---|---|---|---|---|---|---|---|---|---|---|---|---|---|---|
| 225 | | | | 230 | | | | | 235 | | | | | 240 | |

| Ile | Ile | Asn | Leu | Lys | Asn | Lys | Glu | Gly | Thr | Thr | Gln | Asn | His | Ser | Ser |
|---|---|---|---|---|---|---|---|---|---|---|---|---|---|---|---|
| | | | | 245 | | | | | 250 | | | | | 255 | |

| Glu | Asp | Gly | Ile | Ile | Ser | Trp | Leu | Asp | Asn | Gln | Pro | Pro | Ser | Ser | Val |
|---|---|---|---|---|---|---|---|---|---|---|---|---|---|---|---|
| | | | 260 | | | | | 265 | | | | | 270 | | |

| Val | Phe | Leu | Cys | Phe | Gly | Ser | Phe | Gly | Ser | Phe | Asp | Glu | Gly | Gln | Val |
|---|---|---|---|---|---|---|---|---|---|---|---|---|---|---|---|
| | | 275 | | | | | 280 | | | | | 285 | | | |

| Arg | Glu | Ile | Ala | Asn | Gly | Leu | Glu | Gln | Ser | Gly | Gln | Arg | Phe | Leu | Trp |
|---|---|---|---|---|---|---|---|---|---|---|---|---|---|---|---|
| | 290 | | | | | 295 | | | | | 300 | | | | |

| Ser | Leu | Arg | Arg | Arg | Pro | Glu | Lys | Met | Glu | Leu | Pro | Lys | Asp | Tyr | Glu |
|---|---|---|---|---|---|---|---|---|---|---|---|---|---|---|---|
| 305 | | | | | 310 | | | | | 315 | | | | | 320 |

| Asn | Pro | Glu | Glu | Val | Leu | Pro | Glu | Gly | Phe | Ile | Glu | Arg | Thr | Ser | Gly |
|---|---|---|---|---|---|---|---|---|---|---|---|---|---|---|---|
| | | | | 325 | | | | | 330 | | | | | 335 | |

| Met | Gly | Lys | Val | Ile | Gly | Trp | Ala | Pro | Gln | Thr | Ala | Ile | Leu | Ser | His |
|---|---|---|---|---|---|---|---|---|---|---|---|---|---|---|---|
| | | | 340 | | | | | 345 | | | | | 350 | | |

| Pro | Ala | Val | Gly | Gly | Phe | Val | Ser | His | Cys | Gly | Trp | Asn | Ser | Thr | Leu |
|---|---|---|---|---|---|---|---|---|---|---|---|---|---|---|---|
| | | 355 | | | | | 360 | | | | | 365 | | | |

| Glu | Ser | Ile | Trp | Cys | Gly | Val | Pro | Met | Ala | Thr | Trp | Pro | Ile | Tyr | Ala |
|---|---|---|---|---|---|---|---|---|---|---|---|---|---|---|---|
| 370 | | | | | 375 | | | | | 380 | | | | | |

| Glu | Gln | Gln | Ile | Asn | Ala | Phe | Glu | Leu | Val | Lys | Glu | Leu | Gly | Met | Ala |
|---|---|---|---|---|---|---|---|---|---|---|---|---|---|---|---|
| 385 | | | | | 390 | | | | | 395 | | | | | 400 |

| Val | Glu | Ile | Lys | Met | Asp | Tyr | Arg | Glu | Asp | Tyr | Ile | Phe | Ala | Pro | Glu |
|---|---|---|---|---|---|---|---|---|---|---|---|---|---|---|---|
| | | | | 405 | | | | | 410 | | | | | 415 | |

| Asn | Asn | Leu | Val | Val | Thr | Ala | Asp | Gln | Ile | Glu | Lys | Gly | Met | Arg | Cys |
|---|---|---|---|---|---|---|---|---|---|---|---|---|---|---|---|
| | | | 420 | | | | | 425 | | | | | 430 | | |

| Leu | Met | Met | Asp | Gly | Glu | Ser | Glu | Met | Arg | Lys | Lys | Val | Glu | Glu | Met |
|---|---|---|---|---|---|---|---|---|---|---|---|---|---|---|---|
| | | 435 | | | | | 440 | | | | | 445 | | | |

| Lys | Glu | Lys | Ser | Arg | Met | Ala | Met | Val | Lys | Gly | Gly | Ser | Ser | Tyr | Ile |
|---|---|---|---|---|---|---|---|---|---|---|---|---|---|---|---|
| 450 | | | | | 455 | | | | | 460 | | | | | |

| Ser | Leu | Gly | His | Phe | Ile | Glu | Asp | Val | Met | Arg | Asn |
|---|---|---|---|---|---|---|---|---|---|---|---|
| 465 | | | | | 470 | | | | | 475 | |

<210> SEQ ID NO 5
<211> LENGTH: 1353
<212> TYPE: DNA
<213> ORGANISM: Panax ginseng
<220> FEATURE:
<221> NAME/KEY: misc_feature
<223> OTHER INFORMATION: gGT30

<400> SEQUENCE: 5

```
atggcaaccc aaaaatgttt ccgtgtcctc gtgttcccat ggttagctca tggtcacatc      60 tccccttcc  tagaactagc cagaaaactt atagaaaaag aaactttttt catttacttc     120
tgctccactc ctataaatct catctccata agaaaaaac  ttagtggtga tgatcatcaa     180
aattacacca agtcaataca actagtggaa cacaatctac cgaccttacc tcaacttcct     240
cctcactacc acaccaccga cggcctccca ccaaatctca atcctaccct tcgaaaggca     300
tttgaaatgt caaaactatc cttccccaac accctaaaca cttttgaaacc agatctactc     360 atttgtgatg acttatttca atggccagaa atagtagctt catcacatgg tgttccggtt     420
gttcggttcc aaacatgcag cgtgacagcc gctagttttc tagctcatat ttttacgaac     480
ccagacgtta cataccctt  tccagccatt tatcttcatg agtatgaaac tgatcagatc     540
aggcgttgcg ttgacgcggt ttttgaaagc ggcagagaag aatctcgcaa cctgttggtt     600
```

```
gtcaacacgt ctaaagcgat cgaggaaaaa tattttttatt attattctct acttcggggt    660
aacaccaaaa ttatgccagt tggtccgctt attcagcaag ccccaaatgg cgacgaggat    720
atgaaggtca tcgaatggct tgacaagaag gatccgtgtt caaccgtgtt cgtgtccttt    780
gggagcgagt attttatgca aaaagaagag gttgaagaga tggctcatgg tttagagctt    840
agcaacgtca atttcatctg gttttttagg gctccggtgg gagcggaaaa ggttaagctg    900
ccgttagggt ttgttgagag ggttgggggg aggggaattg ttatggaggg gtgggcccca    960
caggcaagga ttttgggaca ttcaagtatt ggtgggtttg tgagtcattg tgggtggaat   1020
tctgtgttgg aaactataaa ttttggtgtt ccaataatag ggatgccaat gaaatttgag   1080
cagcctatga atgctaggct tctatctgaa cttggtgttt gtgttgaaat tgtgggggac   1140
gaaactagga ggtttggaag agaagaggta ggaaatgtaa taagaagagt ggttggtggg   1200
aagatagggg acgatttgag aaggaaagtg aaagaacttg gagcaaagat aaaggaaaaa   1260
caagaggaag agatggatga tgtgcttgat gaattagtac aaatttgtaa caagaaaaaa   1320
cggactgttg tacatcatca tcatcatcat tga                                 1353
```

<210> SEQ ID NO 6
<211> LENGTH: 450
<212> TYPE: PRT
<213> ORGANISM: Panax ginseng
<220> FEATURE:
<221> NAME/KEY: misc_feature
<223> OTHER INFORMATION: gGT30

<400> SEQUENCE: 6

```
Met Ala Thr Gln Lys Cys Phe Arg Val Leu Val Phe Pro Trp Leu Ala
1               5                   10                  15

His Gly His Ile Ser Pro Phe Leu Glu Leu Ala Arg Lys Leu Ile Glu
            20                  25                  30

Lys Gly Asn Phe Phe Ile Tyr Phe Cys Ser Thr Pro Ile Asn Leu Ile
        35                  40                  45

Ser Ile Lys Lys Lys Leu Ser Gly Asp Asp His Gln Asn Tyr Thr Lys
    50                  55                  60

Ser Ile Gln Leu Val Glu His Asn Leu Pro Thr Leu Pro Gln Leu Pro
65                  70                  75                  80

Pro His Tyr His Thr Thr Asp Gly Leu Pro Pro Asn Leu Asn Pro Thr
                85                  90                  95

Leu Arg Lys Ala Phe Glu Met Ser Lys Leu Ser Phe Pro Asn Thr Leu
            100                 105                 110

Asn Thr Leu Lys Pro Asp Leu Leu Ile Cys Asp Asp Leu Phe Gln Trp
        115                 120                 125

Pro Glu Ile Val Ala Ser Ser His Gly Val Pro Val Val Arg Phe Gln
    130                 135                 140

Thr Cys Ser Val Thr Ala Ala Ser Phe Leu Ala His Ile Phe Thr Asn
145                 150                 155                 160

Pro Asp Val Thr Tyr Pro Phe Pro Ala Ile Tyr Leu His Glu Tyr Glu
                165                 170                 175

Thr Asp Gln Ile Arg Arg Cys Val Asp Ala Val Phe Glu Ser Gly Arg
            180                 185                 190

Glu Glu Ser Arg Asn Leu Leu Val Val Asn Thr Ser Lys Ala Ile Glu
        195                 200                 205

Glu Lys Tyr Phe Tyr Tyr Ser Leu Leu Arg Gly Asn Thr Lys Ile
    210                 215                 220
```

```
Met Pro Val Gly Pro Leu Ile Gln Gln Ala Pro Asn Gly Asp Glu Asp
225                 230                 235                 240

Met Lys Val Ile Glu Trp Leu Asp Lys Lys Asp Pro Cys Ser Thr Val
            245                 250                 255

Phe Val Ser Phe Gly Ser Glu Tyr Phe Met Gln Lys Glu Glu Val Glu
        260                 265                 270

Glu Met Ala His Gly Leu Glu Leu Ser Asn Val Asn Phe Ile Trp Val
    275                 280                 285

Phe Arg Ala Pro Val Gly Ala Glu Lys Val Lys Leu Pro Leu Gly Phe
290                 295                 300

Val Glu Arg Val Gly Gly Arg Gly Ile Val Met Glu Gly Trp Ala Pro
305                 310                 315                 320

Gln Ala Arg Ile Leu Gly His Ser Ser Ile Gly Gly Phe Val Ser His
            325                 330                 335

Cys Gly Trp Asn Ser Val Leu Glu Thr Ile Asn Phe Gly Val Pro Ile
        340                 345                 350

Ile Gly Met Pro Met Lys Phe Glu Gln Pro Met Asn Ala Arg Leu Leu
    355                 360                 365

Ser Glu Leu Gly Val Cys Val Glu Ile Val Gly Asp Glu Thr Arg Arg
370                 375                 380

Phe Gly Arg Glu Glu Val Gly Asn Val Ile Arg Glu Val Val Gly Gly
385                 390                 395                 400

Lys Ile Gly Asp Asp Leu Arg Arg Lys Val Lys Glu Leu Gly Ala Lys
            405                 410                 415

Ile Lys Glu Lys Gln Glu Glu Met Asp Asp Val Leu Asp Glu Leu
        420                 425                 430

Val Gln Ile Cys Asn Lys Lys Lys Arg Thr Val Val His His His His
    435                 440                 445

His His
    450

<210> SEQ ID NO 7
<211> LENGTH: 26
<212> TYPE: DNA
<213> ORGANISM: Panax ginseng

<400> SEQUENCE: 7
ccaagttcat tcaagatgaa gtcaga                                        26

<210> SEQ ID NO 8
<211> LENGTH: 28
<212> TYPE: DNA
<213> ORGANISM: Artificial sequece
<220> FEATURE:
<223> OTHER INFORMATION: synthesized nucleotides

<400> SEQUENCE: 8
cataatttcc tcaaatagct tcgccaat                                      28

<210> SEQ ID NO 9
<211> LENGTH: 24
<212> TYPE: DNA
<213> ORGANISM: Artificial sequece
<220> FEATURE:
<223> OTHER INFORMATION: synthesized nucleotides

<400> SEQUENCE: 9
actggagcag ttgcaacata caaa                                          24
```

<210> SEQ ID NO 10
<211> LENGTH: 24
<212> TYPE: DNA
<213> ORGANISM: Artificial sequece
<220> FEATURE:
<223> OTHER INFORMATION: synthesized nucleotides

<400> SEQUENCE: 10
tcatttatgc gctttcctgg atgt                                          24

<210> SEQ ID NO 11
<211> LENGTH: 21
<212> TYPE: DNA
<213> ORGANISM: Artificial sequece
<220> FEATURE:
<223> OTHER INFORMATION: synthesized nucleotides

<400> SEQUENCE: 11
acgagggtgg ttttaatggc a                                             21

<210> SEQ ID NO 12
<211> LENGTH: 27
<212> TYPE: DNA
<213> ORGANISM: Artificial sequece
<220> FEATURE:
<223> OTHER INFORMATION: synthesized nucleotides

<400> SEQUENCE: 12
acaccattca taatcataca acagtcc                                       27

<210> SEQ ID NO 13
<211> LENGTH: 29
<212> TYPE: DNA
<213> ORGANISM: Artificial sequece
<220> FEATURE:
<223> OTHER INFORMATION: synthesized nucleotides

<400> SEQUENCE: 13
atatggtacc atggcagtag ccggcgctg                                     29

<210> SEQ ID NO 14
<211> LENGTH: 57
<212> TYPE: DNA
<213> ORGANISM: Artificial sequece
<220> FEATURE:
<223> OTHER INFORMATION: synthesized nucleotides

<400> SEQUENCE: 14
gcgctctaga ttaatgatga tgatgatgat gttttattat atgttttttg gggtcgc      57

<210> SEQ ID NO 15
<211> LENGTH: 1428
<212> TYPE: DNA
<213> ORGANISM: Panax ginseng
<220> FEATURE:
<221> NAME/KEY: misc_feature
<223> OTHER INFORMATION: gGT25-1

<400> SEQUENCE: 15
atgaagtcag aattgatatt cttgcccgcc ccggccatcg acacctcgt ggggaatggtg    60 gagatggcta aactcttcat cagtcgacat gaaaacctct cggtcaccgt cctcatcgcg   120
aaattctaca tggatacggg ggtagacaac tacaataaat cactcttaac aaaccctacc   180
ccgcgtctca caattgtaaa tctcccggaa accgaccccc aaaactatat gctcaaacca   240

-continued

```
cgccatgcca tctttcctag cgtcatcgag actcagaaga cacacgtgcg agacataata    300
tcaggcatga ctcagtccga gtcgactcgg gtcgttggtt tgctggctga ccttttgttc    360
atcaacatta tggacattgc caatgagttc aatgttccaa cttatgtata ctcccctgcc    420
ggagccggtc atcttggcct cgcgttccat ctccagacac tcaacgacaa aaagcaagat    480
gtgaccgagt tcaggaactc ggacactgag ttattggtac cgagttttgc aaacccggtt    540
cccgccgagg tcttgccgtc gatgtatgtg gataaagaag gtgggtatga ttatttgttt    600
tcattgttcc ggaggtgcag agagtcaaag gcaattatta ttaacacgtt tgaggagctg    660
gaaccctatg cgatcaattc cctccggatg gatagtatga tccctccgat ctacccggtg    720
ggacccatac taaatctcaa cggtgatggc caaaactccg atgaggctgc tgtgatcctt    780
ggttggttag atgatcaacc accttcatct gtggtgtttt tgtgctttgg tagctatgga    840
acctttcaag aaaaccaggt gaaggagatt gcaatgggtc tagagcgcag tgggcatcgc    900
ttcttgtggt ccttgcgtcc gtctatccct aaaggcgaga caaagcttca gcttaaatac    960
tcaaatttgg aagaaattct cccagtcgga ttccttggaca ggacatcatg cgtcggaaaa   1020
gttattggat gggccccgca agtggcggtg ctcggacacg aggcagtcgg agggttcctg   1080
tctcattgtg gttggaattc gacattagag agtgtgtggt gtggcgtgcc cgtcgcaaca   1140
tggccaatgt acggcgagca acaactcaat gcttttgaga tggttaagga gttaggtatt   1200
gcggtggaaa ttgaggtgga ctataagaat gaatatttta acatgaataa tgattttatt   1260
gttagggcag aagaaatcga gacgaaaata aagaagttga tgatggatga aaagaatagt   1320
gaaataagga agaaggtaaa ggaaatgaaa gaaagagta ggcttgcaat gtctgagaat   1380
ggatcatctt ataattcatt ggcgaagcta tttgaggaaa tcatgtaa                1428
```

<210> SEQ ID NO 16
<211> LENGTH: 475
<212> TYPE: PRT
<213> ORGANISM: Panax ginseng
<220> FEATURE:
<221> NAME/KEY: misc_feature
<223> OTHER INFORMATION: gGT25-1

<400> SEQUENCE: 16

```
Met Lys Ser Glu Leu Ile Phe Leu Pro Ala Pro Ala Ile Gly His Leu
1               5                  10                  15

Val Gly Met Val Glu Met Ala Lys Leu Phe Ile Ser Arg His Glu Asn
            20                  25                  30

Leu Ser Val Thr Val Leu Ile Ala Lys Phe Tyr Met Asp Thr Gly Val
        35                  40                  45

Asp Asn Tyr Asn Lys Ser Leu Leu Thr Asn Pro Thr Pro Arg Leu Thr
    50                  55                  60

Ile Val Asn Leu Pro Glu Thr Asp Pro Gln Asn Tyr Met Leu Lys Pro
65                  70                  75                  80

Arg His Ala Ile Phe Pro Ser Val Ile Glu Thr Gln Lys Thr His Val
                85                  90                  95

Arg Asp Ile Ile Ser Gly Met Thr Gln Ser Glu Ser Thr Arg Val Val
            100                 105                 110

Gly Leu Leu Ala Asp Leu Leu Phe Ile Asn Ile Met Asp Ile Ala Asn
        115                 120                 125

Glu Phe Asn Val Pro Thr Tyr Val Tyr Ser Pro Ala Gly Ala Gly His
    130                 135                 140

Leu Gly Leu Ala Phe His Leu Gln Thr Leu Asn Asp Lys Lys Gln Asp
```

```
                145                 150                 155                 160
Val Thr Glu Phe Arg Asn Ser Asp Thr Glu Leu Leu Val Pro Ser Phe
                165                 170                 175

Ala Asn Pro Val Pro Ala Glu Val Leu Pro Ser Met Tyr Val Asp Lys
            180                 185                 190

Glu Gly Gly Tyr Asp Tyr Leu Phe Ser Leu Phe Arg Cys Arg Glu
        195                 200                 205

Ser Lys Ala Ile Ile Ile Asn Thr Phe Glu Glu Leu Glu Pro Tyr Ala
    210                 215                 220

Ile Asn Ser Leu Arg Met Asp Ser Met Ile Pro Pro Ile Tyr Pro Val
225                 230                 235                 240

Gly Pro Ile Leu Asn Leu Asn Gly Asp Gly Gln Asn Ser Asp Glu Ala
                245                 250                 255

Ala Val Ile Leu Gly Trp Leu Asp Asp Gln Pro Pro Ser Ser Val Val
            260                 265                 270

Phe Leu Cys Phe Gly Ser Tyr Gly Thr Phe Gln Glu Asn Gln Val Lys
        275                 280                 285

Glu Ile Ala Met Gly Leu Glu Arg Ser Gly His Arg Phe Leu Trp Ser
    290                 295                 300

Leu Arg Pro Ser Ile Pro Lys Gly Glu Thr Lys Leu Gln Leu Lys Tyr
305                 310                 315                 320

Ser Asn Leu Glu Glu Ile Leu Pro Val Gly Phe Leu Asp Arg Thr Ser
                325                 330                 335

Cys Val Gly Lys Val Ile Gly Trp Ala Pro Gln Val Ala Val Leu Gly
            340                 345                 350

His Glu Ala Val Gly Gly Phe Leu Ser His Cys Gly Trp Asn Ser Thr
        355                 360                 365

Leu Glu Ser Val Trp Cys Gly Val Pro Val Ala Thr Trp Pro Met Tyr
    370                 375                 380

Gly Glu Gln Gln Leu Asn Ala Phe Glu Met Val Lys Glu Leu Gly Ile
385                 390                 395                 400

Ala Val Glu Ile Glu Val Asp Tyr Lys Asn Glu Tyr Phe Asn Met Asn
                405                 410                 415

Asn Asp Phe Ile Val Arg Ala Glu Glu Ile Glu Thr Lys Ile Lys Lys
            420                 425                 430

Leu Met Met Asp Glu Lys Asn Ser Glu Ile Arg Lys Lys Val Lys Glu
        435                 440                 445

Met Lys Glu Lys Ser Arg Leu Ala Met Ser Glu Asn Gly Ser Ser Tyr
    450                 455                 460

Asn Ser Leu Ala Lys Leu Phe Glu Glu Ile Met
465                 470                 475

<210> SEQ ID NO 17
<211> LENGTH: 1428
<212> TYPE: DNA
<213> ORGANISM: Panax ginseng
<220> FEATURE:
<221> NAME/KEY: misc_feature
<223> OTHER INFORMATION: gGT25-3

<400> SEQUENCE: 17
atgaagtcag aattgatatt cttgcccgcc ccggccatcg acacctcgt gggaatggtg    60 gagatggcta aactcttcat cagtcgacat gaaaatctct cggtcaccgt cctcatcgcg   120
aaattctaca tggatacggg ggtagacaac tacaataaat cactcttaac aaaccctacc   180
```

-continued

```
ccgcgtctca caattgtaaa tctcccggaa accgaccccc aaaactatat gctcaaacca    240
cgccacgcca tctttcctag cgtcatcgag actcagaaga cacacgtgcg agacataata    300
tccggtatga ctcagtccga gtcgactcag gtcgttggtt tgctggctga ccttttgttc    360
atcaacatca tggacattgc caatgagttc aatgttccaa cttatgtata ctcccctgcc    420
ggagccggtc atcttggcct cgcgttccat ctccagacac tcaacgacaa aaacaagat    480 gtgaccgagt tcaggaactc ggatactgag ttattggtac cgagttttgc aaacccggtt    540
cccgccgagg tcttgccgtc gatgtatgtg ataaagaag gtgggtatga ttatctgttt    600
tcattgttcc ggaggtgcag agagtcaaag gcaattatta ttaacacgtt tgaggagctg    660
gaaccctatg cgatcaattc cctccggatg gatagtatga tccctccgat ctacccggtg    720
ggacccatac taaatctcaa cggtgatggc caaaactccg atgaggctgc tgtgatcctt    780
ggttggttag atgatcaacc accttcatct gtggtgtttt tgtgctttgg tagctatgga    840
agctttcaag aaaaccaggt gaaggagatt gcaatgggtc tagagcgcag tgggcatcgc    900
ttcttgtggt ccttgcgtcc gtctatccct aaaggcgaga caaagcttca gcttaaatac    960
tcaaatttga agaaattct cccagtagga ttcttggaca ggacatcatg cgtcggaaaa    1020
gtgattggat gggccccgca gtggccgtg ctcggacatg agtcagtcgg agggttcctg    1080
tctcattgcg gttggaattc gacattggag agtgtttggt gtggggtgcc cgttgcaaca    1140
tggccaatgt atggtgagca caactcaat gcttttgaga tggttaagga gttaggtatt    1200
gcggtggaaa ttgaggtgga ctataagaaa gattattta acatgaagaa tgattttatt    1260
gttagggcag aagaaatcga gacaaaaata aagaagttga tgatggatga aaataatagt    1320
gaaataagaa agaaggtaaa ggaaatgaaa gaaagagta gggctgcaat gtctgagaat    1380
ggatcatctt ataattcatt ggcgaagcta tttgaggaaa ttatgtaa                 1428
```

<210> SEQ ID NO 18
<211> LENGTH: 475
<212> TYPE: PRT
<213> ORGANISM: Panax ginseng
<220> FEATURE:
<221> NAME/KEY: misc_feature
<223> OTHER INFORMATION: gGT25-3

<400> SEQUENCE: 18

```
Met Lys Ser Glu Leu Ile Phe Leu Pro Ala Pro Ala Ile Gly His Leu
 1               5                  10                  15

Val Gly Met Val Glu Met Ala Lys Leu Phe Ile Ser Arg His Glu Asn
             20                  25                  30

Leu Ser Val Thr Val Leu Ile Ala Lys Phe Tyr Met Asp Thr Gly Val
         35                  40                  45

Asp Asn Tyr Asn Lys Ser Leu Leu Thr Asn Pro Thr Pro Arg Leu Thr
     50                  55                  60

Ile Val Asn Leu Pro Glu Thr Asp Pro Gln Asn Tyr Met Leu Lys Pro
 65                  70                  75                  80

Arg His Ala Ile Phe Pro Ser Val Ile Glu Thr Gln Lys Thr His Val
                 85                  90                  95

Arg Asp Ile Ile Ser Gly Met Thr Gln Ser Glu Ser Thr Gln Val Val
            100                 105                 110

Gly Leu Leu Ala Asp Leu Leu Phe Ile Asn Ile Met Asp Ile Ala Asn
        115                 120                 125

Glu Phe Asn Val Pro Thr Tyr Val Tyr Ser Pro Ala Gly Ala Gly His
    130                 135                 140
```

Leu Gly Leu Ala Phe His Leu Gln Thr Leu Asn Asp Lys Lys Gln Asp
145                 150                 155                 160

Val Thr Glu Phe Arg Asn Ser Asp Thr Glu Leu Leu Val Pro Ser Phe
            165                 170                 175

Ala Asn Pro Val Pro Ala Glu Val Leu Pro Ser Met Tyr Val Asp Lys
        180                 185                 190

Glu Gly Gly Tyr Asp Tyr Leu Phe Ser Leu Phe Arg Arg Cys Arg Glu
    195                 200                 205

Ser Lys Ala Ile Ile Ile Asn Thr Phe Glu Glu Leu Glu Pro Tyr Ala
210                 215                 220

Ile Asn Ser Leu Arg Met Asp Ser Met Ile Pro Pro Ile Tyr Pro Val
225                 230                 235                 240

Gly Pro Ile Leu Asn Leu Asn Gly Asp Gly Gln Asn Ser Asp Glu Ala
            245                 250                 255

Ala Val Ile Leu Gly Trp Leu Asp Asp Gln Pro Pro Ser Ser Val Val
        260                 265                 270

Phe Leu Cys Phe Gly Ser Tyr Gly Ser Phe Gln Glu Asn Gln Val Lys
    275                 280                 285

Glu Ile Ala Met Gly Leu Glu Arg Ser Gly His Arg Phe Leu Trp Ser
290                 295                 300

Leu Arg Pro Ser Ile Pro Lys Gly Glu Thr Lys Leu Gln Leu Lys Tyr
305                 310                 315                 320

Ser Asn Leu Lys Glu Ile Leu Pro Val Gly Phe Leu Asp Arg Thr Ser
            325                 330                 335

Cys Val Gly Lys Val Ile Gly Trp Ala Pro Gln Val Ala Val Leu Gly
        340                 345                 350

His Glu Ser Val Gly Gly Phe Leu Ser His Cys Gly Trp Asn Ser Thr
    355                 360                 365

Leu Glu Ser Val Trp Cys Gly Val Pro Val Ala Thr Trp Pro Met Tyr
370                 375                 380

Gly Glu Gln Gln Leu Asn Ala Phe Glu Met Val Lys Glu Leu Gly Ile
385                 390                 395                 400

Ala Val Glu Ile Glu Val Asp Tyr Lys Lys Asp Tyr Phe Asn Met Lys
            405                 410                 415

Asn Asp Phe Ile Val Arg Ala Glu Glu Ile Glu Thr Lys Ile Lys Lys
        420                 425                 430

Leu Met Met Asp Glu Asn Asn Ser Glu Ile Arg Lys Val Lys Glu
    435                 440                 445

Met Lys Glu Lys Ser Arg Ala Ala Met Ser Glu Asn Gly Ser Ser Tyr
450                 455                 460

Asn Ser Leu Ala Lys Leu Phe Glu Glu Ile Met
465                 470                 475

<210> SEQ ID NO 19
<211> LENGTH: 1419
<212> TYPE: DNA
<213> ORGANISM: Panax ginseng
<220> FEATURE:
<221> NAME/KEY: misc_feature
<223> OTHER INFORMATION: gGT25-5

<400> SEQUENCE: 19
atgaagtcag aattgatatt cgtgcccgtc ccggccttcg ggcacctcgt ggggatggtg    60
gagatggcta aacttttcat cagtcgacac gaaaacctat cagtcaccgt cctcatttcg   120

-continued

```
aaatttttca ttgatacggg gatagacaac tacaataaat cactcttagc gaaacctacc    180
ccgcgtctca caattataaa tctcccggaa atcgatcccc aaaaatattt gctcaaacca    240
cgttgcgcca tctttccttc cctcatcgag aatcagaaga cacacgtgcg agacgtaatg    300
tcccgcatga ctcagtccga gtcgactcgg gtcgttggtt tgctggcaga cattttgttc    360
gtcgacatct tcgacattgc cgatgagttc aatgttccaa cttatgtata ctcccctgcc    420
ggagccggtt ttcttggcct cgcgttccat ctccagacac tcaacgacga caaaaagcaa    480
gatgtgaccg agttcaggaa ttcggacact gagttattgg taccgagttt tgcaaacccg    540
gtccccgccg agttcttgcc gtcgatattt ttggaaaaag atggtaggca tgatgttttg    600
ttatcattgt actggaggtg cagggaggca aagggaatta ttgttaacac gtttgaggag    660
ctggaaccct atgcgatcaa ttccctccgg atggatagta tgatccctcc gatctacccg    720
gtgggaccca tactaaatct caacggtgag ggacaaaact ccgatgaggc tgctgtgatc    780
cttggttggt tagatgatca accaccttca tctgtggtgt ttttgtgctt tggtagcttt    840
ggaagctttc cagaaaacca ggtgaaggag attgcaatgg gtttagagcg cagcgggcat    900
cgcttcttgt ggtccttgcg tccgtgtatc tctgaaggtg agacaacgct tcaacttaaa    960
tactcaaatt tggaacttcc ggccggattc ttggatagga catcatgcgt cggaaaagtg   1020
attggatggg ccccacaaat ggccatccta gcacacgagg cagtcggagg gttcgtgtct   1080
cattgtggtt ggaattcggt actagagagt gtgtggtatg gcatgcctgt cgcaacatgg   1140
ccaatgtacg gtgagcaaca actcaacgct tttgagatgg ttaaggagtt gggtcttgcg   1200
gtggaaattg aggtggacta taggaatgaa tataacaagt ctgattttat tgttaaggct   1260
gacgaaattg agacaaaaat aaagaagttg atgatggatg gaaagaatag taaaataagg   1320
aagaaggtaa aggaaatgaa agaaaagagt agggttgcca tgtcggagaa tgggtcatct   1380
tatacttcat tggcgaagct atttgaggaa attatgtaa                          1419
```

<210> SEQ ID NO 20
<211> LENGTH: 472
<212> TYPE: PRT
<213> ORGANISM: Panax ginseng
<220> FEATURE:
<221> NAME/KEY: misc_feature
<223> OTHER INFORMATION: gGT25-5

<400> SEQUENCE: 20

```
Met Lys Ser Glu Leu Ile Phe Val Pro Val Pro Ala Phe Gly His Leu
1               5                   10                  15

Val Gly Met Val Glu Met Ala Lys Leu Phe Ile Ser Arg His Glu Asn
            20                  25                  30

Leu Ser Val Thr Val Leu Ile Ser Lys Phe Phe Ile Asp Thr Gly Ile
        35                  40                  45

Asp Asn Tyr Asn Lys Ser Leu Leu Ala Lys Pro Thr Pro Arg Leu Thr
    50                  55                  60

Ile Ile Asn Leu Pro Glu Ile Asp Pro Gln Lys Tyr Leu Leu Lys Pro
65                  70                  75                  80

Arg Cys Ala Ile Phe Pro Ser Leu Ile Glu Asn Gln Lys Thr His Val
                85                  90                  95

Arg Asp Val Met Ser Arg Met Thr Gln Ser Glu Ser Thr Arg Val Val
            100                 105                 110

Gly Leu Leu Ala Asp Ile Leu Phe Val Asp Ile Phe Asp Ile Ala Asp
        115                 120                 125
```

```
Glu Phe Asn Val Pro Thr Tyr Val Tyr Ser Pro Ala Gly Ala Gly Phe
130                 135                 140

Leu Gly Leu Ala Phe His Leu Gln Thr Leu Asn Asp Asp Lys Lys Gln
145                 150                 155                 160

Asp Val Thr Glu Phe Arg Asn Ser Asp Thr Glu Leu Leu Val Pro Ser
                165                 170                 175

Phe Ala Asn Pro Val Pro Ala Glu Phe Leu Pro Ser Ile Phe Leu Glu
            180                 185                 190

Lys Asp Gly Arg His Asp Val Leu Leu Ser Leu Tyr Trp Arg Cys Arg
            195                 200                 205

Glu Ala Lys Gly Ile Ile Val Asn Thr Phe Glu Glu Leu Glu Pro Tyr
210                 215                 220

Ala Ile Asn Ser Leu Arg Met Asp Ser Met Ile Pro Pro Ile Tyr Pro
225                 230                 235                 240

Val Gly Pro Ile Leu Asn Leu Asn Gly Glu Gly Gln Asn Ser Asp Glu
                245                 250                 255

Ala Ala Val Ile Leu Gly Trp Leu Asp Asp Gln Pro Pro Ser Ser Val
            260                 265                 270

Val Phe Leu Cys Phe Gly Ser Phe Gly Ser Phe Pro Glu Asn Gln Val
            275                 280                 285

Lys Glu Ile Ala Met Gly Leu Glu Arg Ser Gly His Arg Phe Leu Trp
290                 295                 300

Ser Leu Arg Pro Cys Ile Ser Glu Gly Glu Thr Thr Leu Gln Leu Lys
305                 310                 315                 320

Tyr Ser Asn Leu Glu Leu Pro Ala Gly Phe Leu Asp Arg Thr Ser Cys
                325                 330                 335

Val Gly Lys Val Ile Gly Trp Ala Pro Gln Met Ala Ile Leu Ala His
            340                 345                 350

Glu Ala Val Gly Gly Phe Val Ser His Cys Gly Trp Asn Ser Val Leu
            355                 360                 365

Glu Ser Val Trp Tyr Gly Met Pro Val Ala Thr Trp Pro Met Tyr Gly
370                 375                 380

Glu Gln Gln Leu Asn Ala Phe Glu Met Val Lys Glu Leu Gly Leu Ala
385                 390                 395                 400

Val Glu Ile Glu Val Asp Tyr Arg Asn Glu Tyr Asn Lys Ser Asp Phe
                405                 410                 415

Ile Val Lys Ala Asp Glu Ile Glu Thr Lys Ile Lys Lys Leu Met Met
            420                 425                 430

Asp Gly Lys Asn Ser Lys Ile Arg Lys Lys Val Lys Glu Met Lys Glu
            435                 440                 445

Lys Ser Arg Val Ala Met Ser Glu Asn Gly Ser Ser Tyr Thr Ser Leu
450                 455                 460

Ala Lys Leu Phe Glu Glu Ile Met
465                 470

<210> SEQ ID NO 21
<211> LENGTH: 1488
<212> TYPE: DNA
<213> ORGANISM: Barbarea vulgaris
<220> FEATURE:
<221> NAME/KEY: misc_feature
<223> OTHER INFORMATION: 3GT1

<400> SEQUENCE: 21
atggtttccg aaatcaccca taaatcttat cctcttcact ttgttctctt cccttttcatg    60
```

```
gctcaaggcc acatgattcc catggttgat attgcaaggc tcttggctca gcgcggtgtg    120
aaaataacaa ttgtcacaac gccgcacaat gcagcgaggt tcgagaatgt cctaagccgt    180
gccattgagt ctggcttgcc catcagcata gtgcaagtca agcttccatc tcaagaagct    240
ggcttaccag aaggaaatga gactttcgat tcacttgtct caacaaagtt gctggtacct    300
ttctttaaag cggttaacat gcttgaagaa ccggtccaga agctctttga agagatgagc    360
cctcaaccaa gctgtataat ttctgatttt tgtttgcctt atacaagcaa aatcgccaag    420
aagttcaata tcccaaagat cctcttccat ggcatgtgtt gcttttgtct tctgtgtatg    480
catgttttac gcaagaaccg tgagatcttg gaaaacttaa agtctgacaa ggagcatttc    540
gttgttcctt attttcctga tcgagttgaa ttcacaagac ctcaagttcc attggcaaca    600
tatgttcctg gggaatggca cgagatcaag gaggatatgg tagaagcgga taagacttcc    660
tatggtgtga tagtcaacac atatcaagag ctcgagcctg cttatgccaa cggctacaag    720
gaggcaaggt ctggtaaagc atggaccatt ggacctgttt ccttgtgcaa caaggtggga    780
gccgacaaag cagagagggg aaacaaagca gacattgatc aagatgagtg tcttaaatgg    840
cttgattcta agaagaagg ttcggttcta tatgtttgcc ttggaagtat ctgcagtctt    900
cctctgtctc agctcaagga gctggggcta ggccttgagg aatcccaaag acctttcatt    960
tgggtcgtaa gaggttggga gaagaacaaa gagttacttg agtggttctc ggagagcgga    1020
tttgaagaaa gagtaaaaga cagagggctt ctcatcaaag gatggtcacc tcaaatgctt    1080
atccttgcac atcattccgt tggagggttc ttaacacact gtggatggaa ctcgaccctc    1140
gaaggaatca cttcaggcgt tccattgctc acttggccac tgtttggaga ccaattctgc    1200
aaccaaaaac ttgtcgtgca ggtgctaaaa gtgggtgtaa gtgccggggt tgaagaggtt    1260
acgaattggg gagaagagga gaaaatagga gtattagtgg ataaagaggg agtgaagaag    1320
gcagtggaag aattaatggg tgagagtgat gatgctaaag aaataagaaa aagagtcaaa    1380
gagcttggac aattagctca caaggctgtg gaggaaggag gctcatctca ttctaatatc    1440
acatccttgc tagaagacat aatgcaacta gcacaaccta ataattaa                 1488
```

<210> SEQ ID NO 22
<211> LENGTH: 495
<212> TYPE: PRT
<213> ORGANISM: Barbarea vulgaris
<220> FEATURE:
<221> NAME/KEY: misc_feature
<223> OTHER INFORMATION: 3GT1

<400> SEQUENCE: 22

Met Val Ser Glu Ile Thr His Lys Ser Tyr Pro Leu His Phe Val Leu
1               5                   10                  15

Phe Pro Phe Met Ala Gln Gly His Met Ile Pro Met Val Asp Ile Ala
            20                  25                  30

Arg Leu Leu Ala Gln Arg Gly Val Lys Ile Thr Ile Val Thr Thr Pro
        35                  40                  45

His Asn Ala Ala Arg Phe Glu Asn Val Leu Ser Arg Ala Ile Glu Ser
    50                  55                  60

Gly Leu Pro Ile Ser Ile Val Gln Val Lys Leu Pro Ser Gln Glu Ala
65                  70                  75                  80

Gly Leu Pro Glu Gly Asn Glu Thr Phe Asp Ser Leu Val Ser Thr Lys
                85                  90                  95

Leu Leu Val Pro Phe Phe Lys Ala Val Asn Met Leu Glu Glu Pro Val
            100                 105                 110

```
Gln Lys Leu Phe Glu Glu Met Ser Pro Gln Pro Ser Cys Ile Ile Ser
            115                 120                 125

Asp Phe Cys Leu Pro Tyr Thr Ser Lys Ile Ala Lys Lys Phe Asn Ile
    130                 135                 140

Pro Lys Ile Leu Phe His Gly Met Cys Phe Cys Leu Leu Cys Met
145                 150                 155                 160

His Val Leu Arg Lys Asn Arg Glu Ile Leu Glu Asn Leu Lys Ser Asp
                165                 170                 175

Lys Glu His Phe Val Val Pro Tyr Phe Pro Asp Arg Val Glu Phe Thr
            180                 185                 190

Arg Pro Gln Val Pro Leu Ala Thr Tyr Val Pro Gly Trp His Glu
            195                 200                 205

Ile Lys Glu Asp Met Val Glu Ala Asp Lys Thr Ser Tyr Gly Val Ile
            210                 215                 220

Val Asn Thr Tyr Gln Glu Leu Glu Pro Ala Tyr Ala Asn Gly Tyr Lys
225                 230                 235                 240

Glu Ala Arg Ser Gly Lys Ala Trp Thr Ile Gly Pro Val Ser Leu Cys
                245                 250                 255

Asn Lys Val Gly Ala Asp Lys Ala Glu Arg Gly Asn Lys Ala Asp Ile
            260                 265                 270

Asp Gln Asp Glu Cys Leu Lys Trp Leu Asp Ser Lys Glu Glu Gly Ser
            275                 280                 285

Val Leu Tyr Val Cys Leu Gly Ser Ile Cys Ser Leu Pro Leu Ser Gln
            290                 295                 300

Leu Lys Glu Leu Gly Leu Gly Leu Glu Glu Ser Gln Arg Pro Phe Ile
305                 310                 315                 320

Trp Val Val Arg Gly Trp Glu Lys Asn Lys Glu Leu Leu Glu Trp Phe
                325                 330                 335

Ser Glu Ser Gly Phe Glu Glu Arg Val Lys Asp Arg Gly Leu Leu Ile
            340                 345                 350

Lys Gly Trp Ser Pro Gln Met Leu Ile Leu Ala His His Ser Val Gly
            355                 360                 365

Gly Phe Leu Thr His Cys Gly Trp Asn Ser Thr Leu Glu Gly Ile Thr
            370                 375                 380

Ser Gly Val Pro Leu Leu Thr Trp Pro Leu Phe Gly Asp Gln Phe Cys
385                 390                 395                 400

Asn Gln Lys Leu Val Val Gln Val Leu Lys Val Gly Val Ser Ala Gly
                405                 410                 415

Val Glu Glu Val Thr Asn Trp Gly Glu Glu Lys Ile Gly Val Leu
            420                 425                 430

Val Asp Lys Glu Gly Val Lys Lys Ala Val Glu Glu Leu Met Gly Glu
            435                 440                 445

Ser Asp Asp Ala Lys Glu Ile Arg Lys Arg Val Lys Glu Leu Gly Gln
            450                 455                 460

Leu Ala His Lys Ala Val Glu Glu Gly Gly Ser Ser His Ser Asn Ile
465                 470                 475                 480

Thr Ser Leu Leu Glu Asp Ile Met Gln Leu Ala Gln Pro Asn Asn
                485                 490                 495

<210> SEQ ID NO 23
<211> LENGTH: 1488
<212> TYPE: DNA
<213> ORGANISM: Barbarea vulgaris
<220> FEATURE:
```

<221> NAME/KEY: misc_feature
<223> OTHER INFORMATION: 3GT2

<400> SEQUENCE: 23

```
atggtttccg aaatcaccca taaatcttat cctcttcact ttgttctctt ccctttcatg      60
gctcaaggcc acatgattcc catggttgat attgcaaggc tcttggccca gcgcggtgtg     120
aaaataacaa ttgtcacaac cccgcacaat gcagcgaggt tcaagaatgt cctaagtcgt     180
gccattgagt ctggcttgcc catcagcata gtgcaagtca agcttccatc tcaagaagct     240
ggcttaccag aaggaaatga gactctcgat tcacttgtct cgatggagtt gatgatacat     300
ttcttaaaag cggttaacat gctggaagaa ccggtccaga agctctttga agagatgagc     360
cctcaaccaa gctgtataat ttctgatttt tgtttgcctt atacaagcaa aatcgccaag     420
aagttcaata tcccaaagat cctcttccat ggcatgtgct gcttttgtct tctgtgtatg     480
catattttac gcaagaaccg tgagatcgtg aaaacttaa agtctgacaa ggagcatttc      540
gttgttcctt attttcctga tcgagttgaa ttcacaagac ctcaagttcc agtggcaaca     600
tatgttcctg gagactggca cgagatcacg gaggatatgg tagaagcgga taagacttcc     660
tatggtgtga tagtcaacac atatcaagag ctcgagcctg cttatgccaa cgactacaag     720
gaggcaaggt ctggtaaagc atggaccatt ggacctgttt ccttgtgcaa caaggtggga     780
gcggacaaag cagagagggg aaacaaagca gacattgatc aagatgagtg tcttaaatgg     840
cttaattcta agaagaagg ttcggttcta tatgtttgcc ttggaagtat ctgcaatctt     900
cctctgtctc agctcaagga gctcgggcta ggccttgagg aatcccaaag acctttcatt     960
tgggtcataa gaggttggga aagaacaaa gagttacatg agtggttctc ggagagcgga    1020
ttcgaagaaa gaatcaaaga cagaggactt ctcatcaaag gatgggctcc tcaaatgctt    1080
atactttcac atcattccgt tggagggttc ttaacacact gtggatggaa ctcgactctt    1140
gaggggctaa ccgctggtct accactgctg catggccgc ttttcgcaga ccagttctgc    1200
aacgagaaac ttgccgtgca ggtattaaaa gccggtgtaa gcgccggggt tgaccagcct    1260
atgaaatggg gagaagagga gaaaatagga gtgttggtgg ataaagaagg agtgaagaag    1320
gcagtggaag aattaatggg tgagagtgat gatgctaaag agataagaag aagagccaaa    1380
gagcttggag aattagctca caaggctgtg gaggaaggag gctcatctca ttctaatatc    1440
acatcccttc tagaagacat aatgcaacta gcacaatcca ataattaa                  1488
```

<210> SEQ ID NO 24
<211> LENGTH: 495
<212> TYPE: PRT
<213> ORGANISM: Barbarea vulgaris
<220> FEATURE:
<221> NAME/KEY: misc_feature
<223> OTHER INFORMATION: 3GT2

<400> SEQUENCE: 24

```
Met Val Ser Glu Ile Thr His Lys Ser Tyr Pro Leu His Phe Val Leu
1               5                   10                  15

Phe Pro Phe Met Ala Gln Gly His Met Ile Pro Met Val Asp Ile Ala
            20                  25                  30

Arg Leu Leu Ala Gln Arg Gly Val Lys Ile Thr Ile Val Thr Thr Pro
        35                  40                  45

His Asn Ala Ala Arg Phe Lys Asn Val Leu Ser Arg Ala Ile Glu Ser
    50                  55                  60

Gly Leu Pro Ile Ser Ile Val Gln Val Lys Leu Pro Ser Gln Glu Ala
```

```
                65                  70                  75                  80
        Gly Leu Pro Glu Gly Asn Glu Thr Leu Asp Ser Leu Val Ser Met Glu
                        85                  90                  95

Leu Met Ile His Phe Leu Lys Ala Val Asn Met Leu Glu Glu Pro Val
                        100                 105                 110

Gln Lys Leu Phe Glu Glu Met Ser Pro Gln Pro Ser Cys Ile Ile Ser
                        115                 120                 125

Asp Phe Cys Leu Pro Tyr Thr Ser Lys Ile Ala Lys Lys Phe Asn Ile
                        130                 135                 140

Pro Lys Ile Leu Phe His Gly Met Cys Cys Phe Cys Leu Leu Cys Met
        145                 150                 155                 160

His Ile Leu Arg Lys Asn Arg Glu Ile Val Glu Asn Leu Lys Ser Asp
                        165                 170                 175

Lys Glu His Phe Val Val Pro Tyr Phe Pro Asp Arg Val Glu Phe Thr
                        180                 185                 190

Arg Pro Gln Val Pro Val Ala Thr Tyr Val Pro Gly Asp Trp His Glu
                        195                 200                 205

Ile Thr Glu Asp Met Val Glu Ala Asp Lys Thr Ser Tyr Gly Val Ile
                        210                 215                 220

Val Asn Thr Tyr Gln Glu Leu Glu Pro Ala Tyr Ala Asn Asp Tyr Lys
        225                 230                 235                 240

Glu Ala Arg Ser Gly Lys Ala Trp Thr Ile Gly Pro Val Ser Leu Cys
                        245                 250                 255

Asn Lys Val Gly Ala Asp Lys Ala Glu Arg Gly Asn Lys Ala Asp Ile
                        260                 265                 270

Asp Gln Asp Glu Cys Leu Lys Trp Leu Asn Ser Lys Glu Glu Gly Ser
                        275                 280                 285

Val Leu Tyr Val Cys Leu Gly Ser Ile Cys Asn Leu Pro Leu Ser Gln
                        290                 295                 300

Leu Lys Glu Leu Gly Leu Gly Leu Glu Glu Ser Gln Arg Pro Phe Ile
        305                 310                 315                 320

Trp Val Ile Arg Gly Trp Glu Lys Asn Lys Glu Leu His Glu Trp Phe
                        325                 330                 335

Ser Glu Ser Gly Phe Glu Glu Arg Ile Lys Asp Arg Gly Leu Leu Ile
                        340                 345                 350

Lys Gly Trp Ala Pro Gln Met Leu Ile Leu Ser His Ser Val Gly
                        355                 360                 365

Gly Phe Leu Thr His Cys Gly Trp Asn Ser Thr Leu Glu Gly Leu Thr
                        370                 375                 380

Ala Gly Leu Pro Leu Leu Thr Trp Pro Leu Phe Ala Asp Gln Phe Cys
        385                 390                 395                 400

Asn Glu Lys Leu Ala Val Gln Val Leu Lys Ala Gly Val Ser Ala Gly
                        405                 410                 415

Val Asp Gln Pro Met Lys Trp Gly Glu Glu Lys Ile Gly Val Leu
                        420                 425                 430

Val Asp Lys Glu Gly Val Lys Lys Ala Val Glu Glu Leu Met Gly Glu
                        435                 440                 445

Ser Asp Asp Ala Lys Glu Ile Arg Arg Arg Ala Lys Glu Leu Gly Glu
                        450                 455                 460

Leu Ala His Lys Ala Val Glu Glu Gly Gly Ser Ser His Ser Asn Ile
        465                 470                 475                 480

Thr Ser Leu Leu Glu Asp Ile Met Gln Leu Ala Gln Ser Asn Asn
                        485                 490                 495
```

<210> SEQ ID NO 25
<211> LENGTH: 1329
<212> TYPE: DNA
<213> ORGANISM: Panax ginseng
<220> FEATURE:
<221> NAME/KEY: misc_feature
<223> OTHER INFORMATION: gGT29

<400> SEQUENCE: 25

| | | | | | |
|---|---|---|---|---|---|
| atggataacc | aaaaaggtag | aatcagtata | gcgttgctac | cattttttagc | ccatggtcac | 60 |
| atatctccct | tctttgagct | agccaaacaa | ctcgcgaaaa | gaaattgcaa | tgttttcctc | 120 |
| tgttctaccc | caatcaatct | tagctccatc | aaggataagg | attcctctgc | ttctataaaa | 180 |
| ctagttgagc | ttcatcttcc | atcttcccct | gatcttcctc | ctcactatca | caccacaaat | 240 |
| ggcctccctt | cccatctcat | gctcccactc | agaaacgcct | ttgaaactgc | aggccccacc | 300 |
| ttctctgaaa | tccttaaaac | cttaaacccc | gatttgctta | tttatgattt | caatccctca | 360 |
| tgggcaccgg | agatcgcttc | gtctcacaat | attccggcag | tttatttcct | aaccacggca | 420 |
| gcagccagct | cttccattgg | cctacatgct | tcaaaaacc | caggtgaaaa | atacccattt | 480 |
| ccagattttt | atgataacag | taatattacc | cctgaaccac | cttctgcaga | taacatgaag | 540 |
| ctacttcatg | attttatcgc | ttgtttcgaa | cgatcttgcg | acattatttt | gattaagagt | 600 |
| tttagagaac | tagaagggaa | atatattgat | ttgcttccca | ctttatctga | taaaactttg | 660 |
| gttcctgttg | gtccactcgt | tcaagatcct | atgggccata | tgaagatccc | aaaaacagag | 720 |
| cagattataa | actggcttga | caaaagggct | gaatctacag | tggtgtttgt | ctgctttgga | 780 |
| agtgagtatt | ttctctccaa | tgaggaattg | gaagaagtag | caattgggct | agagattagc | 840 |
| acggttaatt | tcatatgggc | tgtgagatta | attgaaggag | agaaaaaagg | gattttacca | 900 |
| gaggggtttg | ttcaaagggt | aggagacaga | ggattggttg | tggaggggtg | ggctccacag | 960 |
| gcaagaattt | taggacattc | aagcaccggt | gggtttgtga | gccattgtgg | gtggagttct | 1020 |
| attgcggaga | gtatgaagtt | tggggttcca | gtaattgcca | tggccaggca | tcttgatcag | 1080 |
| cctttgaatg | gtaagctggc | ggcggaggtt | ggtgtgggca | tggaggttgt | gagagatgag | 1140 |
| aatgggaagt | ataagagaga | agggattgca | gaggtaataa | gaaaagtggt | tgtggagaaa | 1200 |
| agtgggaggg | ttatcaggag | gaaagcaagg | gagttgagtg | agaaaatgaa | agagaaagga | 1260 |
| gagcaagaga | ttgatagggc | attggaggag | ctagtacaaa | tttgtaagaa | gaagaaagat | 1320 |
| gaacaatag | | | | | | 1329 |

<210> SEQ ID NO 26
<211> LENGTH: 442
<212> TYPE: PRT
<213> ORGANISM: Panax ginseng
<220> FEATURE:
<221> NAME/KEY: misc_feature
<223> OTHER INFORMATION: gGT29

<400> SEQUENCE: 26

Met Asp Asn Gln Lys Gly Arg Ile Ser Ile Ala Leu Leu Pro Phe Leu
1               5                   10                  15

Ala His Gly His Ile Ser Pro Phe Phe Glu Leu Ala Lys Gln Leu Ala
                20                  25                  30

Lys Arg Asn Cys Asn Val Phe Leu Cys Ser Thr Pro Ile Asn Leu Ser
            35                  40                  45

Ser Ile Lys Asp Lys Asp Ser Ser Ala Ser Ile Lys Leu Val Glu Leu

```
            50                  55                  60
His Leu Pro Ser Ser Pro Asp Leu Pro His Tyr His Thr Thr Asn
 65                  70                  75                  80

Gly Leu Pro Ser His Leu Met Leu Pro Leu Arg Asn Ala Phe Glu Thr
                     85                  90                  95

Ala Gly Pro Thr Phe Ser Glu Ile Leu Lys Thr Leu Asn Pro Asp Leu
                100                 105                 110

Leu Ile Tyr Asp Phe Asn Pro Ser Trp Ala Pro Glu Ile Ala Ser Ser
            115                 120                 125

His Asn Ile Pro Ala Val Tyr Phe Leu Thr Thr Ala Ala Ser Ser
130                 135                 140

Ser Ile Gly Leu His Ala Phe Lys Asn Pro Gly Glu Lys Tyr Pro Phe
145                 150                 155                 160

Pro Asp Phe Tyr Asp Asn Ser Asn Ile Thr Pro Glu Pro Ser Ala
                165                 170                 175

Asp Asn Met Lys Leu Leu His Asp Phe Ile Ala Cys Phe Glu Arg Ser
                180                 185                 190

Cys Asp Ile Ile Leu Ile Lys Ser Phe Arg Glu Leu Glu Gly Lys Tyr
            195                 200                 205

Ile Asp Leu Leu Ser Thr Leu Ser Asp Lys Thr Leu Val Pro Val Gly
            210                 215                 220

Pro Leu Val Gln Asp Pro Met Gly His Asn Glu Asp Pro Lys Thr Glu
225                 230                 235                 240

Gln Ile Ile Asn Trp Leu Asp Lys Arg Ala Glu Ser Thr Val Val Phe
                245                 250                 255

Val Cys Phe Gly Ser Glu Tyr Phe Leu Ser Asn Glu Glu Leu Glu Glu
                260                 265                 270

Val Ala Ile Gly Leu Glu Ile Ser Thr Val Asn Phe Ile Trp Ala Val
                275                 280                 285

Arg Leu Ile Glu Gly Glu Lys Lys Gly Ile Leu Pro Glu Gly Phe Val
            290                 295                 300

Gln Arg Val Gly Asp Arg Gly Leu Val Val Glu Gly Trp Ala Pro Gln
305                 310                 315                 320

Ala Arg Ile Leu Gly His Ser Ser Thr Gly Gly Phe Val Ser His Cys
                325                 330                 335

Gly Trp Ser Ser Ile Ala Glu Ser Met Lys Phe Gly Val Pro Val Ile
                340                 345                 350

Ala Met Ala Arg His Leu Asp Gln Pro Leu Asn Gly Lys Leu Ala Ala
                355                 360                 365

Glu Val Gly Val Gly Met Glu Val Val Arg Asp Glu Asn Gly Lys Tyr
            370                 375                 380

Lys Arg Glu Gly Ile Ala Glu Val Ile Arg Lys Val Val Glu Lys
385                 390                 395                 400

Ser Gly Glu Val Ile Arg Arg Lys Ala Arg Glu Leu Ser Glu Lys Met
                405                 410                 415

Lys Glu Lys Gly Glu Gln Ile Asp Arg Ala Leu Glu Glu Leu Val
                420                 425                 430

Gln Ile Cys Lys Lys Lys Asp Glu Gln
            435                 440

<210> SEQ ID NO 27
<211> LENGTH: 1329
<212> TYPE: DNA
<213> ORGANISM: Panax ginseng
```

```
<220> FEATURE:
<221> NAME/KEY: misc_feature
<223> OTHER INFORMATION: gGT29-3

<400> SEQUENCE: 27
atggataacc aagaaggtag aatcagtata gcgttgctac cattttagc ccatggtcac      60
atatctccct tctttgagct agccaaacaa ctcgcaaaaa gaaattgcaa tgttttcctc     120
tgttctaccc caatcaatct tagctccatc aagaataagg attcctctgc ttctataaaa     180
ctagttgagc ttcatcttcc atcttcccct gatcttcctc ctcactatca caccacaaat     240
ggcctccctt cccatctcat ggtcccactc ataaacgcct ttgaaacagc aggccccacc     300
ttctctgaaa tccttaaaac cttaaacccc gatttgctta tttatgattt caatccctca     360
tgggcaccgg agatcgcttc gtctcacaat attccggcag tttatttcct aaccacggca     420
gcagccagct cttccattgg cctacatgct ttcaaaaacc caggtgaaaa atacccattt     480
ccagattttt atgataacag taataatacc cctgaaccac cttctgcaga taacatgaag     540
ctacttcatg attttatcgc ttgtttcgaa cgatcttgcg acattatttt gattaagagt     600
tttatagaac tagaagggaa atatatcgat ttgctttcca ctttatctga taaaactttg     660
gttcctgttg gtccactcgt tcaagatcct atgggccata tgaagatcc aaaaacagag      720
cagattataa actggcttga caaaagggct gaatctacag tggtgtttgt ctgctttgga     780
agtgagtatt ttctctccaa tgaggaattg aagaagtag caattgggct agagattagc     840
atggttaatt tcatatgggc tgtgagatta attgaaggag agaaaaaagg ggttttacca     900
gagggatttg ttcaaagggt aggagacaga ggattggttg tggaggggtg ggctccacag     960
gcaagaattt taggacattc aagcaccggt gggtttgtga gccattgtgg gtggagttct    1020
attgcggaga gtatgaagtt tggggttcca gtaattgcca tggccaggca tcttgatcag    1080
cctttgaatg gtaagctggc ggcggaggtt ggtgtgggca tggaggttgt gagagatgaa    1140
aatgggaagt ataagagaga agggattgca gaggtaataa gaaagtcgt tgtgagaaa     1200
agtggggagg ttatgaggag gaaagcaagg gaattgagtg agaaaatgaa agagaaagga    1260
gaggaagaga ttgatagggc agtggaggag ctagtacaaa tttgtaagaa gaagaaagat    1320
gcacaatag                                                           1329

<210> SEQ ID NO 28
<211> LENGTH: 442
<212> TYPE: PRT
<213> ORGANISM: Panax ginseng
<220> FEATURE:
<221> NAME/KEY: misc_feature
<223> OTHER INFORMATION: gGT29-3

<400> SEQUENCE: 28

Met Asp Asn Gln Glu Gly Arg Ile Ser Ile Ala Leu Leu Pro Phe Leu
1               5                   10                  15

Ala His Gly His Ile Ser Pro Phe Phe Glu Leu Ala Lys Gln Leu Ala
                20                  25                  30

Lys Arg Asn Cys Asn Val Phe Leu Cys Ser Thr Pro Ile Asn Leu Ser
        35                  40                  45

Ser Ile Lys Asn Lys Asp Ser Ser Ala Ser Ile Lys Leu Val Glu Leu
    50                  55                  60

His Leu Pro Ser Ser Pro Asp Leu Pro Pro His Tyr His Thr Thr Asn
65                  70                  75                  80

Gly Leu Pro Ser His Leu Met Val Pro Leu Ile Asn Ala Phe Glu Thr
```

```
            85                  90                  95
Ala Gly Pro Thr Phe Ser Glu Ile Leu Lys Thr Leu Asn Pro Asp Leu
            100                 105                 110

Leu Ile Tyr Asp Phe Asn Pro Ser Trp Ala Pro Glu Ile Ala Ser Ser
        115                 120                 125

His Asn Ile Pro Ala Val Tyr Phe Leu Thr Thr Ala Ala Ser Ser
    130                 135                 140

Ser Ile Gly Leu His Ala Phe Lys Asn Pro Gly Glu Lys Tyr Pro Phe
145                 150                 155                 160

Pro Asp Phe Tyr Asp Asn Ser Asn Asn Thr Pro Glu Pro Pro Ser Ala
                165                 170                 175

Asp Asn Met Lys Leu Leu His Asp Phe Ile Ala Cys Phe Glu Arg Ser
            180                 185                 190

Cys Asp Ile Ile Leu Ile Lys Ser Phe Ile Glu Leu Glu Gly Lys Tyr
            195                 200                 205

Ile Asp Leu Leu Ser Thr Leu Ser Asp Lys Thr Leu Val Pro Val Gly
        210                 215                 220

Pro Leu Val Gln Asp Pro Met Gly His Asn Glu Asp Pro Lys Thr Glu
225                 230                 235                 240

Gln Ile Ile Asn Trp Leu Asp Lys Arg Ala Glu Ser Thr Val Val Phe
                245                 250                 255

Val Cys Phe Gly Ser Glu Tyr Phe Leu Ser Asn Glu Glu Leu Glu Glu
            260                 265                 270

Val Ala Ile Gly Leu Glu Ile Ser Met Val Asn Phe Ile Trp Ala Val
            275                 280                 285

Arg Leu Ile Glu Gly Glu Lys Lys Gly Val Leu Pro Glu Gly Phe Val
        290                 295                 300

Gln Arg Val Gly Asp Arg Gly Leu Val Val Glu Gly Trp Ala Pro Gln
305                 310                 315                 320

Ala Arg Ile Leu Gly His Ser Ser Thr Gly Gly Phe Val Ser His Cys
                325                 330                 335

Gly Trp Ser Ser Ile Ala Glu Ser Met Lys Phe Gly Val Pro Val Ile
            340                 345                 350

Ala Met Ala Arg His Leu Asp Gln Pro Leu Asn Gly Lys Leu Ala Ala
            355                 360                 365

Glu Val Gly Val Gly Met Glu Val Val Arg Asp Glu Asn Gly Lys Tyr
        370                 375                 380

Lys Arg Glu Gly Ile Ala Glu Val Ile Arg Lys Val Val Glu Lys
385                 390                 395                 400

Ser Gly Glu Val Met Arg Arg Lys Ala Arg Glu Leu Ser Glu Lys Met
                405                 410                 415

Lys Glu Lys Gly Glu Glu Ile Asp Arg Ala Val Glu Glu Leu Val
            420                 425                 430

Gln Ile Cys Lys Lys Lys Lys Asp Ala Gln
            435                 440

<210> SEQ ID NO 29
<211> LENGTH: 20
<212> TYPE: DNA
<213> ORGANISM: Artificial sequece
<220> FEATURE:
<223> OTHER INFORMATION: synthesized nucleotides

<400> SEQUENCE: 29
atggtttccg aaatcaccca                                             20
```

<210> SEQ ID NO 30
<211> LENGTH: 24
<212> TYPE: DNA
<213> ORGANISM: Artificial sequece
<220> FEATURE:
<223> OTHER INFORMATION: synthesized nucleotides

<400> SEQUENCE: 30
ttaattattr grttgtgcta gttg                                          24

<210> SEQ ID NO 31
<211> LENGTH: 35
<212> TYPE: DNA
<213> ORGANISM: Artificial sequece
<220> FEATURE:
<223> OTHER INFORMATION: synthesized nucleotides

<400> SEQUENCE: 31
gactggatcc atggtttccg aaatcaccca taaat                              35

<210> SEQ ID NO 32
<211> LENGTH: 30
<212> TYPE: DNA
<213> ORGANISM: Artificial sequece
<220> FEATURE:
<223> OTHER INFORMATION: synthesized nucleotides

<400> SEQUENCE: 32
gcgcgtcgac attattaggt tgtgctagtt                                    30

<210> SEQ ID NO 33
<211> LENGTH: 30
<212> TYPE: DNA
<213> ORGANISM: Artificial sequece
<220> FEATURE:
<223> OTHER INFORMATION: synthesized nucleotides

<400> SEQUENCE: 33
gcgcgtcgac attattggat tgtgctagtt                                    30

<210> SEQ ID NO 34
<211> LENGTH: 26
<212> TYPE: DNA
<213> ORGANISM: Artificial sequece
<220> FEATURE:
<223> OTHER INFORMATION: synthesized nucleotides

<400> SEQUENCE: 34
agtaagaaaa acagagttca tcatgg                                        26

<210> SEQ ID NO 35
<211> LENGTH: 20
<212> TYPE: DNA
<213> ORGANISM: Artificial sequece
<220> FEATURE:
<223> OTHER INFORMATION: synthesized nucleotides

<400> SEQUENCE: 35
gcctcggtta ggctagctgt                                               20

<210> SEQ ID NO 36
<211> LENGTH: 35
<212> TYPE: DNA
<213> ORGANISM: Artificial sequece
<220> FEATURE:

-continued

<223> OTHER INFORMATION: synthesized nucleotides

<400> SEQUENCE: 36
ggcgggtacc atggataacc aaaaaggtag aatca                         35

<210> SEQ ID NO 37
<211> LENGTH: 56
<212> TYPE: DNA
<213> ORGANISM: Artificial sequece
<220> FEATURE:
<223> OTHER INFORMATION: synthesized nucleotides

<400> SEQUENCE: 37
gccgctcgag tcaatgatga tgatgatgat gttgttcatc tttcttcttc ttacaa    56

<210> SEQ ID NO 38
<211> LENGTH: 35
<212> TYPE: DNA
<213> ORGANISM: Artificial sequece
<220> FEATURE:
<223> OTHER INFORMATION: synthesized nucleotides

<400> SEQUENCE: 38
ggcgggtacc atggataacc aagaaggtag aatca                         35

<210> SEQ ID NO 39
<211> LENGTH: 56
<212> TYPE: DNA
<213> ORGANISM: Artificial sequece
<220> FEATURE:
<223> OTHER INFORMATION: synthesized nucleotides

<400> SEQUENCE: 39
gccgctcgag tcaatgatga tgatgatgat gttgtgcatc tttcttcttc ttacaa    56

<210> SEQ ID NO 40
<211> LENGTH: 1494
<212> TYPE: DNA
<213> ORGANISM: Medicago truncatula
<220> FEATURE:
<221> NAME/KEY: misc_feature
<223> OTHER INFORMATION: 3GT3

<400> SEQUENCE: 40
atggaaggtg ttgaagttga acaaccattg aaagtttact tcattccatt tcttgcatct     60
ggacatatga tccctctttt tgacatagca actatgtttg catcccgtgg ccagcaagta    120
acagtcatca ccactcccgc caacgcaaaa tcccttacca atctctctc atccgacgct    180 ccttcattcc ttcgtcttca caccgttgac ttcccctccc aacaagtcgg cctccctgaa    240
ggtattgaat ctatgtcttc aactacggac cccaccacca cttggaagat ccatactggc    300
gcgatgctcc ttaaagaacc tattggggat ttcattgaga atgatccacc ggattgtatc    360
atctccgact ccacgtaccc atgggttaat gacttggccg ataagtttca gatcccaaac    420
atcacattca atggattgtg ccttttttgct gtctccctcg tggaaaccct caaaacaaac    480
aatttactta agtctcagac agattctgat tcggattcaa gttcctttgt tgttccaaat    540
tttcctcacc atatcacctt gtgtggaaaa ccgccaaagg taatcggtat attcatggga    600
atgatgcttg agacggtgct taaaagtaaa gcactaatca tcaacaactt cagtgaactt    660
gatggagaag agtgcataca acactacgag aaagccacgg gtcacaaggt ttggcatctt    720
ggtccaactt ctcttattcg caaaactgct caagagaaat cagagagggg aaatgagggt    780

```
gctgtgaatg tgcacgagag cctgagttgg ctcgattcag agagagttaa ctcagtgttg      840
tacatatgtt ttggaagcat caactatttt tctgataaac aactatacga gatggcatgt      900
gcgatagaag catccggtca cccattcata tgggttgttc ctgagaagaa agggaaagaa      960
gatgagagcg aagaagagaa agaaaagtgg ttaccgaagg gatttgaaga gagaaatatc     1020
gggaagaagg gtttgatcat tagggggttgg gccccacagg ttaagatatt gagccaccct     1080
gcagtggggg gatttatgac gcattgcggg gggaactcaa ccgtagaggc tgttagtgcg     1140
ggagttccaa tgataacgtg gccggttcat ggagatcaat tctacaatga gaaactgata     1200
acacaattcc gaggaattgg agttgaagtc ggtgcaacag aatggtgtac gagtggtgtc     1260
gcggagagaa agaagttagt gagcagagat agcatagaga aggctgtaag gagattgatg     1320
gacggtggtg atgaagctga aaatatcagg ctacgtgctc gagagtttgg agaaaaagct     1380
atacaagcta ttcaagaagg tggctcgtct tataataatt tgttggcttt gattgacgaa     1440
cttaaaagat cgagagacct taaaagattg agagacctca agctggatga ttaa           1494
```

<210> SEQ ID NO 41
<211> LENGTH: 497
<212> TYPE: PRT
<213> ORGANISM: Medicago truncatula
<220> FEATURE:
<221> NAME/KEY: misc_feature
<223> OTHER INFORMATION: 3GT3

<400> SEQUENCE: 41

```
Met Glu Gly Val Glu Val Glu Gln Pro Leu Lys Val Tyr Phe Ile Pro
1               5                   10                  15

Phe Leu Ala Ser Gly His Met Ile Pro Leu Phe Asp Ile Ala Thr Met
            20                  25                  30

Phe Ala Ser Arg Gly Gln Gln Val Thr Val Ile Thr Thr Pro Ala Asn
        35                  40                  45

Ala Lys Ser Leu Thr Lys Ser Leu Ser Ser Asp Ala Pro Ser Phe Leu
    50                  55                  60

Arg Leu His Thr Val Asp Phe Pro Ser Gln Gln Val Gly Leu Pro Glu
65                  70                  75                  80

Gly Ile Glu Ser Met Ser Ser Thr Thr Asp Pro Thr Thr Thr Trp Lys
                85                  90                  95

Ile His Thr Gly Ala Met Leu Leu Lys Glu Pro Ile Gly Asp Phe Ile
            100                 105                 110

Glu Asn Asp Pro Pro Asp Cys Ile Ile Ser Asp Ser Thr Tyr Pro Trp
        115                 120                 125

Val Asn Asp Leu Ala Asp Lys Phe Gln Ile Pro Asn Ile Thr Phe Asn
    130                 135                 140

Gly Leu Cys Leu Phe Ala Val Ser Leu Val Glu Thr Leu Lys Thr Asn
145                 150                 155                 160

Asn Leu Leu Lys Ser Gln Thr Asp Ser Asp Ser Asp Ser Ser Phe
                165                 170                 175

Val Val Pro Asn Phe Pro His His Ile Thr Leu Cys Gly Lys Pro Pro
            180                 185                 190

Lys Val Ile Gly Ile Phe Met Gly Met Met Leu Glu Thr Val Leu Lys
        195                 200                 205

Ser Lys Ala Leu Ile Ile Asn Asn Phe Ser Glu Leu Asp Gly Glu Glu
    210                 215                 220

Cys Ile Gln His Tyr Glu Lys Ala Thr Gly His Lys Val Trp His Leu
225                 230                 235                 240
```

```
Gly Pro Thr Ser Leu Ile Arg Lys Thr Ala Gln Lys Ser Glu Arg
            245                 250                 255

Gly Asn Glu Gly Ala Val Asn Val His Glu Ser Leu Ser Trp Leu Asp
        260                 265                 270

Ser Glu Arg Val Asn Ser Val Leu Tyr Ile Cys Phe Gly Ser Ile Asn
        275                 280                 285

Tyr Phe Ser Asp Lys Gln Leu Tyr Glu Met Ala Cys Ala Ile Glu Ala
        290                 295                 300

Ser Gly His Pro Phe Ile Trp Val Val Pro Glu Lys Gly Lys Glu
305                 310                 315                 320

Asp Glu Ser Glu Glu Lys Glu Lys Trp Leu Pro Lys Gly Phe Glu
            325                 330                 335

Glu Arg Asn Ile Gly Lys Lys Gly Leu Ile Ile Arg Gly Trp Ala Pro
        340                 345                 350

Gln Val Lys Ile Leu Ser His Pro Ala Val Gly Gly Phe Met Thr His
            355                 360                 365

Cys Gly Gly Asn Ser Thr Val Glu Ala Val Ser Ala Gly Val Pro Met
370                 375                 380

Ile Thr Trp Pro Val His Gly Asp Gln Phe Tyr Asn Glu Lys Leu Ile
385                 390                 395                 400

Thr Gln Phe Arg Gly Ile Gly Val Glu Val Gly Ala Thr Glu Trp Cys
            405                 410                 415

Thr Ser Gly Val Ala Glu Arg Lys Lys Leu Val Ser Arg Asp Ser Ile
            420                 425                 430

Glu Lys Ala Val Arg Arg Leu Met Asp Gly Gly Asp Glu Ala Glu Asn
        435                 440                 445

Ile Arg Leu Arg Ala Arg Glu Phe Gly Glu Lys Ala Ile Gln Ala Ile
        450                 455                 460

Gln Glu Gly Gly Ser Ser Tyr Asn Asn Leu Leu Ala Leu Ile Asp Glu
465                 470                 475                 480

Leu Lys Arg Ser Arg Asp Leu Lys Arg Leu Arg Asp Leu Lys Leu Asp
            485                 490                 495

Asp

<210> SEQ ID NO 42
<211> LENGTH: 1374
<212> TYPE: DNA
<213> ORGANISM: Panax ginseng
<220> FEATURE:
<221> NAME/KEY: misc_feature
<223> OTHER INFORMATION: 3GT4

<400> SEQUENCE: 42
atggagagag aaatgttgag caaaactcac attatgttca tcccattccc agctcaaggc      60
cacatgagcc caatgatgca attcgccaag cgtttagcct ggaaaggcct gcgaatcacg     120
atagttcttc cggctcaaat tcgagatttc atgcaaataa ccaacccatt gatcaacact     180
gagtgcatct cctttgattt tgataaagac gatgggatgc catacagcat gcaggcttat     240
atgggagttg taaaactcaa ggtcacaaat aaactgagtg acctactcga gaagcaagga     300
acaaatggct accctgttaa tttgctagtg gttgattcat tatatccatc tcgggtagaa     360
atgtgccacc aacttggggt aaaaggagct ccattttttca ctcactcttg tgctgttggt     420
gccatttatt ataatgctcg cttagggaaa ttgaagatac ctcctgagga agggttgact     480
tctgtttcat tgccttcaat tccattgttg gggagagatg atttgccaat tattaggact     540
```

```
ggcacctttc ctgatctctt tgagcatttg gggaatcagt ttcagatct tgataaagcg      600
gattggatct ttttcaatac ttttgataag cttgaaaatg aggaagcaaa atggctatct    660
agccaatggc caattacatc catcggacca ttaatccctt caatgtactt agacaaacaa    720
ttaccaaatg acaagacaa tggcattaat ttctacaagg cagacgtcgg atcgtgcatc     780
aagtggctag acgccaaaga ccctggctcg gtagtctacg cctcattcgg gagcgtgaag    840
cacaacctcg gcgatgacta catggacgaa gtagcatggg gcttgttaca tagcaaatat    900
cacttcatat gggttgttat agaatccgaa cgtacaaagc tctctagcga tttcttggca    960
gaggcagagg cagaggaaaa aggcctaata gtgagttggt gccctcaact ccaagttttg   1020
tcacataaat ctatagggag ttttatgact cattgtggtt ggaactcgac ggttgaggca   1080
ttgagtttgg gcgtgccaat ggtggcactg ccacaacagt ttgatcagcc tgctaatgcc   1140
aagtatatcg tggatgtatg gcaaattggg gttcgggttc cgattggtga agaggggtt    1200
gttttgaggg gagaagttgc taactgtata aaggatgtta tggagggga aatagggat    1260
gagcttagag ggaatgcttt gaaatggaag gggttggctg tggaggcaat ggagaaggg    1320
ggtagctctg ataagaatat tgatgagttc atttcaaagc ttgtttcctc ctga          1374
```

<210> SEQ ID NO 43
<211> LENGTH: 457
<212> TYPE: PRT
<213> ORGANISM: Panax ginseng
<220> FEATURE:
<221> NAME/KEY: misc_feature
<223> OTHER INFORMATION: 3GT4

<400> SEQUENCE: 43

```
Met Glu Arg Glu Met Leu Ser Lys Thr His Ile Met Phe Ile Pro Phe
1               5                   10                  15

Pro Ala Gln Gly His Met Ser Pro Met Met Gln Phe Ala Lys Arg Leu
            20                  25                  30

Ala Trp Lys Gly Leu Arg Ile Thr Ile Val Leu Pro Ala Gln Ile Arg
        35                  40                  45

Asp Phe Met Gln Ile Thr Asn Pro Leu Ile Asn Thr Glu Cys Ile Ser
    50                  55                  60

Phe Asp Phe Asp Lys Asp Asp Gly Met Pro Tyr Ser Met Gln Ala Tyr
65                  70                  75                  80

Met Gly Val Val Lys Leu Lys Val Thr Asn Lys Leu Ser Asp Leu Leu
                85                  90                  95

Glu Lys Gln Arg Thr Asn Gly Tyr Pro Val Asn Leu Val Val Asp
            100                 105                 110

Ser Leu Tyr Pro Ser Arg Val Glu Met Cys His Gln Leu Gly Val Lys
        115                 120                 125

Gly Ala Pro Phe Phe Thr His Ser Cys Ala Val Gly Ala Ile Tyr Tyr
    130                 135                 140

Asn Ala Arg Leu Gly Lys Leu Lys Ile Pro Glu Glu Gly Leu Thr
145                 150                 155                 160

Ser Val Ser Leu Pro Ser Ile Pro Leu Gly Arg Asp Leu Pro
                165                 170                 175

Ile Ile Arg Thr Gly Thr Phe Pro Asp Leu Phe Glu His Leu Gly Asn
            180                 185                 190

Gln Phe Ser Asp Leu Asp Lys Ala Asp Trp Ile Phe Phe Asn Thr Phe
        195                 200                 205
```

```
Asp Lys Leu Glu Asn Glu Glu Ala Lys Trp Leu Ser Ser Gln Trp Pro
    210                 215                 220
Ile Thr Ser Ile Gly Pro Leu Ile Pro Ser Met Tyr Leu Asp Lys Gln
225                 230                 235                 240
Leu Pro Asn Asp Lys Asp Asn Gly Ile Asn Phe Tyr Lys Ala Asp Val
                245                 250                 255
Gly Ser Cys Ile Lys Trp Leu Asp Ala Lys Asp Pro Gly Ser Val Val
            260                 265                 270
Tyr Ala Ser Phe Gly Ser Val Lys His Asn Leu Gly Asp Asp Tyr Met
        275                 280                 285
Asp Glu Val Ala Trp Gly Leu Leu His Ser Lys Tyr His Phe Ile Trp
    290                 295                 300
Val Val Ile Glu Ser Glu Arg Thr Lys Leu Ser Ser Asp Phe Leu Ala
305                 310                 315                 320
Glu Ala Glu Ala Glu Glu Lys Gly Leu Ile Val Ser Trp Cys Pro Gln
                325                 330                 335
Leu Gln Val Leu Ser His Lys Ser Ile Gly Ser Phe Met Thr His Cys
            340                 345                 350
Gly Trp Asn Ser Thr Val Glu Ala Leu Ser Leu Gly Val Pro Met Val
        355                 360                 365
Ala Leu Pro Gln Gln Phe Asp Gln Pro Ala Asn Ala Lys Tyr Ile Val
    370                 375                 380
Asp Val Trp Gln Ile Gly Val Arg Val Pro Ile Gly Glu Glu Gly Val
385                 390                 395                 400
Val Leu Arg Gly Glu Val Ala Asn Cys Ile Lys Asp Val Met Glu Gly
                405                 410                 415
Glu Ile Gly Asp Glu Leu Arg Gly Asn Ala Leu Lys Trp Lys Gly Leu
            420                 425                 430
Ala Val Glu Ala Met Glu Lys Gly Gly Ser Ser Asp Lys Asn Ile Asp
        435                 440                 445
Glu Phe Ile Ser Lys Leu Val Ser Ser
    450                 455

<210> SEQ ID NO 44
<211> LENGTH: 24
<212> TYPE: DNA
<213> ORGANISM: Artificial sequece
<220> FEATURE:
<223> OTHER INFORMATION: synthesized nucleotides

<400> SEQUENCE: 44
atggaaggtg ttgaagttga acaa                                          24

<210> SEQ ID NO 45
<211> LENGTH: 24
<212> TYPE: DNA
<213> ORGANISM: Artificial sequece
<220> FEATURE:
<223> OTHER INFORMATION: synthesized nucleotides

<400> SEQUENCE: 45
ttaatcatcc agcttgaggt ctct                                          24

<210> SEQ ID NO 46
<211> LENGTH: 25
<212> TYPE: DNA
<213> ORGANISM: Artificial sequece
<220> FEATURE:
<223> OTHER INFORMATION: synthesized nucleotides
```

<400> SEQUENCE: 46
tacataaata tataatacat aggca                                                25

<210> SEQ ID NO 47
<211> LENGTH: 25
<212> TYPE: DNA
<213> ORGANISM: Artificial sequece
<220> FEATURE:
<223> OTHER INFORMATION: synthesized nucleotides

<400> SEQUENCE: 47
aaaatacata caaaatcttg aaata                                                25

<210> SEQ ID NO 48
<211> LENGTH: 45
<212> TYPE: DNA
<213> ORGANISM: Artificial sequece
<220> FEATURE:
<223> OTHER INFORMATION: synthesized nucleotides

<400> SEQUENCE: 48
actttaagaa ggagatatac catggaaggt gttgaagttg aacaa                          45

<210> SEQ ID NO 49
<211> LENGTH: 45
<212> TYPE: DNA
<213> ORGANISM: Artificial sequece
<220> FEATURE:
<223> OTHER INFORMATION: synthesized nucleotides

<400> SEQUENCE: 49
ctcgagtgcg gccgcaagct tatcatccag cttgaggtct ctcaa                          45

<210> SEQ ID NO 50
<211> LENGTH: 46
<212> TYPE: DNA
<213> ORGANISM: Artificial sequece
<220> FEATURE:
<223> OTHER INFORMATION: synthesized nucleotides

<400> SEQUENCE: 50
actttaagaa ggagatatac catggagaga gaaatgttga gcaaaa                         46

<210> SEQ ID NO 51
<211> LENGTH: 46
<212> TYPE: DNA
<213> ORGANISM: Artificial sequece
<220> FEATURE:
<223> OTHER INFORMATION: synthesized nucleotides

<400> SEQUENCE: 51
ctcgagtgcg gccgcaagct tggaggaaac aagctttgaa atgaac                         46

<210> SEQ ID NO 52
<211> LENGTH: 27
<212> TYPE: DNA
<213> ORGANISM: Artificial sequece
<220> FEATURE:
<223> OTHER INFORMATION: synthesized nucleotides

<400> SEQUENCE: 52
ggtatatctc cttcttaaag ttaaaca                                              27

<210> SEQ ID NO 53

-continued

```
<211> LENGTH: 27
<212> TYPE: DNA
<213> ORGANISM: Artificial sequece
<220> FEATURE:
<223> OTHER INFORMATION: synthesized nucleotides

<400> SEQUENCE: 53
aagcttgcgg ccgcactcga gcaccac                                           27

<210> SEQ ID NO 54
<211> LENGTH: 1341
<212> TYPE: DNA
<213> ORGANISM: Panax ginseng
<220> FEATURE:
<221> NAME/KEY: misc_feature
<223> OTHER INFORMATION: gGT29-4

<400> SEQUENCE: 54
atggataacc aaaaaggtag aatcagtata gcgttgctac cattttttagc ccatggccac       60 atttctccat tctttgagct agccaagcat ctctcaaaaa gaaattgtaa tatattcctc      120
tgttctaccc caatcaatct tagctccatc aagaacagaa tatctgataa ggattcctct      180
gcttctataa aactagtaga gcttcatctt ccatcttccc ctgatcttcc tcctcactac      240
cacaccacaa atggcctccc ttcccatctc atggtccac tcagaaacgc ctttgaaaca       300
gcagccccca ccttctctga aatccttaaa accttaaacc ctgatttgct tatttatgat      360
ttcaatccct catgggcacc ggagatcgct tcgtctcaca atattccggc agtttgtttc      420
ataattgggg gagcagcctc cttttccatg agcctacata gtttcaaaaa cccaggtgaa      480
aaatacccat ttctagattt tgatgataac agtaatatta cccctgaacc accttcagca      540
gataacatga gttattact tgattttatg acttgtttcg aacgatcttg cgacattatt      600
ttgattaaga gttttagaga actagaaggg aaatattttg atttttattc tactttatct      660
gataaaactt tggttcctgt tggtccactc gttcaagatc ctatgggcca taatgaagat      720
ccaaaaacag agcagtttat aaactggctt gacaaaaggg ctgaatctac agtggtgttt      780
gtctgctttg gaagtgagta ttttctctcc aatgaggaat ggaagaagt agcaattggg      840 ctagagatta gcatggttaa tttcatatgg gctgtgagat taattgaagg agagaaaaaa      900
ggggttttac cagagggtt tgttcaaagg gtaggagaca gaggattggt tgtggagggg      960
tgggctccac aggcaagaat tttaggacat tcaagcaccg gtgggtttgt gagccattgt     1020
gggtggagtt ctattacgga gagtatgaag tttgggttc cagtaattgc catggccagg     1080
catcttgatc agcctttgaa tggtaagctg gcggcggagg ttggtgtggg catggaggtt     1140
gtgagagatg aaaatgggaa gtataagaga gaagggattg cagaggtaat aagaaaagtc     1200
gttgtggaga aaagtgggga ggttatgagg aggaaagcaa gggaattgag tgagaaaatg     1260
aaagagaaag gagaggaaga gattgatagg gcagtggagg agctagtaca aatttgtaag     1320
aagaagaaag atgaacaata g                                             1341

<210> SEQ ID NO 55
<211> LENGTH: 446
<212> TYPE: PRT
<213> ORGANISM: Panax ginseng
<220> FEATURE:
<221> NAME/KEY: misc_feature
<223> OTHER INFORMATION: gGT29-4

<400> SEQUENCE: 55

Met Asp Asn Gln Lys Gly Arg Ile Ser Ile Ala Leu Leu Pro Phe Leu
```

```
              1               5              10              15
            Ala His Gly His Ile Ser Pro Phe Phe Glu Leu Ala Lys His Leu Ser
                            20              25              30

Lys Arg Asn Cys Asn Ile Phe Leu Cys Ser Thr Pro Ile Asn Leu Ser
                            35              40              45

Ser Ile Lys Asn Arg Ile Ser Asp Lys Asp Ser Ser Ala Ser Ile Lys
             50              55              60

Leu Val Glu Leu His Leu Pro Ser Ser Pro Asp Leu Pro Pro His Tyr
             65              70              75              80

His Thr Thr Asn Gly Leu Pro Ser His Leu Met Val Pro Leu Arg Asn
                            85              90              95

Ala Phe Glu Thr Ala Ala Pro Thr Phe Ser Glu Ile Leu Lys Thr Leu
                            100             105             110

Asn Pro Asp Leu Leu Ile Tyr Asp Phe Asn Pro Ser Trp Ala Pro Glu
                            115             120             125

Ile Ala Ser Ser His Asn Ile Pro Ala Val Cys Phe Ile Ile Gly Gly
                            130             135             140

Ala Ala Ser Phe Ser Met Ser Leu His Ser Phe Lys Asn Pro Gly Glu
            145             150             155             160

Lys Tyr Pro Phe Leu Asp Phe Asp Asn Ser Asn Ile Thr Pro Glu
                            165             170             175

Pro Pro Ser Ala Asp Asn Met Lys Leu Leu Leu Asp Phe Met Thr Cys
                            180             185             190

Phe Glu Arg Ser Cys Asp Ile Ile Leu Ile Lys Ser Phe Arg Glu Leu
                            195             200             205

Glu Gly Lys Tyr Phe Asp Phe Tyr Ser Thr Leu Ser Asp Lys Thr Leu
                            210             215             220

Val Pro Val Gly Pro Leu Val Gln Asp Pro Met Gly His Asn Glu Asp
            225             230             235             240

Pro Lys Thr Glu Gln Phe Ile Asn Trp Leu Asp Lys Arg Ala Glu Ser
                            245             250             255

Thr Val Val Phe Val Cys Phe Gly Ser Glu Tyr Phe Leu Ser Asn Glu
                            260             265             270

Glu Leu Glu Glu Val Ala Ile Gly Leu Glu Ile Ser Met Val Asn Phe
                            275             280             285

Ile Trp Ala Val Arg Leu Ile Glu Gly Glu Lys Lys Gly Val Leu Pro
                            290             295             300

Glu Gly Phe Val Gln Arg Val Gly Asp Arg Gly Leu Val Val Glu Gly
            305             310             315             320

Trp Ala Pro Gln Ala Arg Ile Leu Gly His Ser Ser Thr Gly Gly Phe
                            325             330             335

Val Ser His Cys Gly Trp Ser Ser Ile Thr Glu Ser Met Lys Phe Gly
                            340             345             350

Val Pro Val Ile Ala Met Ala Arg His Leu Asp Gln Pro Leu Asn Gly
                            355             360             365

Lys Leu Ala Ala Glu Val Gly Val Gly Met Glu Val Val Arg Asp Glu
                            370             375             380

Asn Gly Lys Tyr Lys Arg Glu Gly Ile Ala Glu Val Ile Arg Lys Val
            385             390             395             400

Val Val Glu Lys Ser Gly Glu Val Met Arg Arg Lys Ala Arg Glu Leu
                            405             410             415

Ser Glu Lys Met Lys Glu Lys Gly Glu Glu Ile Asp Arg Ala Val
                            420             425             430
```

Glu Glu Leu Val Gln Ile Cys Lys Lys Lys Lys Asp Glu Gln
        435                 440                 445

<210> SEQ ID NO 56
<211> LENGTH: 1341
<212> TYPE: DNA
<213> ORGANISM: Panax ginseng
<220> FEATURE:
<221> NAME/KEY: misc_feature
<223> OTHER INFORMATION: gGT29-5

<400> SEQUENCE: 56

| | | |
|---|---|---|
| atggataacc aaaagggtag aatcagtata gttatgctgc catttttagc ccatggccac | 60 |
| atttctccat tctttgagct agccaagcat ctctcaaaaa gaaattgtaa tatattcctc | 120 |
| tgttctaccc caatcaatct tagctccatc aagaacagaa tatctgataa ggattcctct | 180 |
| gcttctataa aactagtaga gcttcatctt ccatcttccc ctgatcttcc tcctcactac | 240 |
| cacaccacaa atggcctccc ttcccatctc atggtcccac tcagaaacgc ctttgaaaca | 300 |
| gcagcccca ccttctctga atccttaaaa accttaaacc ctgatttgct tatttatgat | 360 |
| ttcaatccct catgggcacc ggagatcgct tcgtctcaca atattccggc agtttgtttc | 420 |
| ataattgggg gagcagcctc cttttccatg agcctacata gtttcaaaaa cccaggtgaa | 480 |
| aaatacccat ttctagattt tgatgataac agtaatatta ccctgaacc accttcagca | 540 |
| gataacatga agttattact tgattttatg acttgtttcg aacgatcttg cgacattatt | 600 |
| ttgattaaga gttttagaga actagaaggg aaatatatcg atttgctttc cactttatct | 660 |
| gataaaactt tggttcctgt tggtccactc gttcaagatc ctatgggcca taatgaagat | 720 |
| ccaaaaacag agcagattat aaactggctt gacaaaaggg ctgaatctac agtggtgttt | 780 |
| gtctgctttg gaagtgagta ttttctctcc aatgaggaat tggaagaagt agcaattggg | 840 |
| ctagagatta gcatggttaa tttcatatgg gctgtgagat taattgaagg agagaaaaaa | 900 |
| ggggttttac cagagggatt tgttcaaagg gtaggagaca gaggattggt tgtggagggg | 960 |
| tgggctccac aggcaagaat tttaggacat tcaagcaccg gtgggtttgt gagccattgt | 1020 |
| gggtggagtt ctattgcgga gagtatgaag tttggggttc cagtaattgc catggccagg | 1080 |
| catcttgatc agcctttgaa tggtaagctg gcggcggagg ttggtgtggg catggaggtt | 1140 |
| gtgagagatg aaaatgggaa gtataagaga aagggattg cagaggtaat aagaaaagtc | 1200 |
| gttgtggaga aagtgggga ggttatcagg aggaaagcaa gggaattgag tgagaaaatg | 1260 |
| aaagagatag gagagcaatt gattgatagg gcagtggagg agctagtaca aatttgtaag | 1320 |
| aagaagaaag atgaacaata g | 1341 |

<210> SEQ ID NO 57
<211> LENGTH: 446
<212> TYPE: PRT
<213> ORGANISM: Panax ginseng
<220> FEATURE:
<221> NAME/KEY: misc_feature
<223> OTHER INFORMATION: gGT29-5

<400> SEQUENCE: 57

Met Asp Asn Gln Lys Gly Arg Ile Ser Ile Val Met Leu Pro Phe Leu
1               5                   10                  15

Ala His Gly His Ile Ser Pro Phe Phe Glu Leu Ala Lys His Leu Ser
            20                  25                  30

Lys Arg Asn Cys Asn Ile Phe Leu Cys Ser Thr Pro Ile Asn Leu Ser

```
            35                  40                  45
Ser Ile Lys Asn Arg Ile Ser Asp Lys Asp Ser Ser Ala Ser Ile Lys
 50                  55                  60

Leu Val Glu Leu His Leu Pro Ser Ser Pro Asp Leu Pro His Tyr
 65                  70                  75                  80

His Thr Thr Asn Gly Leu Pro Ser His Leu Met Val Pro Leu Arg Asn
                     85                  90                  95

Ala Phe Glu Thr Ala Ala Pro Thr Phe Ser Glu Ile Leu Lys Thr Leu
                100                 105                 110

Asn Pro Asp Leu Leu Ile Tyr Asp Phe Asn Pro Ser Trp Ala Pro Glu
            115                 120                 125

Ile Ala Ser Ser His Asn Ile Pro Ala Val Cys Phe Ile Ile Gly Gly
        130                 135                 140

Ala Ala Ser Phe Ser Met Ser Leu His Ser Phe Lys Asn Pro Gly Glu
145                 150                 155                 160

Lys Tyr Pro Phe Leu Asp Phe Asp Asn Ser Asn Ile Thr Pro Glu
                165                 170                 175

Pro Pro Ser Ala Asp Asn Met Lys Leu Leu Leu Asp Phe Met Thr Cys
            180                 185                 190

Phe Glu Arg Ser Cys Asp Ile Ile Leu Ile Lys Ser Phe Arg Glu Leu
        195                 200                 205

Glu Gly Lys Tyr Ile Asp Leu Leu Ser Thr Leu Ser Asp Lys Thr Leu
210                 215                 220

Val Pro Val Gly Pro Leu Val Gln Asp Pro Met Gly His Asn Glu Asp
225                 230                 235                 240

Pro Lys Thr Glu Gln Ile Ile Asn Trp Leu Asp Lys Arg Ala Glu Ser
                245                 250                 255

Thr Val Val Phe Val Cys Phe Gly Ser Glu Tyr Phe Leu Ser Asn Glu
            260                 265                 270

Glu Leu Glu Glu Val Ala Ile Gly Leu Glu Ile Ser Met Val Asn Phe
        275                 280                 285

Ile Trp Ala Val Arg Leu Ile Glu Gly Glu Lys Lys Gly Val Leu Pro
    290                 295                 300

Glu Gly Phe Val Gln Arg Val Gly Asp Arg Gly Leu Val Val Glu Gly
305                 310                 315                 320

Trp Ala Pro Gln Ala Arg Ile Leu Gly His Ser Ser Thr Gly Gly Phe
                325                 330                 335

Val Ser His Cys Gly Trp Ser Ser Ile Ala Glu Ser Met Lys Phe Gly
            340                 345                 350

Val Pro Val Ile Ala Met Ala Arg His Leu Asp Gln Pro Leu Asn Gly
        355                 360                 365

Lys Leu Ala Ala Glu Val Gly Val Gly Met Glu Val Val Arg Asp Glu
    370                 375                 380

Asn Gly Lys Tyr Lys Arg Glu Gly Ile Ala Glu Val Ile Arg Lys Val
385                 390                 395                 400

Val Val Glu Lys Ser Gly Glu Val Ile Arg Arg Lys Ala Arg Glu Leu
                405                 410                 415

Ser Glu Lys Met Lys Glu Ile Gly Glu Gln Leu Ile Asp Arg Ala Val
            420                 425                 430

Glu Glu Leu Val Gln Ile Cys Lys Lys Lys Asp Glu Gln
        435                 440                 445

<210> SEQ ID NO 58
```

<211> LENGTH: 1341
<212> TYPE: DNA
<213> ORGANISM: Panax ginseng
<220> FEATURE:
<221> NAME/KEY: misc_feature
<223> OTHER INFORMATION: gGT29-6

<400> SEQUENCE: 58

```
atggataacc aaaagggtag aatcagtata gttatgctgc cattttagc ccatggccac      60
atttctccat tctttgagct agccaagcat ctctcaaaaa gaaattgtaa tatattcctc    120
tgttctaccc caatcaatct tagctccatc aagaacagaa tatctgataa ggattcctct    180
gcttctataa aactagtaga gcttcatctt ccatcttccc ctgatcttcc tcctcactac    240
cacaccacaa atggcctccc ttcccatctc atggtccac tcagaaacgc ctttgaaaca    300
gcagccccca ccttctctga aatccttaaa accttaaacc ctgatttgct tatttatgat    360
ttcaatccct catgggcacc ggagatcgct tcgtctcaca atattccggc agtttatttc    420
ctaaccacgg cagcagccag ctcttccatt ggcctacatg ctttcaaaaa cccaggtgaa    480
aaatacccat ttccagattt ttatgataac agtaataata cccctgaacc accttctgca    540
gataacatga agctacttca tgattttatc gcttgtttcg aacgatcttg cgacattatt    600
ttgattaaga gttttataga actagaaggg aaatatatcg atttgctttc cactttatct    660
gataaaactt tggttcctgt tggtccactc gttcaagatc ctatgggcca taatgaagat    720
ccaaaaacag agcagattat aaactggctt gacaaaaggg ctgaatctac agtggtgttt    780
gtctgctttg gaagtgagta tttttctctcc aatgaggaat tggaagaagt agcaattggg    840
ctagagatta gcatggttaa tttcatatgg gctgtgagat taattgaagg agagaaaaaa    900
ggggttttac cagagggatt tgttcaaagg gtaggagaca gaggattggt tgtggagggg    960
tgggctccac aggcaagaat tttaggacat tcaagcaccg gtggtttgt gagccattgt   1020
gggtggagtt ctattgcgga gagtatgaag tttggggttc cagtaattgc catggccagg   1080
catcttgatc agcctttgaa tggtaagctg gcggcggagt tggtgtggg catggaggtt   1140
gtgagagatg aaaatgggaa gtataagaga aagatattg cagggtgtaat aagaaaagtc   1200
gtggtggaga aagtgggga ggttatcagg aggaaagcaa gggaattgag tgagaaaatg   1260
aaagagatag gagagcaatt gattgatagg gcagtggagg agctagtaca aatttgtaag   1320
aagaagaaag atgaacaata g                                             1341
```

<210> SEQ ID NO 59
<211> LENGTH: 446
<212> TYPE: PRT
<213> ORGANISM: Panax ginseng
<220> FEATURE:
<221> NAME/KEY: misc_feature
<223> OTHER INFORMATION: gGT29-6

<400> SEQUENCE: 59

```
Met Asp Asn Gln Lys Gly Arg Ile Ser Ile Val Met Leu Pro Phe Leu
1               5                   10                  15

Ala His Gly His Ile Ser Pro Phe Phe Glu Leu Ala Lys His Leu Ser
            20                  25                  30

Lys Arg Asn Cys Asn Ile Phe Leu Cys Ser Thr Pro Ile Asn Leu Ser
        35                  40                  45

Ser Ile Lys Asn Arg Ile Ser Asp Lys Asp Ser Ser Ala Ser Ile Lys
    50                  55                  60

Leu Val Glu Leu His Leu Pro Ser Ser Pro Asp Leu Pro Pro His Tyr
```

|       |       |       |       |  65  |       |       |       |       |  70  |       |       |       |       |  75  |       |       |       |       |  80  |
|-------|-------|-------|-------|------|-------|-------|-------|-------|------|-------|-------|-------|-------|------|-------|-------|-------|-------|------|

His Thr Thr Asn Gly Leu Pro Ser His Leu Met Val Pro Leu Arg Asn
                   85                   90                 95

Ala Phe Glu Thr Ala Ala Pro Thr Phe Ser Glu Ile Leu Lys Thr Leu
             100                105               110

Asn Pro Asp Leu Leu Ile Tyr Asp Phe Asn Pro Ser Trp Ala Pro Glu
         115               120              125

Ile Ala Ser Ser His Asn Ile Pro Ala Val Tyr Phe Leu Thr Thr Ala
         130               135              140

Ala Ala Ser Ser Ile Gly Leu His Ala Phe Lys Asn Pro Gly Glu
145              150              155             160

Lys Tyr Pro Phe Pro Asp Phe Tyr Asp Asn Ser Asn Thr Pro Glu
             165                170             175

Pro Pro Ser Ala Asp Asn Met Lys Leu Leu His Asp Phe Ile Ala Cys
         180               185              190

Phe Glu Arg Ser Cys Asp Ile Ile Leu Ile Lys Ser Phe Ile Glu Leu
         195               200              205

Glu Gly Lys Tyr Ile Asp Leu Leu Ser Thr Leu Ser Asp Lys Thr Leu
         210               215              220

Val Pro Val Gly Pro Leu Val Gln Asp Pro Met Gly His Asn Glu Asp
225              230              235             240

Pro Lys Thr Glu Gln Ile Ile Asn Trp Leu Asp Lys Arg Ala Glu Ser
             245                250             255

Thr Val Val Phe Val Cys Phe Gly Ser Glu Tyr Phe Leu Ser Asn Glu
         260               265              270

Glu Leu Glu Glu Val Ala Ile Gly Leu Glu Ile Ser Met Val Asn Phe
         275               280              285

Ile Trp Ala Val Arg Leu Ile Glu Gly Lys Lys Gly Val Leu Pro
         290               295              300

Glu Gly Phe Val Gln Arg Val Gly Asp Arg Gly Leu Val Val Glu Gly
305              310              315             320

Trp Ala Pro Gln Ala Arg Ile Leu Gly His Ser Ser Thr Gly Gly Phe
             325                330             335

Val Ser His Cys Gly Trp Ser Ser Ile Ala Glu Ser Met Lys Phe Gly
         340               345              350

Val Pro Val Ile Ala Met Ala Arg His Leu Asp Gln Pro Leu Asn Gly
         355               360              365

Lys Leu Ala Ala Glu Val Gly Val Gly Met Glu Val Val Arg Asp Glu
         370               375              380

Asn Gly Lys Tyr Lys Arg Glu Asp Ile Ala Gly Val Ile Arg Lys Val
385              390              395             400

Val Val Glu Lys Ser Gly Glu Val Ile Arg Arg Lys Ala Arg Glu Leu
             405                410             415

Ser Glu Lys Met Lys Glu Ile Gly Glu Gln Leu Ile Asp Arg Ala Val
             420                425             430

Glu Glu Leu Val Gln Ile Cys Lys Lys Lys Asp Glu Gln
         435               440              445

<210> SEQ ID NO 60
<211> LENGTH: 1341
<212> TYPE: DNA
<213> ORGANISM: Panax ginseng
<220> FEATURE:
<221> NAME/KEY: misc_feature
<223> OTHER INFORMATION: gGT29-7

<400> SEQUENCE: 60

```
atggataacc aaaaaggtag aatcagtata gcgttgctac catttttagc ccatggtcac    60
atatctccct tctttgagct agccaaacaa ctcgcaaaaa gaaattgcaa tgttttcctc   120
tgttctaccc caatcaatct tagctccatc aagaacagag tatctgataa ggattcctct   180
gcttctataa aactagtaga gcttcatctt ccatcttccc ctgatcttcc tcctcactac   240
cacaccacaa atggcctccc ttcccatctc atgatcccac tcagaaacgc ctttgataca   300
gcaggcccca ccttctctga aatccttaaa accttaaacc ctgatttgct tatttatgat   360
ttcaatccct catgggcacc ggagatcgct tcgtctcaca atattccggc agtttgtttc   420
ataattggtg gagcagcctc ctcttccatg agcctacata gtttcaaaaa cccaggtgaa   480
aaatacccat ttctagattt tgatgataac agtaatatta cccctgaacc accttcagca   540
gataacatga agctattaat taattttatg acttgtttcg aacgatcttg cgacattatt   600
ttgattaaga gttttagaga actagaaggg aaatattttg atttttttc cacttttatct  660
gataaaacttt tggttcctgt tggtccactc gttcaagatc ctatgggcca taatgaagat   720
ccaaaaacag agcagtttat aaactggctt gacaaaggg ctgaatctac agtggtgttt    780
gtctgctttg gaagtgagtg ttttctctcc aatgaggaat tggaagaagt agcgattggg   840
ctagagatta gcatggttaa tttcatatgg gctgtgagat taattgaagg agagaaaaaa   900
ggggttttac cagaggggtt tgttcaaagg gtaggagaca gaggattggt tgtggaggag   960
tgggctccac aggcaagaat tttaggacat tcaagcaccg gtgggtttgt gagccattgt  1020
gggtggaatt ctattacgga gagtatgaag tttggggttc cagtaattgc catggccagg  1080
cattttgatc agccttttgaa tggtaagctg gcggcggagg ttggtgtggg catggaggtt  1140
gtgagagatg aaaatgggaa gtaagagaa aagggattg cagaggtaat aagaaaagtc    1200
gttgtggaga aagtgggga ggttatcagg aggaaagcaa gggaattgag tgagaaaatg    1260
aaagagaaag gagagcaaga gattgatagg gtagtggagg agctagtaca aatttgtaag  1320
aagaagaaag atgaacaata g                                            1341
```

<210> SEQ ID NO 61  
<211> LENGTH: 446  
<212> TYPE: PRT  
<213> ORGANISM: Panax ginseng  
<220> FEATURE:  
<221> NAME/KEY: misc_feature  
<223> OTHER INFORMATION: gGT29-7

<400> SEQUENCE: 61

```
Met Asp Asn Gln Lys Gly Arg Ile Ser Ile Ala Leu Leu Pro Phe Leu
1               5                   10                  15

Ala His Gly His Ile Ser Pro Phe Phe Glu Leu Ala Lys Gln Leu Ala
                20                  25                  30

Lys Arg Asn Cys Asn Val Phe Leu Cys Ser Thr Pro Ile Asn Leu Ser
            35                  40                  45

Ser Ile Lys Asn Arg Val Ser Asp Lys Asp Ser Ser Ala Ser Ile Lys
        50                  55                  60

Leu Val Glu Leu His Leu Pro Ser Ser Pro Asp Leu Pro Pro His Tyr
65                  70                  75                  80

His Thr Thr Asn Gly Leu Pro Ser His Leu Met Ile Pro Leu Arg Asn
                85                  90                  95

Ala Phe Asp Thr Ala Gly Pro Thr Phe Ser Glu Ile Leu Lys Thr Leu
```

```
                100              105              110
Asn Pro Asp Leu Leu Ile Tyr Asp Phe Asn Pro Ser Trp Ala Pro Glu
            115                  120                  125

Ile Ala Ser Ser His Asn Ile Pro Ala Val Cys Phe Ile Gly Gly
            130                  135              140

Ala Ala Ser Ser Ser Met Ser Leu His Ser Phe Lys Asn Pro Gly Glu
145                 150                  155                  160

Lys Tyr Pro Phe Leu Asp Phe Asp Asn Ser Asn Ile Thr Pro Glu
            165                  170                  175

Pro Pro Ser Ala Asp Asn Met Lys Leu Leu Ile Asn Phe Met Thr Cys
            180                  185                  190

Phe Glu Arg Ser Cys Asp Ile Ile Leu Ile Lys Ser Phe Arg Glu Leu
            195                  200                  205

Glu Gly Lys Tyr Phe Asp Phe Phe Ser Thr Leu Ser Asp Lys Thr Leu
            210                  215                  220

Val Pro Val Gly Pro Leu Val Gln Asp Pro Met Gly His Asn Glu Asp
225                 230                  235                  240

Pro Lys Thr Glu Gln Phe Ile Asn Trp Leu Asp Lys Arg Ala Glu Ser
                245                  250                  255

Thr Val Val Phe Val Cys Phe Gly Ser Glu Cys Phe Leu Ser Asn Glu
                260                  265                  270

Glu Leu Glu Glu Val Ala Ile Gly Leu Glu Ile Ser Met Val Asn Phe
                275                  280                  285

Ile Trp Ala Val Arg Leu Ile Glu Gly Glu Lys Lys Gly Val Leu Pro
                290                  295                  300

Glu Gly Phe Val Gln Arg Val Gly Asp Arg Gly Leu Val Val Glu Glu
305                 310                  315                  320

Trp Ala Pro Gln Ala Arg Ile Leu Gly His Ser Ser Thr Gly Gly Phe
                325                  330                  335

Val Ser His Cys Gly Trp Asn Ser Ile Thr Glu Ser Met Lys Phe Gly
                340                  345                  350

Val Pro Val Ile Ala Met Ala Arg His Phe Asp Gln Pro Leu Asn Gly
                355                  360                  365

Lys Leu Ala Ala Glu Val Gly Val Gly Met Glu Val Val Arg Asp Glu
            370                  375                  380

Asn Gly Lys Tyr Lys Arg Glu Gly Ile Ala Glu Val Ile Arg Lys Val
385                 390                  395                  400

Val Val Glu Lys Ser Gly Glu Val Ile Arg Arg Lys Ala Arg Glu Leu
                405                  410                  415

Ser Glu Lys Met Lys Glu Lys Gly Glu Gln Glu Ile Asp Arg Val Val
                420                  425                  430

Glu Glu Leu Val Gln Ile Cys Lys Lys Lys Asp Glu Gln
            435                  440                  445
```

<210> SEQ ID NO 62
<211> LENGTH: 26
<212> TYPE: DNA
<213> ORGANISM: Artificial sequece
<220> FEATURE:
<223> OTHER INFORMATION: synthesized nucleotides

<400> SEQUENCE: 62
acagcaagag agagacacag agttca                                      26

<210> SEQ ID NO 63

```
<211> LENGTH: 23
<212> TYPE: DNA
<213> ORGANISM: Artificial sequece
<220> FEATURE:
<223> OTHER INFORMATION: synthesized nucleotides

<400> SEQUENCE: 63
gttcaaagcc caacctaagc gca                                            23

<210> SEQ ID NO 64
<211> LENGTH: 25
<212> TYPE: DNA
<213> ORGANISM: Artificial sequece
<220> FEATURE:
<223> OTHER INFORMATION: synthesized nucleotides

<400> SEQUENCE: 64
atgaaattat acagagaggg agaga                                          25

<210> SEQ ID NO 65
<211> LENGTH: 25
<212> TYPE: DNA
<213> ORGANISM: Artificial sequece
<220> FEATURE:
<223> OTHER INFORMATION: synthesized nucleotides

<400> SEQUENCE: 65
tggttttctt cacaacacaa agtac                                          25

<210> SEQ ID NO 66
<211> LENGTH: 43
<212> TYPE: DNA
<213> ORGANISM: Artificial sequece
<220> FEATURE:
<223> OTHER INFORMATION: synthesized nucleotides

<400> SEQUENCE: 66
ctggtgccgc gcggcagcat ggataaccaa aagggtagaa tca                      43

<210> SEQ ID NO 67
<211> LENGTH: 43
<212> TYPE: DNA
<213> ORGANISM: Artificial sequece
<220> FEATURE:
<223> OTHER INFORMATION: synthesized nucleotides

<400> SEQUENCE: 67
ctggtgccgc gcggcagcat ggataaccaa aaaggtagaa tca                      43

<210> SEQ ID NO 68
<211> LENGTH: 43
<212> TYPE: DNA
<213> ORGANISM: Artificial sequece
<220> FEATURE:
<223> OTHER INFORMATION: synthesized nucleotides

<400> SEQUENCE: 68
tgcggccgca agcttgtctt gttcatcttt cttcttctta caa                      43

<210> SEQ ID NO 69
<211> LENGTH: 30
<212> TYPE: DNA
<213> ORGANISM: Artificial sequece
<220> FEATURE:
<223> OTHER INFORMATION: synthesized nucleotides

<400> SEQUENCE: 69
```

```
gctgccgcgc ggcaccaggc cgctgctgtg                               30
```

<210> SEQ ID NO 70
<211> LENGTH: 30
<212> TYPE: DNA
<213> ORGANISM: Artificial sequece
<220> FEATURE:
<223> OTHER INFORMATION: synthesized nucleotides

<400> SEQUENCE: 70

```
tccgtcgaca agcttgcggc cgcactcgag                               30
```

UNITED STATES PATENT AND TRADEMARK OFFICE
CERTIFICATE OF CORRECTION

PATENT NO. : 9,976,167 B2
APPLICATION NO. : 14/650203
DATED : May 22, 2018
INVENTOR(S) : Zhihua Zhou et al.

Page 1 of 1

It is certified that error appears in the above-identified patent and that said Letters Patent is hereby corrected as shown below:

In the Claims

At Column 135, Claim 7, Lines 35-36, "SEQ ID NOs.: 2, 16, 18, 20, 22, 24, 26, 28, 43, 55, 57, 59 and 61." should read -- SEQ ID NOs.: 2, 16, 18, 20, 26, 28, 43, 55, 57, 59 and 61. --

Signed and Sealed this
Sixteenth Day of October, 2018

Andrei Iancu
*Director of the United States Patent and Trademark Office*